US012582650B2

(12) United States Patent
Lin et al.

(10) Patent No.: US 12,582,650 B2
(45) Date of Patent: Mar. 24, 2026

(54) IRAK4 KINASE INHIBITOR AND PREPARATION METHOD THEREFOR

(71) Applicant: ZHUHAI YUFAN BIOTECHNOLOGIES CO., LTD, Guangdong (CN)

(72) Inventors: Xingyu Lin, Guangdong (CN); Tingting Lu, Guangdong (CN)

(73) Assignee: Guangzhou Yufan Nantu Biotechnologies Co., Ltd, Guangzhou (CN)

( * ) Notice: Subject to any disclaimer, the term of this patent is extended or adjusted under 35 U.S.C. 154(b) by 999 days.

(21) Appl. No.: 17/630,114

(22) PCT Filed: Jul. 24, 2020

(86) PCT No.: PCT/CN2020/103930
§ 371 (c)(1),
(2) Date: Apr. 7, 2022

(87) PCT Pub. No.: WO2021/018012
PCT Pub. Date: Feb. 4, 2021

(65) Prior Publication Data

US 2022/0305009 A1 Sep. 29, 2022

(30) Foreign Application Priority Data

Jul. 26, 2019 (CN) ......................... 201910683845.8

(51) Int. Cl.

| | |
|---|---|
| ***A61P 35/00*** | (2006.01) |
| ***A61K 31/437*** | (2006.01) |
| ***A61K 31/4985*** | (2006.01) |
| ***A61K 31/5377*** | (2006.01) |
| ***A61K 45/06*** | (2006.01) |
| ***A61P 35/02*** | (2006.01) |
| ***C07D 471/14*** | (2006.01) |
| ***C07D 487/14*** | (2006.01) |
| *A61P 11/06* | (2006.01) |

(52) U.S. Cl.
CPC ........ *A61K 31/4985* (2013.01); *A61K 31/437* (2013.01); *A61K 31/5377* (2013.01); *A61K 45/06* (2013.01); *C07D 471/14* (2013.01)

(58) Field of Classification Search
None
See application file for complete search history.

(56) References Cited

U.S. PATENT DOCUMENTS 6,673,908 B1 * 1/2004 Stanton, Jr. ........ C07K 14/7151 435/6.16
8,426,411 B2 4/2013 Wishart et al.
8,461,328 B2 * 6/2013 Babu ....................... A61P 35/02 544/126
8,962,629 B2 2/2015 Wishart et al.
9,365,579 B2 6/2016 Wishart et al.
RE47,221 E 2/2019 Wishart et al.
11,236,093 B2 2/2022 Surleraux et al.
2009/0312338 A1 12/2009 Wishart et al.
2011/0201593 A1 8/2011 Babu et al.
2013/0216497 A1 * 8/2013 Wishart .................... A61P 9/12 424/85.4
2015/0210708 A1 7/2015 Wishart et al.
2016/0222020 A1 8/2016 Wishart et al.
2016/0326181 A1 11/2016 Wishart et al.
2018/0291029 A1 10/2018 Wishart et al.
2019/0127379 A1 5/2019 Surleraux et al.

FOREIGN PATENT DOCUMENTS

CN 102118968 7/2011
CN 102711476 10/2012
CN 102712640 10/2012
(Continued)

OTHER PUBLICATIONS

Epps, S. V. et al., Design and Synthesis of Tricyclic Cores for Kinase Inhibition, Bioorganic & Medicinal Letters, vol. 23, pp. 694-696. (Year: 2012).*
Golub et al., Science, vol. 286, Oct. 15, 1999, pp. 531-537 (Year: 1999).*
Cleveland Clinic "Autoimmune Diseases" (Year: 2024).*
Cleveland Clinic "Cancer" (Year: 2024).*
Cleveland Clinic Atherosclerosis (Year: 2024).*
Sylvia Adams (2009) Toll-Like Receptor Agonists in Cancer Therapy, Immunotherapy, 1:6, 949-964 (Year: 2009).*
PubChem 1310723-13-7, Mar. 31, 2015 (Year: 2015).*
International Search Report for PCT/CN2020/103930 dated Oct. 27, 2020, 12 pages.
(Continued)

*Primary Examiner* — Kortney L. Klinkel
*Assistant Examiner* — Alison Azar Salamatian
(74) *Attorney, Agent, or Firm* — NIXON & VANDERHYE, PC

(57) ABSTRACT

The present invention provides a compound of general formula I, and a pharmaceutically acceptable salt, a stereoisomer, an ester, a prodrug, a solvate and a deuterated compound thereof, wherein the compound is an IRAK4 kinase inhibitor, and can be used for preventing and/or treating diseases related to IRAK4, such as autoimmune diseases, inflammatory diseases, cancers, heteroimmune diseases, thromboembolism, atherosclerosis, myocardial infarction and metabolic syndrome.

(I)

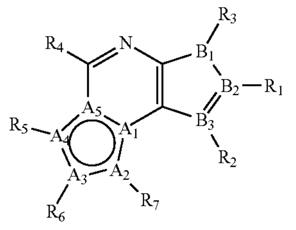

10 Claims, 4 Drawing Sheets

(56) References Cited

FOREIGN PATENT DOCUMENTS

| | | |
|---|---|---|
| CN | 109311882 | 2/2019 |
| JP | 2012-505152 | 3/2012 |
| JP | 2019-516688 | 6/2019 |
| WO | 2011/068881 | 6/2011 |
| WO | 2011/086053 | 7/2011 |

OTHER PUBLICATIONS

Written Opinion of the ISA for PCT/CN2020/103930 dated Oct. 27, 2020, 5 pages.
CAS RN 1353428-82-6 et.al., STN entry dates, 2010-2012.
Janusz J.Kulagowski et.al, "Identification of Imidazo-Pyrrolopyridines as Novel and Potent JAK1 Inhibitors", Journal of Medicinal Chemistry, vol. 55 , No. 12, pp. 5901-5921, May 6, 2012.
William T.Mcelroy: "Interleukin-1 Receptor-Associated Kinase 4(IRAK4) Inhibitors:An Updated Patent Review (2016-2018)", Expert Opinion on the Rapeutic Patents, vol. 29, No. 4, Mar. 29, 2019 (Mar. 29, 2019), pp. 243-259, XP055727413,GB ISSN:1354-3776,DOI: 10.1080/13543776.2019.1597850.
Supplementary European Search Report issued in International Application No. 20848526.8-1110 dated Aug. 17, 2022, 7 pages.

* cited by examiner

IRAK4 KINASE INHIBITOR AND PREPARATION METHOD THEREFOR

CROSS REFERENCE TO RELATED APPLICATION

This application is the U.S. national phase application of International patent application No. PCT/CN2020/103930, filed on Jul. 24, 2020, which claims the benefit and priority of Chinese patent application No. CN201910683845.8, filed on Jul. 26, 2019, the content of each of which is incorporated herein by reference in its entirety for all purposes.

TECHNICAL FIELD

The present invention relates to the field of pharmaceuticals, and particularly relates to an IRAK4 kinase inhibitor and a preparation method thereof and use thereof.

BACKGROUND

Interleukin-1 receptor-associated kinase-4 (IRAK4) is an intracellular serine/threonine protein kinase and is a member of the IRAK family. The IRAK4 kinase mainly consists of a conserved N-terminal death domain (DD), a hinge region and a C-terminal central kinase domain (KD). The DD region is a region in which IRAK4 binds to the adaptor protein myeloid differentiation factor 88 (MyD88), and it plays an important role in molecular recognition and activation of downstream signaling pathways in IRAK4. The KD region consists of 12 subregions, with typical serine/threonine kinase domain characteristics. The primary function of IRAK4 is to phosphorylate its substrate via the KD region, thereby activating downstream signaling molecules. Research shows that IRAK4 is a key factor in the downstream of a toll-like receptor (TLR)/interleukin-1 receptor (IL-1R)-mediated inflammatory signal transduction pathway and plays an important role in body inflammatory response.

TLRs/IL-1R signaling pathways are not only the primary routes for the innate immune system to recognize pathogen-associated molecular patterns (PAMPs), but also involve in the regulation of the adaptive immune response. Research shows that, after binding of TLRs and IL-1R to ligands, MyD88 protein is recruited through the TIR domain of the TLRs, and then MyD88 molecule further recruits IRAK4 into the TLRs/IL-1R complex through the DD region at the N terminal of the molecule and is in close contact with IRAK1, IRAK4 is subjected to autophosphorylation through the KD region and then activates IRAK1, so that signals are transmitted downstream to E3 ubiquitin ligase TNF receptor-associated factor 6 (TRAF6), and activates serine/threonine kinase TAK1, and then activates NF-κB and MAPK signaling pathways, thereby releasing various inflammatory cytokines and anti-apoptotic molecules.

Overactivation of IRAK4-dependent TLR/IL-1R signaling pathway has been shown to be associated with occurrence and development of the following diseases: gout, atherosclerosis, rheumatoid arthritis, myocardial infarction, systemic lupus erythematosus, multiple sclerosis, metabolic syndrome, sepsis, inflammatory bowel disease, asthma, allergy, and rejection after organ transplantation. In recent years, it has been founded that leucine at the $265^{th}$ position in the MyD88 protein coding region is mutated into proline (L265P) in various hematologic tumors, which leads to continuous activation and amplification of IRAK4-mediated NF-kB signaling pathway, thereby promoting malignant proliferation of cells. In diffuse large B-cell lymphoma, mutation of L265P in the MyD88 protein leads to over-activation of IRAK4. Over-activation of IRAK4 caused by mutation of MyD88L265P has also been confirmed in chronic lymphatic leukemia and Waldenstrom's macroglobulinemia. By inhibiting activity of IRAK4, the intracellular IL-6 and IL-10 levels can be reduced, thereby inhibiting malignant proliferation and differentiation of cells. Therefore, IRAK4 has become an important target in the treatment of inflammation, immune-associated diseases and hematologic tumor.

Patent document CN101389630A discloses a compound for inhibiting protein kinase, and the compound for inhibiting protein kinase has a general structural formula of

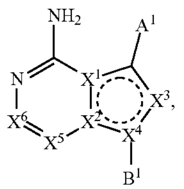

and can be used for treating bladder cancer, breast cancer, neck cancer, colon cancer, endometrial cancer, esophageal cancer, lung cancer, ovarian cancer, pancreatic cancer, prostate cancer, rectal cancer, skin cancer, stomach cancer or thyroid cancer.

Patent document CN109311882A discloses an adenine derivative of a protein kinase inhibitor having a structural formula of

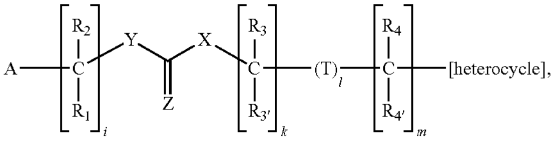

and the compound can be used for treating related diseases mediated by protein kinase, such as cancers, inflammatory diseases, cardiovascular diseases, diseases caused by virus, circulatory diseases, fibroproliferative diseases and pain-sensitized diseases.

Patent document CN102892768A discloses a substituted pyrroloaminopyrimidine compound having a general structural formula of

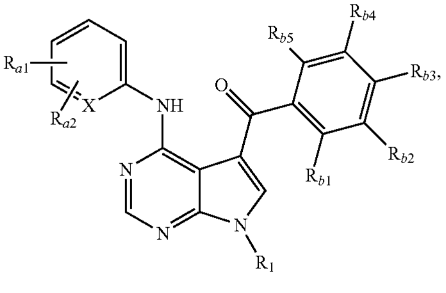

and the compound can be used for treating cell proliferative disorders such as cancers.

Patent document CN02811932.0 discloses pyrrolopyrimidine as a protein kinase inhibitor having a structural formula of

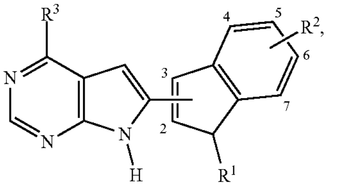

and the compound can be used for treating inflammatory diseases and cancers.

SUMMARY

One objective of the present invention is to provide a compound of general formula I and a preparation method therefor, wherein the compound is an IRAK4 kinase inhibitor; another objective of the present invention is to provide use of the compound.

The objectives of the present invention are implemented through the following technical solutions.

The present invention provides a compound of general formula I:

(I)

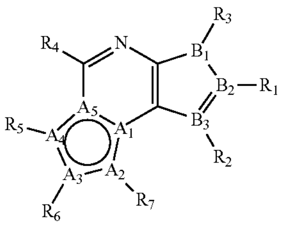

wherein $A_1$, $A_3$, $A_4$ and $A_5$ are independently selected from C and N, $A_2$ is C, N, O or S, and when any one of $A_2$, $A_3$ and $A_4$ is N and the N is bonded to a double bond, corresponding $R_7$, $R_6$ or $R_5$ does not exist.

Preferably, at least one of $A_1$, $A_2$, $A_3$, $A_4$ and $A_5$ is N, and for example, one is N, two are N, or three are N.

More preferably, $A_1$, $A_2$, $A_3$ and $A_5$ are C, and $A_4$ is N; or, $A_3$, $A_4$ and $A_5$ are C, and $A_1$ and $A_2$ are N; or, $A_2$, $A_3$ and $A_5$ are C, and $A_1$ and $A_4$ are N; or, $A_1$, $A_3$ and $A_5$ are C, and $A_2$ and $A_4$ are N; or, $A_1$, $A_2$ and $A_5$ are C, and $A_3$ and $A_4$ are N; or, $A_1$, $A_4$ and $A_5$ are C, and $A_2$ and $A_3$ are N; or, $A_1$, $A_3$ and $A_4$ are C, and $A_2$ and $A_5$ are N; or, $A_1$, $A_2$ and $A_3$ are C, and $A_4$ and $A_5$ are N; or, $A_3$ and $A_5$ are C, and $A_1$, $A_2$ and $A_4$ are N; or, $A_1$ and $A_5$ are C, and $A_2$, $A_3$ and $A_4$ are N; or, $A_1$ and $A_3$ are C, and $A_2$, $A_4$ and $A_5$ are N.

$B_1$, $B_2$ and $B_3$ are independently selected from C and N, and when $B_2$ or $B_3$ is N, corresponding $R_1$ or $R_2$ does not exist.

Preferably, $B_1$ is N, and $B_2$ and $B_3$ are C.

Preferably, the compound has the following structural formula:

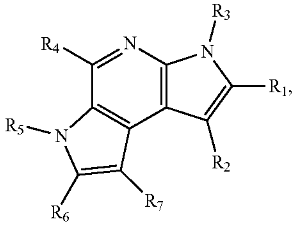

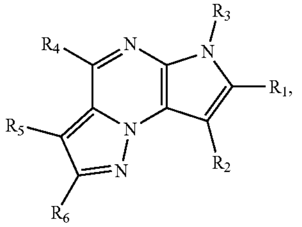

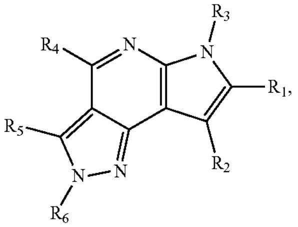

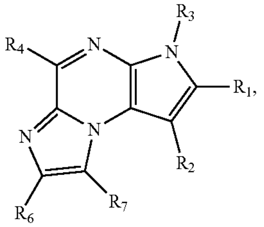

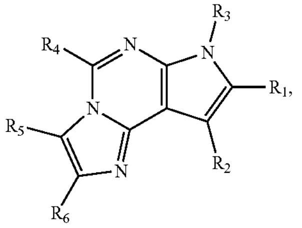

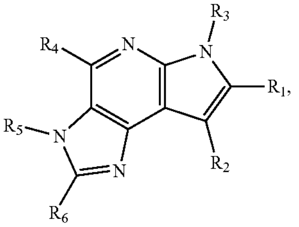

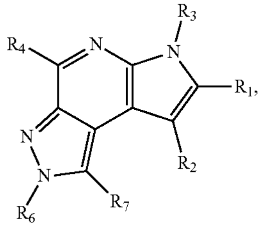

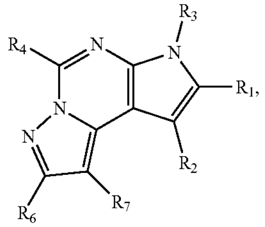

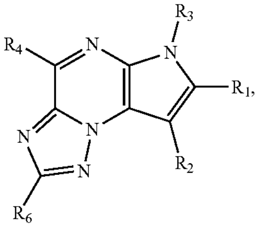

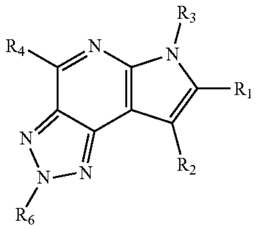

or

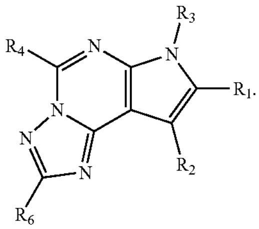

$R_1$, $R_3$ and $R_4$ are independently selected from —H, -D, —OH, halogen, —CN, —$NO_2$, —$CF_3$, —$OCF_3$, $C_{1-5}$ linear/ branched alkyl, —N($C_{0-10}$ alkyl)($C_{0-10}$ alkyl), —N($C_{0-10}$ alkyl)CO($C_{0-10}$ alkyl), —N($C_{0-10}$ alkyl)CON($C_{0-10}$ alkyl), —N($C_{0-10}$ alkyl)$SO_2$($C_{0-10}$ alkyl), —$OC_{0-10}$ alkyl, —$SC_{0-10}$ alkyl, —SO($C_{0-10}$ alkyl), —$SO_2$($C_{0-10}$ alkyl), —$SO_2N$($C_{0-10}$ alkyl)($C_{0-10}$ alkyl), —COO($C_{0-10}$ alkyl), —OCO($C_{0-10}$ alkyl), —CON($C_{0-10}$ alkyl)($C_{0-10}$ alkyl), —CO($C_{0-10}$ alkyl), $C_{3-6}$ cycloalkyl, —O heterocycloalkyl, —N heterocycloalkyl, —S heterocycloalkyl, —N heterocycloaryl, —O heterocycloaryl and —S heterocycloaryl.

Preferably, $R_1$ is selected from —H, -D, —OH, —F, —Cl, —Br, —I, —CN, —$NO_2$, —$CF_3$, —$NH_2$, —O heterocycloalkyl and —N heterocycloalkyl.

$R_3$ is selected from —H, -D, —CN, —$CF_3$, $C_{1-5}$ linear/branched alkyl, $C_{3-6}$ cycloalkyl and —O heterocycloalkyl.

$R_4$ is selected from —H, -D, —OH, —F, —Cl, —Br, —I, —CN, —$NO_2$, —$CF_3$, —$NH_2$, —O heterocycloalkyl and —N heterocycloalkyl.

In a preferred embodiment of the present invention, $R_1$, $R_3$ and $R_4$ are independently selected from —H.

Preferably, the compound has the following structural formula:

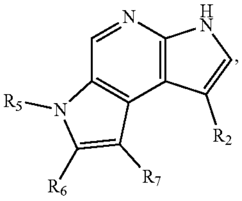,
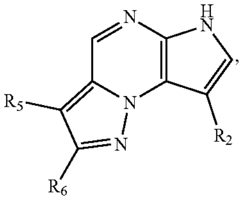,
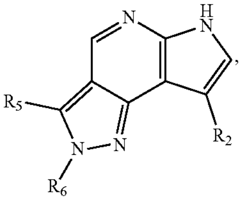,
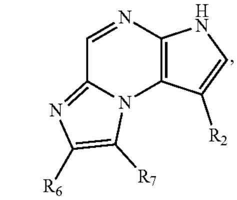,
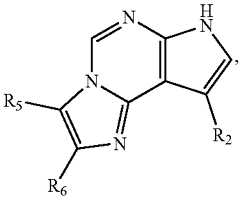,
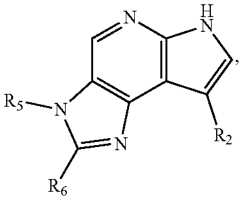,
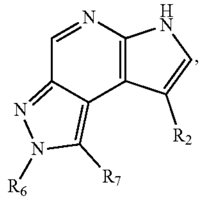,
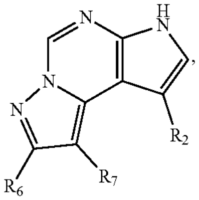,
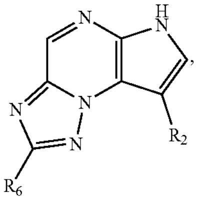,
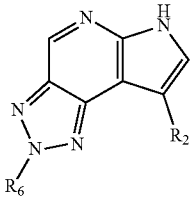 or -continued

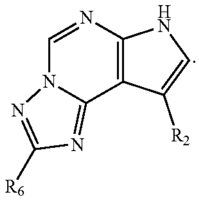.

$R_2$ is selected from —H, -D, halogen, —CN, —$CF_3$, $C_{1-5}$ linear/branched alkyl, —N($C_{0-10}$ alkyl)($C_{0-10}$ alkyl), —$OC_{0-10}$ alkyl, $C_{3-8}$ cycloalkyl, heterocycloalkyl, phenyl, heterocycloaryl, $C_{4-8}$ bridged cycloalkyl, $C_{5-10}$ spirohydrocarbyl and $C_{7-10}$ fused cycloalkyl, wherein H of the groups can be substituted with one or two or more of the following substituents: —OH, —$NH_2$, halogen, —CN, —$NO_2$, —$CF_3$, —$OCF_3$, =O, —N alkyl, —O alkyl, —S alkyl, —SO-alkyl, —$SO_2$-alkyl, —COO-alkyl, —CON alkyl, —CO-alkyl, —OCO-alkyl, —N-alkyl-CON-alkyl, —N alkyl-CO-alkyl, —N alkyl-$SO_2$-alkyl, substituted or unsubstituted aryl, and substituted or unsubstituted cycloalkyl.

Preferably, $R_2$ is selected from $C_{1-5}$ linear/branched alkyl,

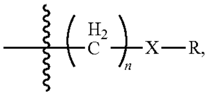,
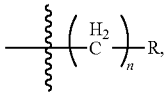,
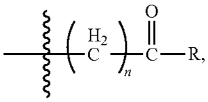,
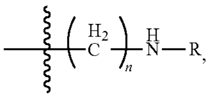,
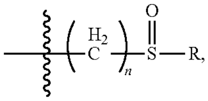,
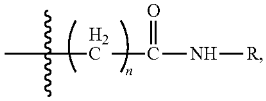,
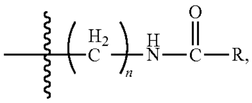,
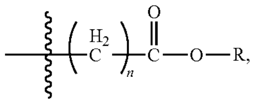,
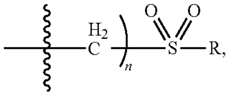,
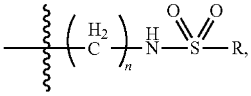,
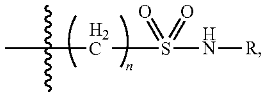,
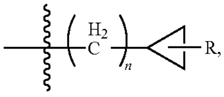,
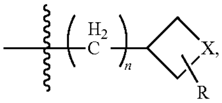,
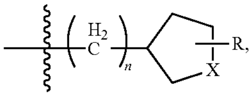,
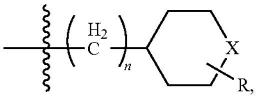,
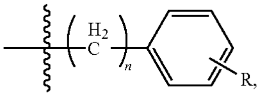,
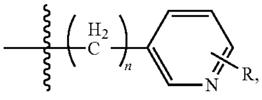,
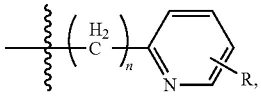,
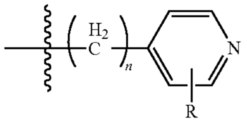 and -continued

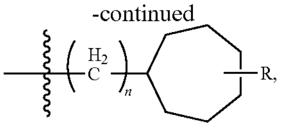

wherein H on the C atom can be substituted with the following substituents: —OH, —$NH_2$, halogen, —CN, and —$NO_2$, wherein n is an integer between 0 and 5, for example, 0, 1, 2, 3, 4 or 5, and when n is 0, —$CH_2$-does not exist; preferably, n is 0, 1 or 2;

X is selected from C, N, O and S, and preferably, X is selected from C and O;

R is selected from —H, —OH, ═O, —CN, halogen, —$CF_3$, —CON($C_{0-5}$ alkyl)($C_{0-5}$ alkyl), $C_{1-5}$ linear/branched alkyl, $C_{1-5}$ unsaturated alkyl, —$OC_{0-5}$ alkyl, —$NHC_{0-5}$ alkyl, cycloalkyl, heterocycloalkyl, phenyl and heterocycloaryl; and preferably, R is selected from —H, —OH, —$CONH_2$, —CN, —F, —$CF_3$, —$CH_3$, —$CH_2CH_3$, —$CH_2CH$═$CHCH_3$, —$NHCH_3$,

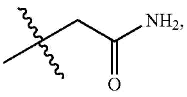,
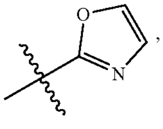,
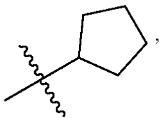,
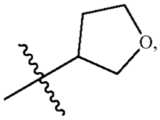,
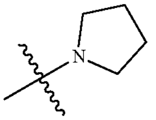,
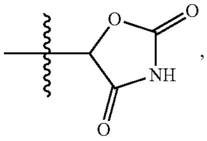,
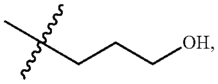,
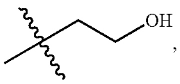,
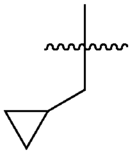,
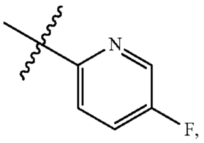,
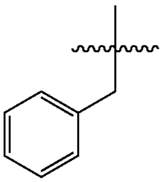
and
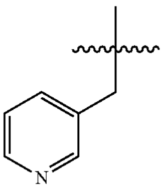.

In a preferred embodiment of the present invention, $R_2$ is selected from

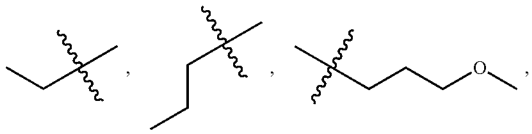,

-continued

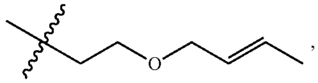,
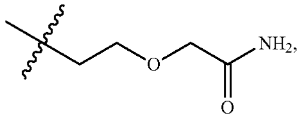,
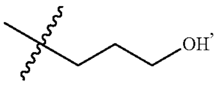,
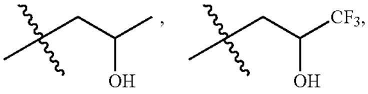,
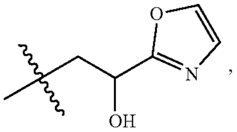,
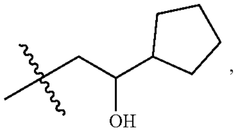,
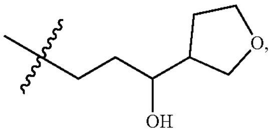,
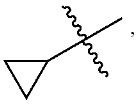,
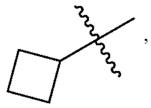,
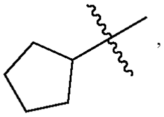,
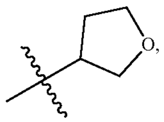,
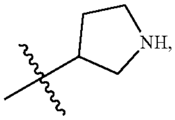,
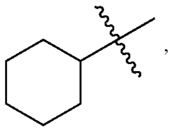,
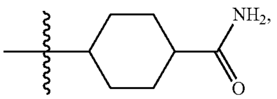,
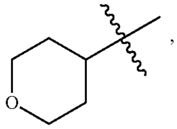,
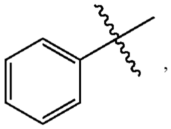,
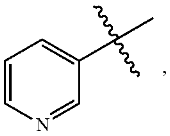,
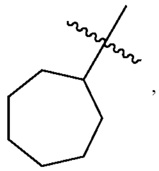,
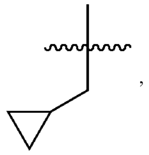,
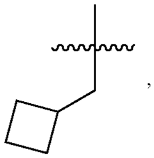,
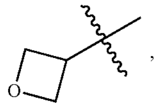,
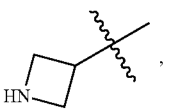,
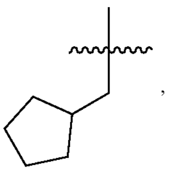,
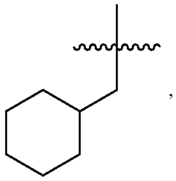,
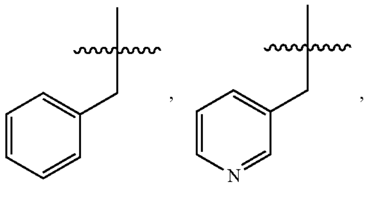, -continued

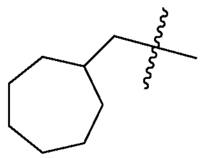
,
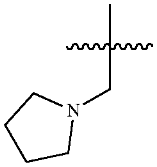
,
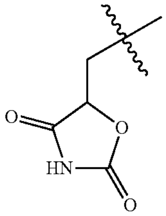
,
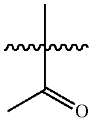
,
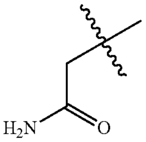
,
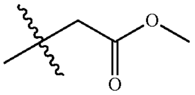
,
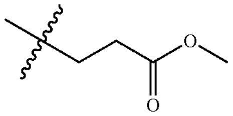
,
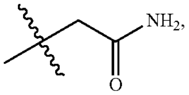
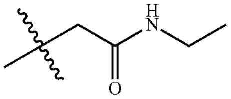
,
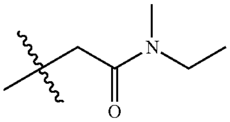
,
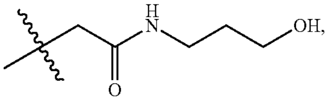
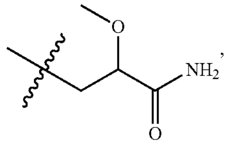
,
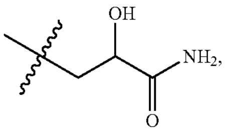
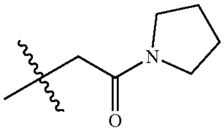
,
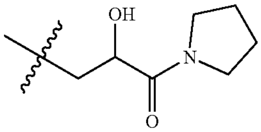
,
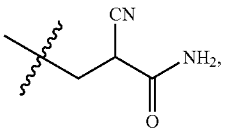
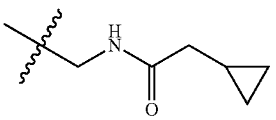
,
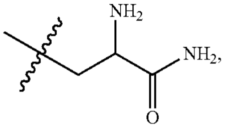
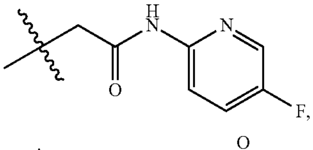
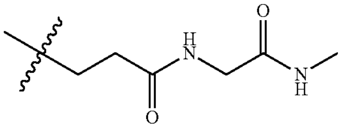
,
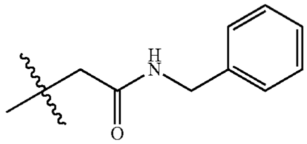
, -continued

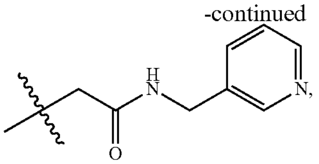
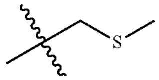
,
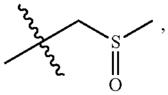
,
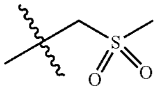
,
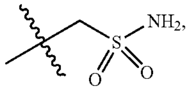
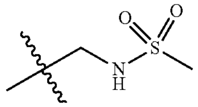
,
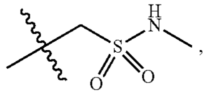
,
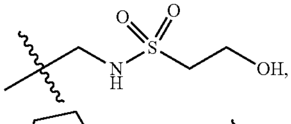
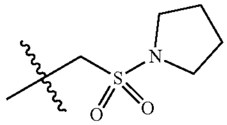
and
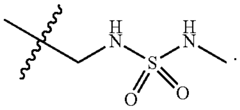
.

$R_5$ is selected from —H, -D, halogen, —CN, —$CF_3$, $C_{1-5}$ linear/branched alkyl, —N($C_{0-10}$ alkyl)($C_{0-10}$ alkyl), —$OC_{0-10}$ alkyl, $C_{3-8}$ cycloalkyl, heterocycloalkyl, phenyl, heterocycloaryl, $C_{4-8}$ bridged cycloalkyl, $C_{5-10}$ spirohydrocarbyl and $C_{7-10}$ fused cycloalkyl, wherein H of the groups can be substituted with one or two or more of the following substituents: —OH, —$NH_2$, halogen, —CN, —$NO_2$, —$CF_3$, —$OCF_3$, ═O, —N alkyl, —O alkyl, —S alkyl, —SO-alkyl, —$SO_2$-alkyl, —COO-alkyl, —CON alkyl, —CO-alkyl, —OCO-alkyl, —N-alkyl-CON-alkyl, —N alkyl-CO-alkyl, —N alkyl-$SO_2$-alkyl, substituted or unsubstituted aryl, and substituted or unsubstituted cycloalkyl.

Preferably, $R_5$ is selected from $C_{1-5}$ linear/branched alkyl

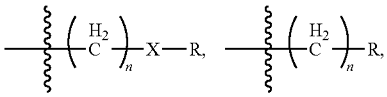
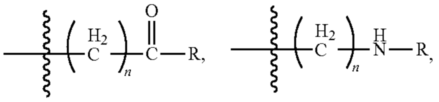
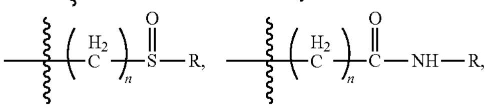
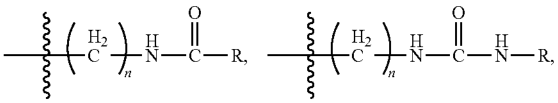
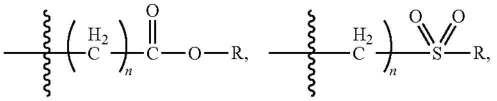
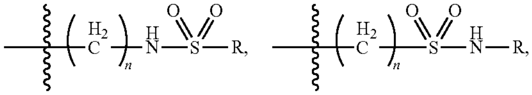
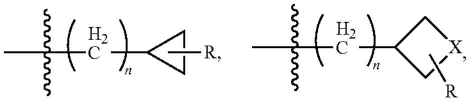

-continued

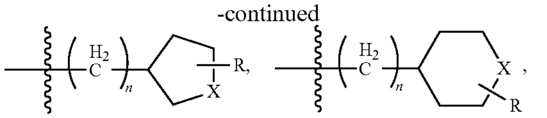

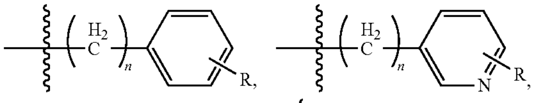

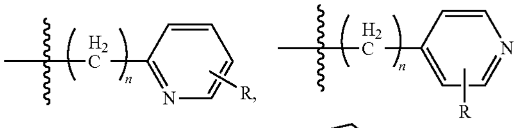

and

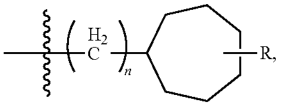

wherein H on the C atom can be substituted with the following substituents: —OH, —$NH_2$, halogen, —CN, and —$NO_2$, wherein n is an integer between 0 and 5, for example, 0, 1, 2, 3, 4 or 5, and when n is 0, —$CH_2$-does not exist; preferably, n is 0, 1 or 2.

X is selected from C, N, O and S, and preferably, X is selected from C and O;

R is selected from —H, —OH, =O, —CN, halogen, —$CF_3$, $C_{1-5}$ linear/branched alkyl, $C_{1-5}$ unsaturated alkyl, —$OC_{0-5}$ alkyl, —$NHC_{0-5}$ alkyl, cycloalkyl, heterocycloalkyl, phenyl and heterocycloaryl; and preferably, R is selected from —H, —OH, —CN, —F, —$CF_3$, —$CH_3$, —$CH_2CH_3$, —$CH_2CH$═$CHCH_3$, —$NHCH_3$,

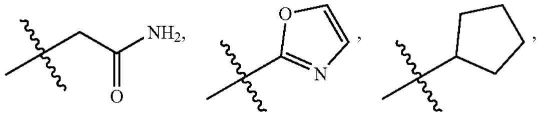

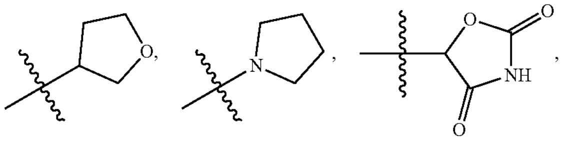

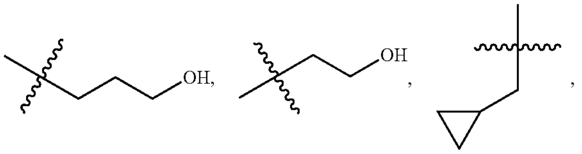

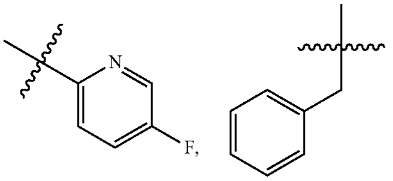

and

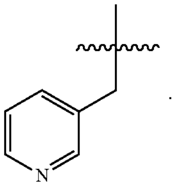

In a preferred embodiment of the present invention, $R_5$ is selected from —H, —$CH_3$,

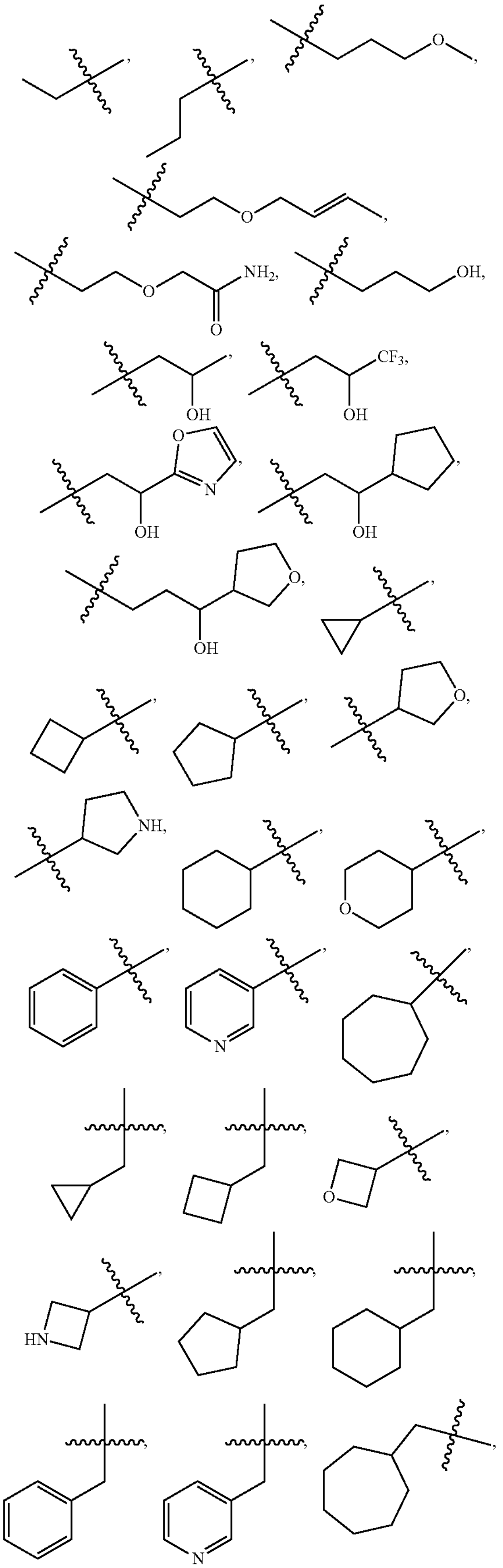

-continued

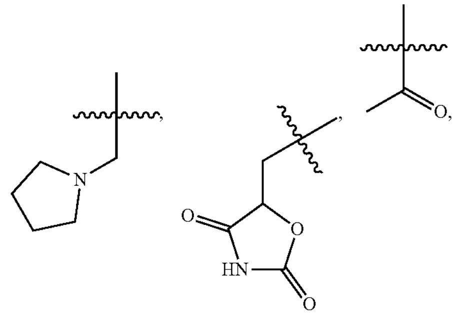

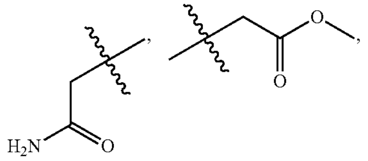

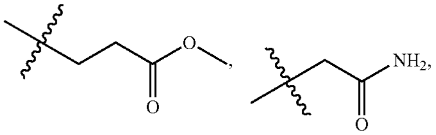

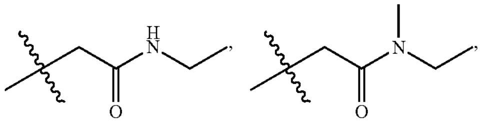

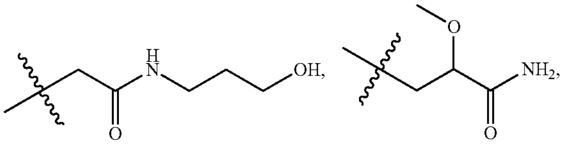

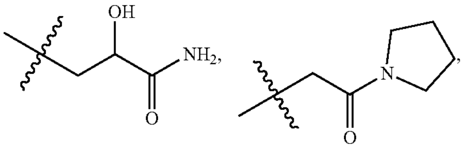

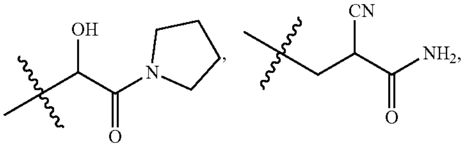

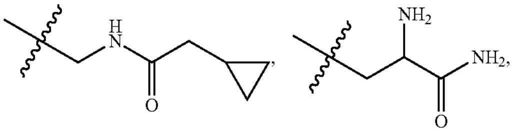

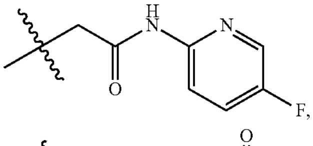

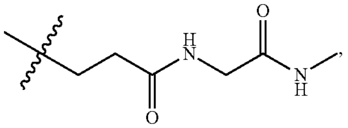

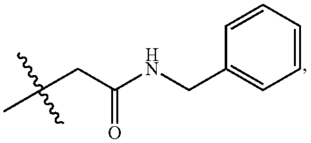

-continued

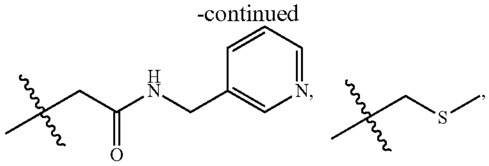

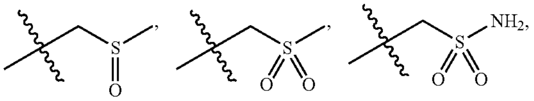

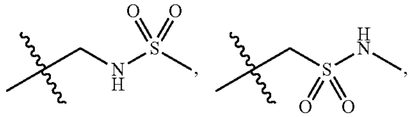

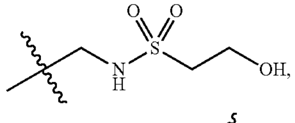

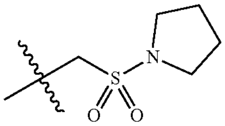

and

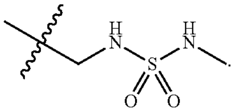

$R_6$ is selected from —H, -D, halogen, —CN, —$CF_3$, —$CHF_2$, —$CH_2F$, —$CH_2CF_3$, $C_{1-5}$ linear/branched alkyl, —N($C_{0-10}$ alkyl)($C_{0-10}$ alkyl), —$OC_{0-10}$ alkyl, $C_{3-8}$ cycloalkyl, heterocycloalkyl, phenyl, heterocycloaryl, $C_{4-8}$ bridged cycloalkyl, $C_{5-10}$ spirocycloalkyl and $C_{7-10}$ fused cycloalkyl, wherein H of the groups can be substituted with one or two or more of the following substituents: —OH, —$NH_2$, halogen, —CN, —$NO_2$, —$CF_3$, —$OCF_3$, ═O, —N alkyl, —O alkyl, —S alkyl, —SO-alkyl, —$SO_2$-alkyl, —COO-alkyl, —CON alkyl, —CO-alkyl, —OCO-alkyl, —N-alkyl-CON-alkyl, —N alkyl-CO-alkyl, —N alkyl-$SO_2$-alkyl, substituted or unsubstituted aryl, and substituted or unsubstituted cycloalkyl.

Preferably, $R_6$ is selected from —H, —$CF_3$, —$CHF_2$, —$CH_2F$, —$CH_2CF_3$, —CN, $C_{1-5}$ linear/branched alkyl,

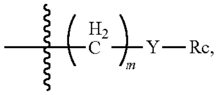

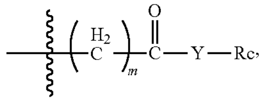

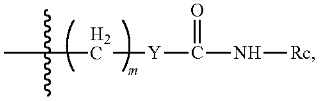

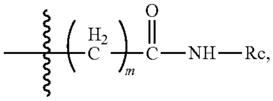

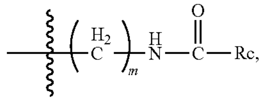

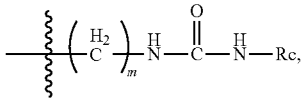

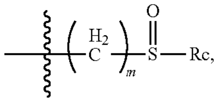

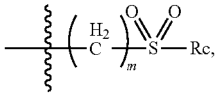

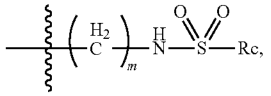

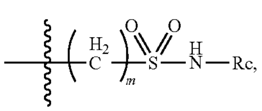

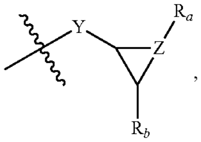

-continued

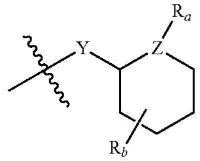,
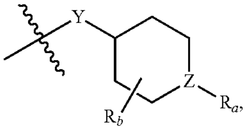
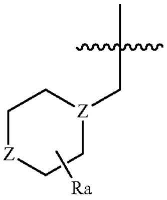,
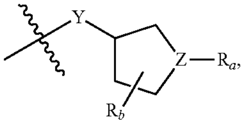
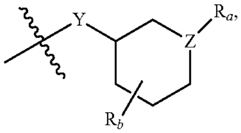
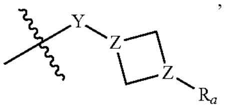,
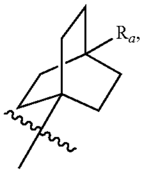
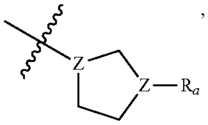,
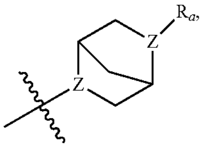
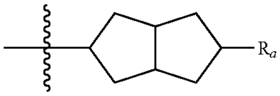,
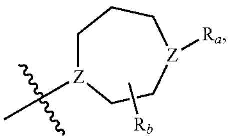
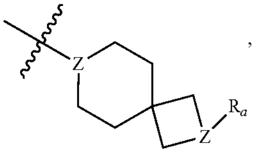,
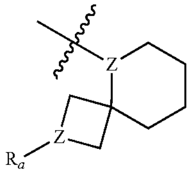,
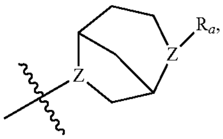
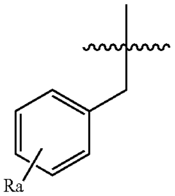,
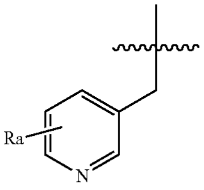,
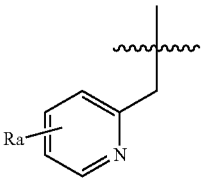,
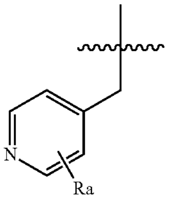,
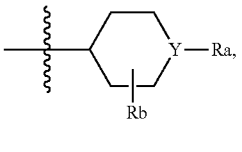
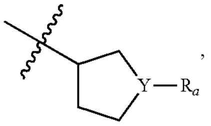, and -continued

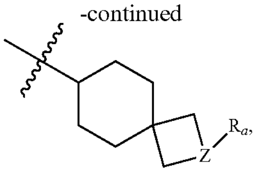

wherein H on the C atom can be substituted with the following substituents: —OH, —$NH_2$, —$CF_3$, halogen, —CN, and —$NO_2$, wherein m is an integer between 0 and 5, for example, 0, 1, 2, 3, 4 or 5, and when m is 0, —$CH_2$-does not exist; preferably, m is 0, 1 or 2;

Y is selected from C, N, O and S, and preferably, Y is selected from C, N and O;

Z is selected from C and N;

Rb is selected from —H, —OH, —CN, halogen, —$CF_3$ and $C_{1-5}$ linear/branched alkyl;

Ra is selected from —H, -D, —OH, —CN, halogen, —$NH_2$, N($C_{0-5}$ alkyl)($C_{0-5}$ alkyl), $C_{1-5}$ linear/branched alkyl, cycloalkyl, heterocycloalkyl,

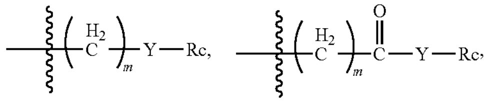
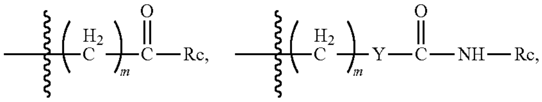
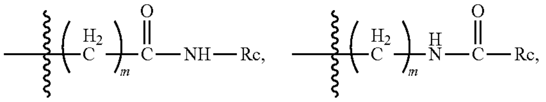
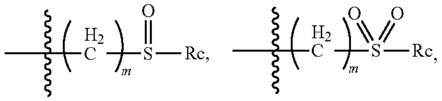
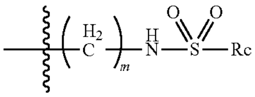 and
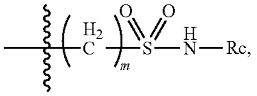

wherein m is 0, 1 or 2, and Y is selected from C, N and O;

Rc is selected from —H, —OH, —CN, halogen, —$CF_3$, $C_{1-5}$ linear/branched alkyl, $C_{1-5}$ unsaturated alkyl, —$OC_{0-5}$ alkyl, —$NHC_{0-5}$ alkyl, cycloalkyl, heterocycloalkyl, phenyl, or heterocycloaryl, wherein H on the C atom can be substituted with the following substituents: —OH, —$NH_2$, halogen, —CN, and —$NO_2$.

Preferably, Rc is selected from —H, —OH, —$CH_3$, —$CH_2CH_3$,

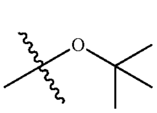,
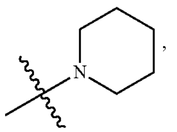,
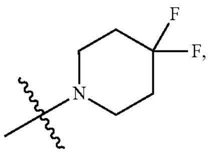

-continued
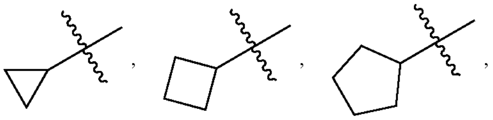
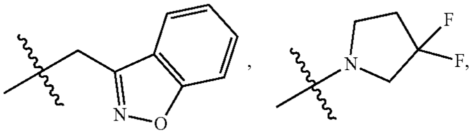
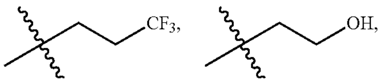
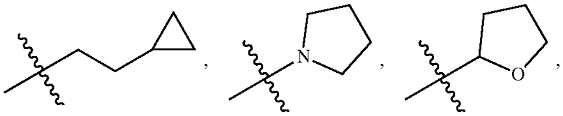
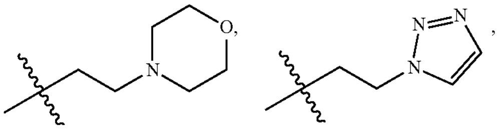
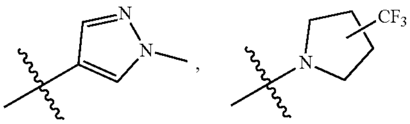
and
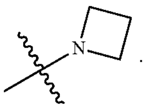
Preferably, Ra is selected from —H, -D, —OH, halogen, $—CH_3$, $—CH_2CH_3$, $—NH_2$,
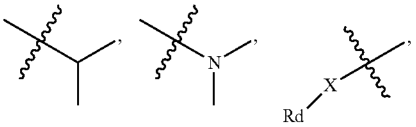
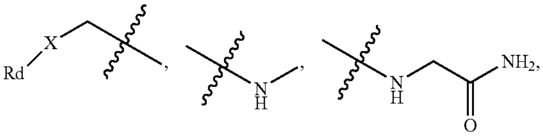
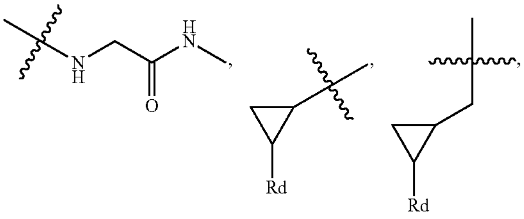
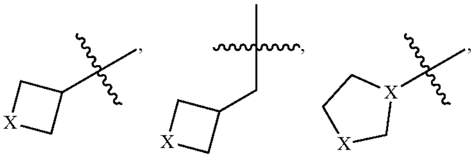
-continued
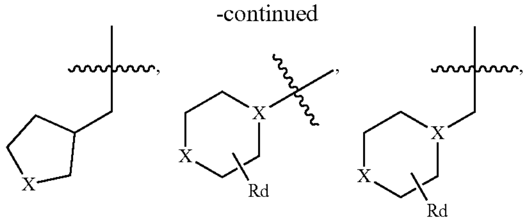
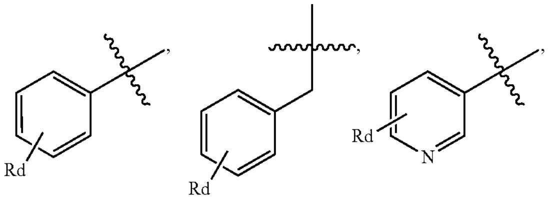
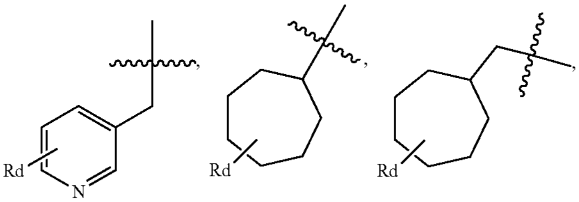
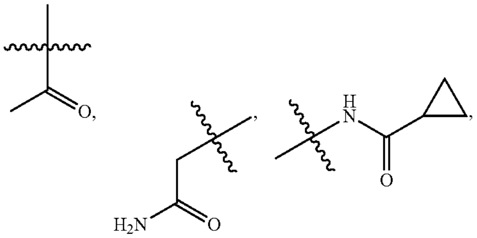
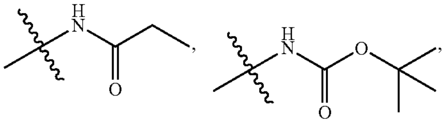
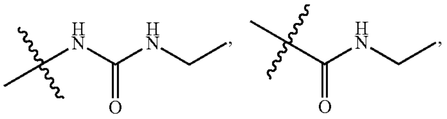
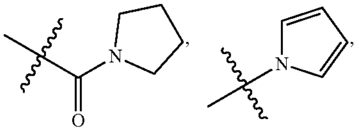
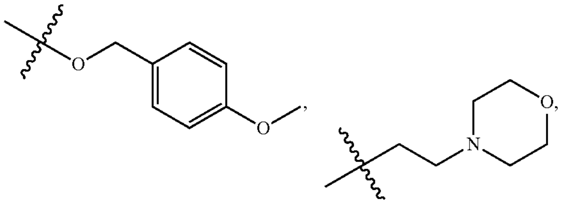
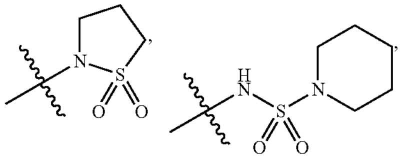
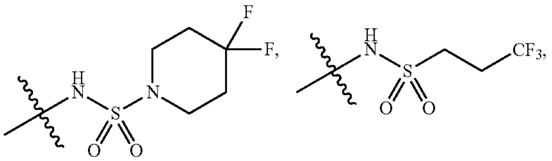

-continued

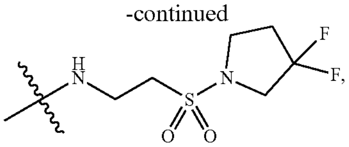

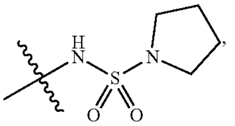

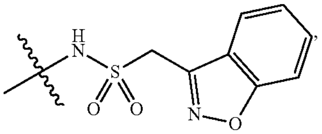

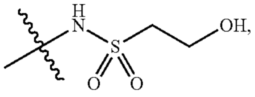

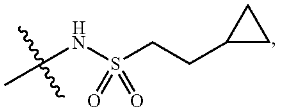

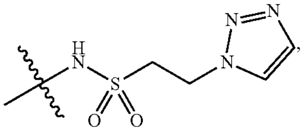

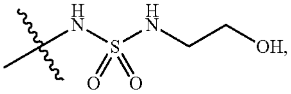

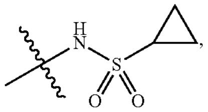

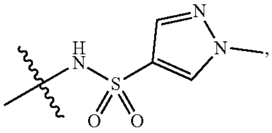

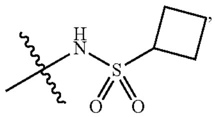

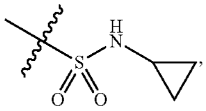

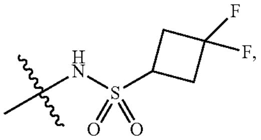

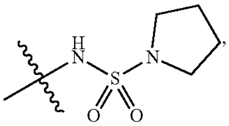

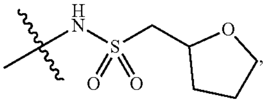

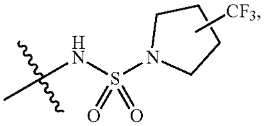

and

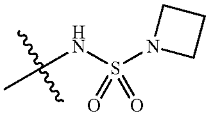

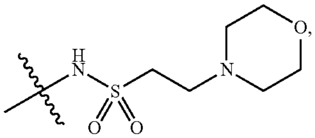

wherein X is selected from C, N, O and S.

Rd is selected from —H, -D, halogen, $C_{1-5}$ linear/branched alkyl, $C_{3-8}$ cycloalkyl, heterocycloalkyl, phenyl, heterocycloaryl, $C_{4-8}$ bridged cycloalkyl, $C_{5-10}$ spirocycloalkyl and $C_{7-10}$ fused cycloalkyl, wherein H of the groups can be substituted with one or two or more of the following substituents: —OH, —$NH_2$, halogen, —CN, —$CF_3$, —$OCF_3$, —N alkyl, —O alkyl, —S alkyl, —SO-alkyl, —$SO_2$-alkyl, —COO-alkyl, —CON alkyl, —CO-alkyl, —N alkyl-CO-alkyl, —N alkyl-$SO_2$-alkyl, substituted or unsubstituted aryl, and substituted or unsubstituted cycloalkyl.

In a preferred embodiment of the present invention, Ra is selected from —H, -D, —OH, halogen, —$CH_3$, —$CH_2CH_3$, —$NH_2$,

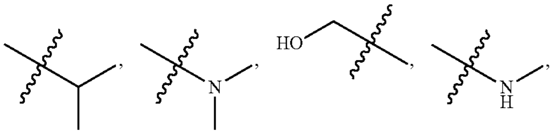

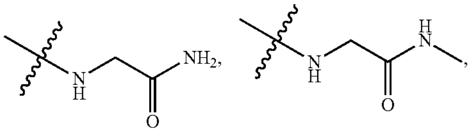

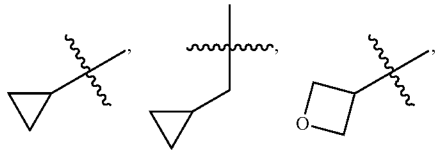

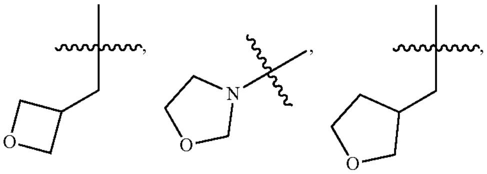

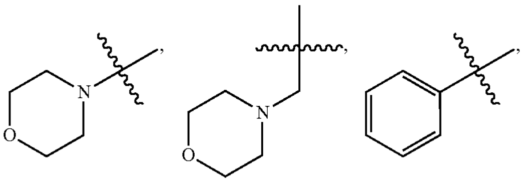

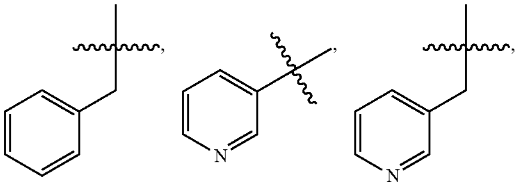

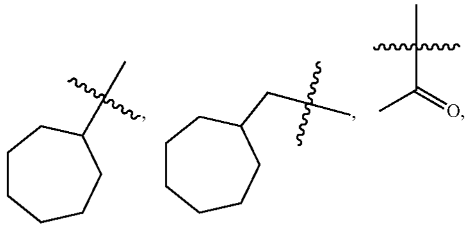

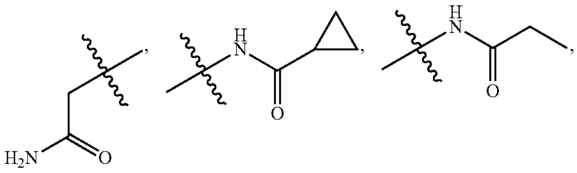

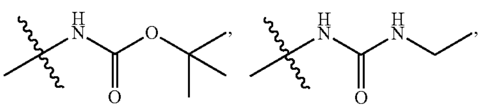

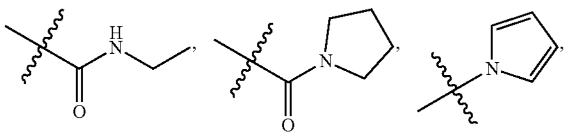

-continued
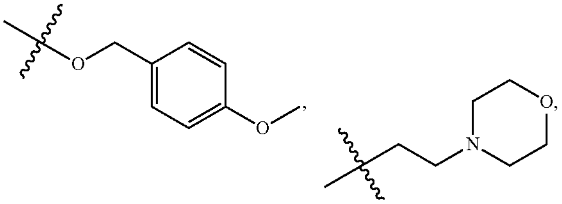
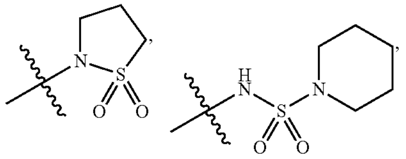
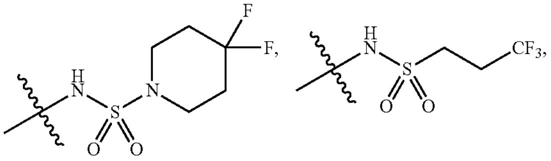
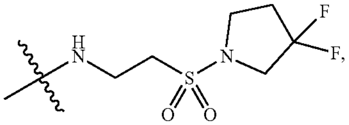
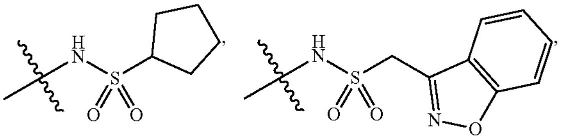
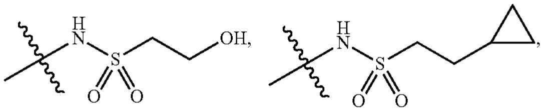
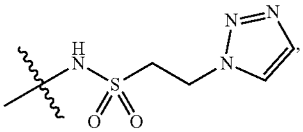
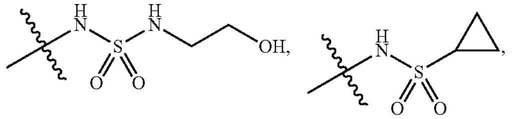
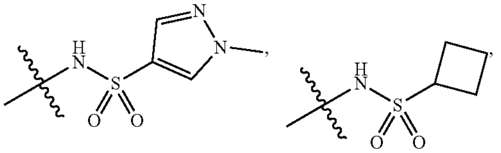
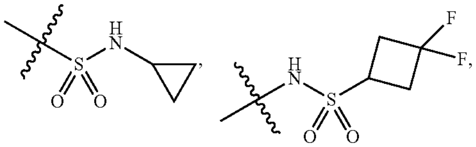
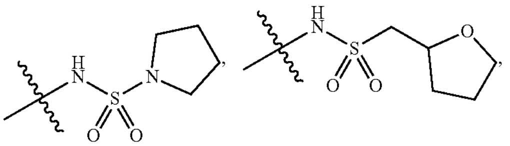
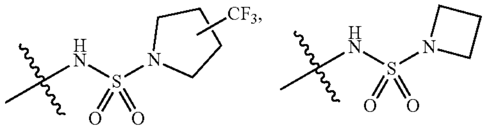
and
-continued
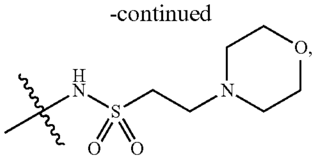
In a preferred embodiment of the present invention, $R_6$ is selected from —H, —$CF_3$, —$CHF_2$, —$CH_2F$, —$CH_2CF_3$, —CN,
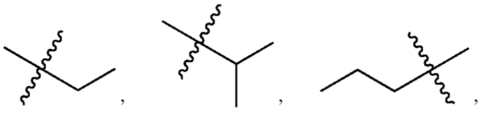
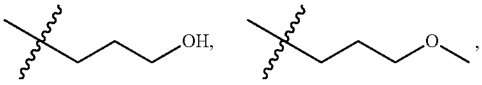
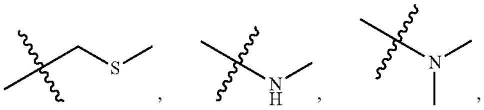
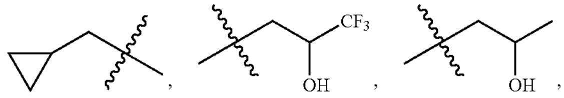
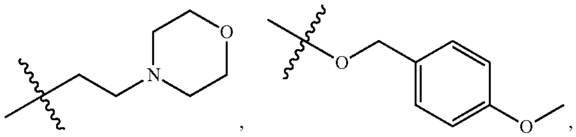
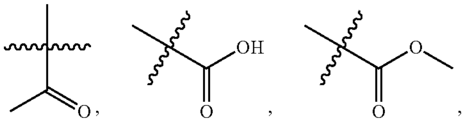
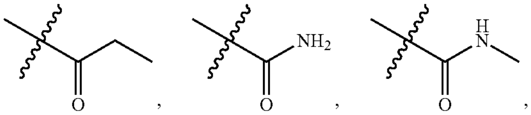
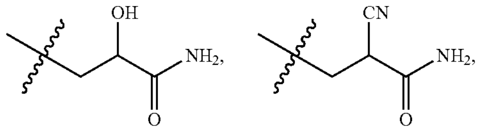
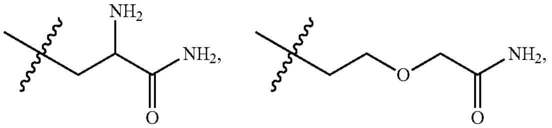
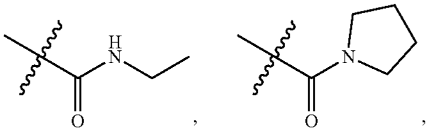
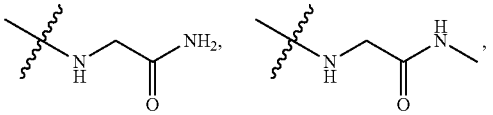
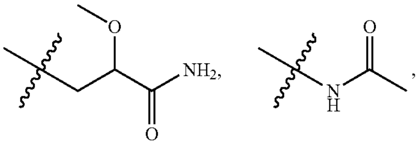

-continued
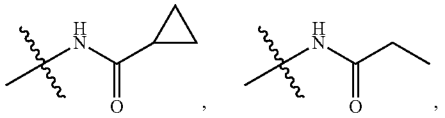
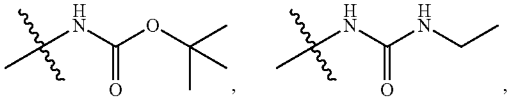
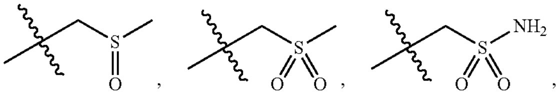
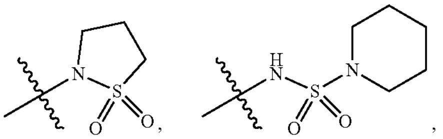
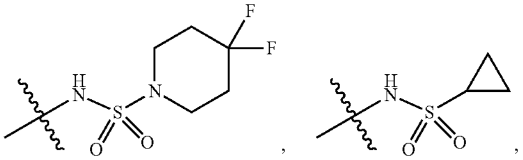
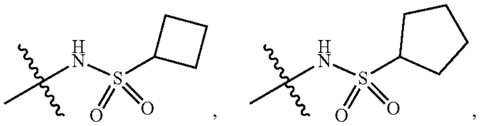
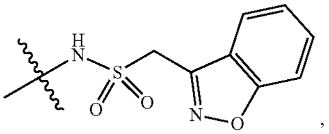
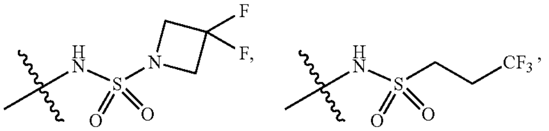
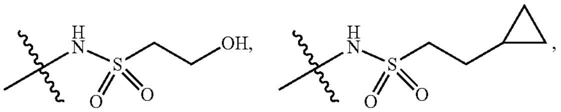
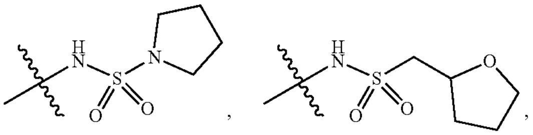
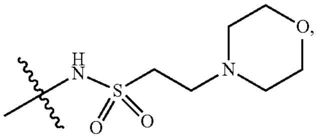
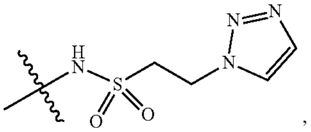
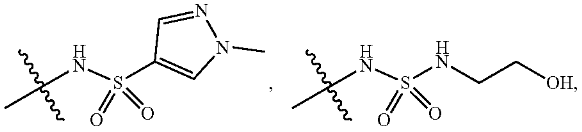
-continued
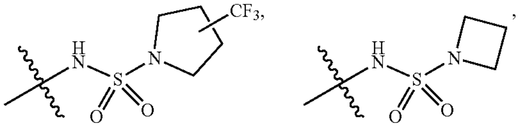
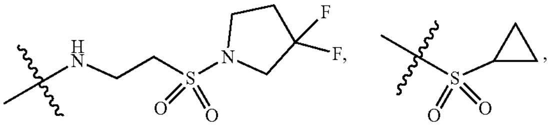
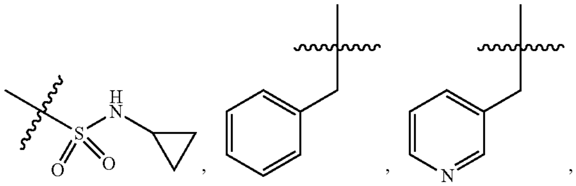
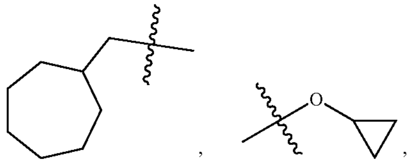
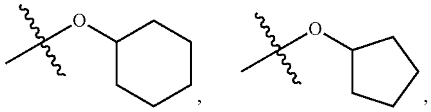
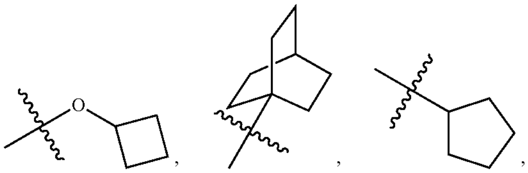
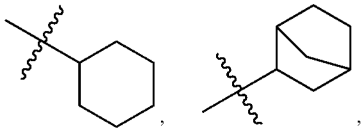
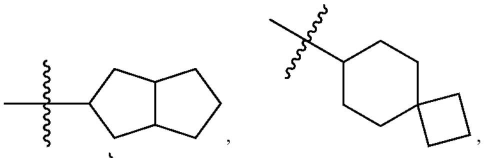
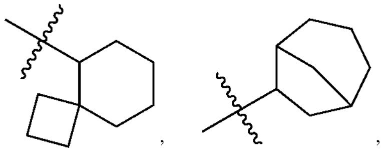
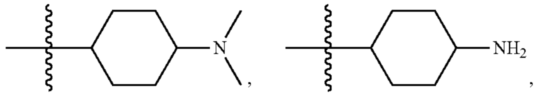
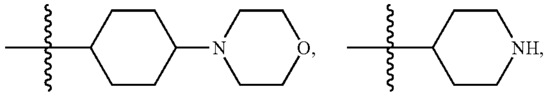
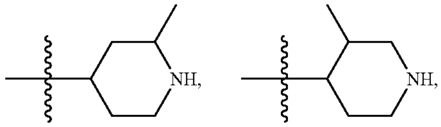
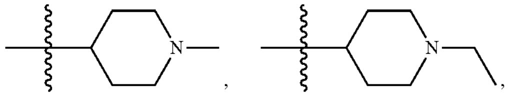

-continued

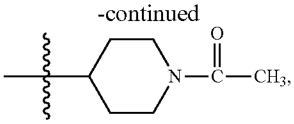,

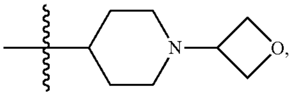, 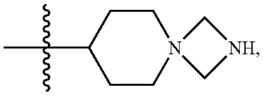,

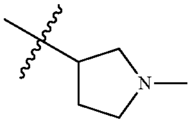, 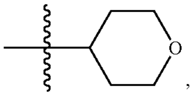,

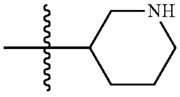.

$R_7$ is selected from —H, -D, —OH, halogen, —CN, —$NO_2$, —$CF_3$, —$OCF_3$, =O, $C_{1-5}$ linear/branched alkyl, —N($C_{0-10}$ alkyl)($C_{0-10}$ alkyl), —N($C_{0-10}$ alkyl)CO($C_{0-10}$ alkyl), —N($C_{0-10}$ alkyl)CON($C_{0-10}$ alkyl), —N($C_{0-10}$ alkyl) $SO_2$($C_{0-10}$ alkyl), —$OC_{0-10}$ alkyl, —$SC_{0-10}$ alkyl, —SO($C_{0-10}$ alkyl), —$SO_2$($C_{0-10}$ alkyl), —$SO_2$N($C_{0-10}$ alkyl) ($C_{0-10}$ alkyl), —COO($C_{0-10}$ alkyl), —OCO($C_{0-10}$ alkyl), —CON($C_{0-10}$ alkyl)($C_{0-10}$ alkyl), —CO($C_{0-10}$ alkyl), $C_{3-6}$ cycloalkyl, —O heterocycloalkyl, —N heterocycloalkyl, —S heterocycloalkyl, —N heterocycloaryl, —O heterocycloaryl and —S heterocycloaryl.

Preferably, $R_7$ is selected from —H, -D, —OH, —F, —Cl, —Br, —I, —CN, —$NO_2$, —$CF_3$, —$NH_2$, $C_{1-5}$ linear/branched alkyl, $C_{3-6}$ cycloalkyl, —O heterocycloalkyl and —N heterocycloalkyl.

In a preferred embodiment of the present invention, $R_7$ is selected from —H.

The compound of general formula I disclosed herein further encompasses a pharmaceutically acceptable salt, a stereoisomer, an ester, a prodrug, a solvate and a deuterated compound.

In specific embodiments of the present invention, the compound of general formula I has the following structure:

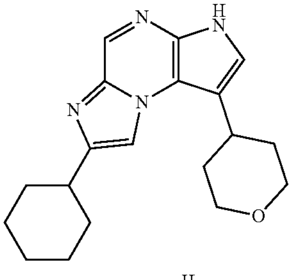, 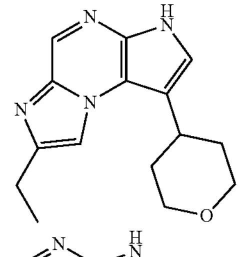,

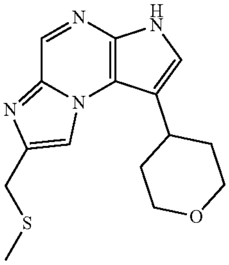, 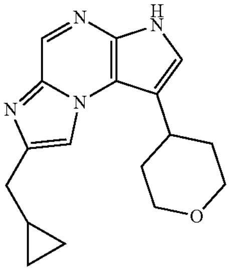,

-continued

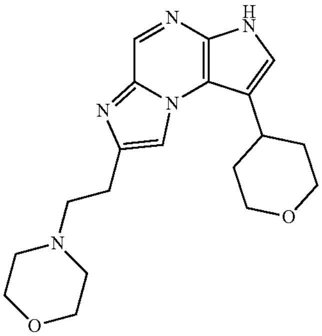,

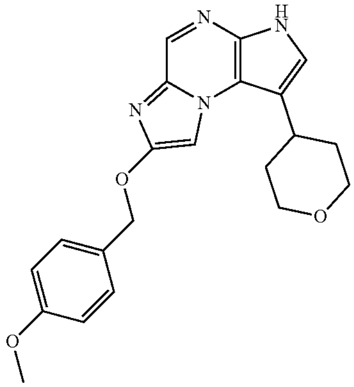,

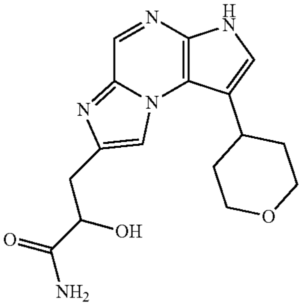,

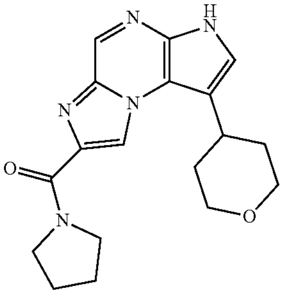,

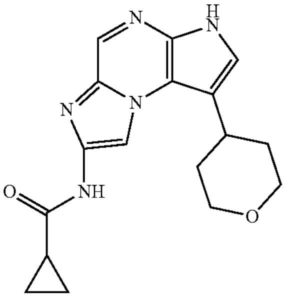,

-continued
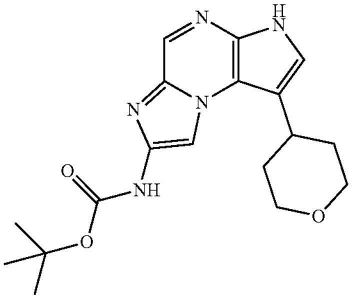
,
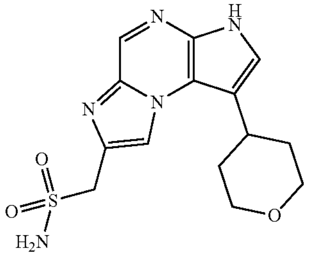
,
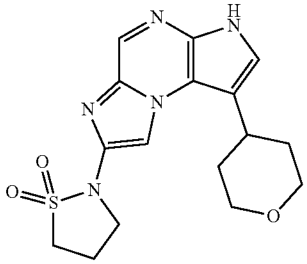
,
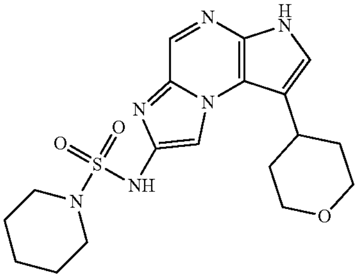
,
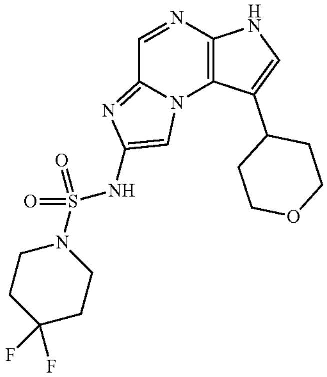
,
-continued
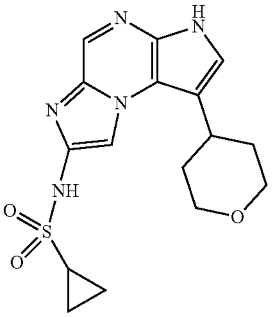
,
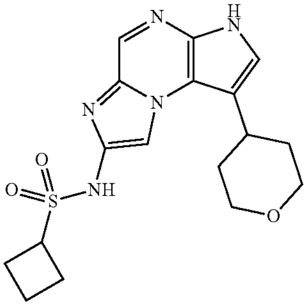
,
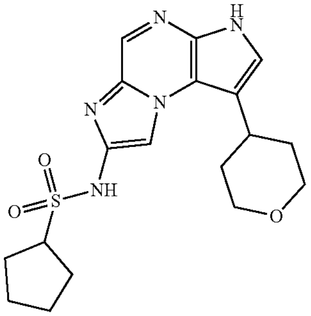
,
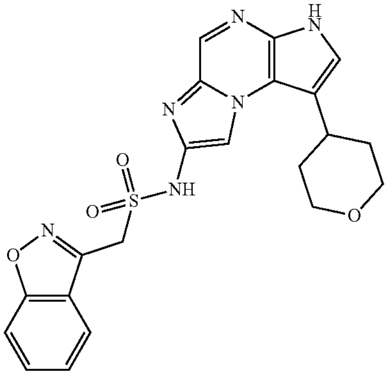
,
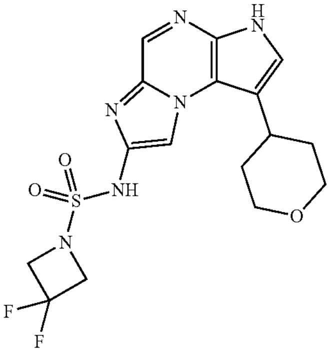
, -continued
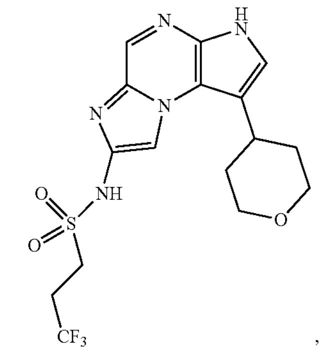
,
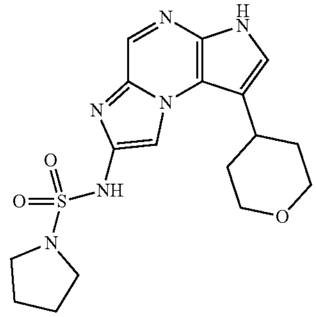
,
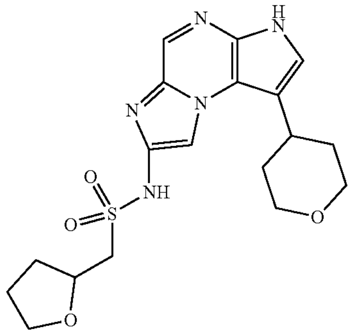
,
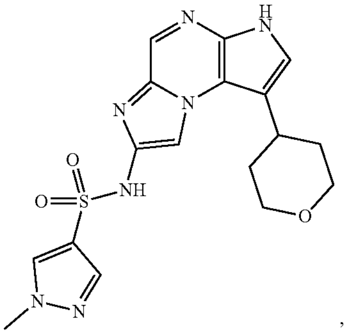
,
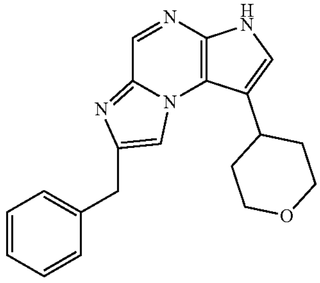
,
-continued
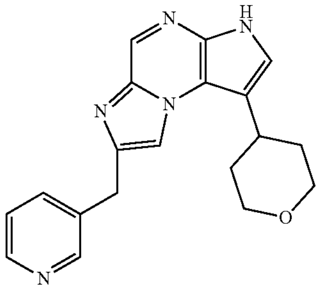
,
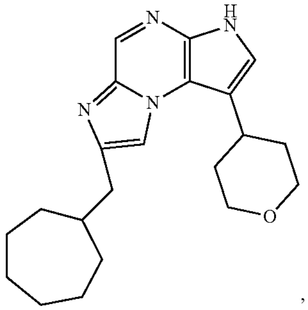
,
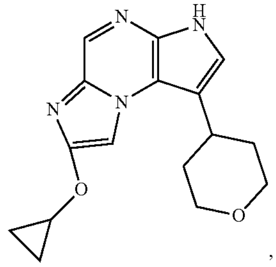
,
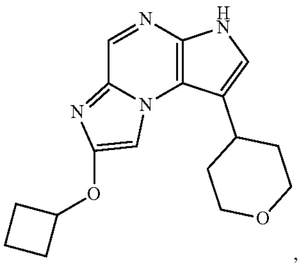
,
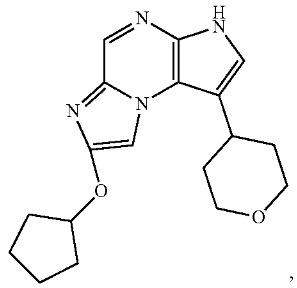
,
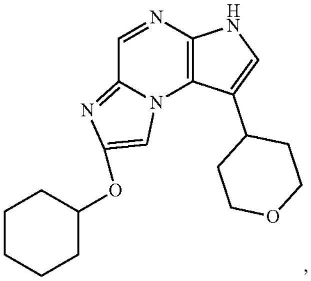
, -continued
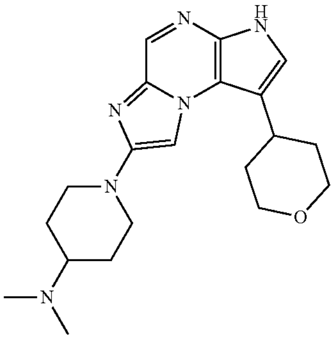
,
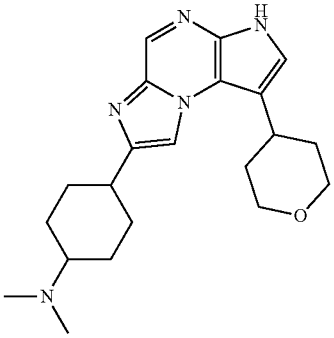
,
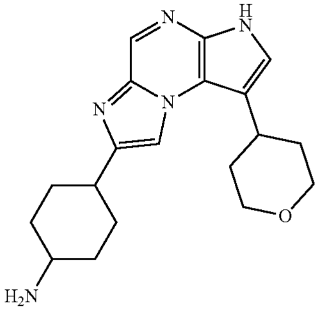
,
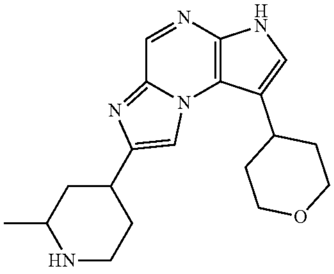
,
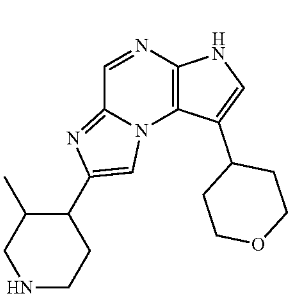
,
-continued
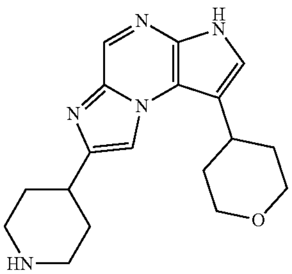
,
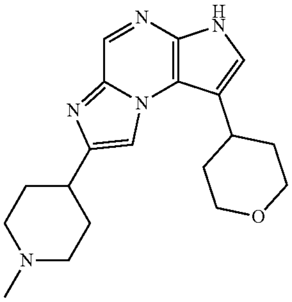
,
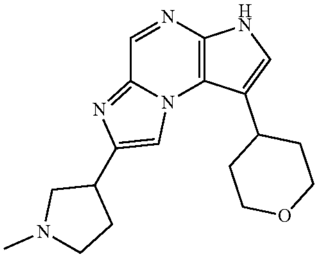
,
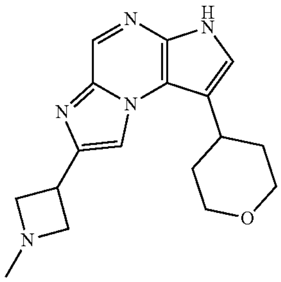
,
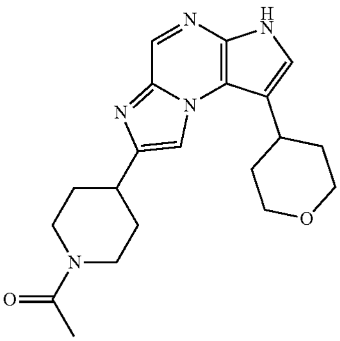
,

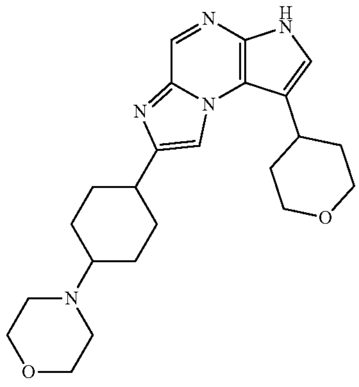
,
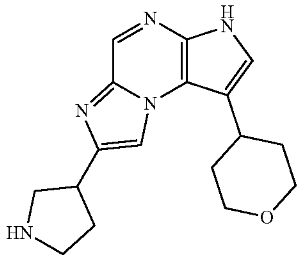
,
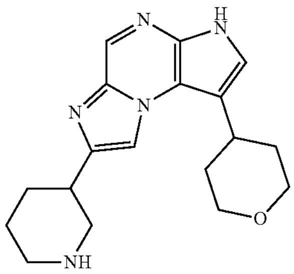
,
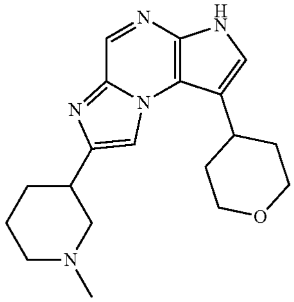
,
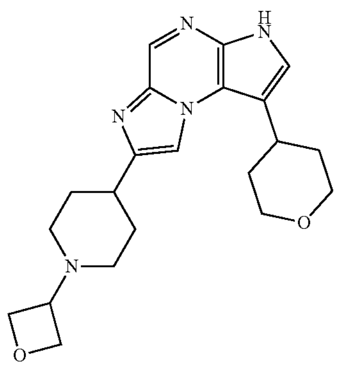
,
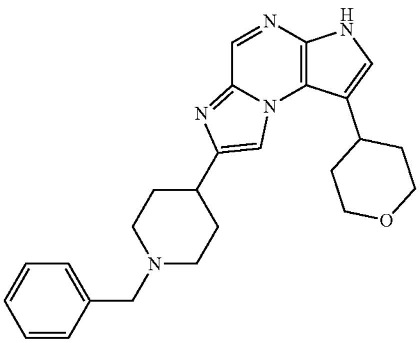
,
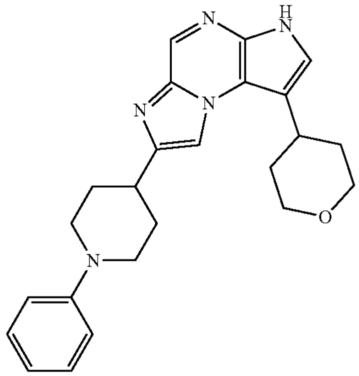
,
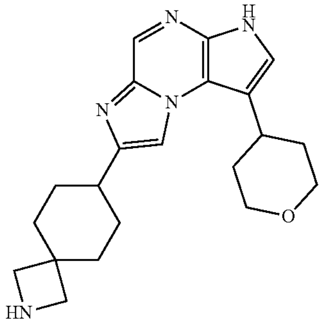
,
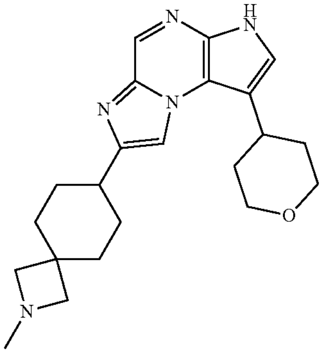
,
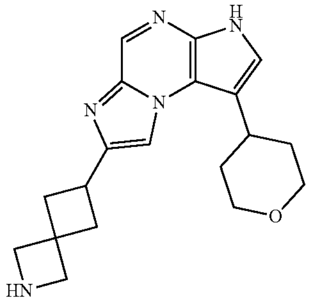
, -continued
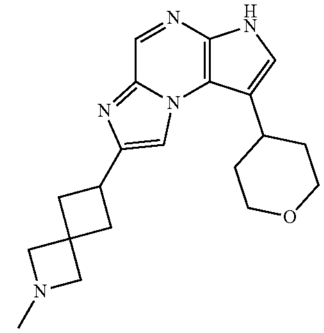
,
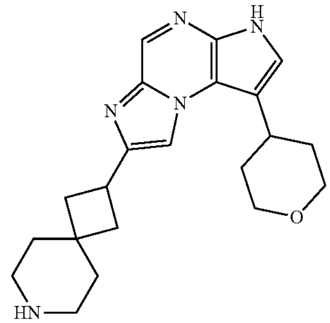
,
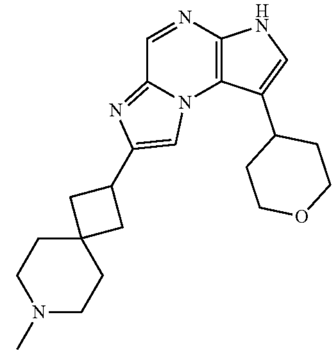
,
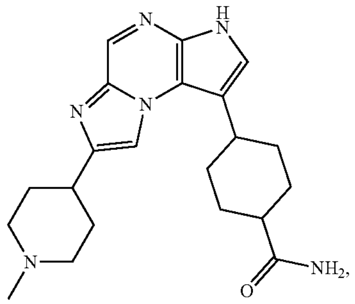
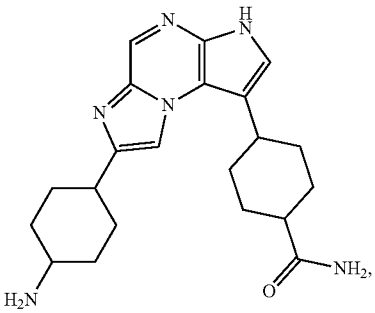
-continued
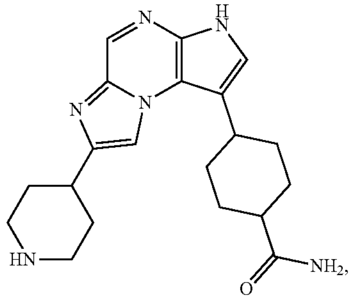
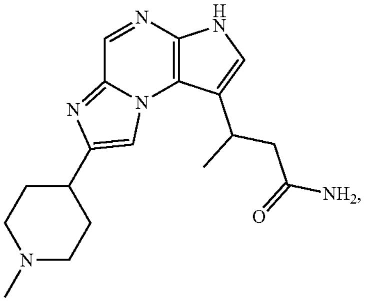
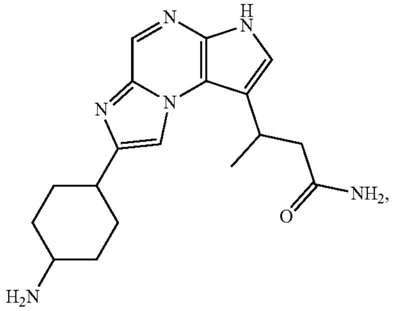
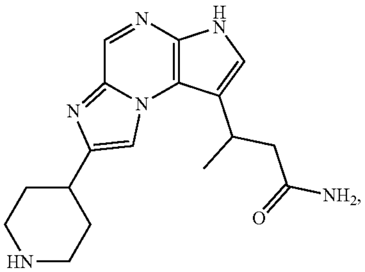
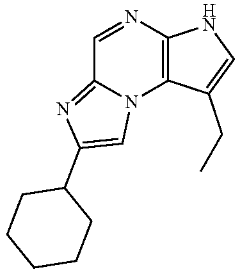
,
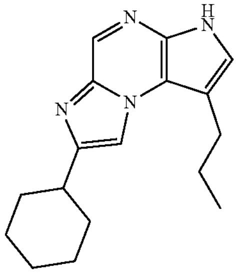
, -continued
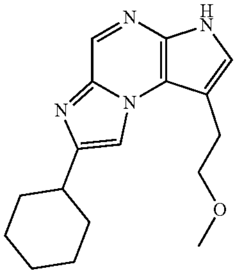
,
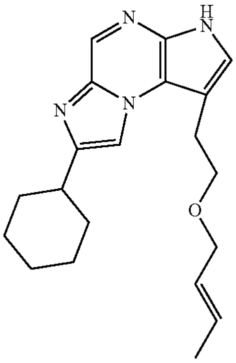
,
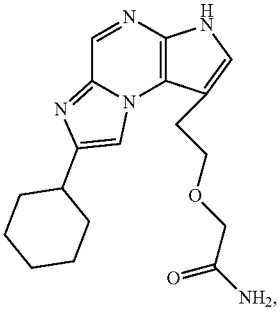
,
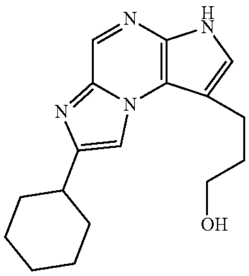
,
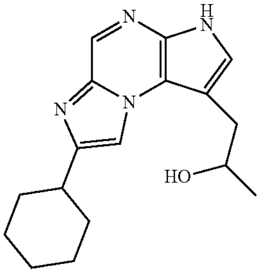
,
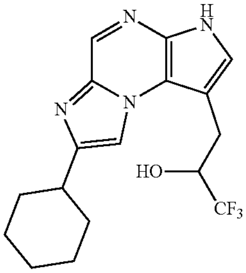
,
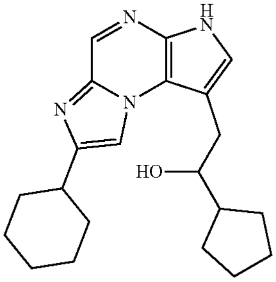
,
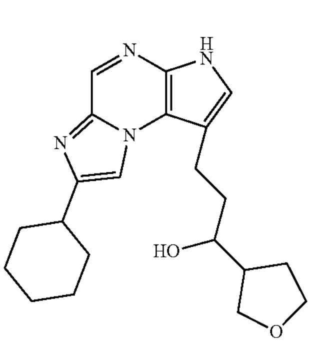
,
-continued
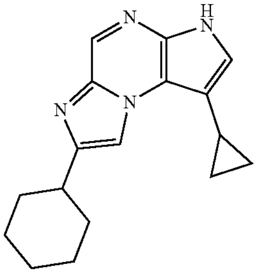
,
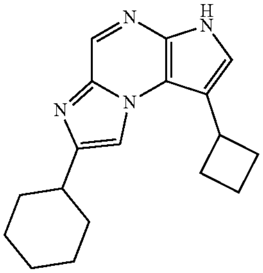
,
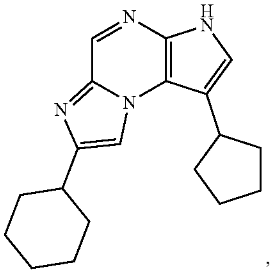
,
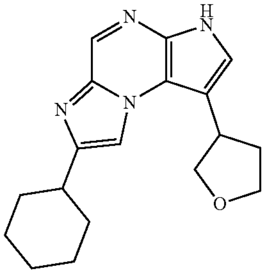
,
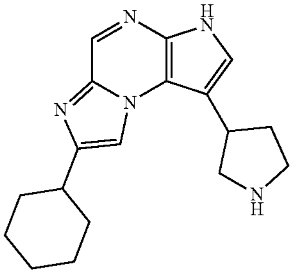
,
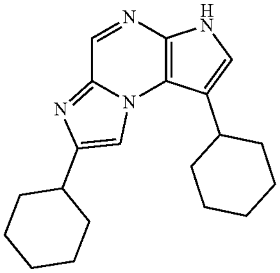
,
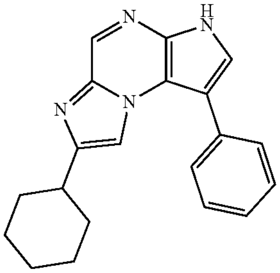
,
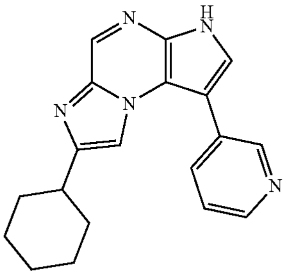
, -continued
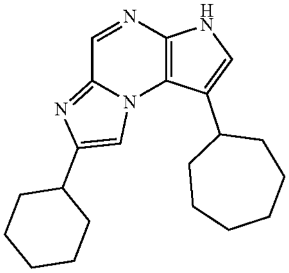
,
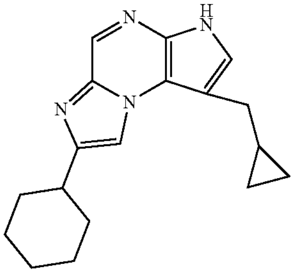
,
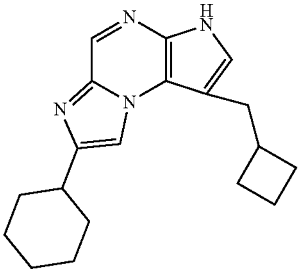
,
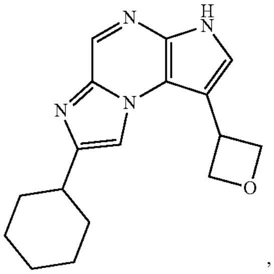
,
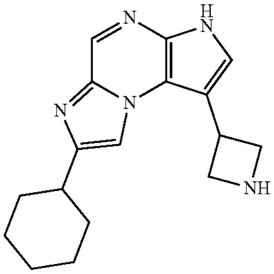
,
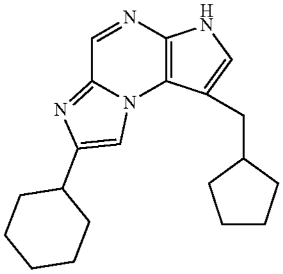
,
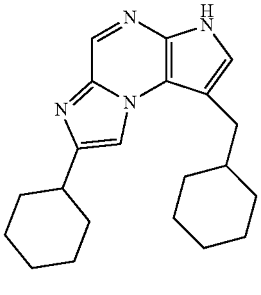
,
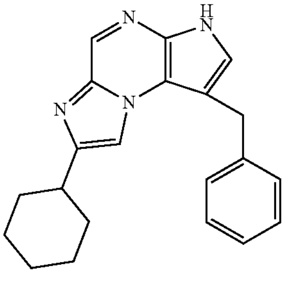
,
-continued
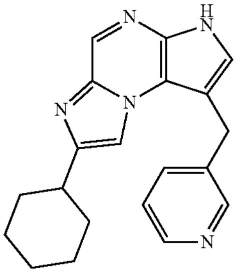
,
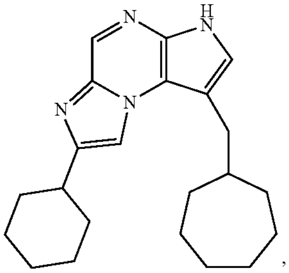
,
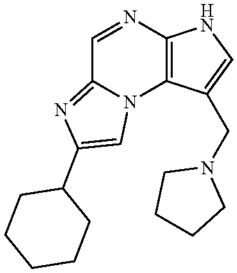
,
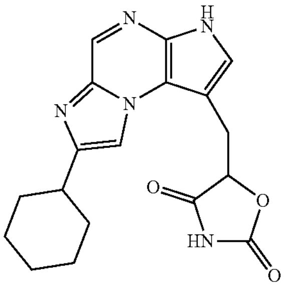
,
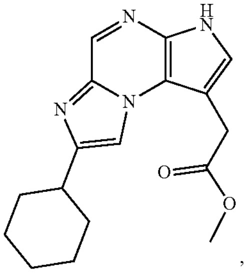
,
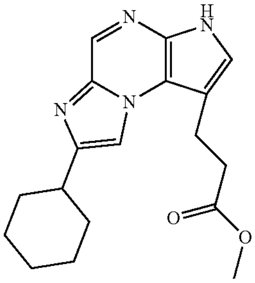
,
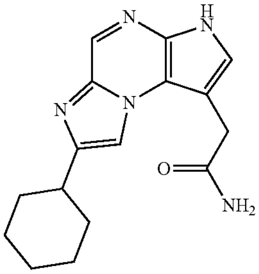
,
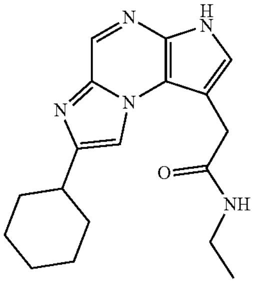
,
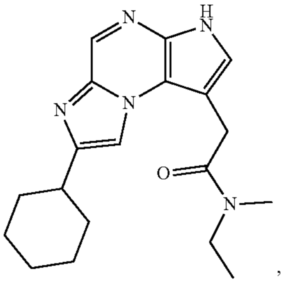
,
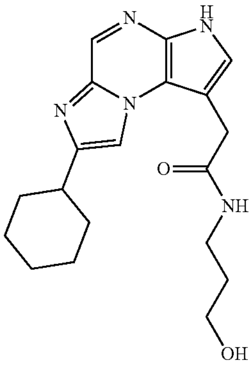
, -continued
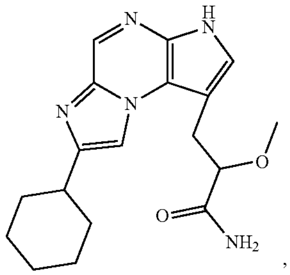
,
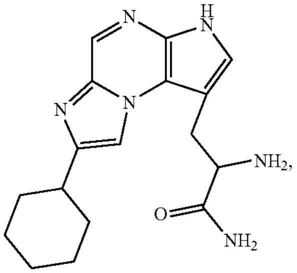
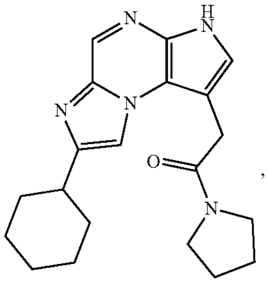
,
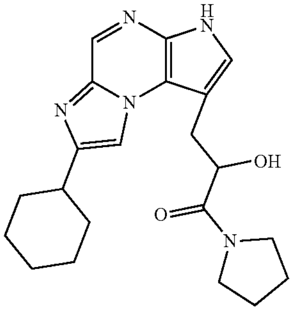
,
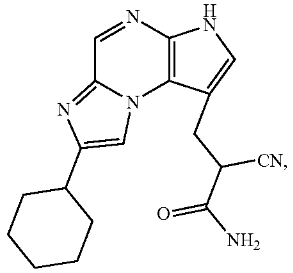
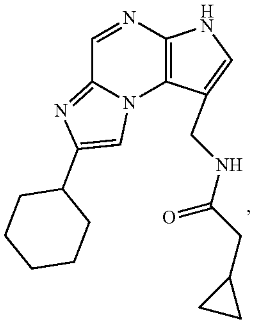
,
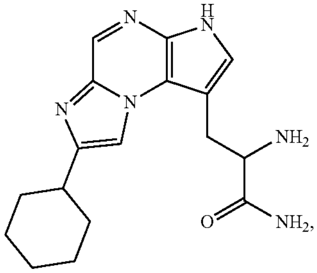
-continued
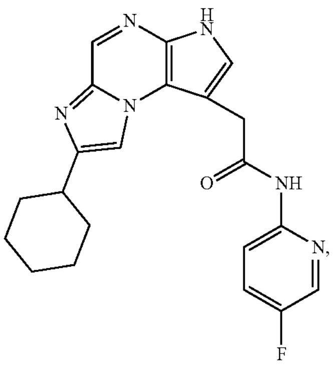
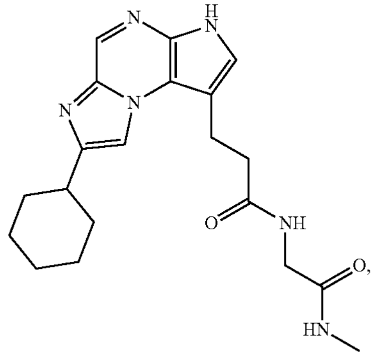
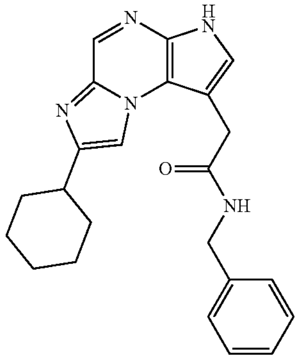
,
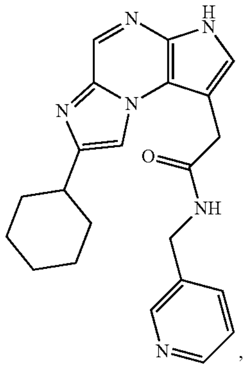
,
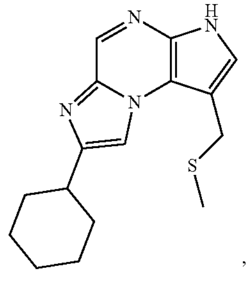
,
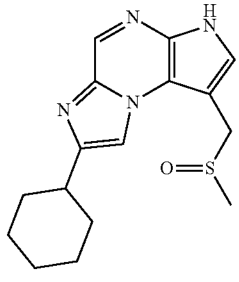
,
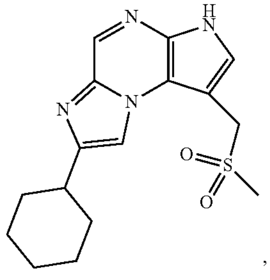
,
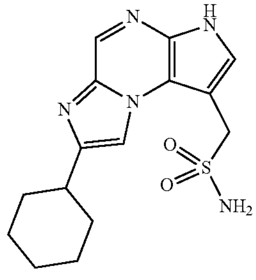
, -continued
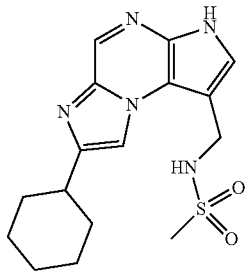
,
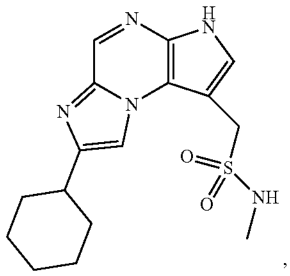
,
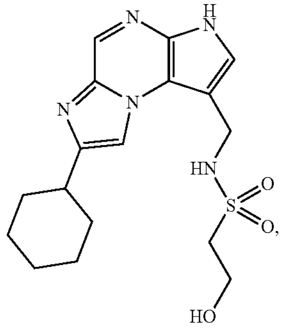
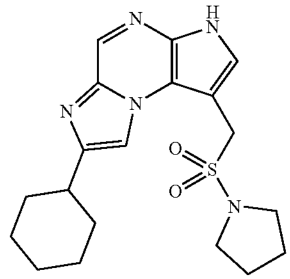
,
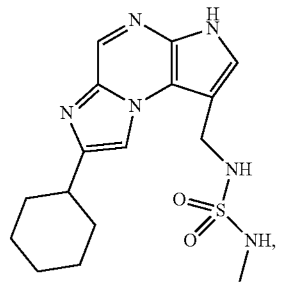
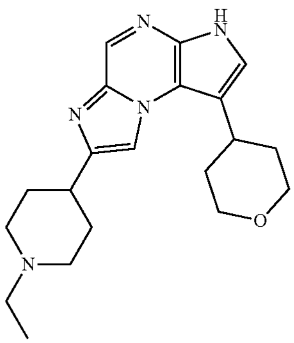
,
-continued
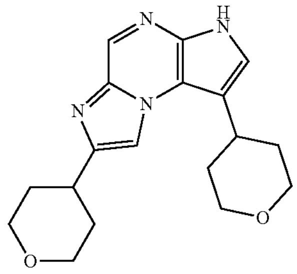
,
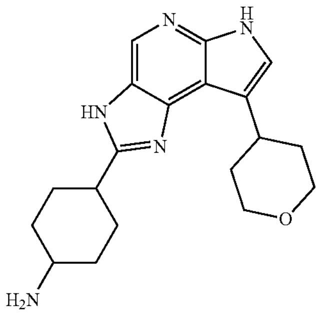
,
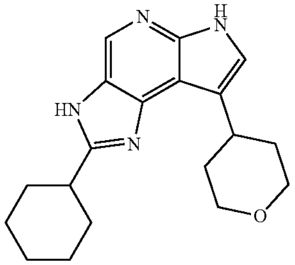
, and
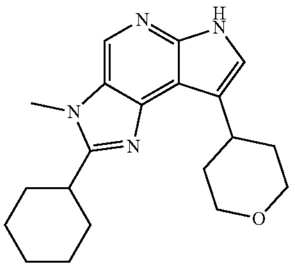
.
In specific embodiments of the present invention, specific compounds are further provided as follows:
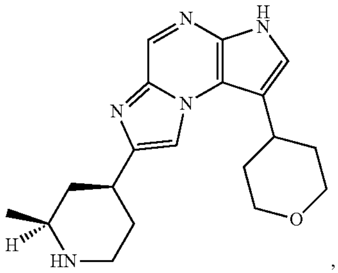
, -continued

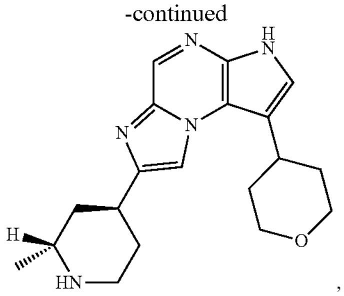

,

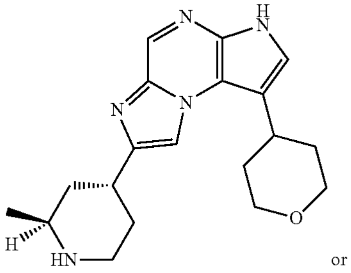

or

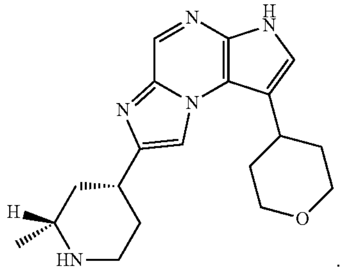

.

The present invention provides a pharmaceutical composition, which comprises the compound of general formula I, or a pharmaceutically acceptable salt, a stereoisomer, an ester, a prodrug, a solvate and a deuterated compound thereof, and which further comprises a pharmaceutically acceptable excipient, wherein the excipient is selected from carriers, diluents, binders, lubricants and wetting agents. Preferably, the pharmaceutical composition comprises a therapeutically effective amount of the compound of general formula I. In certain embodiments, the pharmaceutical compositions can be used alone or in combination with other formulations.

The pharmaceutical composition is suitable for parenteral or non-parenteral administration, for example by intravenous, intramuscular, intradermal and subcutaneous routes of administration, and therefore, preferably, the pharmaceutical composition further comprises an antioxidant, a buffer, a bacteriostat, a solute which renders a formulation isotonic with the blood of a subject, and aqueous and non-aqueous sterile suspensions which may comprise suspending agents, solubilizers, thickening agents, stabilizers and preservatives.

The compound disclosed herein can be formulated as pharmaceutical formulations in the form of injections, syrups, elixirs, suspensions, powders, granules, tablets, capsules, lozenges, creams, ointments, lotions, gels, emulsions and the like.

In the preparation of injections, any carrier commonly used in the art can be used, for example, water, ethanol, propylene glycol, ethoxylated isostearyl alcohol, polyethoxylated isostearyl alcohol, and fatty acid esters of polyethylene sorbitan. In addition, conventional solvents and buffers can be added.

The pharmaceutical formulation is preferably in unit dosage form. In this form, the formulation is subdivided into unit dosages containing an appropriate amount of active components. The unit dosage form can be capsules, tablets or any other dosage forms; in addition, the unit dosage form can be packaged formulations such as tablets, capsules and powders packaged in vials or ampoules.

The amount of active components of the formulation in unit dosage can be varied or adjusted from 0.1 to 1000 mg, depending on the specific application and the potency of active components. The composition may further contain other suitable therapeutic agents, if desired.

The present invention provides use of the compound of general formula I, and the pharmaceutically acceptable salt, the stereoisomer, the ester, the prodrug, the solvate and the deuterated compound thereof for preparing a medicament for treating diseases associated with interleukin-1 receptor-associated kinase-4 (IRAK4).

The diseases associated with IRAK4 are selected from autoimmune diseases, inflammatory diseases, cancers, heteroimmune diseases, thromboembolism, atherosclerosis, myocardial infarction and metabolic syndrome.

The autoimmune diseases include, but are not limited to, one or more of organ-specific autoimmune diseases, systemic lupus erythematosus, rheumatoid arthritis, systemic vasculitis, scleroderma, pemphigus, dermatomyositis, mixed connective tissue disease, autoimmune hemolytic anemia, thyroid autoimmune disease and ulcerative colitis.

The inflammatory diseases include, but are not limited to, one or more of osteoarthritis, gout, chronic obstructive pulmonary disease, periodic fever, rash, lymphadenectasis, sepsis, inflammatory bowel disease, asthma and allergy.

The cancers include, but are not limited to, one or more of B-cell chronic lymphocytic leukemia, acute lymphocytic leukemia, non-Hodgkin's lymphoma, Hodgkin's lymphoma, acute myelogenous leukemia, diffuse large B-cell lymphoma, multiple myeloma, Waldenstrom's macroglobulinemia, blastoma, medulloblastoma, retinoblastoma, sarcoma, liposarcoma, synovial cell sarcoma, neuroendocrine tumor, carcinoid tumor, gastrinoma, islet cell carcinoma, mesothelioma, schwannoma, acoustic neuroma, meningioma, adenocarcinoma, melanoma, leukemia or lymphoid malignancy, squamous cell carcinoma, epithelial squamous cell carcinoma, lung carcinoma, small cell lung carcinoma, non-small cell lung carcinoma, adenocarcinoma lung carcinoma, squamous lung carcinoma, peritoneal carcinoma, hepatocellular carcinoma, gastric carcinoma, intestinal carcinoma, pancreatic carcinoma, glioblastoma, cervical carcinoma, ovarian carcinoma, liver carcinoma, bladder carcinoma, liver carcinoma, breast carcinoma, metastatic breast carcinoma, colon carcinoma, rectal carcinoma, colorectal carcinoma, uterine carcinoma, salivary gland carcinoma, kidney carcinoma, prostate carcinoma, vulval carcinoma, thyroid carcinoma, liver carcinoma, anal carcinoma, penile carcinoma, Merkel cell carcinoma, esophageal carcinoma, biliary tract carcinoma, head and neck carcinoma and hematological malignancies.

The heteroimmune disease is transplant rejection after organ transplantation.

Preferably, the compound of general formula I, and the pharmaceutically acceptable salt, the stereoisomer, the ester, the prodrug, the solvate and the deuterated compound thereof can be used alone or in combination with other types of pharmaceutical formulations and/or treatment methods.

The other types of pharmaceutical formulations and/or treatment methods include, but are not limited to, immunosuppressants, targeted antineoplastic drugs, glucocorticoids, non-steroidal anti-inflammatory drugs, antineoplastic vaccines, agonists and inhibitors of TLRs (Toll-like receptors), and adoptive cellular immunotherapy or radiotherapy.

Preferably, the other types of pharmaceutical formulations and/or treatment methods are selected from agonists and inhibitors of TLRs.

The immunosuppressants include, but are not limited to, 6-mercaptopurine, cyclosporine, tacrolimus, anti-lymphocyte globulin and daclizumab.

The glucocorticoids include, but are not limited to, hydrocortisone, dexamethasone, betamethasone and prednisone.

The non-steroidal anti-inflammatory drugs include, but are not limited to, aspirin, ibuprofen, diclofenac, and rofecoxib.

The targeted antitumor drugs include, but are not limited to, protein kinase inhibitors, proteasome inhibitors, isocitrate dehydrogenase inhibitors, epigenetic-based antitumor drugs or cell cycle signaling pathway inhibitors.

The protein kinase inhibitors include, but are not limited to, BTK inhibitors, PI3K inhibitors, SYK inhibitors and JAK inhibitors.

Agonists of TLRs include, but are not limited to, a TLR3 agonist Poly-ICLC, a TLR4 agonist MPLA, a TLR7 agonist GS-9620, a TLR8 agonist ssRNA40, a TLR7 agonist TLR7-agonist-1, a TLR8 agonist Motolimod, and a TLR9 agonist CPG7079 or 1018ISS.

Inhibitors of TLRs include, but are not limited to, a TLR1/2 inhibitor CU CPT 22, a TLR4 inhibitor Atractylenolide, a TLR2 inhibitor C29, a TLR8 inhibitor CU-CPT-9a, and a TLR7/8/9 inhibitor CPG-52364.

The present invention provides use of the compound of general formula I, and the pharmaceutically acceptable salt, the stereoisomer, the ester, the prodrug, the solvate and the deuterated compound thereof for preventing and/or treating autoimmune diseases, inflammatory diseases, cancers, heteroimmune diseases, thromboembolism, atherosclerosis, myocardial infarction and metabolic syndrome.

The present invention provides use of the compound of general formula I, and the pharmaceutically acceptable salt, the stereoisomer, the ester, the prodrug, the solvate and the deuterated compound thereof for preparing a medicament for preventing and/or treating autoimmune diseases, inflammatory diseases, cancers, heteroimmune diseases, thromboembolism, atherosclerosis, myocardial infarction and metabolic syndrome.

For the term $C_{0-5}$ alkyl described herein, $C_0$ alkyl refers to H, and thus, $C_{0-10}$ alkyl comprises H, $C_1$ alkyl, $C_2$ alkyl, $C_3$ alkyl, $C_4$ alkyl and $C_5$ alkyl.

The term $C_{3-10}$ cycloalkyl described herein comprises $C_3$ cycloalkyl, $C_4$ cycloalkyl, $C_5$ cycloalkyl, $C_6$ cycloalkyl, $C_7$ cycloalkyl, $C_8$ cycloalkyl, $C_9$ cycloalkyl and $C_{10}$ cycloalkyl.

The term $C_{1-6}$ linear alkyl described herein comprises methyl, ethyl, $C_3$ linear alkyl, $C_4$ linear alkyl, $C_5$ linear alkyl and $C_6$ linear alkyl.

The term halogen described herein comprises fluorine, chlorine, bromine and iodine.

The term heterocycloalkyl described herein refers to a non-aromatic saturated monocyclic or polycyclic ring system containing 3 to 10 ring atoms, preferably 5 to 10 ring atoms, wherein one or more ring atoms are not carbon atoms, but are, for example, nitrogen, oxygen or sulfur atoms.

Preferred heterocycloalkyl contains 5 to 6 ring atoms. The prefix aza, oxa or thia before heterocycloalkyl means that there is at least one nitrogen, oxygen or sulfur atom as a ring atom.

Representative monocyclic heterocycloalkyl includes piperidinyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothienyl, tetrahydrothiopyranyl, and the like.

The term heterocycloaryl described herein refers to an aromatic monocyclic or polycyclic ring system containing 5 to 14 ring atoms, preferably 5 to 10 ring atoms, wherein one or more ring atoms are not carbon atoms, but are, for example, nitrogen, oxygen or sulfur atoms. Preferred heterocycloaryl contains 5 to 6 ring atoms. Representative heterocycloaryl includes pyrazinyl, furyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, 2,3-naphthyridinyl, imidazo[1,2-a]pyridine, imidazo[2,1-b]thiazolyl, benzofurazanyl, indolyl, azaindolyl, benzimidazolyl, benzothienyl, quinolyl, imidazolyl, thienopyridyl, quinazolinyl, thienopyrimidinyl, pyrrolopyridyl, imidazopyridinyl, isoquinolyl, benzoazaindolyl, 1,2,4-triazinyl, benzothiazolyl, and the like.

DETAILED DESCRIPTION

Figure 1:
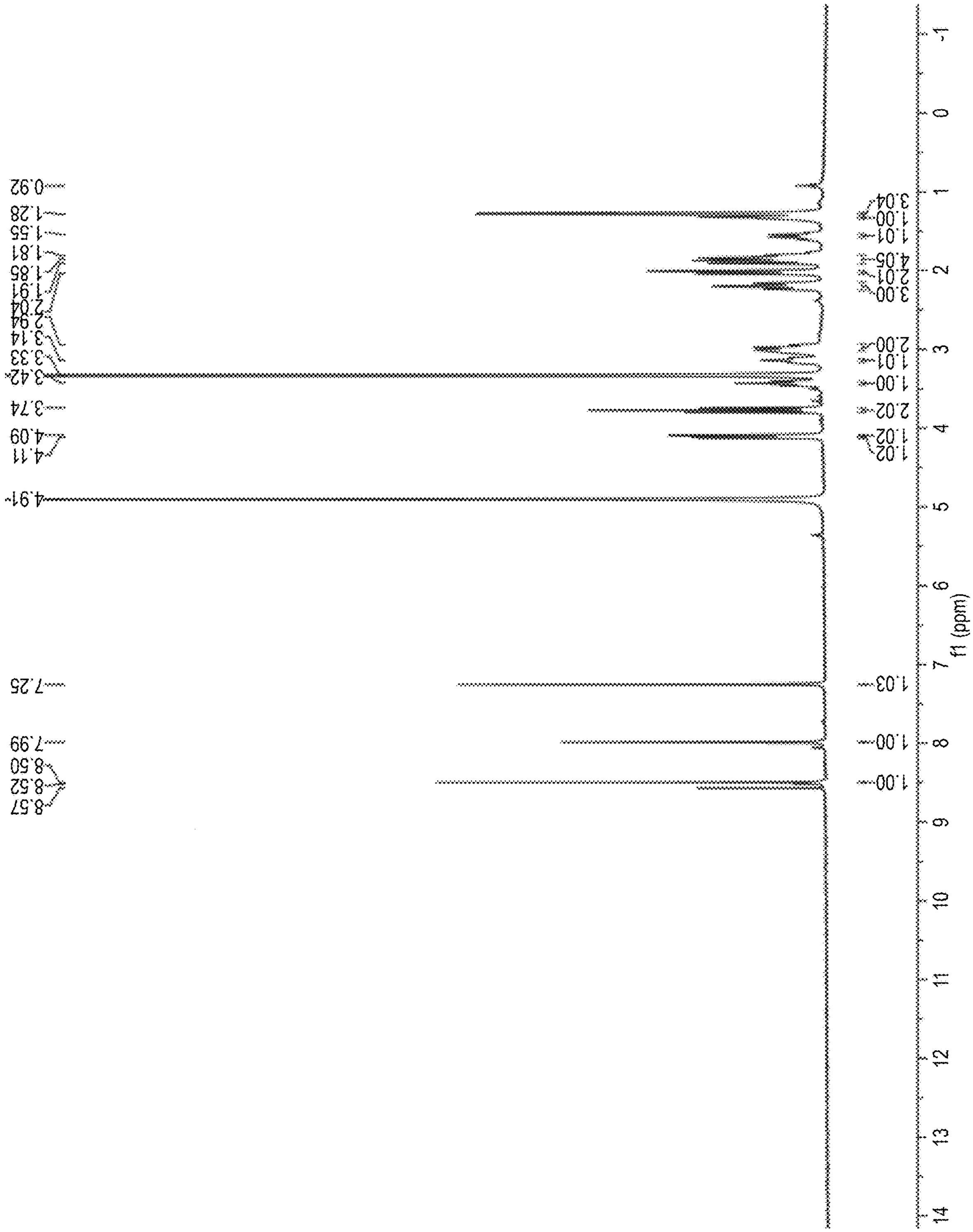
FIG. 1 is a $^1$H-NMR spectrum of compound E-1.

The technical solutions in the examples of the present invention will be described clearly and completely below, and it is apparent that the examples described herein are only some examples of the present invention, but not all of them. Based on the examples of the present invention, all other examples obtained by those of ordinary skill in the art without creative work shall fall within the protection scope of the present invention.

Example 1: Preparation of IRAK4 Kinase Inhibitor

The synthetic route is as follows.

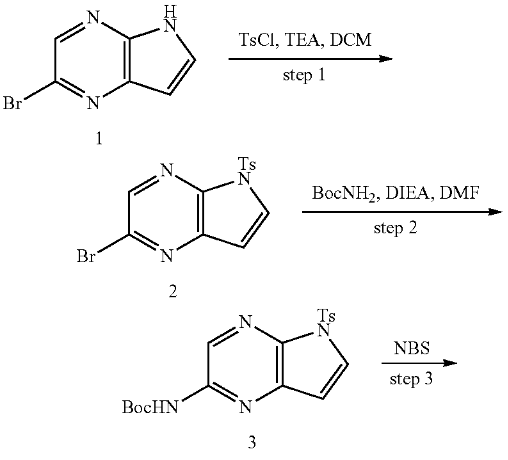

1

2

3

-continued
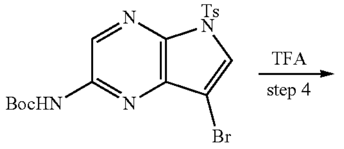
4
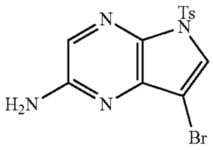
5
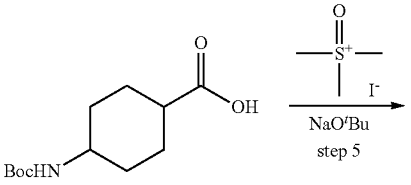
6
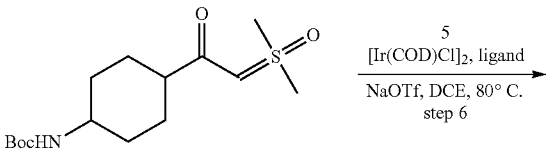
7
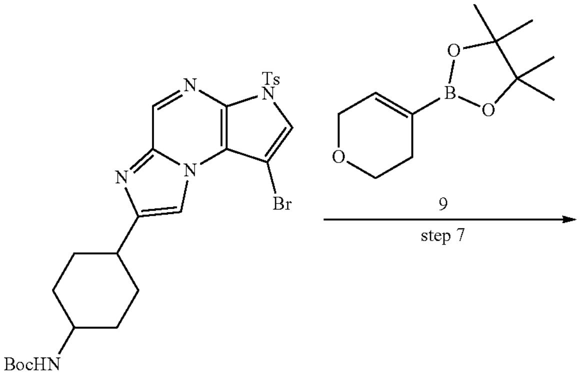
8
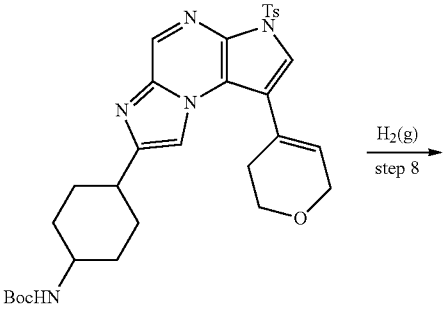
10
-continued
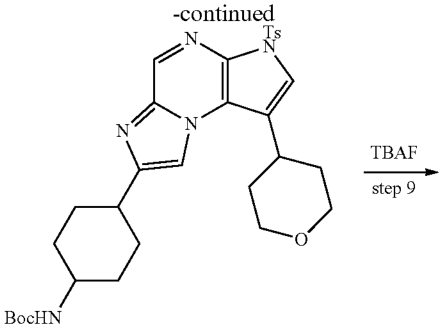
11
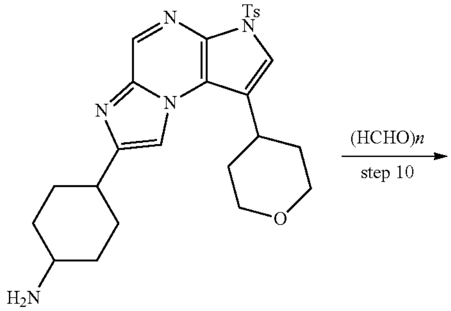
12
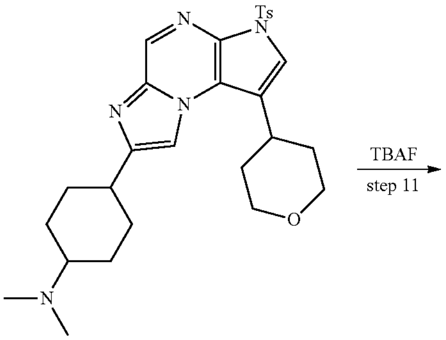
13
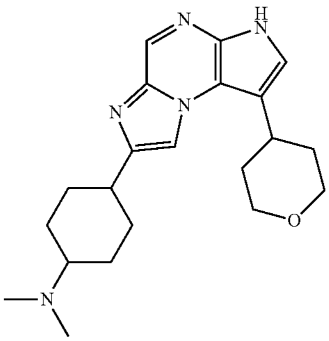
Compound A Step 1

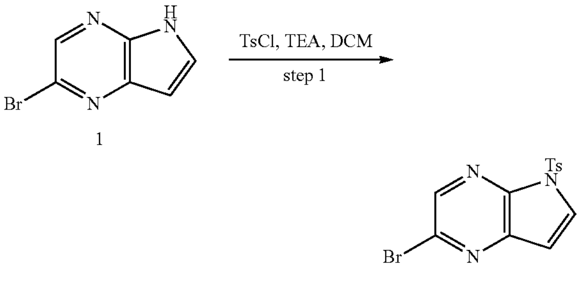

1

2

To a 250 mL single-neck flask were added 1 (8.0 g, 40.62 mmol), dichloromethane (80 mL), triethylamine (8.23 g, 81.23 mmol) and TsCl (9.29 g, 48.74 mmol), and the mixture was stirred at room temperature for 3 h and added with water. The reaction system was extracted with ethyl acetate (100 mL×3), washed with saturated brine (50 mL×2), dried over anhydrous sodium sulfate, concentrated by rotary evaporation, and purified by column chromatography (petroleum ether:ethyl acetate=4:1) to give a target product (8.0 g, yield: 56.1%) in the form of a yellow solid; LC-MS: 352 $[M+H]^+$.

Step 2

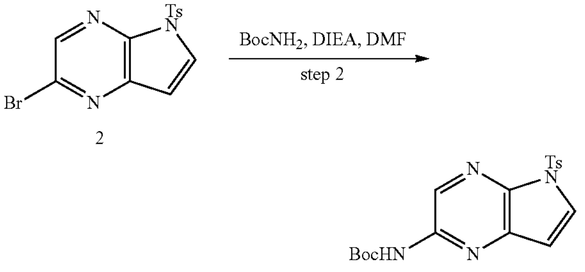

2

3

To a 100 mL single-neck round-bottom flask were added 2 (8.0 g, 22.79 mmol), tert-butyl carbamate (3.20 g, 27.35 mmol), DIEA (5.88 g, 45.58 mmol) and DMF (40.0 mL), and the mixture was reacted at 100° C. for 18 h. The reaction system was added with water and extracted with ethyl acetate (100 mL×3). The organic phase was washed with saturated brine (50 mL×2), dried over anhydrous sodium sulfate and concentrated by rotary evaporation to give a crude product (9.0 g) in the form of a yellow solid; LC-MS: 389 $[M+H]^+$.

Step 3

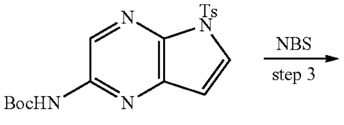

3

-continued

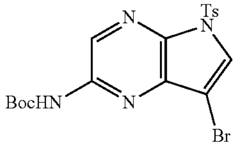

4

To a 250 mL single-neck flask were added 3 (9.0 g, 23.19 mmol), acetonitrile (90 mL) and NBS (4.95 g, 27.83 mmol), and the mixture was reacted at room temperature for 4 h. The reaction system was added with water (50 mL) to quench the reaction, extracted with ethyl acetate (100 mL×3), washed with saturated brine (50 mL×2), dried over anhydrous sodium sulfate, concentrated by rotary evaporation, and purified by column chromatography (petroleum ether:ethyl acetate=8:1) to give a target product (4.5 g, yield: 41.6%) in the form of a yellow solid; LC-MS: 467 $[M+H]^+$.

Step 4

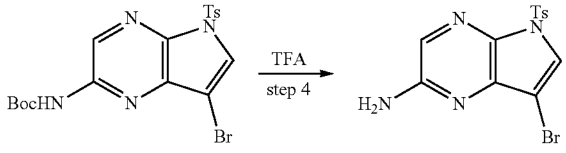

4

5

To a 100 mL single-neck flask were added 4 (4.5 g, 9.66 mmol), dichloromethane (45.0 mL) and TFA (9 mL), and the mixture was reacted at room temperature for 2 h. The reaction system was concentrated, added with acetone, and filtered under vacuum. The solid was dried to give a target product (3.3 g, yield: 93.3%) in the form of a yellow solid; LC-MS: 367 $[M+H]^+$.

Step 5

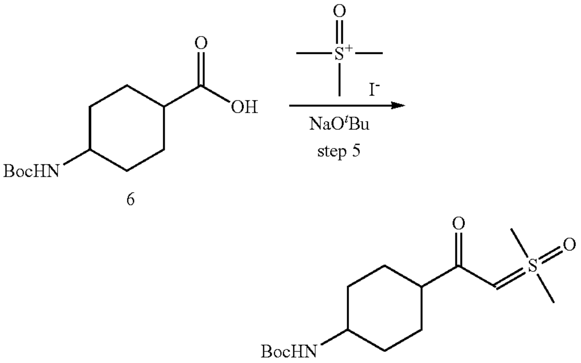

6

7

To a 100 mL single-neck flask were added 6 (5.0 g, 20.56 mmol), HATU (11.72 g, 30.85 mmol) and tetrahydrofuran (50 mL), and the mixture was reacted at room temperature for 2 h to give a mixture 1. To another 250 mL single-neck flask were added trimethylsulfoxonium iodide (4.52 g, 20.56 mmol), sodium tert-butoxide (2.96 g, 30.85 mmol) and tetrahydrofuran (30 mL), and the mixture was reacted at room temperature for 3 h to give a mixture 2. The mixture 1 was added slowly to a mixture 2, and the resulting mixture was reacted under reflux for 12 h. The reaction system was added with water, extracted with ethyl acetate (50 mL×3), washed with saturated brine (50 mL×3), dried over anhydrous sodium sulfate, concentrated by rotary evaporation, and purified by column chromatography (PE:EA=6:1) to give a target product (6.50 g, crude) in the form of a white solid; LC-MS: 318 $[M+H]^+$.

Step 6

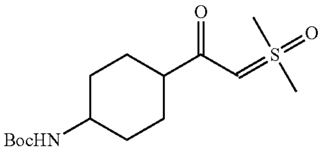

7

5

$[Ir(COD)Cl]_2$, ligand

NaOTf, DCE, 80° C.

step 6

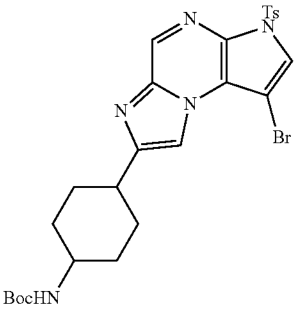

8

To a 50 mL single-neck flask were added 5 (2.65 g, 7.25 mmol), 7 (2.76 g, 8.70 mmol), $[Ir(COD)Cl]_2$ (122 mg, 0.181 mmol), 1,10-phenanthroline (65 mg, 0.363 mmol), NaOTf (62 mg, 0.363 mmol) and 1,2-dichloroethane (30.0 mL), and the mixture was reacted at 80° C. for 24 h under nitrogen atmosphere. The reaction system was filtered under vacuum, and the filtrate was concentrated by rotary evaporation and purified by column chromatography (dichloromethane:ethyl acetate=8:1) to give a target product (382 mg, yield: 9.0%) in the form of a yellow solid; LC-MS: 588 $[M+H]^+$.

Step 7

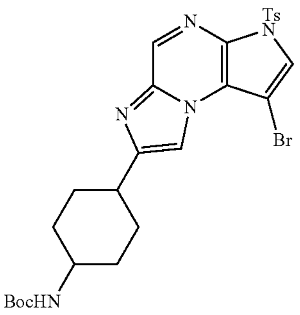

8

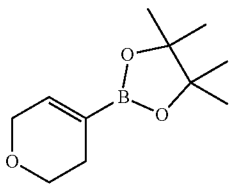

9 step 7

-continued

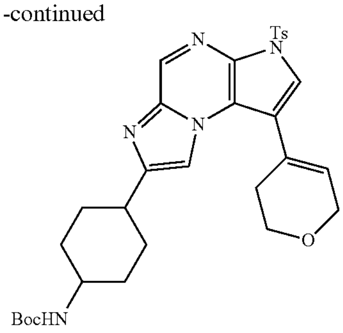

10

To a 25 mL single-neck flask were added 8 (382 mg, 0.65 mmol), 9 (205 mg, 0.98 mmol), dioxane (4 mL), water (1 mL), [1,1'-bis(diphenylphosphino)ferrocene]dichloropalladium (26 mg, 0.03 mmol) and potassium carbonate (179 mg, 1.30 mmol), and the mixture was reacted at 80° C. for 18 h under nitrogen atmosphere. The reaction system was added with water to quench the reaction, extracted with ethyl acetate (10 mL×3), washed with saturated brine (10 mL×3), dried over anhydrous sodium sulfate, concentrated by rotary evaporation, and purified by column chromatography (petroleum ether:ethyl acetate=1:1) to give a target product (239 mg, yield: 62.2%) in the form of a yellow solid; LC-MS: 592 $[M+H]^+$.

Step 8

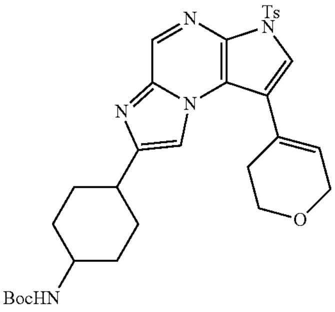

10

$H_2(g)$ step 8

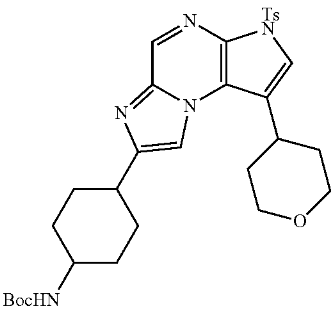

11

To a 25 mL single-neck flask were added 10 (239 mg, 0.40 mmol), methanol (1 mL) and $Pd(OH)_2$ (24 mg), and the mixture was reacted at room temperature for 18 h under hydrogen atmosphere. The reaction system was filtered under vacuum, and the filtrate was concentrated by rotary evaporation to give a crude product (160 mg); LC-MS: 594 $[M+H]^+$.

Step 9

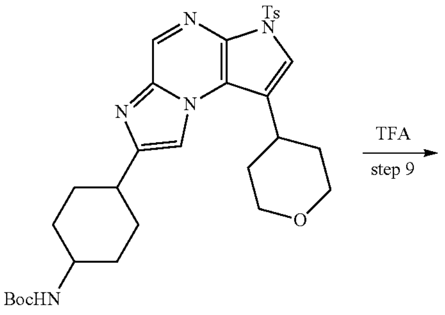

11

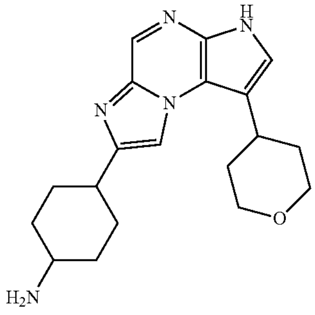

12

To a 25 mL single-neck flask were added 11 (120 mg, 0.202 mmol), dichloromethane (5.0 mL) and trifluoroacetic acid (1 mL), and the mixture was reacted at room temperature for 2 h, and then concentrated to give a crude product (150 mg, crude); LC-MS: 494 $[M+H]^+$.

Step 10

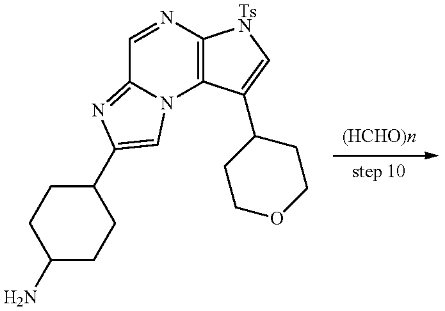

12

-continued

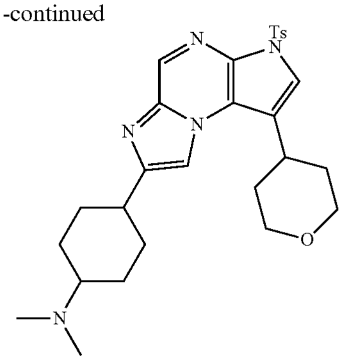

13

To a 25 mL single-neck flask were added 12 (99.5 mg, 0.202 mmol), paraformaldehyde (60.6 mg, 2.02 mmol), dichloromethane (5 mL), triethylamine (61.2 mg, 0.606 mmol) and sodium triacetoxyborohydride (128 mg, 0.606 mmol), and the mixture was reacted at room temperature for 16 h, concentrated, and purified by column chromatography (DCM:MeOH=20:1) to give a white solid (55 mg, yield: 52.3%); LC-MS: 522 $[M+H]^+$.

Step 11

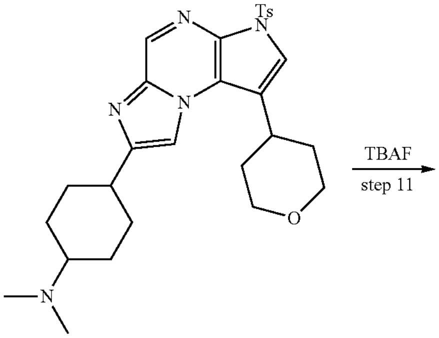

13

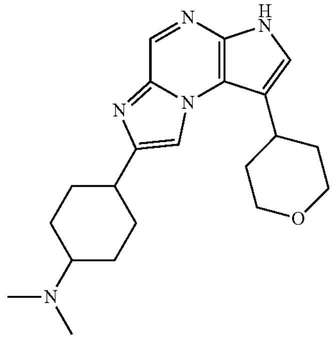

Compound A

To a 25 mL single-neck flask were added 13 (55 mg, 0.106 mmol) and a solution of tetrabutylammonium fluoride in tetrahydrofuran (1 M, 2 mL), and the mixture was reacted at 60° C. for 12 h and concentrated to prepare a target product compound A (5 mg, yield: 12.9%) in the form of a white solid; LC-MS: 368 $[M+H]^+$.

$^1H$ NMR (400 MHz, DMSO) δ 11.97 (s, 1H), 8.50 (s, 1H), 8.19 (s, 1H), 8.00 (s, 1H), 7.24 (d, J=2.7 Hz, 1H), 3.98-3.94

(m, 2H), 3.63 (d, J=11.3 Hz, 3H), 2.77 (d, J=12.2 Hz, 2H), 2.18 (d, J=11.8 Hz, 3H), 2.03 (d, J=10.6 Hz, 3H), 1.87 (d, J=12.7 Hz, 2H), 1.76-1.57 (m, 6H), 1.54-1.43 (m, 3H).
Example 2: Preparation of IRAK4 Kinase Inhibitor
The synthetic route is as follows:
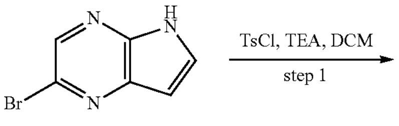
1
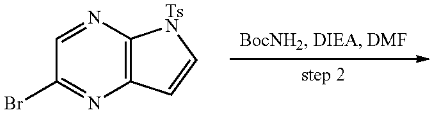
2
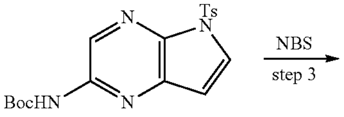
3
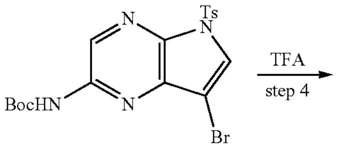
4
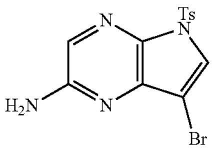
5
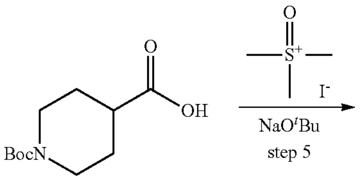
14
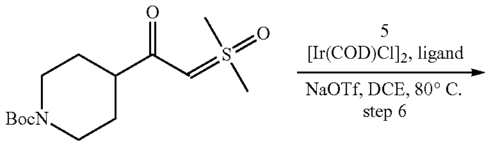
15
-continued
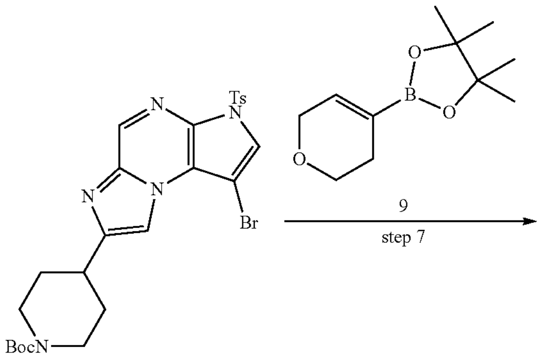
16
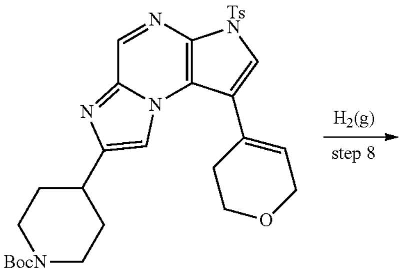
17
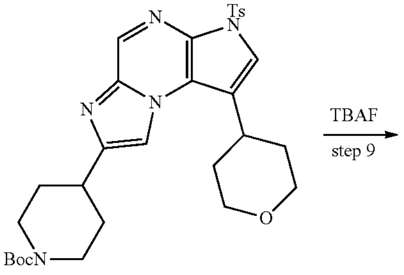
18
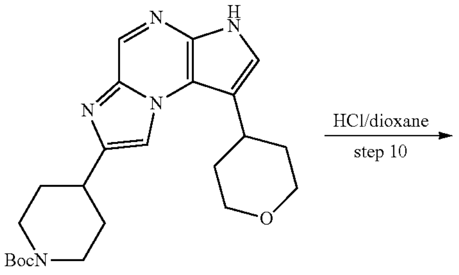
19
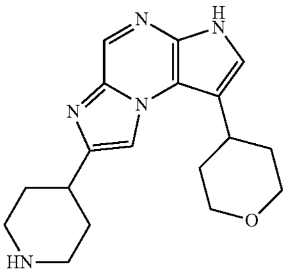
Compound B Step 1

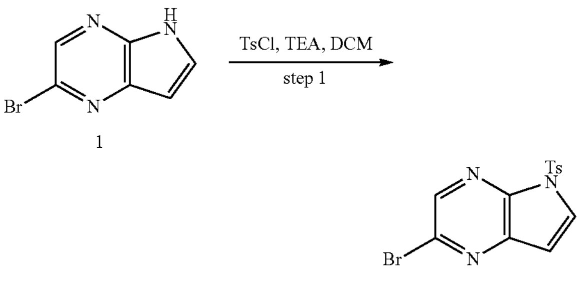

1

2

To a 250 mL single-neck flask were added 1 (8.0 g, 40.62 mmol), dichloromethane (80 mL), triethylamine (8.23 g, 81.23 mmol) and TsCl (9.29 g, 48.74 mmol), and the mixture was stirred at room temperature for 3 h. The reaction system was added with water, extracted with ethyl acetate (100 mL×3), washed with saturated brine (50 mL×2), dried over anhydrous sodium sulfate, concentrated by rotary evaporation, and purified by column chromatography (petroleum ether:ethyl acetate=4:1) to give a target product (8.0 g, yield: 56.1%) in the form of a yellow solid; LC-MS: 352 $[M+H]^+$.

Step 2

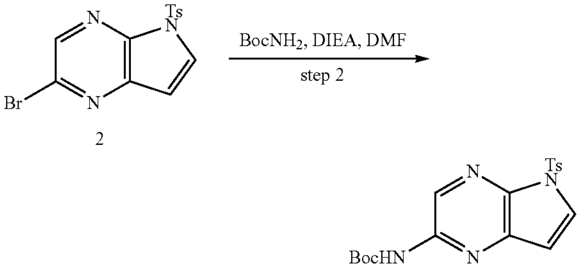

2

3

To a 100 mL single-neck round-bottom flask were added 2 (8.0 g, 22.79 mmol), tert-butyl carbamate (3.20 g, 27.35 mmol), DTEA (5.88 g, 45.58 mmol) and DMtF (40.0 mL), and the mixture was reacted at 100° C. for 18 h. The reaction system was added with water and extracted with ethyl acetate (100 mL×3). The organic phase was washed with saturated brine (50 mL×2), dried over anhydrous sodium sulfate and concentrated by rotary evaporation to give a crude product (9.0 g) in the form of a yellow solid; LC-MS: 389 $[M+H]^+$.

Step 3

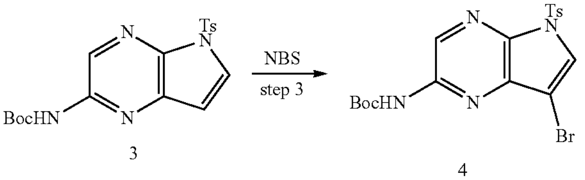

3

4

To a 250 mL single-neck flask were added 3 (9.0 g, 23.19 mmol), acetonitrile (90 mL) and NBS (4.95 g, 27.83 mmol), and the mixture was reacted at room temperature for 4 h. The reaction system was added with water (50 mL) to quench the reaction, extracted with ethyl acetate (100 mL×3), washed with saturated brine (50 mL×2), dried over anhydrous sodium sulfate, concentrated by rotary evaporation, and purified by column chromatography (petroleum ether:ethyl acetate=8:1) to give a target product (4.5 g, yield: 41.6%) in the form of a yellow solid; LC-MS: 467 $[M+H]^+$.

Step 4

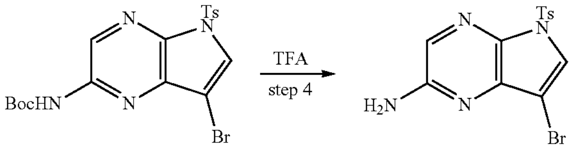

4

5

To a 100 mL single-neck flask were added 4 (4.5 g, 9.66 mmol), dichloromethane (45.0 mL) and TFA (9 mL), and the mixture was reacted at room temperature for 2 h. The reaction system was concentrated, added with acetone, and filtered under vacuum. The resulting solid was dried to give a target product (3.3 g, yield: 93.3%) in the form of a yellow solid; LC-MS: 367 $[M+H]^+$.

Step 5

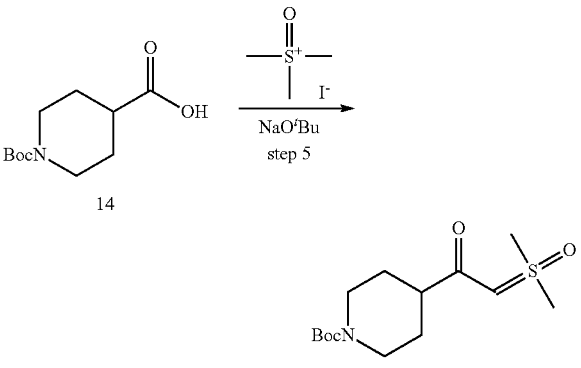

14

15

To a 100 mL single-neck flask were added 14 (5.0 g, 21.82 mmol), HATU (12.44 g, 32.73 mmol) and tetrahydrofuran (50 mL), and the mixture was reacted at room temperature for 2 h to give a mixture 1. To another 250 mL single-neck flask were added trimethylsulfoxonium iodide (4.80 g, 21.82 mmol), sodium tert-butoxide (3.15 g, 32.73 mmol) and tetrahydrofuran (30 mL), and the mixture was reacted at room temperature for 3 h to give a mixture 2. The mixture 1 was added slowly to a mixture 2, and the resulting mixture was reacted under reflux for 12 h. The reaction system was added with water, extracted with ethyl acetate (80 mL×3), washed with saturated brine (80 mL×3), dried over anhydrous sodium sulfate, concentrated by rotary evaporation, and purified by column chromatography (PE:EA=10:1) to give a target product (4.7 g, yield: 71.1%) in the form of a white solid; LC-MS: 304 $[M+H]^+$.

Step 6

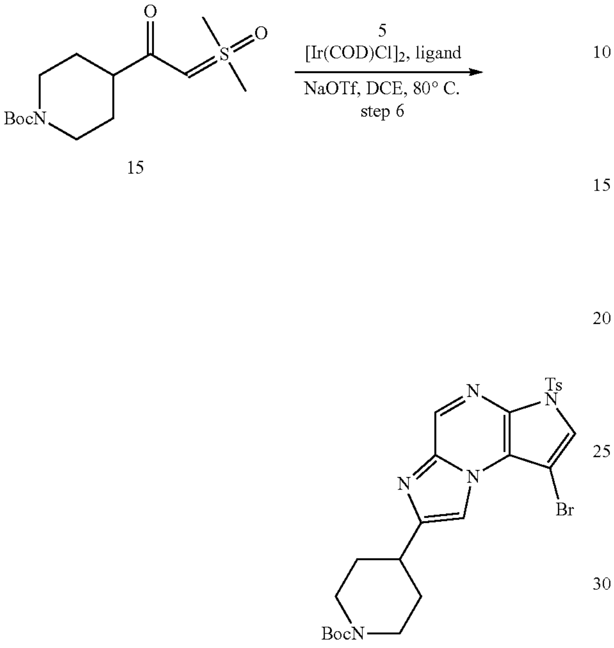

15

16

To a 50 mL single-neck flask were added 5 (1.29 g, 3.52 mmol), 15 (1.6 g, 5.28 mmol), $[Ir(COD)Cl]_2$ (59 mg, 0.088 mmol), 1,10-phenanthroline (32 mg, 0.176 mmol), NaOTf (30 mg, 0.176 mmol) and 1,2-dichloroethane (15 mL), and the mixture was reacted at 80° C. for 24 h under nitrogen atmosphere. The reaction system was filtered under vacuum, and the filtrate was concentrated by rotary evaporation and purified by column chromatography (dichloromethane:ethyl acetate=10:1) to give a target product (300 mg, yield: 14.9%) in the form of a yellow solid; LC-MS: 574 $[M+H]^+$.

Step 7

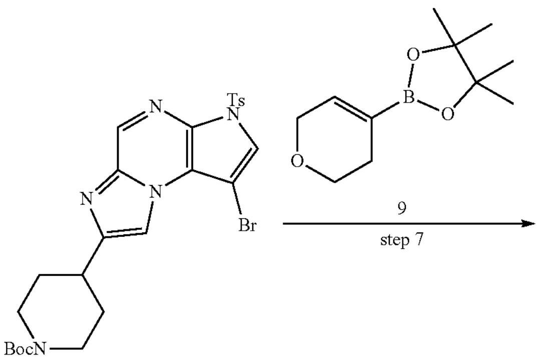

16

-continued

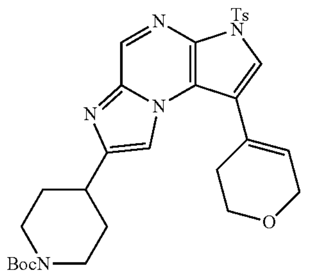

17

To a 25 mL single-neck flask were added 16 (300 mg, 0.52 mmol), 9 (165 mg, 0.78 mmol), dioxane (4 mL), water (1 mL), [1,1'-bis(diphenylphosphino)ferrocene]dichloropalladium (21 mg, 0.03 mmol) and potassium carbonate (144 mg, 1.04 mmol), and the mixture was reacted at 80° C. for 18 h under nitrogen atmosphere. The reaction system was added with water to quench the reaction, extracted with ethyl acetate (10 mL×3), washed with saturated brine (10 mL×3), dried over anhydrous sodium sulfate, concentrated by rotary evaporation, and purified by column chromatography (petroleum ether:ethyl acetate=2:1) to give a target product (187 mg, yield: 62.3%) in the form of a yellow solid; LC-MS: 578 $[M+H]^+$.

Step 8

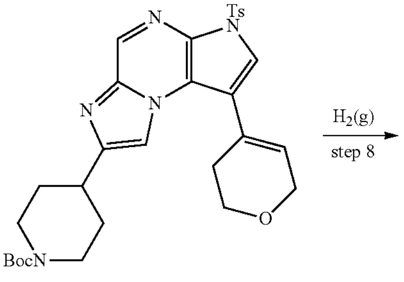

17

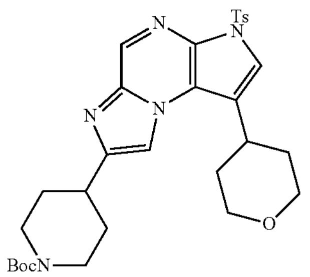

18

To a 25 mL single-neck flask were added 17 (187 mg, 0.32 mmol), methanol (1 mL) and $Pd(OH)_2$ (20 mg), and the mixture was reacted at room temperature for 18 h under hydrogen atmosphere. The reaction system was filtered under vacuum, and the filtrate was concentrated by rotary evaporation to give a crude product (170 mg); LC-MS: 580 $[M+H]^+$.

Step 9

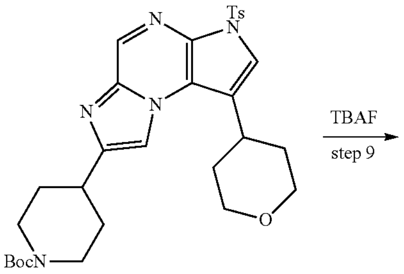

18

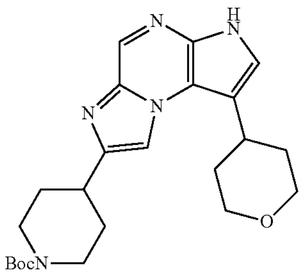

19

To a 25 mL single-neck flask were added 18 (85 mg, 0.20 mmol), THE (1.0 mL) and tetrabutylammonium fluoride (55 mg, 0.21 mmol), and the mixture was reacted at 60° C. for 12 h, concentrated and added with dichloromethane and brine. The organic phase was dried over anhydrous sodium sulfate and concentrated to prepare a target product 19 (82 mg, yield: 19.3%) in the form of a white solid; LC-MS: 425.8 $[M+H]^+$.

$^1$H NMR (400 MHz, $CDCl_3$) δ 9.17 (s, 1H), 8.66 (s, 1H), 7.67 (s, 1H), 7.05 (d, J=2.8 Hz, 1H), 4.20-4.15 (m, 2H), 3.70 (dd, J=11.7, 9.9 Hz, 2H), 3.33 (s, 2H), 3.25 (dd, J=9.7, 5.8 Hz, 1H), 3.09-3.04 (m, 1H), 2.94 (s, 2H), 2.13 (s, 1H), 2.01 (s, 1H), 1.93 (d, J=4.3 Hz, 1H), 1.90 (d, J=4.1 Hz, 1H), 1.87 (d, J=3.0 Hz, 1H), 1.70 (d, J=8.4 Hz, 3H), 1.50 (d, J=4.5 Hz, 9H).

Step 10

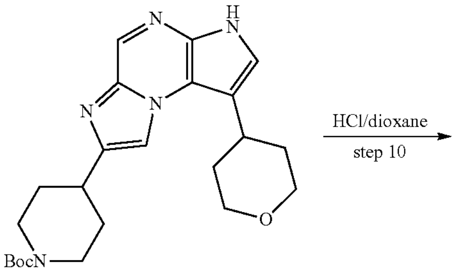

19

-continued

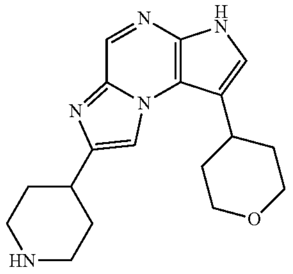

Compound B

To a 25 mL single-neck flask were added 19 (80 mg, 0.19 mmol) and a solution of hydrogen chloride in 1,4-dioxane (2.0 mL), and the mixture was reacted at room temperature for 2 h and concentrated to prepare a target product compound B (15 mg, yield: 24.3%) in the form of a white solid; LC-MS: 326.2 $[M+H]^+$.

$^1$H NMR (400 MHz, DMSO) δ 11.96 (s, 1H), 8.51 (s, 1H), 8.00 (s, 1H), 7.23 (s, 1H), 3.96 (dd, J=11.1, 3.3 Hz, 2H), 3.67 (d, J=10.4 Hz, 2H), 3.35 (s, 2H), 3.06 (d, J=11.9 Hz, 2H), 2.88 (d, J=11.5 Hz, 1H), 2.63 (d, J=11.8 Hz, 2H), 1.94 (d, J=12.1 Hz, 2H), 1.87 (d, J=11.3 Hz, 2H), 1.74-1.66 (m, 4H).

Example 3: Preparation of IRAK4 Kinase Inhibitor

The synthetic route is as follows:

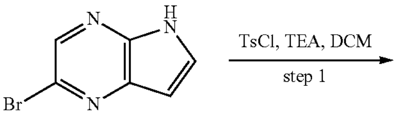

1

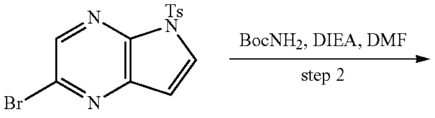

2

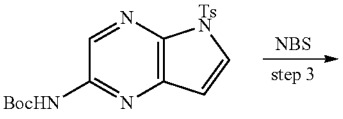

3

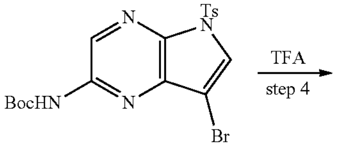

4

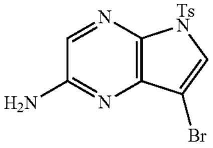

5

-continued

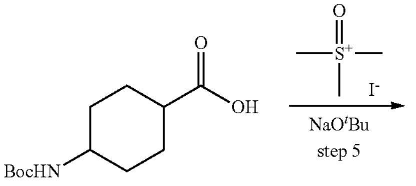

6

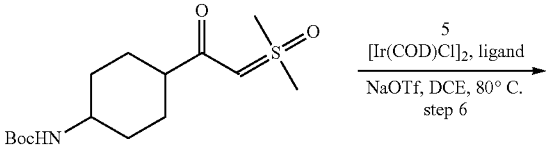

7

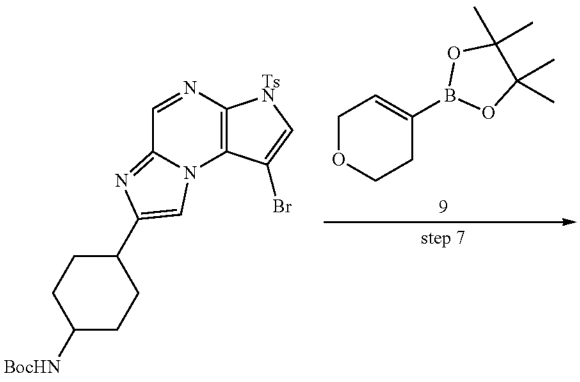

8

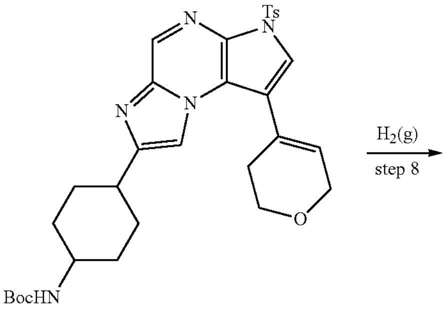

10

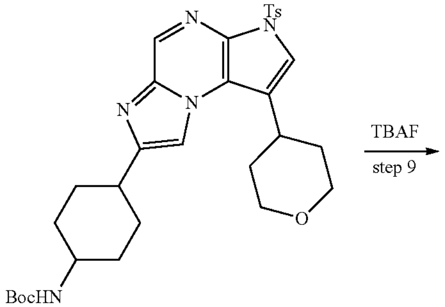

11

-continued

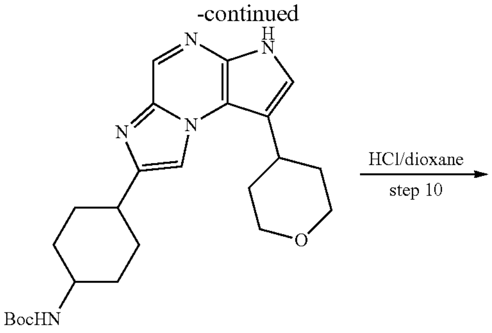

20

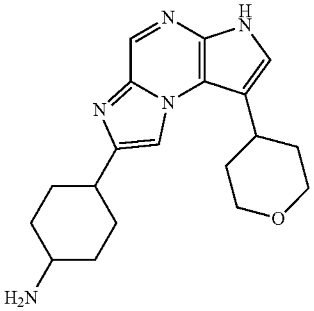

Compound C

Step 1

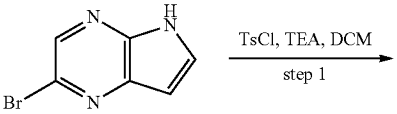

1

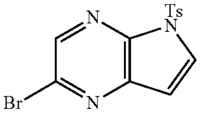

2

To a 250 mL single-neck flask were added 1 (8.0 g, 40.62 mmol), dichloromethane (80 mL), triethylamine (8.23 g, 81.23 mmol) and TsCl (9.29 g, 48.74 mmol), and the mixture was stirred at room temperature for 3 h. The reaction system was added with water, extracted with ethyl acetate (100 mL×3), washed with saturated brine (50 mL×2), dried over anhydrous sodium sulfate, concentrated by rotary evaporation, and purified by column chromatography (petroleum ether:ethyl acetate=4:1) to give a target product (8.0 g, yield: 56.1%) in the form of a yellow solid; LC-MS: 352 [M+H]$^+$.

Step 2

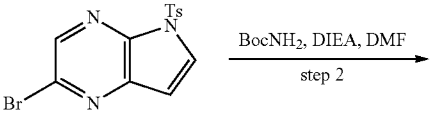

2

-continued

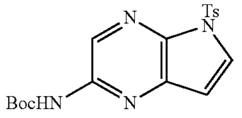

3

To a 100 mL single-neck round-bottom flask were added 2 (8.0 g, 22.79 mmol), tert-butyl carbamate (3.20 g, 27.35 mmol), DIEA (5.88 g, 45.58 mmol) and DMF (40.0 mL), and the mixture was reacted at 100° C. for 18 h. The reaction system was added with water and extracted with ethyl acetate (100 mL×3). The organic phase was washed with saturated brine (50 mL×2), dried over anhydrous sodium sulfate and concentrated by rotary evaporation to give a crude product (9.0 g) in the form of a yellow solid; LC-MS: 389 $[M+H]^+$.

Step 3

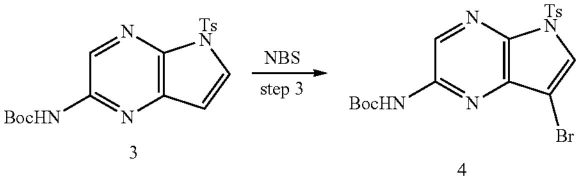

3 4

To a 250 mL single-neck flask were added 3 (9.0 g, 23.19 mmol), acetonitrile (90 mL) and NBS (4.95 g, 27.83 mmol), and the mixture was reacted at room temperature for 4 h. The reaction system was added with water (50 mL) to quench the reaction, extracted with ethyl acetate (100 mL×3), washed with saturated brine (50 mL×2), dried over anhydrous sodium sulfate, concentrated by rotary evaporation, and purified by column chromatography (petroleum ether:ethyl acetate=8:1) to give a target product (4.5 g, yield: 41.6%) in the form of a yellow solid; LC-MS: 467 $[M+H]^+$.

Step 4

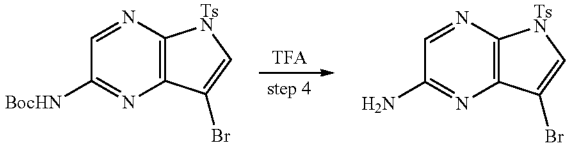

4 5

To a 100 mL single-neck flask were added 4 (4.5 g, 9.66 mmol), dichloromethane (45.0 mL) and TFA (9 mL), and the mixture was reacted at room temperature for 2 h. The reaction system was concentrated, added with acetone, and filtered under vacuum. The relusting solid was dried to give a target product (3.3 g, yield: 93.3%) in the form of a yellow solid; LC-MS: 367 $[M+H]^+$.

Step 5

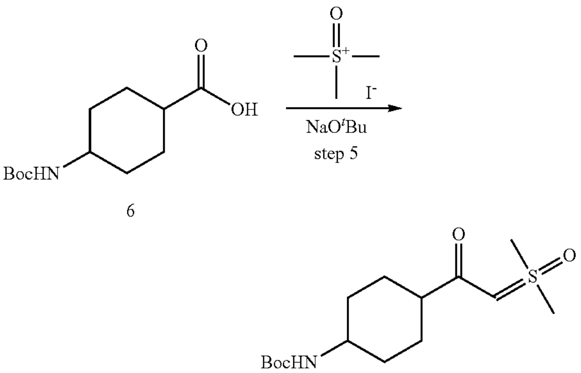

6

7

To a 100 mL single-neck flask were added 6 (5.0 g, 20.56 mmol), HATU (11.72 g, 30.85 mmol) and tetrahydrofuran (50 mL), and the mixture was reacted at room temperature for 2 h to give a mixture 1. To another 250 mL single-neck flask were added trimethylsulfoxonium iodide (4.52 g, 20.56 mmol), sodium tert-butoxide (2.96 g, 30.85 mmol) and tetrahydrofuran (30 mL), and the mixture was reacted at room temperature for 3 h to give a mixture 2. The mixture 1 was added slowly to a mixture 2, and the resulting mixture was reacted under reflux for 12 h. The reaction system was added with water, extracted with ethyl acetate (50 mL×3), washed with saturated brine (50 mL×3), dried over anhydrous sodium sulfate, concentrated by rotary evaporation, and purified by column chromatography (PE:EA=6:1) to give a target product (6.50 g, crude) in the form of a white solid; LC-MS: 318 $[M+H]^+$.

Step 6

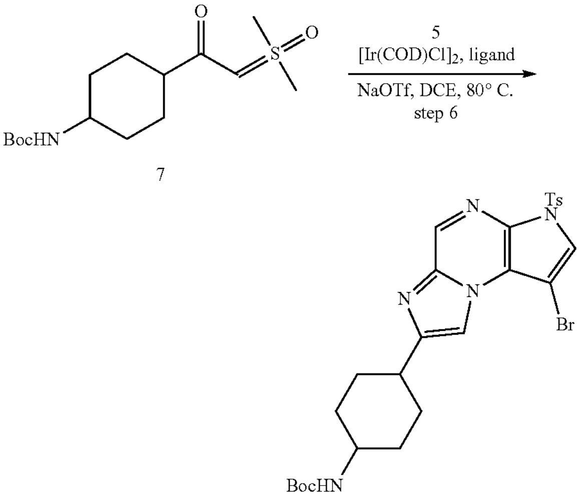

7

8

To a 50 mL single-neck flask were added 5 (2.65 g, 7.25 mmol), 7 (2.76 g, 8.70 mmol), $[Ir(COD)Cl]_2$ (122 mg, 0.181 mmol), 1,10-phenanthroline (65 mg, 0.363 mmol), NaOTf (62 mg, 0.363 mmol) and 1,2-dichloroethane (30.0 mL), and the mixture was reacted at 80° C. for 24 h under nitrogen atmosphere. The reaction system was filtered under vacuum, and the filtrate was concentrated by rotary evaporation and purified by column chromatography (dichloromethane:ethyl acetate=8:1) to give a target product (382 mg, yield: 9.0%) in the form of a yellow solid; LC-MS: 588 $[M+H]^+$.

Step 7

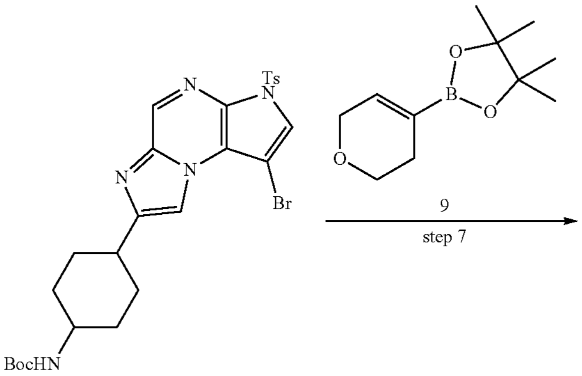

8

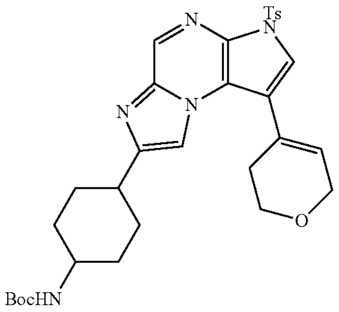

10

To a 25 mL single-neck flask were added 8 (382 mg, 0.65 mmol), 9 (205 mg, 0.98 mmol), dioxane (4 mL), water (1 mL), [1,1'-bis(diphenylphosphino)ferrocene]dichloropalladium (26 mg, 0.03 mmol) and potassium carbonate (179 mg, 1.30 mmol), and the mixture was reacted at 80° C. for 18 h under nitrogen atmosphere. The reaction system was added with water to quench the reaction, extracted with ethyl acetate (10 mL×3), washed with saturated brine (10 mL×3), dried over anhydrous sodium sulfate, concentrated by rotary evaporation, and purified by column chromatography (petroleum ether:ethyl acetate=1:1) to give a target product (239 mg, yield: 62.2%) in the form of a yellow solid; LC-MS: 592 $[M+H]^+$.

Step 8

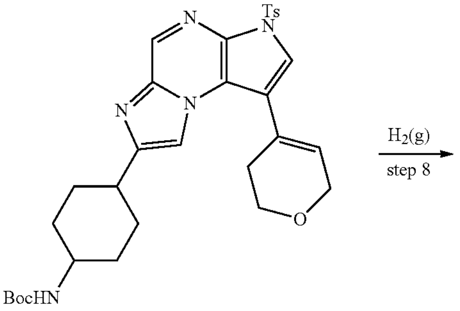

10

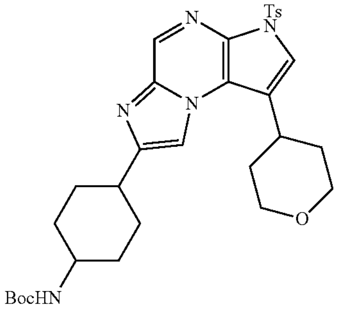

11

To a 25 mL single-neck flask were added 10 (239 mg, 0.40 mmol), methanol (1 mL) and $Pd(OH)_2$ (24 mg), and the mixture was reacted at room temperature for 18 h under hydrogen atmosphere. The reaction system was filtered under vacuum, and the filtrate was concentrated by rotary evaporation to give a crude product (160 mg); LC-MS: 594 $[M+H]^+$.

Step 9

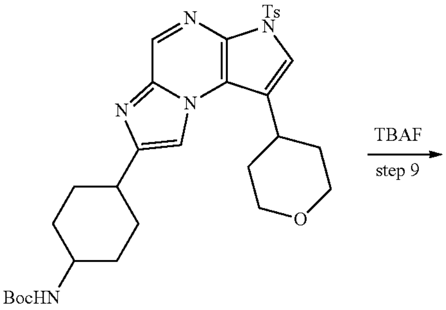

11

-continued

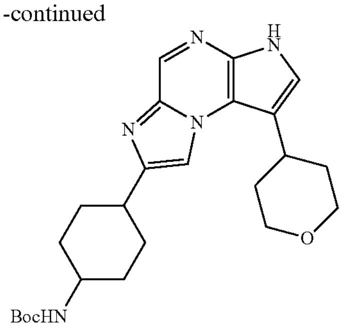

20

To a 25 mL single-neck flask were added 11 (160 mg, 0.27 mmol), THE (1.0 mL) and tetrabutylammonium fluoride (74 mg, 0.28 mmol), and the mixture was reacted at 60° C. for 12 h, concentrated and added with dichloromethane and brine. The organic phase was dried over anhydrous sodium sulfate and concentrated to give a crude product (300 mg, crude); LC-MS: 440 $[M+H]^+$.

Step 10

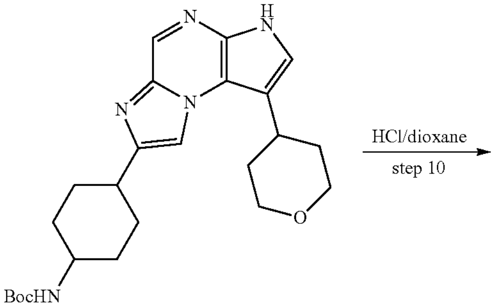

20

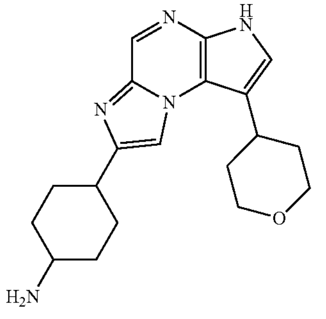

Compound C

To a 25 mL single-neck flask were added 20 (300 mg, 0.68 mmol) and a solution of hydrogen chloride in 1,4-dioxane (3.0 mL), and the mixture was reacted at room temperature for 2 h and concentrated to prepare a target product compound C (45 mg, yield: 19.5%) in the form of a white solid; LC-MS: 339.9 $[M+H]^+$.

$^1H$ NMR (400 MHz, $CDCl_3$) δ 8.71 (s, 1H), 8.23 (s, 1H), 7.87 (s, 1H), 7.55 (s, 1H), 3.96 (dd, J=11.0, 3.3 Hz, 2H), 3.65 (dd, J=11.6, 10.0 Hz, 2H), 3.41 (dd, J=11.6, 3.6 Hz, 1H), 3.11 (s, 1H), 2.95 (d, J=12.5 Hz, 1H), 2.16-2.05 (m, 4H), 1.86 (d, J=12.8 Hz, 2H), 1.76-1.65 (m, 4H), 1.50 (dd, J=23.2, 10.9 Hz, 2H).

Example 4: Preparation of IRAK4 Kinase Inhibitor

The synthetic route is as follows:

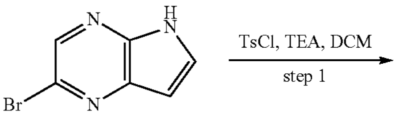

1

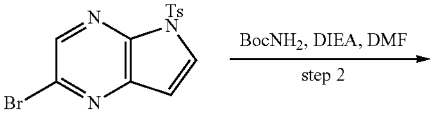

2

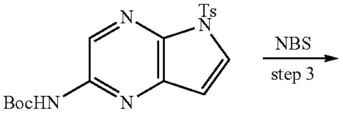

3

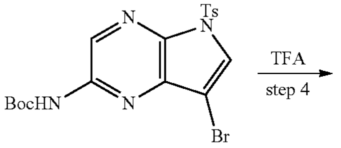

4

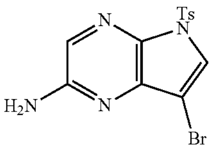

5

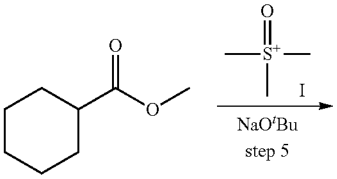

21

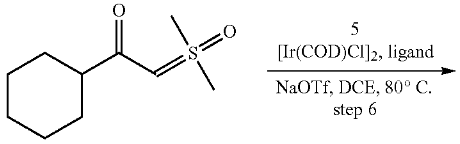

22

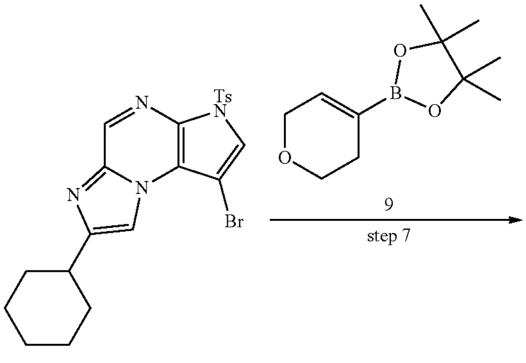

23

-continued

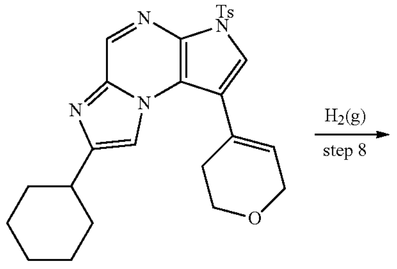

24

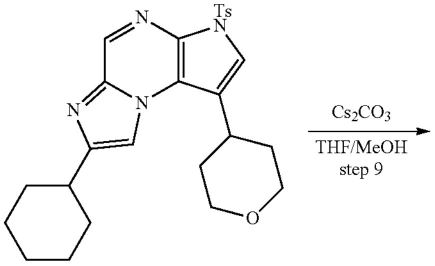

25

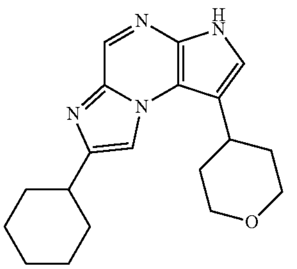

Compound D

Step 1

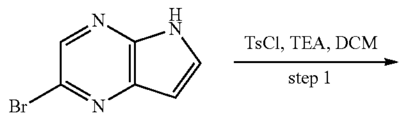

1

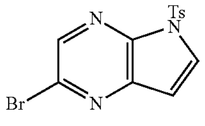

2

To a 250 mL single-neck flask were added 1 (8.0 g, 40.62 mmol), dichloromethane (80 mL), triethylamine (8.23 g, 81.23 mmol) and TsCl (9.29 g, 48.74 mmol), and the mixture was stirred at room temperature for 3 h. The reaction system was added with water, extracted with ethyl acetate (100 mL×3), washed with saturated brine (50 mL×2), dried over anhydrous sodium sulfate, concentrated by rotary evaporation, and purified by column chromatography (petroleum ether:ethyl acetate=4:1) to give a target product (8.0 g, yield: 56.1%) in the form of a yellow solid; LC-MS: 352 $[M+H]^+$.

Step 2

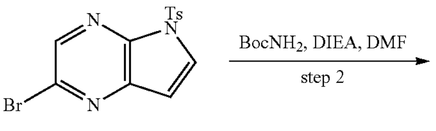

2

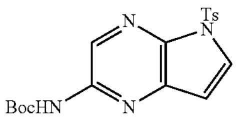

3

To a 100 mL single-neck round-bottom flask were added 2 (8.0 g, 22.79 mmol), tert-butyl carbamate (3.20 g, 27.35 mmol), DIEA (5.88 g, 45.58 mmol) and DMF (40.0 mL), and the mixture was reacted at 100° C. for 18 h. The reaction system was added with water and extracted with ethyl acetate (100 mL×3). The organic phase was washed with saturated brine (50 mL×2), dried over anhydrous sodium sulfate and concentrated by rotary evaporation to give a crude product (9.0 g) in the form of a yellow solid; LC-MS: 389 $[M+H]^+$.

Step 3

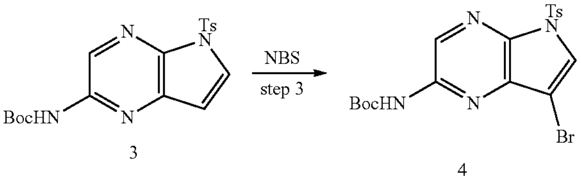

3 4

To a 250 mL single-neck flask were added 3 (9.0 g, 23.19 mmol), acetonitrile (90 mL) and NBS (4.95 g, 27.83 mmol), and the mixture was reacted at room temperature for 4 h. The reaction system was added with water (50 mL) to quench the reaction, extracted with ethyl acetate (100 mL×3), washed with saturated brine (50 mL×2), dried over anhydrous sodium sulfate, concentrated by rotary evaporation, and purified by column chromatography (petroleum ether:ethyl acetate=8:1) to give a target product (4.5 g, yield: 41.6%) in the form of a yellow solid; LC-MS: 467 $[M+H]^+$.

Step 4

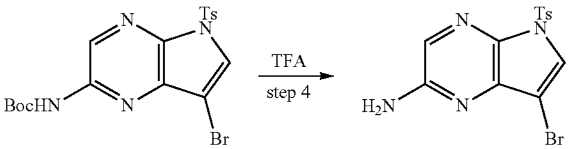

4 5

To a 100 mL single-neck flask were added 4 (4.5 g, 9.66 mmol), dichloromethane (45.0 mL) and TFA (9 mL), and the mixture was reacted at room temperature for 2 h. The reaction system was concentrated, added with acetone, and filtered under vacuum. The solid was dried to give a target product (3.3 g, yield: 93.3%) in the form of a yellow solid; LC-MS: 367 [M+H]$^+$.

Step 5

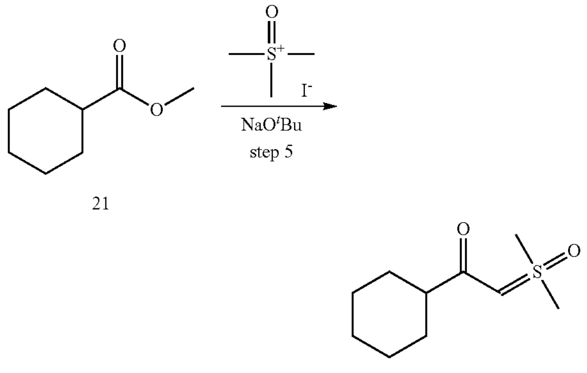

21

22

To a 250 mL single-neck flask were added trimethylsulfoxonium iodide (23.22 g, 105.56 mmol), THE (150 mL) and sodium tert-butoxide (10.65 mmol, 110.85 mmol), and the mixture was reacted under reflux for 2 h, cooled to room temperature, added with 21 (5.0 g, 35.19 mmol) and reacted at room temperature for 18 h. The reaction system was added with water to quench the reaction, extracted with ethyl acetate (200 mL×3), washed with saturated brine (100 mL×2), dried over anhydrous sodium sulfate, concentrated by rotary evaporation, and re-crystallized from ethyl acetate to give a target product (6.0 g, yield: 84.4%) in the form of a white solid; LC-MS: 203 [M+H]$^+$.

Step 6

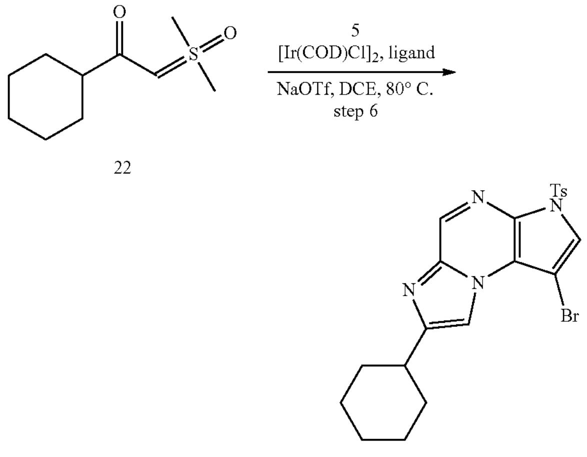

22

23

To a 25 mL single-neck flask were added 5 (483 mg, 1.32 mmol), 22 (400 mg, 1.98 mmol), $[Ir(COD)Cl]_2$ (22 mg, 0.033 mmol), 1,10-phenanthroline (12 mg, 0.066 mmol), NaOTf (11 mg, 0.066 mmol) and 1,2-dichloroethane (5 mL), and the mixture was reacted at 80° C. for 24 h under nitrogen atmosphere. The reaction system was filtered under vacuum, and the filtrate was concentrated by rotary evaporation and purified by column chromatography (dichloromethane:ethyl acetate=10:1) to give a target product (135 mg, yield: 21.7%) in the form of a yellow solid; LC-MS: 473 [M+H]$^+$.

Step 7

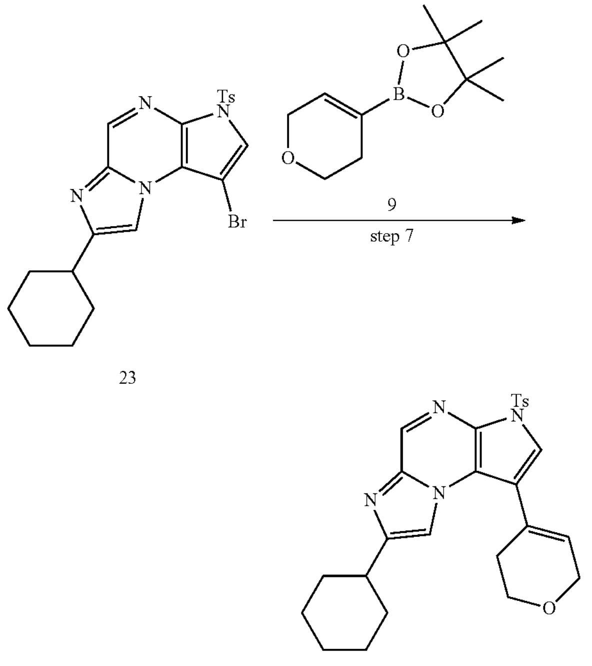

23

24

To a 25 mL single-neck flask were added 23 (135 mg, 0.29 mmol), 9 (90 mg, 0.43 mmol), dioxane (4 mL), water (1 mL), [1,1'-bis(diphenylphosphino)ferrocene]dichloropalladium (12 mg, 0.01 mmol) and potassium carbonate (80 mg, 0.58 mmol), and the mixture was reacted at 80° C. for 18 h under nitrogen atmosphere. The reaction system was added with water to quench the reaction, extracted with ethyl acetate (10 mL×3), washed with saturated brine (10 mL×3), dried over anhydrous sodium sulfate, concentrated by rotary evaporation, and purified by column chromatography (petroleum ether:ethyl acetate=2:1) to give a target product (70 mg, yield: 50.7%) in the form of a yellow solid; LC-MS: 477 [M+H]$^+$.

Step 8

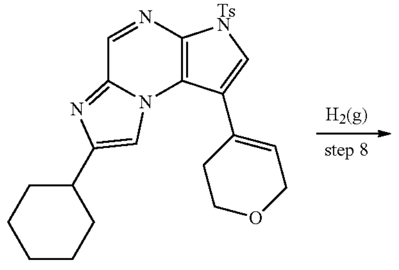

24

-continued

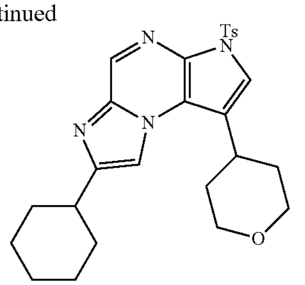

25

To a 25 mL single-neck flask were added 24 (70 mg, 0.15 mmol), methanol (1 mL) and $Pd(OH)_2$ (10 mg), and the mixture was reacted at room temperature for 18 h under hydrogen atmosphere. The reaction system was filtered under vacuum, and the filtrate was concentrated by rotary evaporation to give a target product (55 mg, yield: 76.7%) in the form of a yellow solid; LC-MS: 479 $[M+H]^+$.

Step 9

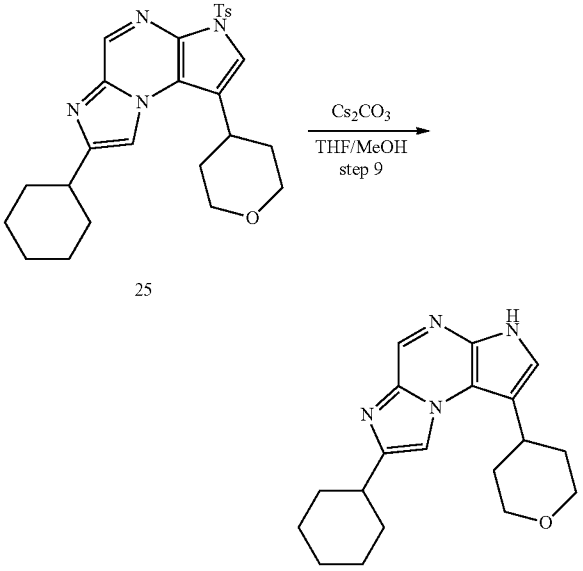

25

Compound D

To a 25 mL single-neck flask were added 25 (70 mg, 0.12 mmol), THF/MeOH (1.0 mL) and cesium carbonate (78 mg, 0.24 mmol), and the mixture was reacted under reflux for 12 h, concentrated and added with dichloromethane and brine. The organic phase was dried over anhydrous sodium sulfate and concentrated to prepare a target product compound D (10 mg, yield: 25.7%) in the form of a white solid; LC-MS: 325.0 $[M+H]^+$.

$^1H$ NMR (400 MHz, DMSO) δ 11.96 (s, 1H), 8.50 (s, 1H), 7.98 (s, 1H), 7.23 (d, J=2.8 Hz, 1H), 3.95 (dd, J=11.1, 3.3 Hz, 2H), 3.65 (t, J=10.9 Hz, 2H), 3.37 (ddd, J=11.7, 8.2, 3.5 Hz, 2H), 2.81 (ddd, J=11.6, 8.1, 3.5 Hz, 1H), 2.04 (d, J=11.5 Hz, 2H), 1.89-1.79 (m, 4H), 1.73-1.68 (m, 2H), 1.61-1.53 (m, 2H), 1.40 (dt, J=12.5, 4.7 Hz, 2H), 1.28 (dt, J=12.3, 3.2 Hz, 1H).

Example 5: Preparation of IRAK4 Kinase Inhibitor

The synthetic route is as follows:

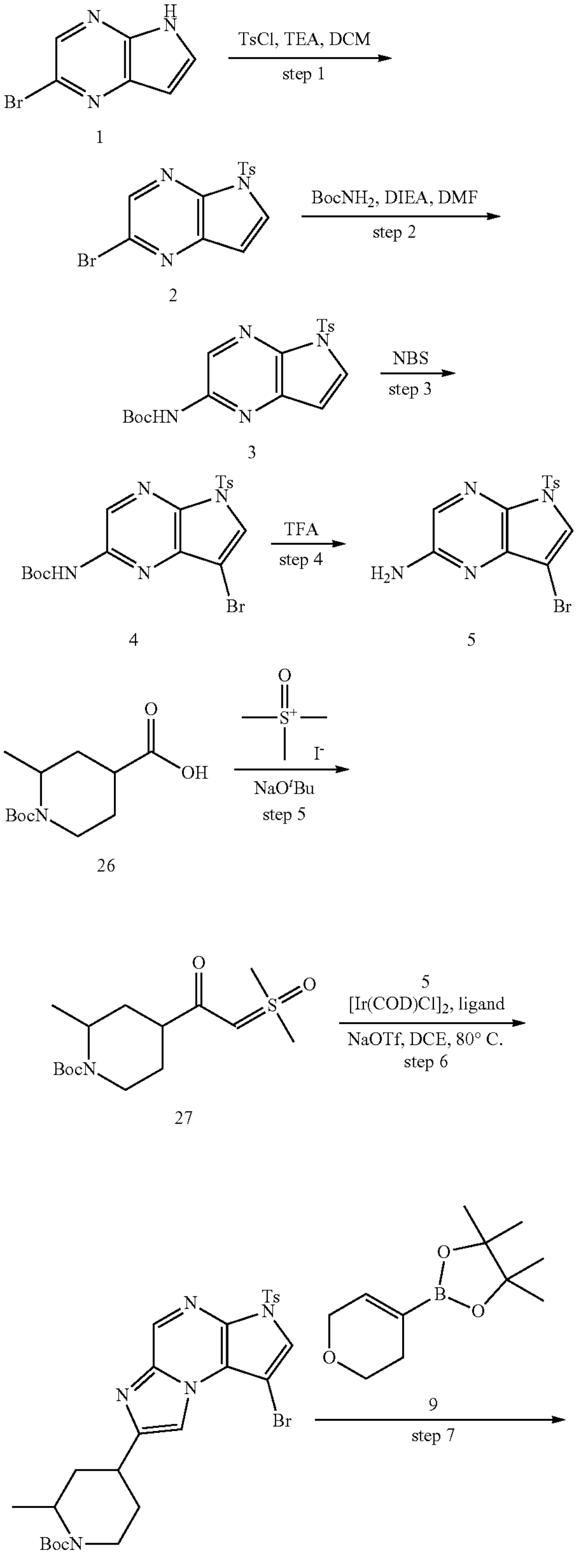

1, 2, 3, 4, 5, 26, 27, 28

-continued

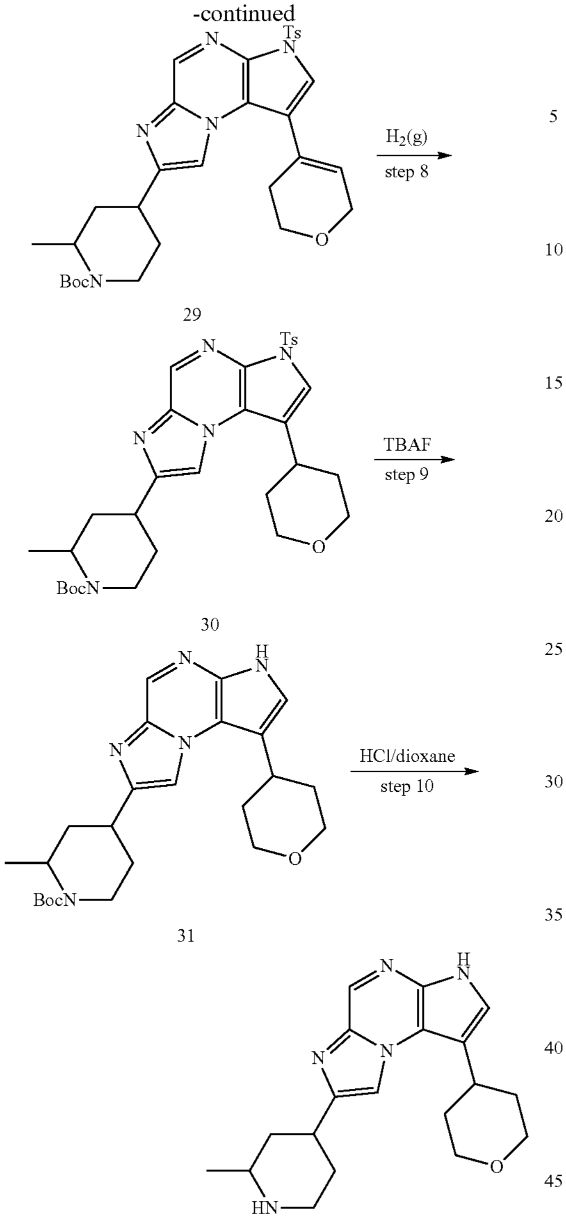

29

30

31

Compound E

Step 1

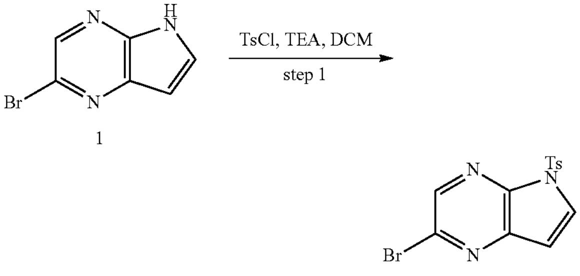

1

2

To a 250 mL single-neck flask were added 1 (8.0 g, 40.62 mmol), dichloromethane (80 mL), triethylamine (8.23 g, 81.23 mmol) and TsCl (9.29 g, 48.74 mmol), and the mixture was stirred at room temperature for 3 h and added with water. The reaction system was extracted with ethyl acetate (100 mL×3), washed with saturated brine (50 mL×2), dried over anhydrous sodium sulfate, concentrated by rotary evaporation, and purified by column chromatography (petroleum ether:ethyl acetate=4:1) to give a target product (8.0 g, yield: 56.1%) in the form of a yellow solid; LC-MS: 352 $[M+H]^+$.

Step 2

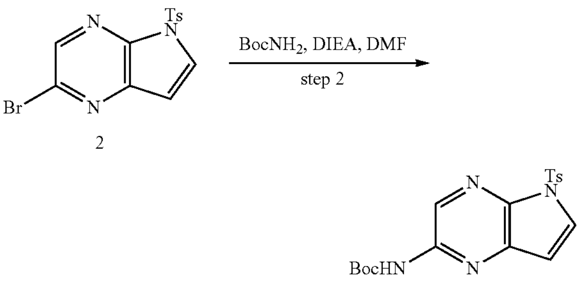

2

3

To a 100 mL single-neck round-bottom flask were added 2 (8.0 g, 22.79 mmol), tert-butyl carbamate (3.20 g, 27.35 mmol), DIEA (5.88 g, 45.58 mmol) and DMF (40.0 mL), and the mixture was reacted at 100° C. for 18 h. The reaction system was added with water and extracted with ethyl acetate (100 mL×3). The organic phase was washed with saturated brine (50 mL×2), dried over anhydrous sodium sulfate and concentrated by rotary evaporation to give a crude product (9.0 g) in the form of a yellow solid; LC-MS: 389 $[M+H]^+$.

Step 3

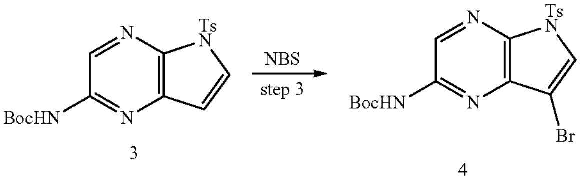

3

4

To a 250 mL single-neck flask were added 3 (9.0 g, 23.19 mmol), acetonitrile (90 mL) and NBS (4.95 g, 27.83 mmol), and the mixture was reacted at room temperature for 4 h. The reaction system was added with water (50 mL) to quench the reaction, extracted with ethyl acetate (100 mL×3), washed with saturated brine (50 mL×2), dried over anhydrous sodium sulfate, concentrated by rotary evaporation, and purified by column chromatography (petroleum ether:ethyl acetate=8:1) to give a target product (4.5 g, yield: 41.6%) in the form of a yellow solid; LC-MS: 467 $[M+H]^+$.

Step 4

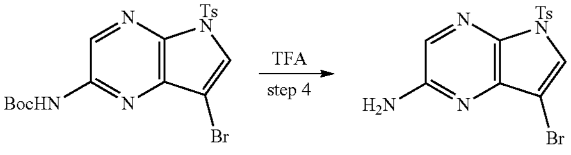

4

5

To a 100 mL single-neck flask were added 4 (4.5 g, 9.66 mmol), dichloromethane (45.0 mL) and TFA (9 mL), and the mixture was reacted at room temperature for 2 h. The reaction system was concentrated, added with acetone, and filtered under vacuum. The resulting solid was dried to give a target product (3.3 g, yield: 93.3%) in the form of a yellow solid; LC-MS: 367 $[M+H]^+$.

Step 5

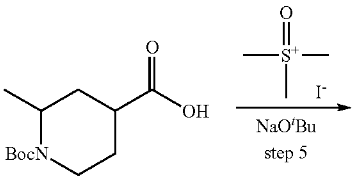

26

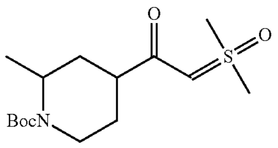

27

To a 100 mL single-neck flask were added 26 (1.00 g, 4.12 mmol), HATU (4.70 g, 12.4 mmol) and tetrahydrofuran (10 mL), and the mixture was reacted at room temperature for 2 h to give a mixture 1. To another 250 mL single-neck flask were added trimethylsulfoxonium iodide (1.82 g, 8.24 mmol), sodium tert-butoxide (791 mg, 8.24 mmol) and tetrahydrofuran (10 mL), and the mixture was reacted at room temperature for 3 h to give a mixture 2. The mixture 1 was added slowly to a mixture 2, and the resulting mixture was reacted under reflux for 12 h. The reaction system was added with water, extracted with ethyl acetate (50 mL×3), washed with saturated brine (50 mL×3), dried over anhydrous sodium sulfate and concentrated by rotary evaporation to give a target product (1.05 g, crude) in the form of a white solid; LC-MS: 318 $[M+H]^+$.

Step 6

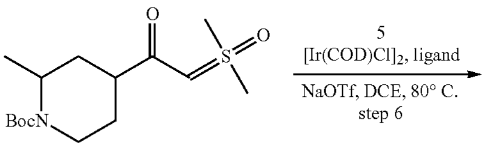

27

-continued

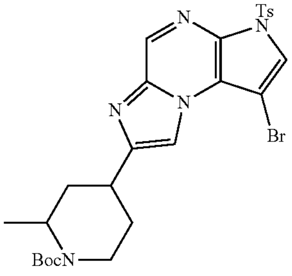

28

To a 50 mL single-neck flask were added 27 (1.00 g, 3.15 mmol), 5 (578 mg, 1.58 mmol), $[Ir(COD)Cl]_2$ (50.4 mg, 0.075 mmol), 1,10-phenanthroline (42.6 mg, 0.237 mmol), NaOTf (455 mg, 4.74 mmol) and 1,2-dichloroethane (25 mL), and the mixture was reacted at 80° C. for 24 h under nitrogen atmosphere. The reaction system was filtered under vacuum, and the filtrate was concentrated by rotary evaporation and purified by column chromatography (dichloromethane:ethyl acetate=10:1) to give a target product (120 mg, yield: 12.9%) in the form of a yellow solid; LC-MS: 588 $[M+H]^+$.

Step 7

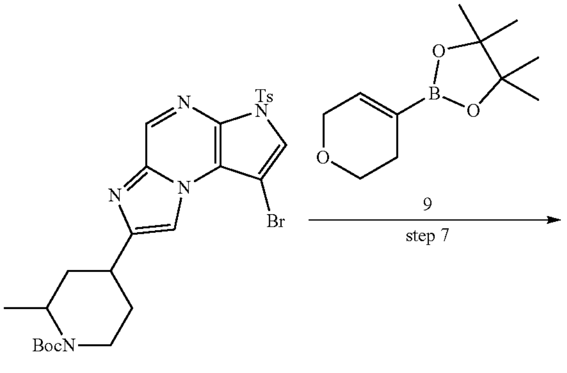

28

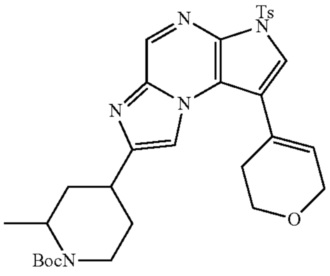

29

To a 25 mL single-neck flask were added 28 (120 mg, 0.204 mmol), 9 (51.5 mg, 0.245 mmol), dioxane (5 mL), water (1 mL), [1,1'-bis(diphenylphosphino)ferrocene]dichloropalladium (4.45 mg, 0.00612 mmol) and potassium carbonate (84.5 mg, 0.612 mmol), and the mixture was reacted at 80° C. for 18 h under nitrogen atmosphere. The reaction system was added with water to quench the reaction, extracted with ethyl acetate (10 mL×3), washed with saturated brine (10 mL×3), dried over anhydrous sodium sulfate, concentrated by rotary evaporation, and purified by column chromatography (petroleum ether:ethyl acetate=2:1) to give a target product (90 mg, yield: 74.5%) in the form of a yellow solid; LC-MS: 592 $[M+H]^+$.

Step 8

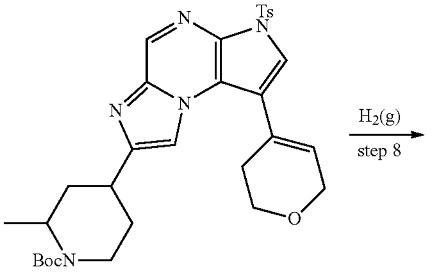

29

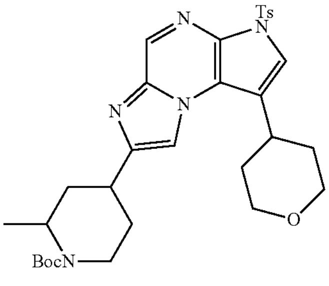

30

To a 25 mL single-neck flask were added 29 (90.0 mg, 0.152 mmol), methanol (5 mL) and $Pd(OH)_2$ (20 mg), and the mixture was reacted at room temperature for 18 h under hydrogen atmosphere. The reaction system was filtered under vacuum, and the filtrate was concentrated by rotary evaporation to give a crude product (57 mg); LC-MS: 594 $[M+H]^+$.

Step 9

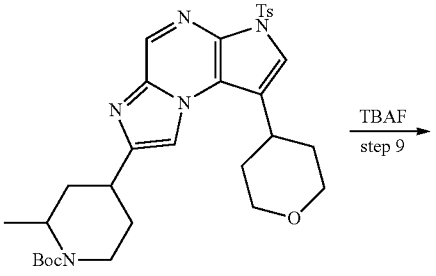

30

-continued

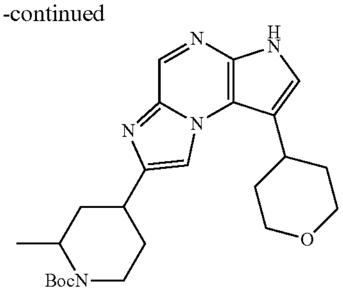

31

To a 25 mL single-neck flask were added 30 (57 mg, 0.0961 mmol) and a solution of tetrabutylammonium fluoride in tetrahydrofuran (1 M, 4 mL), and the mixture was reacted at 60° C. for 12 h, concentrated and added with dichloromethane and brine. The organic phase was dried over anhydrous sodium sulfate and concentrated to give a crude product (100 mg, crude); LC-MS: 440 $[M+H]^+$.

Step 10

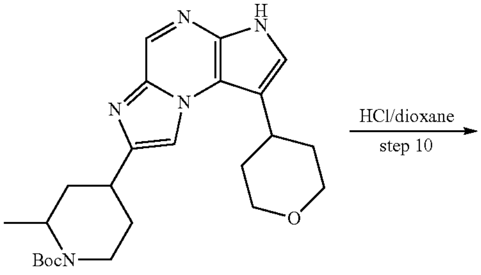

31

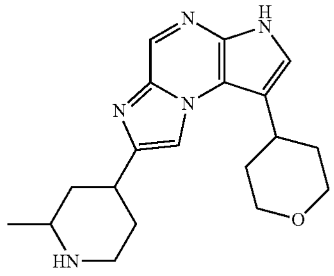

Compound E

Figure 2:
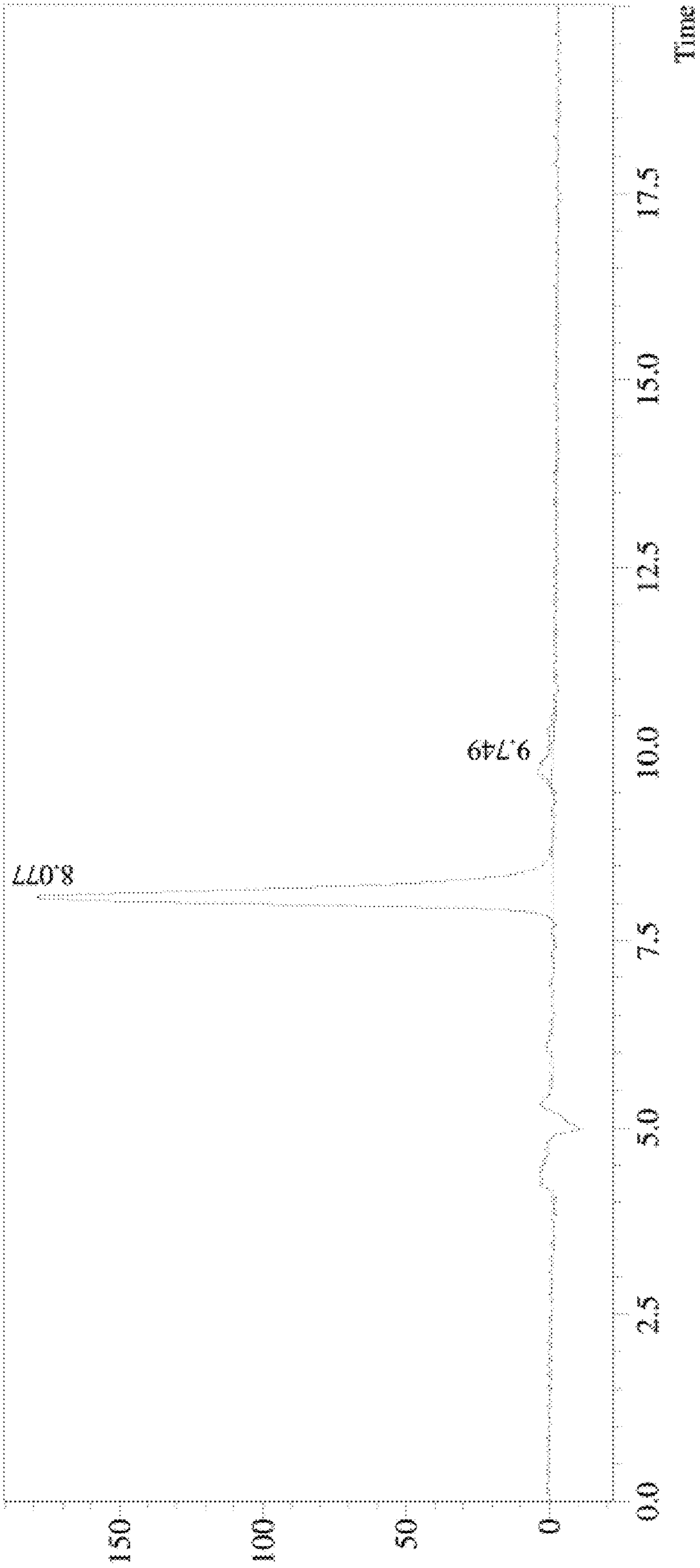
FIG. 2 is a chiral high performance liquid chromatogram of compound E-1.
Figure 3:
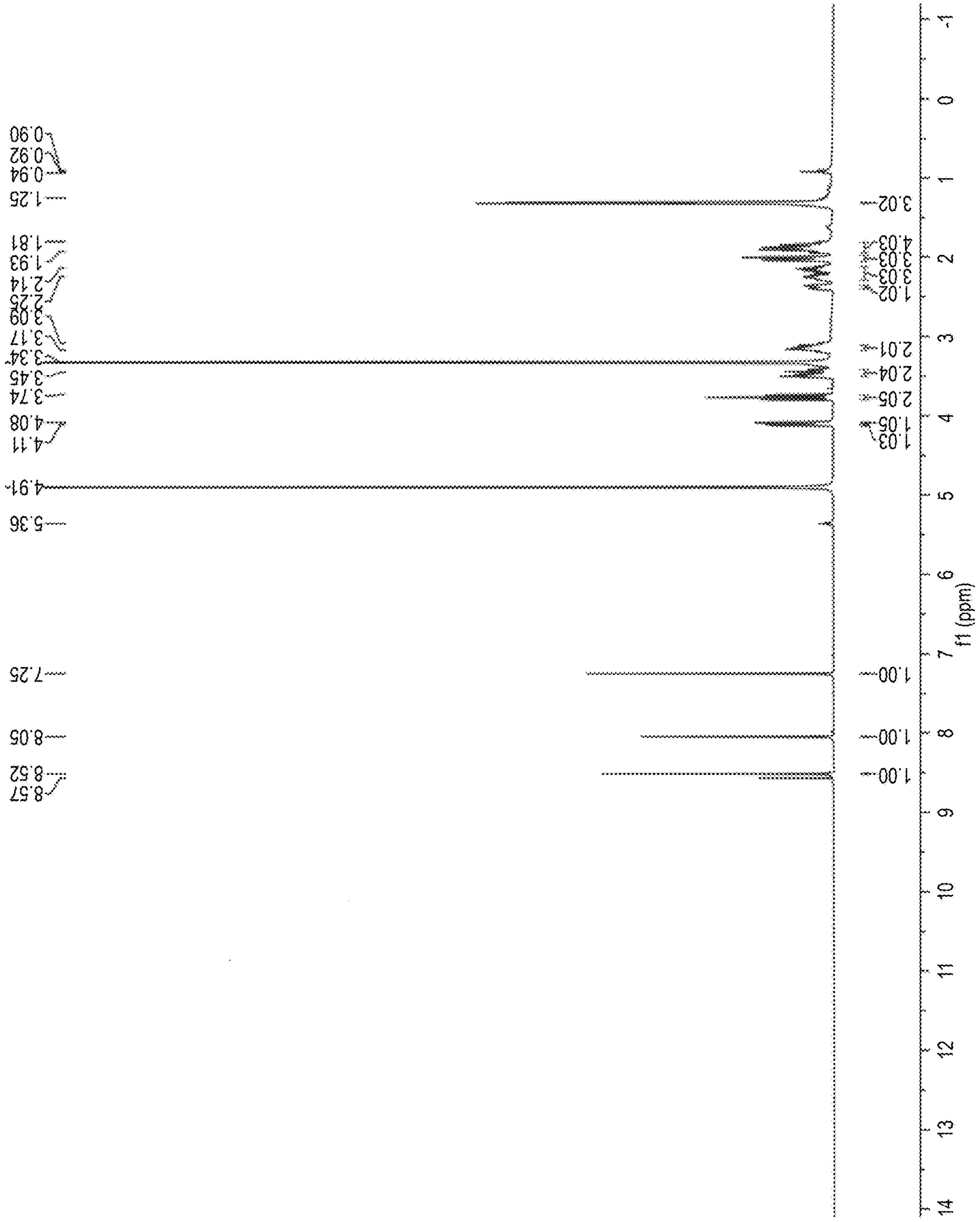
FIG. 3 is a $^1$H-NMR spectrum of compound E-2.
Figure 4:
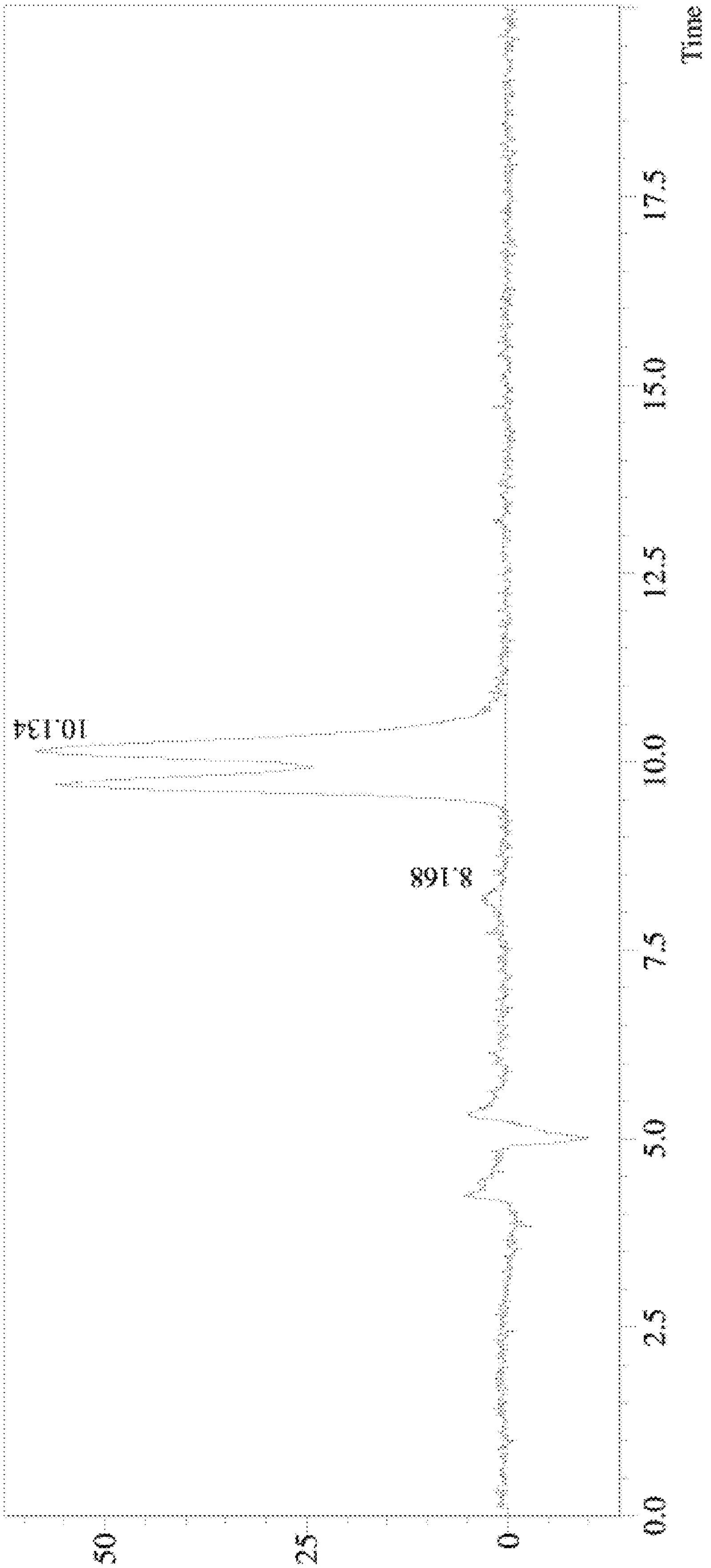
FIG. 4 is a chiral high performance liquid chromatogram of compound E-2.

To a 25 mL single-neck flask were added 31 (100 mg, 0.228 mmol) and a solution of hydrogen chloride in 1,4-dioxane (5.0 mL), and the mixture was reacted at room temperature for 2 h and concentrated to prepare a target product compound E in the form of a white solid which was then resolved by chiral HPLC to give target products E-1 and E-2, wherein the column is DAICEL CHRAL IC (250 mm×30 mm, 10 um), the running time is 20 min, the mobile phase is 20% EtOH/80% n-hexane (containing 0.2% DEA), the flow rate is 18 mL/min, the chiral HPLC spectra are shown in FIGS. 2 and 4, $^1H$ NMR spectra are shown in FIGS. 1 and 3, and the yields of the products E-1 and E-2 are 3 mg, yield: 7.77% and 5 mg, yield: 12.9%, respectively.

Compound E-1: LC-MS: 340 $[M+H]^+$, $^1H$ NMR (400 MHz, MeOD) δ 8.50 (s, 1H), 7.99 (s, 1H), 7.25 (s, 1H), 4.12 (d, J=3.7 Hz, 1H), 4.09 (d, J=3.2 Hz, 1H), 3.77 (dd, J=11.7, 10.0 Hz, 2H), 3.45-3.41 (m, 1H), 3.14 (s, 1H), 3.02-2.93 (m, 2H), 2.20 (t, J=14.5 Hz, 3H), 2.02 (d, J=13.2 Hz, 2H), 1.86 (ddd, J=16.8, 11.7, 3.8 Hz, 4H), 1.56 (d, J=12.2 Hz, 1H), 1.32 (s, 1H), 1.27 (d, J=6.3 Hz, 3H).
Compound E-2: LC-MS: 340 $[M+H]^+$, $^1H$ NMR (400 MHz, MeOD) δ 8.52 (s, 1H), 8.05 (s, 1H), 7.25 (s, 1H), 4.12 (d, J=3.6 Hz, 1H), 4.09 (d, J=3.4 Hz, 1H), 3.77 (dd, J=11.7, 10.0 Hz, 2H), 3.46 (ddd, J=11.5, 9.3, 5.0 Hz, 2H), 3.18-3.11 (m, 2H), 2.38 (dd, J=9.7, 4.9 Hz, 1H), 2.29-2.12 (m, 3H), 2.06-1.98 (m, 3H), 1.95-1.82 (m, 4H), 1.31 (d, J=6.5 Hz, 3H).
Example 6: Preparation of IRAK4 Kinase Inhibitor
The synthetic route is as follows:
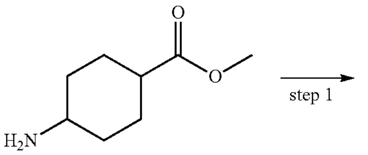
1
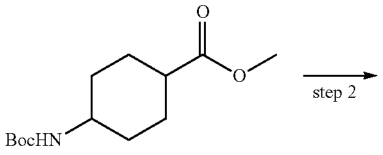
2
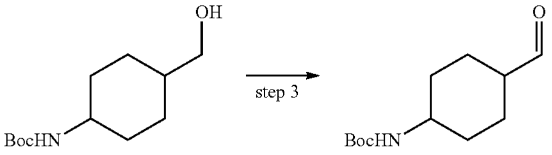
3 4
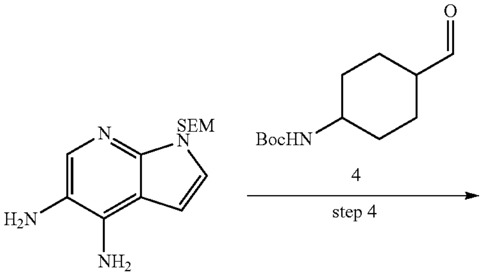
5
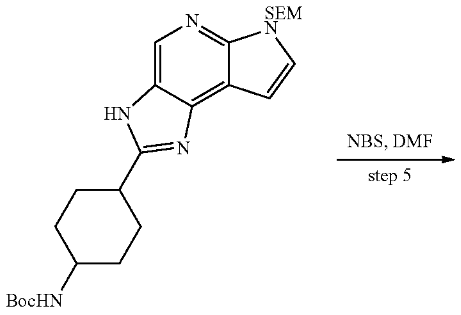
6
-continued
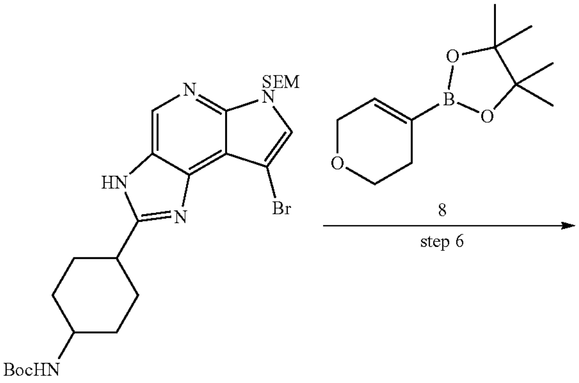
7
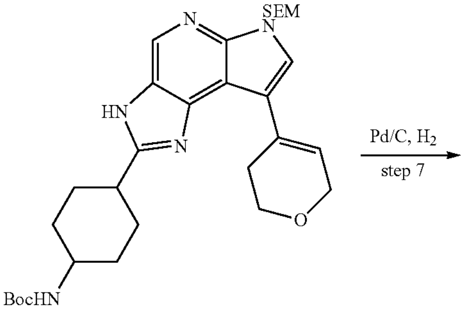
9
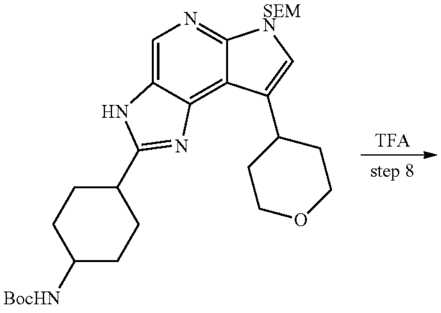
10
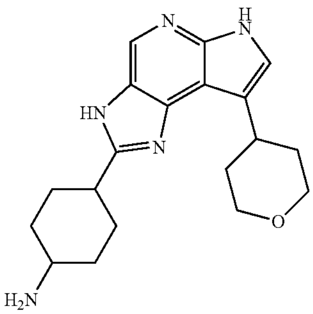
F Step 1

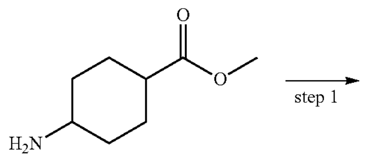

1

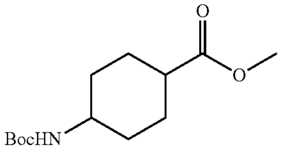

2

In a 500 mL single-neck flask, 1 (8.95 g, 57.0 mmol) was dissolved in DMF (70 mL), and $(Boc)_2O$ (24.8 g, 114 mmol), TEA (17.4 g, 171 mmol) and DMAP (10.4 g, 85.5 mmol) were added and reacted at 90° C. for 18 h. The reaction system was filtered under vacuum, concentrated and purified by column chromatography (petroleum ether: ethyl acetate=60:1) to give a target product (6.2 g, yield: 44%) in the form of a yellow oil. LC-MS: 258 $[M+H]^+$.

Step 2

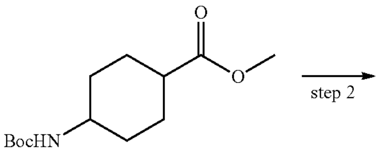

2

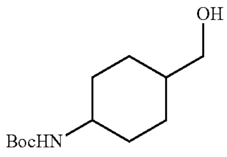

3

In a 500 mL three-neck flask, $LiAlH_4$ (2.6 g, 68.6 mmol) was dissolved in THE (40 mL) and cooled to −5° C., and 2 (5.89 g, 22.8 mmol) was dissolved in THE (20 mL) and added dropwise slowly to the system. The mixture was reacted at 0° C. for 1 h, added with ice water to quench the reaction, washed with a 15% aqueous NaOH solution, then added with ice water for washing, filtered under vacuum, concentrated, extracted with ethyl acetate (100 mL×3), washed with saturated saline solution (100 mL×3), dried over anhydrous sodium sulfate, and spin-dried to give a target product (3.3 g, crude) in the form of a colorless oil. LC-MS: 230 $[M+H]^+$.

Step 3

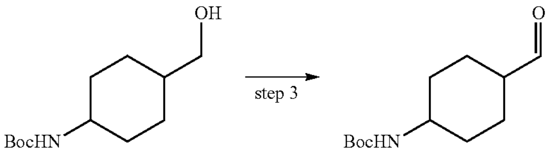

3 4

In a 250 mL three-neck flask, 3 (1.94 g, 8.47 mmol) was dissolved in DCM (40 mL), cooled to 0° C. in an ice bath, and Dess-Martin (3.6 g, 8.47 mmol) was added. The mixture was reacted at room temperature for 1 h, filtered under vacuum, added with a saturated aqueous $NaHCO_3$ solution to quench the reaction, extracted with dichloromethane (80 mL×3), washed with saturated brine (80 mL×2), dried over anhydrous sodium sulfate, and concentrated to give a target product (2.6 g, crude) in the form of a yellow oil. LC-MS: 228 $[M+H]^+$.

Step 4

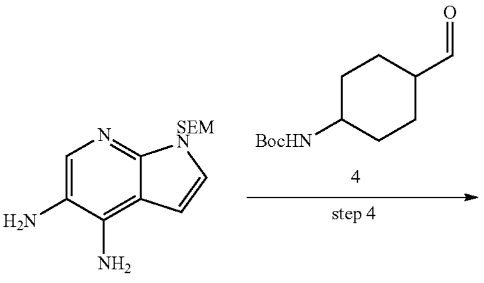

5

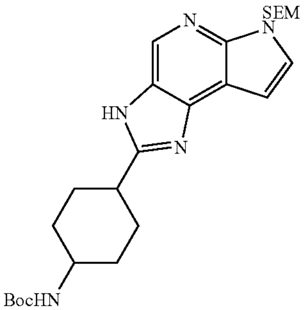

6

To a 100 mL single-neck flask were added 5 (432 mg, 1.55 mmol), 4 (352 mg, 1.55 mmol), AcOH (279 mg, 4.66 mmol) and methanol (10 mL), and the mixture was reacted at room temperature for 16 h, concentrated, added with ice water to quench the reaction, extracted with dichloromethane (50 mL×4), washed with saturated saline (50 mL×2), dried over anhydrous sodium sulfate, and spin-dried to give a target product (640 mg, crude) in the form of a yellow oil. LC-MS: 486 $[M+H]^+$.

Step 5

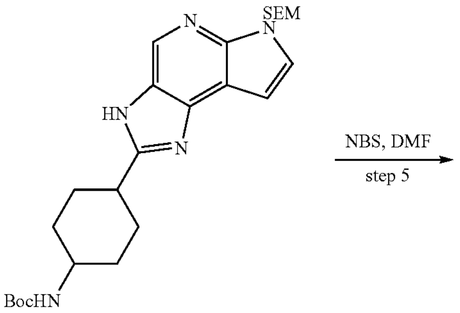

6

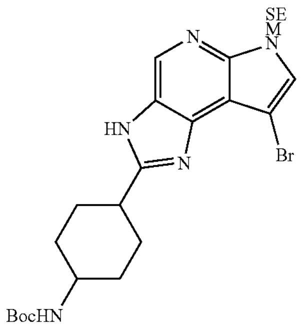

7

To a 100 mL single-neck flask were added 6 (640 mg, 1.319 mmol), NBS (281.8 mg, 1.583 mmol) and DMF (10 mL), and the mixture was reacted at room temperature for 16 h, added with ice water to quench the reaction, extracted with ethyl acetate (50 mL×3), washed with saturated brine (50 mL×3), dried over anhydrous sodium sulfate, and spin-dried to give a target product (979 mg, crude) in the form of a yellow oil. LC-MS: 566 $[M+H]^+$.

Step 6

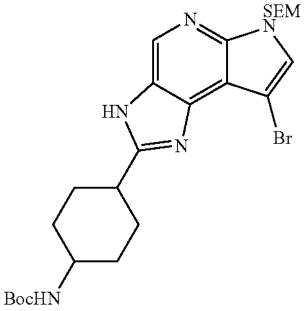

7

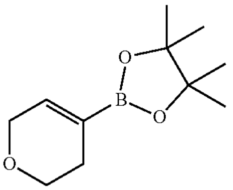

8

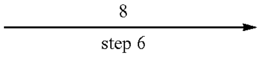

-continued

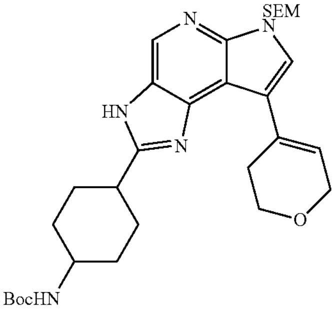

9

To a 100 mL single-neck flask were added 7 (979 mg, 1.73 mmol), 8 (546 mg, 2.6 mmol), $Pd_2(dppf)Cl_2 \cdot CH_2Cl_2$ (71 mg, 0.0866 mmol), $K_2CO_3$ (717 g, 5.2 mmol), dioxane (20 mL) and $H_2O$ (4 mL), and the mixture was reacted at 80° C. for 16 h under nitrogen atmosphere, spin-dried, and purified by column chromatography (dichloromethane:methanol=20:1) to give a target product (466 mg, yield: 47.3%) in the form of a yellow oil. LC-MS: 568 $[M+H]^+$.

Step 7

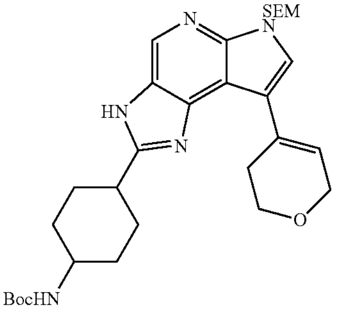

9

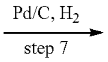

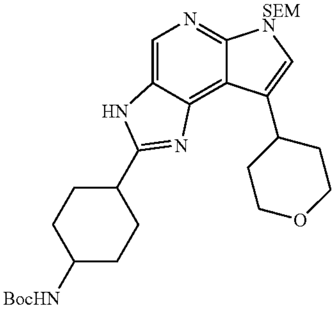

10

To a 100 mL single-neck flask were added 9 (466 mg, 0.821 mmol), $Pd(OH)_2$ (210 mg) and THE (10 mL), the mixture was reacted at room temperature for 16 h under hydrogen atmosphere, and filtered under vacuum, and the filtrate was concentrated to give a target product (325 mg, yield: 69.5%) in the form of a yellow oil. LC-MS: 570 $[M+H]^+$.

Step 8

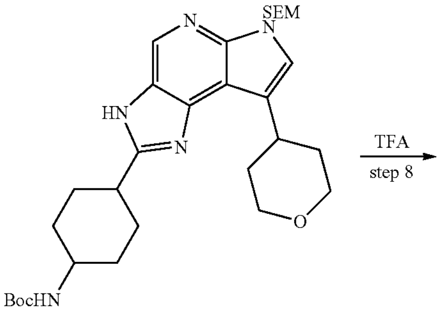

10

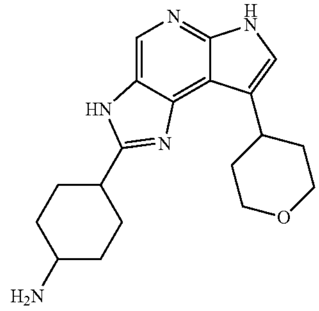

F

To a 100 mL single-neck flask were added 10 (325 mg, 0.571 mmol), TFA (2.6 mL) and DCM (8 mL), and the mixture was reacted at room temperature for 16 h, and concentrated to give a crude product (300 mg) in the form of a yellow oil. The crude product was added with $NH_3H_2O$ (1 mL) and dioxane (5 mL), reacted at 70° C. for 16 h, concentrated, and resolved by chiral HPLC (column: DAICEL CHRAL OD (250 mm×30 mm, 10 um); Gradient Time: 20 min; Condition: 0.2% DEA EtOH & Hexane; Flow Rate: 18 mL/min; 75% of B) to give two target products (F1: 50 mg, yield: 51.7%; F2: 25 mg, yield: 25.9%) in the form of white solids. LC-MS: 340 [M+H]+. 1H NMR (400 MHz, DMSO) δ 12.26 (s, 1H), 8.79 (s, 1H), 7.93-7.92 (m, 1H), 7.47 (d, J=2.1 Hz, 1H), 3.97 (dd, J=11.0, 3.3 Hz, 4H), 3.60 (s, 1H), 3.40 (s, 1H), 3.15 (s, 1H), 2.23 (d, J=11.4 Hz, 2H), 2.11 (d, J=10.3 Hz, 2H), 1.96 (s, 2H), 1.81-1.72 (m, 6H), 1.53 (d, J=9.9 Hz, 2H);

1H NMR (400 MHz, DMSO) δ 12.32 (s, 1H), 8.81 (s, 1H), 7.87 (s, 1H), 7.44 (s, 1H), 3.98 (d, J=10.6 Hz, 4H), 3.60 (s, 1H), 3.39 (s, 1H), 3.29 (s, 1H), 2.34-2.25 (m, 4H), 1.99 (d, J=3.9 Hz, 2H), 1.97 (s, 2H), 1.85 (s, 4H), 1.78 (s, 2H).

Example 7: Preparation of IRAK4 Kinase Inhibitor

The synthetic route is as follows:

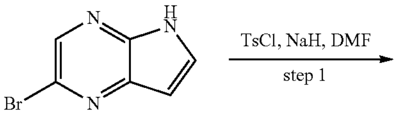

1

-continued

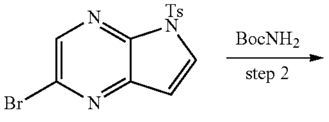

2

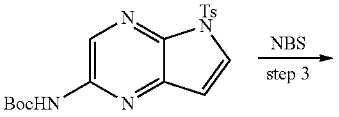

3

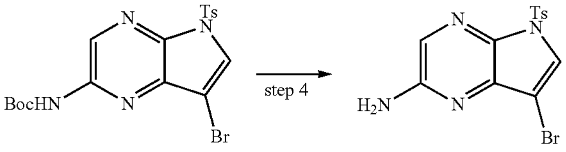

4 int 2-1

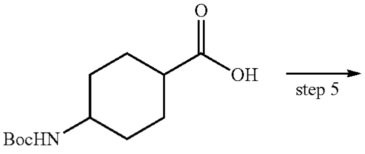

5

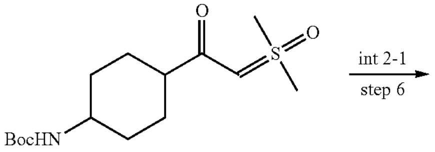

6

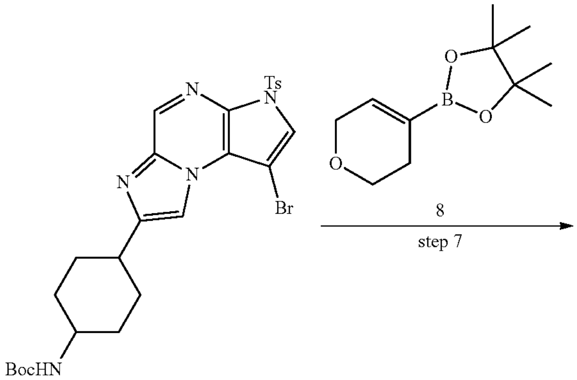

7

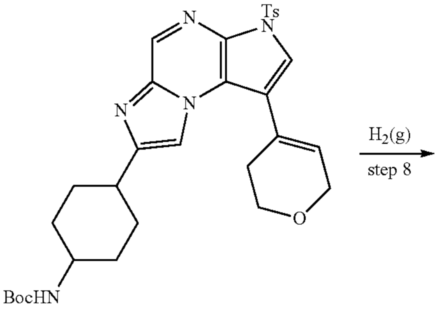

9

-continued

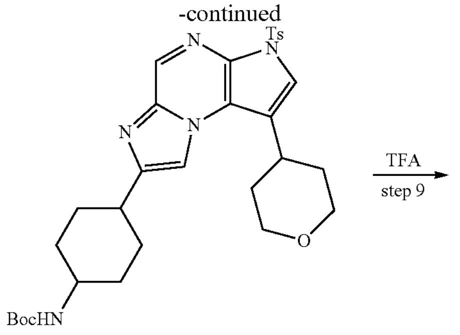

10

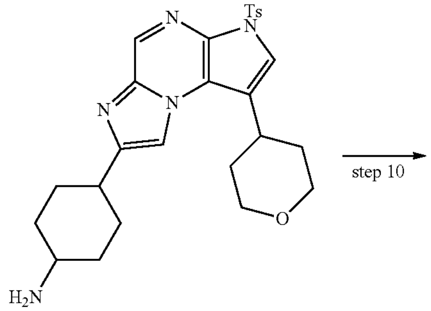

11

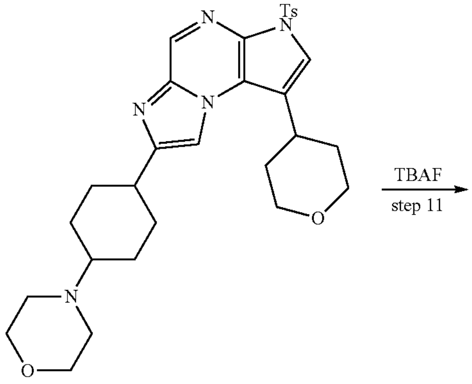

12

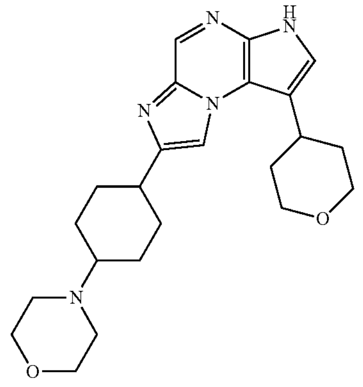

G

Step 1

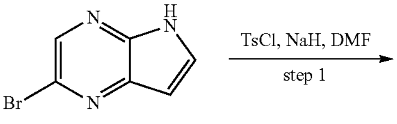

1

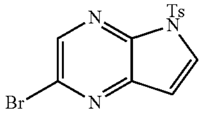

2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352 $[M+H]^+$.

Step 2

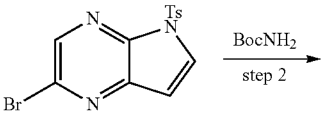

2

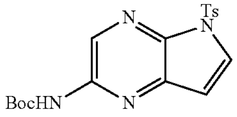

3

To a 500 mL single-neck round-bottom flask were added 2 (22.70 g, 64.6 mmol), $BocNH_2$ (11.3 g, 97.0 mmol), $Pd(OAc)_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 $[M+H]^+$.

Step 3

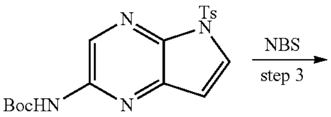

3

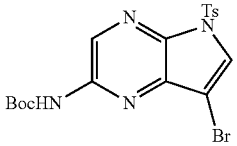

4

In a 500 mL single-neck flask, 3 (12.80 g, 32.9 mmol) was dissolved in DMF (100 mL), and added with NBS (7.04 g, 39.5 mmol) at 0° C. The mixture was reacted at room temperature for 1.5 h, added with ice water to quench the reaction, and filtered to give a target product (15.0 g, crude) in the form of a yellow solid. LC-MS: 467 $[M+H]^+$.

Step 4

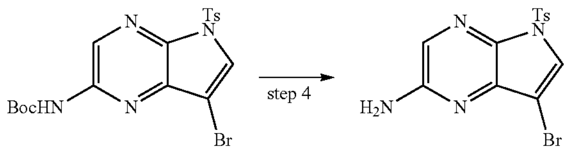

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 $[M+H]^+$.

Step 5

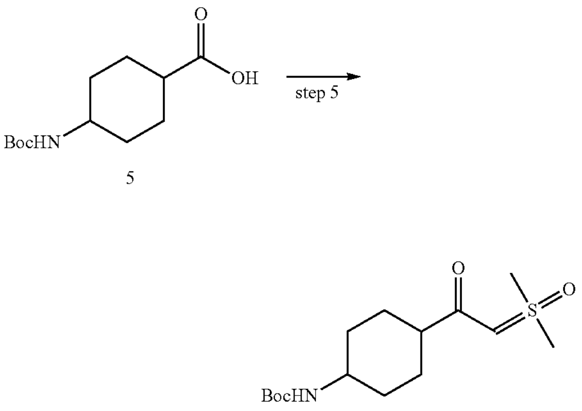

5

6

To a 250 mL single-neck flask were added 5 (5.00 g, 20.5 mmol), HATU (7.81 g, 20.5 mmol), triethylamine (7.28 g, 71.9 mmol) and THE (60 mL), and the mixture was reacted at room temperature for 3 h to give an activated ester. To another 1000 mL single-neck flask were added trimethylsulfoxonium iodide (13.5 g, 61.6 mmol), potassium tert-butoxide (7.26 g, 64.7 mmol) and THE (60 mL), and the mixture was reacted at 65° C. for 3 h, then cooled to 0° C. in an ice bath, and added dropwise with the activated ester. The resulting mixture was reacted at room temperature for 16 h, added with ice water to quench the reaction, stirred at room temperature for 5 h, concentrated, and filtered to give a target product (6.50 g, crude) in the form of a white solid.

LC-MS: 318 $[M+H]^+$.

Step 6

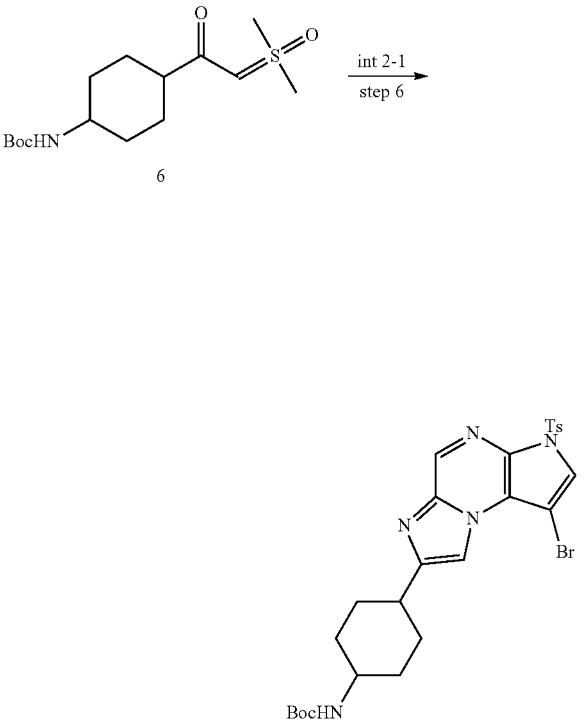

6

7

To a 100 mL single-neck flask were added 6 (2.76 g, 8.72 mmol), int 2-1 (800 mg, 2.18 mmol), chloro(1,5-cyclooctadiene)iridium(I) dimer (439 mg, 0.654 mmol), 1,10-phenanthroline (615 mg, 2.83 mmol), sodium triflate (697 mg, 4.05 mmol), dichloroethane (20 mL) and MS-4A, the mixture was reacted at 80° C. for 36 h under nitrogen atmosphere, and filtered under vacuum, and the filtrate was concentrated, and purified by TLC (petroleum ether:ethyl acetate=1:1) to give a target product (630 mg, yield: 52.5%) in the form of a yellow solid. LC-MS: 588 $[M+H]^+$.

Step 7

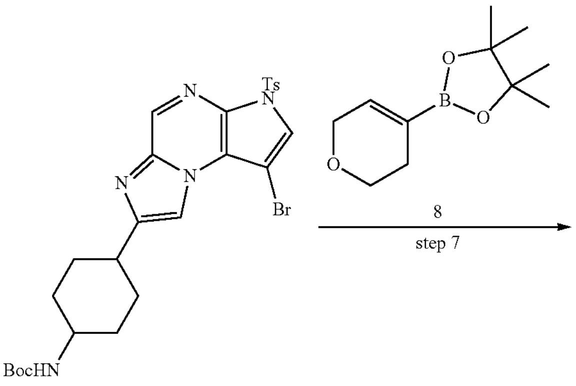

7

-continued

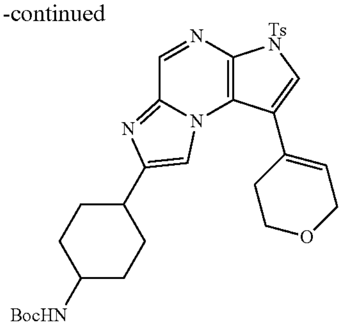

9

To a 100 mL single-neck flask were added 7 (630 mg, 1.07 mmol), 8 (338 mg, 1.60 mmol), $Pd_2(dppf)Cl_2 \cdot CH_2Cl_2$ (44 mg, 0.0536 mmol), $K_2CO_3$ (444 mg, 3.22 mmol), dioxane (10 mL) and $H_2O$ (2 mL), and the mixture was reacted at 80° C. for 16 h under nitrogen atmosphere, added with ice water to quench the reaction, extracted with dichloromethane (50 mL×3), washed with saturated brine (50 mL×2), dried over anhydrous sodium sulfate, spin-dried, and purified by TLC (petroleum ether:ethyl acetate=1:1) to give a target product (289 mg, yield: 45.0%) in the form of a yellow solid. LC-MS: 592 $[M+H]^+$.

Step 8

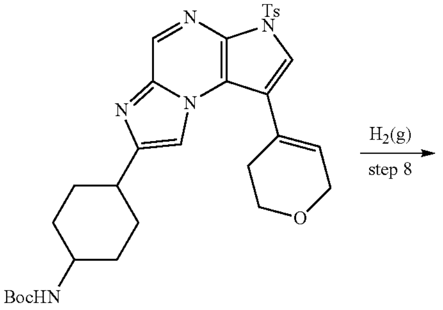

9

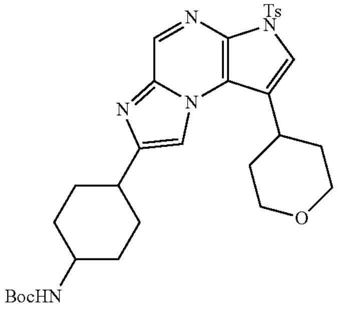

10

To a 100 mL single-neck flask were added 9 (289 mg, 0.489 mmol), $Pd(OH)_2$ (115 mg, 0.0981 mmol) and THE (10 mL), the mixture was reacted at room temperature for 24 h under hydrogen atmosphere, and filtered under vacuum, and the filtrate was concentrated, and purified by TLC (petroleum ether:ethyl acetate=1:1) to give a target product (200 mg, yield: 69.2%) in the form of a yellow oil. LC-MS: 594 $[M+H]^+$.

Step 9

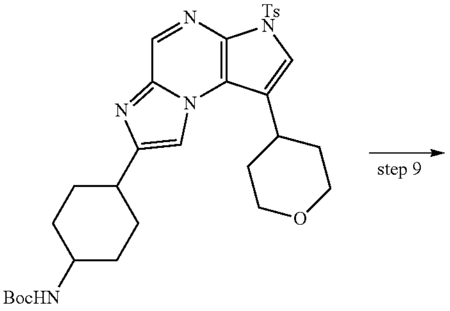

10

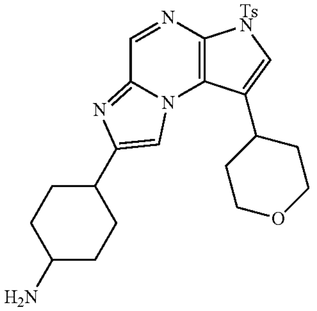

11

To a 100 mL single-neck flask were added 10 (200 mg, 0.337 mmol), TFA (1.5 mL) and DCM (8 mL), and the mixture was reacted at room temperature for 5 h, added with ice water to quench the reaction, adjusted to pH=9 with a saturated $Na_2CO_3$ solution, extracted with dichloromethane (20 mL×3), washed with saturated brine (20 mL×2), dried over anhydrous sodium sulfate, concentrated, and purified by TLC (dichloromethane:methanol=15:1) to give a target product (119 mg, yield: 71.6%) in the form of a yellow oil. LC-MS: 494 $[M+H]^+$.

Step 10

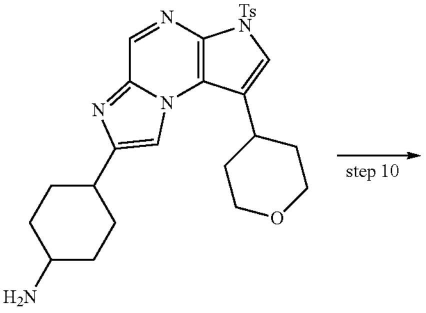

11

-continued

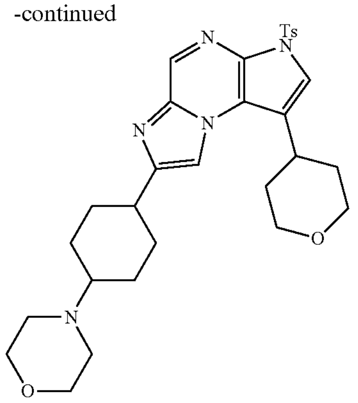

12

To a 100 mL single-neck flask were added 11 (82 mg, 0.165 mmol), 2,2'-dibromodiethyl ether (58 mg, 0.248 mmol), $K_2CO_3$ (68.7 mg, 0.497 mmol) and acetonitrile (5 mL), the mixture was reacted at 60° C. for 12 h, and filtered under vacuum, and the filtrate was concentrated, and purified by TLC (dichloromethane:methanol=15:1) to give a target product (36 mg, yield: 38.7%) in the form of a yellow oil. LC-MS: 564 [M+H]+.

Step 11

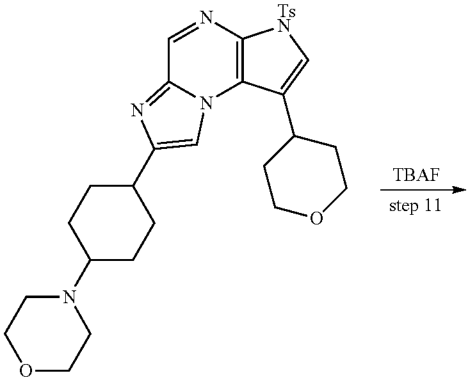

12

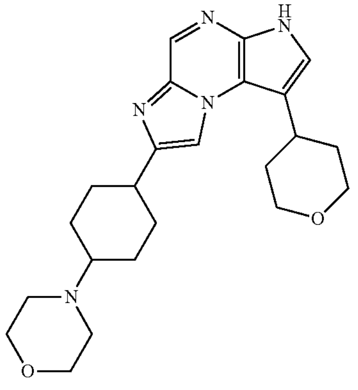

G

To a 100 mL single-neck flask were added 12 (36 mg, 0.0638 mmol) and TBAF (1.0 mL), and the mixture was reacted at 70° C. for 16 h, concentrated, and subjected to preparative high pressure liquid chromatography to give a target product (5.0 mg, yield: 19.2%) in the form of a white solid. LC-MS: 410 [M+H]+, 0.1H NMR (400 MHz, DMSO) δ 11.96 (s, 1H), 8.50 (s, 1H), 8.15 (s, 1H), 8.00 (s, 1H), 7.23 (d, J=2.9 Hz, 1H), 3.98-3.93 (m, 3H), 3.68 (s, 1H), 3.64 (d, J=2.3 Hz, 3H), 2.76 (t, J=3.4 Hz, 1H), 2.68-2.60 (m, 5H), 2.44 (s, 1H), 2.14 (d, J=11.9 Hz, 2H), 2.00 (d, J=11.1 Hz, 2H), 1.87 (d, J=11.0 Hz, 2H), 1.74-1.71 (m, 1H), 1.67 (d, J=8.8 Hz, 1H), 1.58 (d, J=10.6 Hz, 2H), 1.43 (d, J=12.1 Hz, 1H), 1.39 (s, 1H).

Example 8: Preparation of IRAK4 Kinase Inhibitor

The synthetic route is as follows:

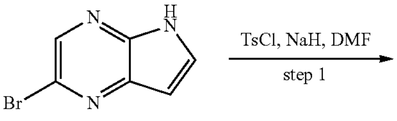

1

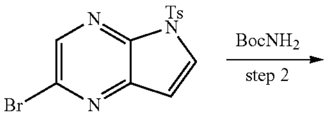

2

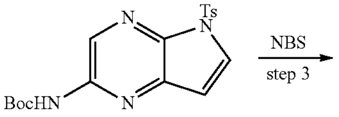

3

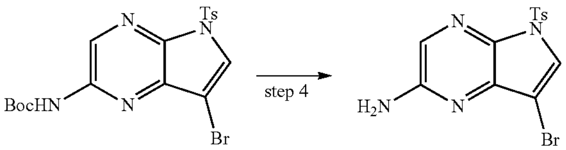

4 int 2-1

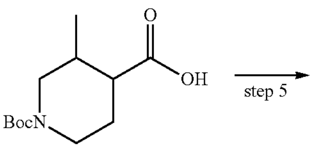

5

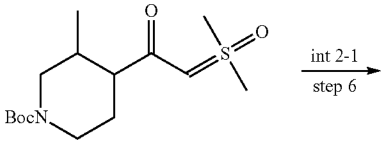

6

-continued

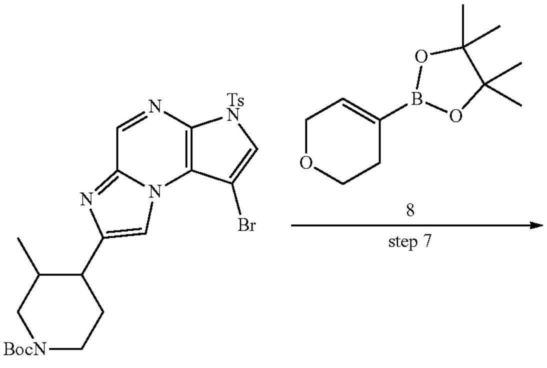

7

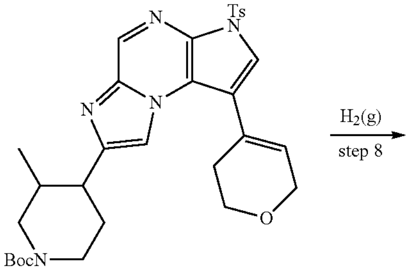

9

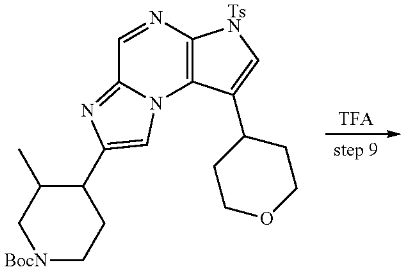

10

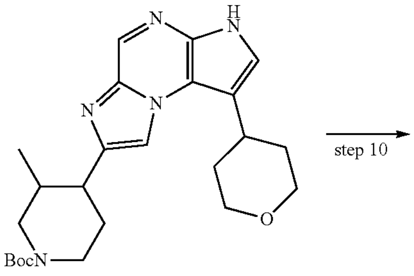

11

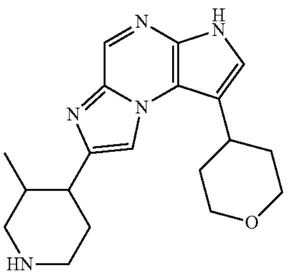

H

Step 1

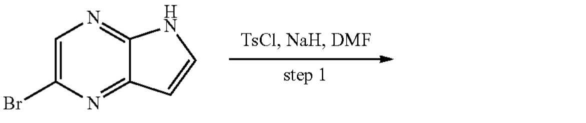

1

2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352 $[M+H]^+$.

Step 2

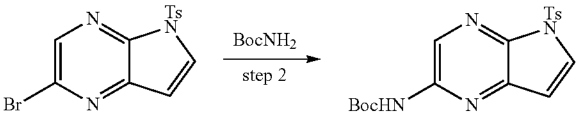

2

3

To a 500 mL single-neck round-bottom flask were added 2 (22.70 g, 64.6 mmol), $BocNH_2$ (11.3 g, 97.0 mmol), $Pd(OAc)_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 $[M+H]^+$.

Step 3

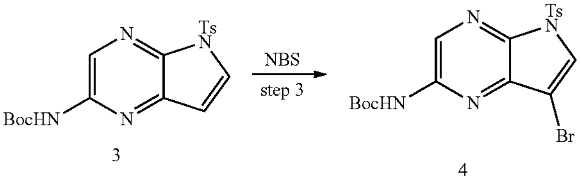

3

4

In a 500 mL single-neck flask, 3 (12.80 g, 32.9 mmol) was dissolved in DMF (100 mL), and added with NBS (7.04 g, 39.5 mmol) at 0° C. The mixture was reacted at room temperature for 1.5 h, added with ice water to quench the reaction, and filtered to give a target product (15.0 g, crude) in the form of a yellow solid. LC-MS: 467 [M+H]+.

Step 4

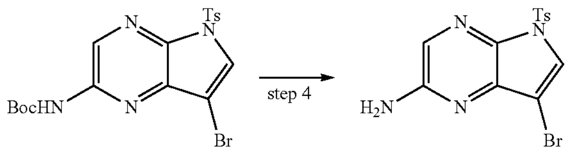

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 [M+H]+.

Step 5

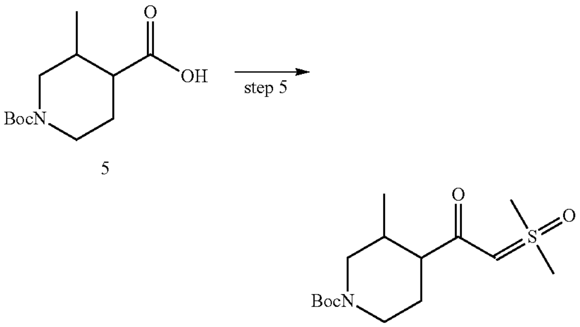

5 6

To a 100 mL single-neck flask were added 5 (1.028 g, 4.22 mmol), HATU (1.60 g, 4.22 mmol), triethylamine (1.50 g, 14.7 mmol) and THE (20 mL), and the mixture was reacted at room temperature for 3 h to give an activated ester. To another 500 mL single-neck flask were added trimethylsulfoxonium iodide (2.78 g, 12.6 mmol), potassium tert-butoxide (1.50 g, 13.3 mmol) and THE (20 mL), and the mixture was reacted at 65° C. for 3 h, then cooled to 0° C. in an ice bath, and added dropwise with the activated ester. The resulting mixture was reacted at room temperature for 16 h, added with ice water to quench the reaction, stirred at room temperature for 5 h, and filtered under vacuum, and the filtrate was concentrated and extracted with dichloromethane (60 mL×5), washed with saturated brine (50 mL×3), dried over anhydrous sodium sulfate, and spin-dried to give a target product (1.2 g, yield: 92.3%) in the form of a yellow solid. LC-MS: 318 [M+H]+.

Step 6

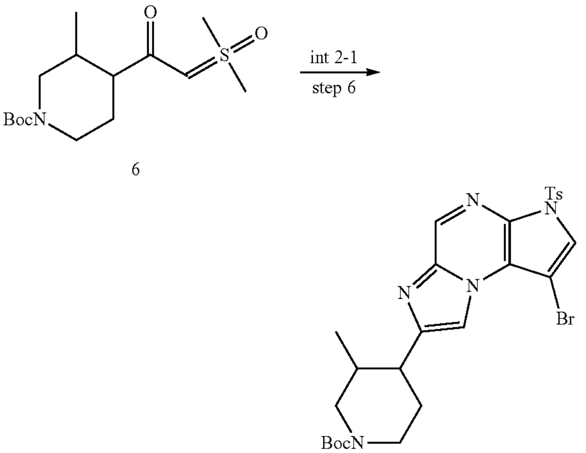

6 7

To a 100 mL single-neck flask were added 6 (1.2 g, 5.44 mmol), int 2-1 (500 mg, 1.360 mmol), chloro(1,5-cyclooctadiene)iridium(I) dimer (274 mg, 0.408 mmol), 1,10-phenanthroline (384 mg, 1.77 mmol), sodium triflate (435 mg, 2.53 mmol), dichloroethane (20 mL) and MS-4A, the mixture was reacted at 80° C. for 36 h under nitrogen atmosphere, and filtered under vacuum, and the filtrate was concentrated, and purified by TLC (petroleum ether:ethyl acetate=1:1) to give a target product (184 mg, yield: 8.3%) in the form of a yellow oil. LC-MS: 588 [M+H]+.

Step 7

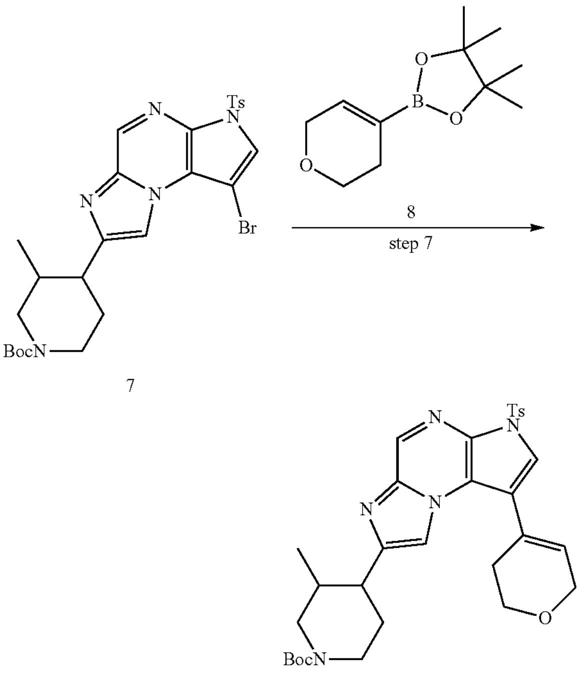

8 7 9

To a 100 mL single-neck flask were added 7 (184 mg, 0.312 mmol), 8 (98.5 mg, 0.468 mmol), $Pd_2(dppf)Cl_2 \cdot CH_2Cl_2$ (12.8 mg, 0.0156 mmol), $K_2CO_3$ (129.4 mg, 0.937 mmol), dioxane (10 mL) and $H_2O$ (2 mL), and the mixture was reacted at 80° C. for 16 h under nitrogen atmosphere, added with ice water to quench the reaction, extracted with dichloromethane (20 mL×3), washed with saturated brine (20 mL×2), dried over anhydrous sodium sulfate, spin-dried, and purified by TLC (petroleum ether: ethyl acetate=1:1) to give a target product (64 mg, yield: 34.5%) in the form of a yellow oil. LC-MS: 592 $[M+H]^+$.

Step 8

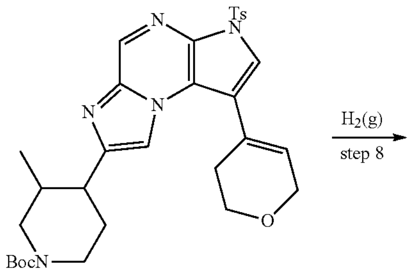

9

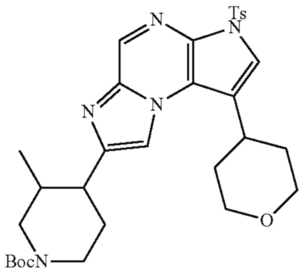

10

To a 100 mL single-neck flask were added 9 (60 mg, 0.101 mmol), $Pd(OH)_2$ (30 mg, 0.253 mmol) and THE (10 mL), the mixture was reacted at room temperature for 24 h under hydrogen atmosphere, and filtered under vacuum, and the filtrate was concentrated, and purified by TLC (petroleum ether:ethyl acetate=1:1) to give a target product (55 mg, yield: 85.9%) in the form of a yellow oil. LC-MS: 594 $[M+H]^+$.

Step 9

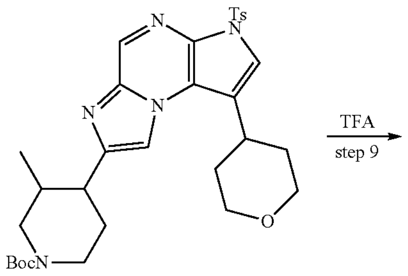

10

-continued

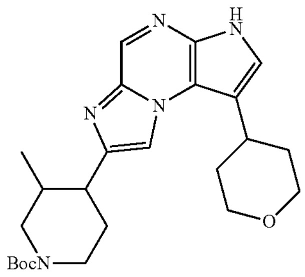

11

To a 100 mL single-neck flask were added 10 (55 mg, 0.0927 mmol) and TBAF (2.0 mL), and the mixture was reacted at 70° C. for 16 h, and concentrated to give a target product (30 mg, yield: 75.0%) in the form of a yellow oil. LC-MS: 440 $[M+H]^+$.

Step 10

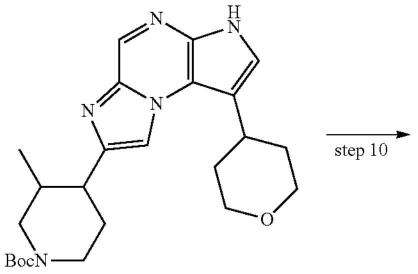

11

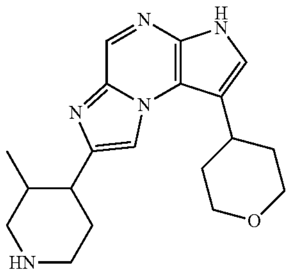

H

To a 100 mL single-neck flask were added 11 (30 mg, 0.0682 mmol), TFA (1.0 mL) and DCM (5 mL), and the mixture was reacted at room temperature for 5 h, concentrated, and subjected to prep-HPLC to give a target product (2 mg, yield: 8.6%) in the form of a white solid, LC-MS: 340 $[M+H]^+$, 0.1H NMR (400 MHz, MeOD) δ 8.51 (s, 1H), 8.04 (s, 1H), 7.25 (s, 1H), 4.10 (d, J=11.7 Hz, 2H), 3.78 (dd, J=11.7, 9.9 Hz, 2H), 3.42 (td, J=8.0, 4.2 Hz, 1H), 3.22 (dd, J=14.0, 10.6 Hz, 2H), 2.84-2.78 (m, 1H), 2.74-2.69 (m, 1H), 2.47 (d, J=12.3 Hz, 1H), 2.03 (d, J=11.3 Hz, 4H), 1.95 (dd, J=9.0, 5.9 Hz, 2H), 1.89-1.86 (m, 1H), 1.83 (dd, J=9.5, 4.4 Hz, 1H), 0.81 (d, J=6.6 Hz, 3H).

Example 9: Preparation of IRAK4 Kinase Inhibitor
The synthetic route is as follows:
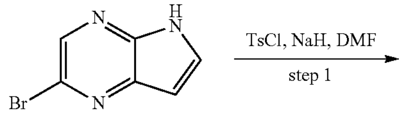
1
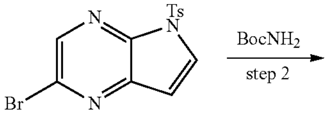
2
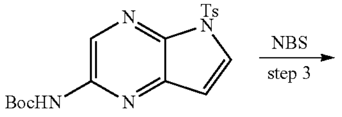
3
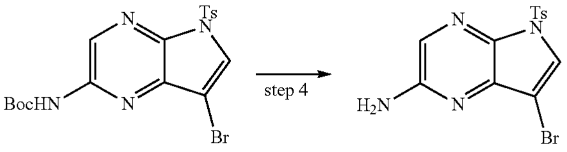
4 int 2-1
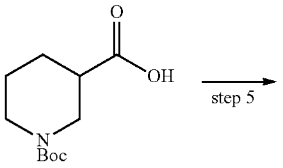
5
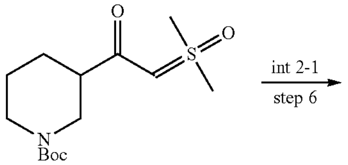
6
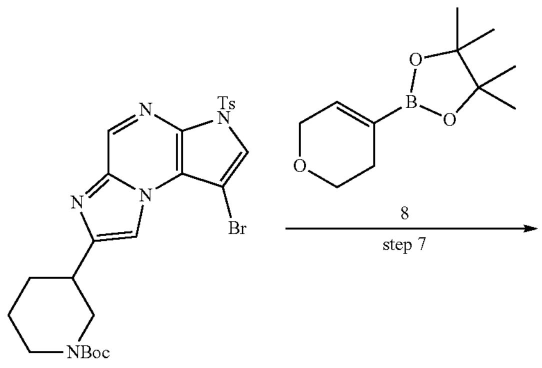
7
-continued
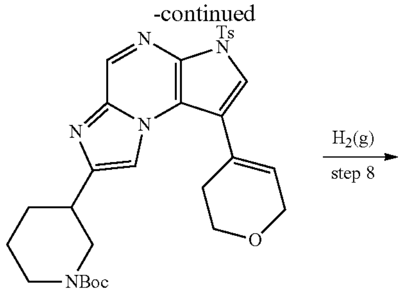
9
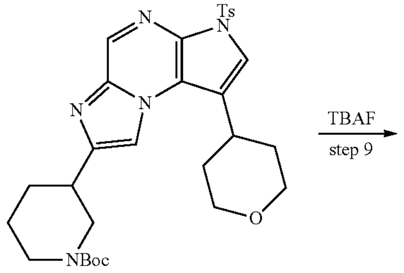
10
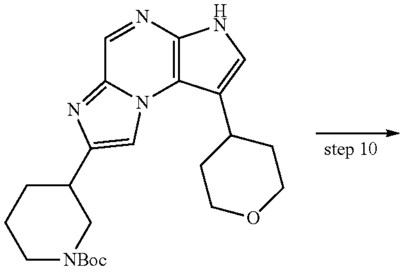
11
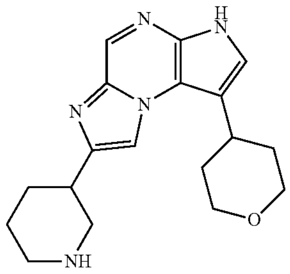
I
Step 1
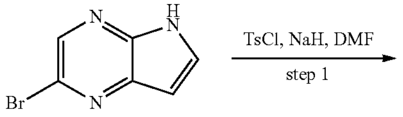
1
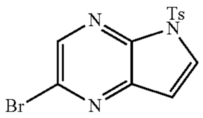
2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352 [M+H]$^+$.

Step 2

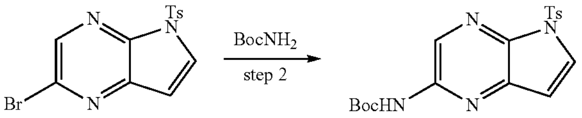

2 3

To a 500 mL single-neck round-bottom flask were added 2 (22.70 g, 64.6 mmol), BocNH$_2$ (11.3 g, 97.0 mmol), Pd(OAc)$_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 [M+H]$^+$.

Step 3

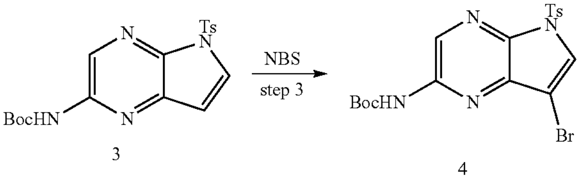

3 4

In a 500 mL single-neck flask, 3 (12.80 g, 32.9 mmol) was dissolved in DMF (100 mL), and added with NBS (7.04 g, 39.5 mmol) at 0° C. The mixture was reacted at room temperature for 1.5 h, added with ice water to quench the reaction, and filtered to give a target product (15.0 g, crude) in the form of a yellow solid. LC-MS: 467 [M+H]$^+$.

Step 4

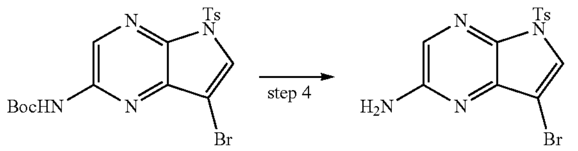

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 [M+H]$^+$.

Step 5

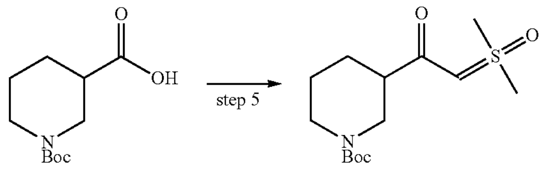

5 6

To a 100 mL single-neck flask were added 5 (3.00 g, 13.1 mmol), HATU (4.97 g, 13.1 mmol), triethylamine (4.63 g, 45.8 mmol) and THE (40 mL), and the mixture was reacted at room temperature for 3 h to give an activated ester. To another 1000 mL single-neck flask were added trimethylsulfoxonium iodide (8.64 g, 39.2 mmol), potassium tert-butoxide (4.62 g, 41.2 mmol) and THE (50 mL), and the mixture was reacted at 65° C. for 3 h, then cooled to 0° C. in an ice bath, and added dropwise with the activated ester. The resulting mixture was reacted at room temperature for 16 h, added with ice water to quench the reaction, stirred at room temperature for 5 h, and filtered under vacuum, and the filtrate was concentrated and extracted with dichloromethane (80 mL×5), washed with saturated brine (80 mL×3), dried over anhydrous sodium sulfate, and spin-dried to give a target product (3.10 g, yield: 79.4%) in the form of a white solid. LC-MS: 304 [M+H]$^+$.

Step 6

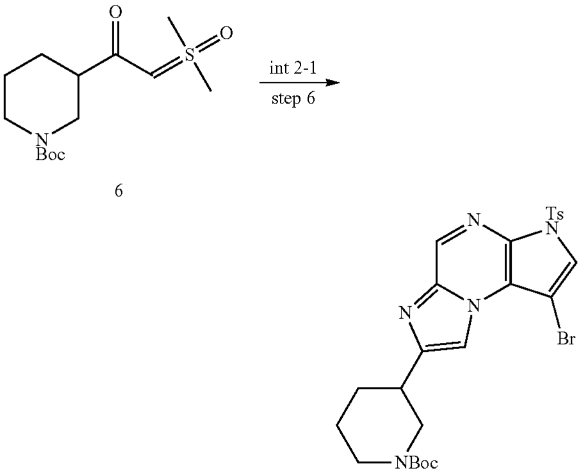

6

7

To a 100 mL single-neck flask were added 6 (2.64 g, 8.71 mmol), int 2-1 (800 mg, 2.17 mmol), chloro(1,5-cyclooctadiene)iridium(I) dimer (439 mg, 0.653 mmol), 1,10-phenanthroline (510 mg, 2.83 mmol), sodium triflate (374 mg, 2.17 mmol), dichloroethane (20 mL) and MS-4A, the mixture was reacted at 80° C. for 36 h under nitrogen atmosphere, and filtered under vacuum, and the filtrate was concentrated, and purified by TLC (petroleum ether:ethyl acetate=1:1) to give a target product (210 mg, yield: 4.2%) in the form of a yellow oil. LC-MS: 574 $[M+H]^+$.

Step 7

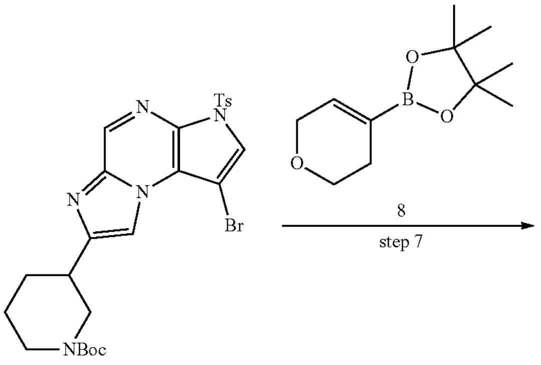

7

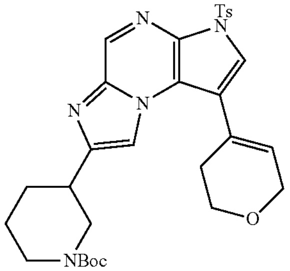

9

To a 100 mL single-neck flask were added 7 (210 mg, 0.365 mmol), 8 (115 mg, 0.548 mmol), $Pd_2(dppf)Cl_2 \cdot CH_2Cl_2$ (26.7 mg, 0.0365 mmol), $K_2CO_3$ (151 mg, 1.09 mmol), dioxane (10 mL) and $H_2O$ (2 mL), and the mixture was reacted at 80° C. for 16 h under nitrogen atmosphere, added with ice water to quench the reaction, extracted with ethyl acetate (20 mL×3), washed with saturated brine (20 mL×2), dried over anhydrous sodium sulfate, spin-dried, and purified by TLC (petroleum ether:ethyl acetate=1:1) to give a target product (100 mg, yield: 47.3%) in the form of a yellow oil. LC-MS: 578 $[M+H]^+$.

Step 8

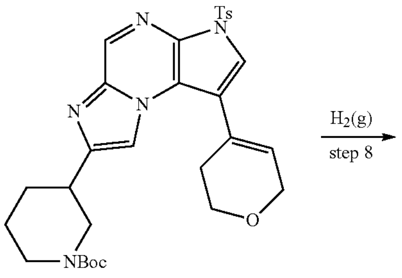

9

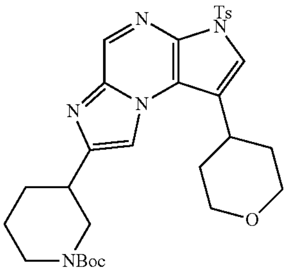

10

To a 100 mL single-neck flask were added 9 (100 mg, 0.173 mmol), $Pd(OH)_2$ (50 mg, 0.432 mmol) and THE (10 mL), the mixture was reacted at room temperature for 24 h under hydrogen atmosphere, and filtered under vacuum, and the filtrate was concentrated, and purified by TLC (petroleum ether:ethyl acetate=1:1) to give a target product (95 mg, yield: 95%) in the form of a yellow oil. LC-MS: 580 $[M+H]^+$.

Step 9

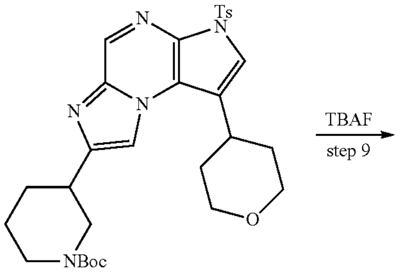

10

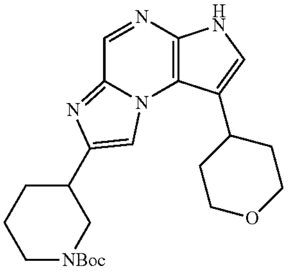

11

To a 100 mL single-neck flask were added 10 (95 mg, 0.164 mmol) and TBAF (2.0 mL), and the mixture was reacted at 70° C. for 16 h, and concentrated to give a target product (50 mg, yield: 76.9%) in the form of a yellow oil. LC-MS: 426 $[M+H]^+$.

Step 10

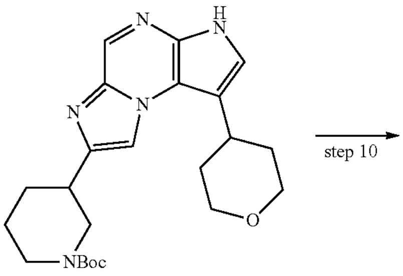

11

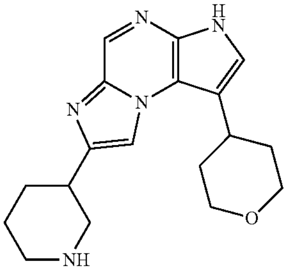

I

To a 100 mL single-neck flask were added 11 (50 mg, 0.117 mmol), TFA (1.0 mL) and DCM (5 mL), and the mixture was reacted at room temperature for 5 h, concentrated, and subjected to prep-HPLC to give a target product (5 mg, yield: 13.1%) in the form of a white solid. LC-MS: 326 $[M+H]^+$, $^{1}$H NMR (400 MHz, MeOD) δ 8.57 (s, 1H), 8.16 (s, 1H), 7.32 (s, 1H), 4.10 (dd, J=11.2, 3.4 Hz, 2H), 3.77 (dd, J=11.6, 10.4 Hz, 2H), 3.69 (d, J=11.7 Hz, 1H), 3.48 (s, 1H), 3.47-3.40 (m, 2H), 3.38 (d, J=11.6 Hz, 1H), 3.15 (dd, J=16.5, 7.4 Hz, 1H), 2.31 (d, J=11.3 Hz, 1H), 2.12 (d, J=13.7 Hz, 1H), 2.05 (d, J=11.4 Hz, 1H), 2.00 (s, 2H), 1.93 (s, 1H), 1.91-1.87 (m, 1H), 1.83 (dd, J=12.5, 3.9 Hz, 1H).

Example 10: Preparation of IRAK4 Kinase Inhibitor

The synthetic route is as follows:

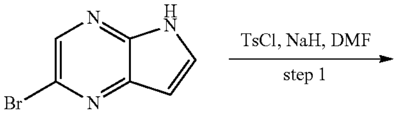

1

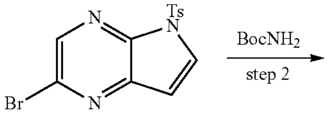

2

-continued

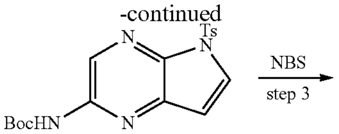

3

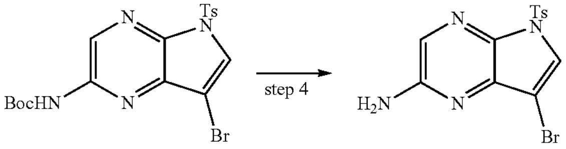

4 int 2-1

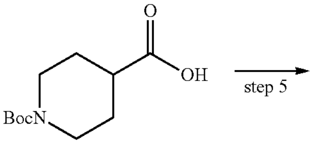

5

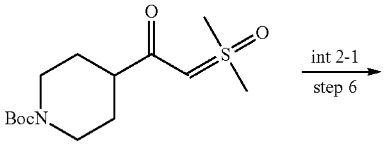

6

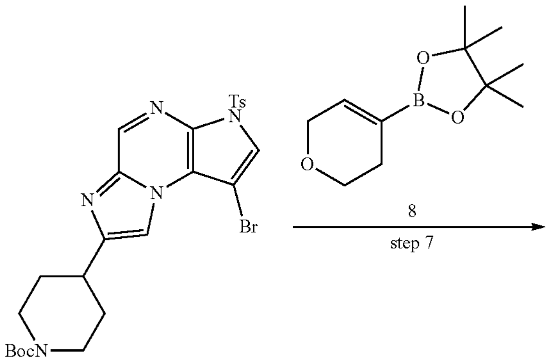

7

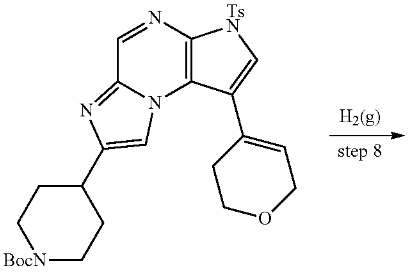

9

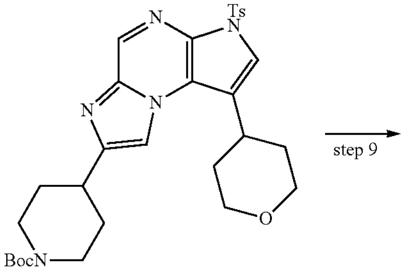

10

-continued

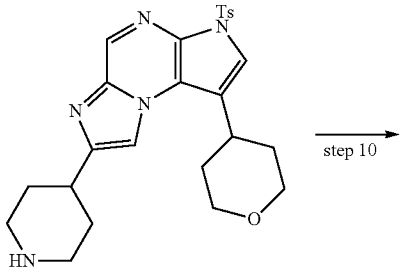

11

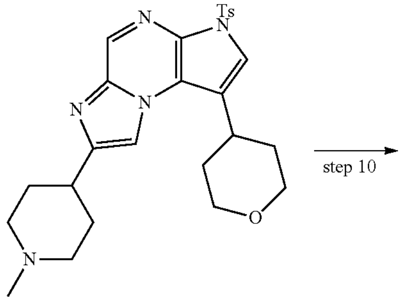

12

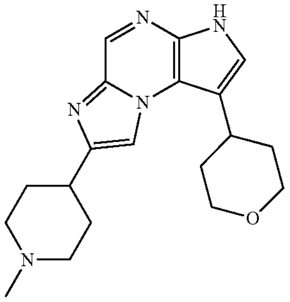

J

Step 1

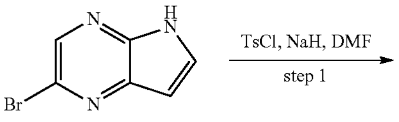

1

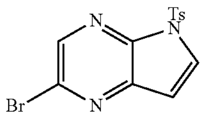

2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352[M+H]$^+$.

Step 2

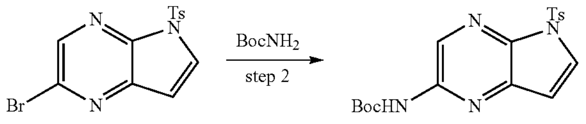

2 3

To a 500 mL single-neck round-bottom flask were added 2 (22.70 g, 64.6 mmol), $BocNH_2$ (11.3 g, 97.0 mmol), $Pd(OAc)_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 [M+H]$^+$.

Step 3

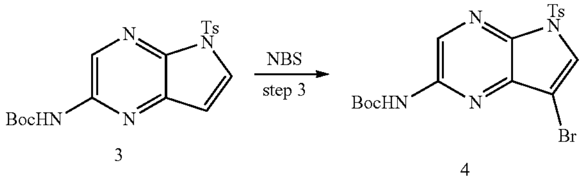

3 4

In a 500 mL single-neck flask, 3 (12.80 g, 32.9 mmol) was dissolved in DMF (100 mL), and added with NBS (7.04 g, 39.5 mmol) at 0° C. The mixture was reacted at room temperature for 1.5 h, added with ice water to quench the reaction, and filtered to give a target product (15.0 g, crude) in the form of a yellow solid. LC-MS: 467 [M+H]$^+$.

Step 4

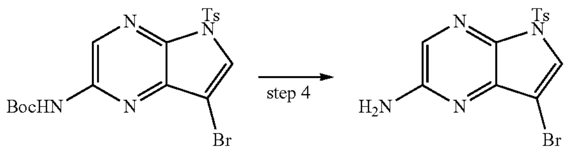

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 [M+H]$^+$.

Step 5

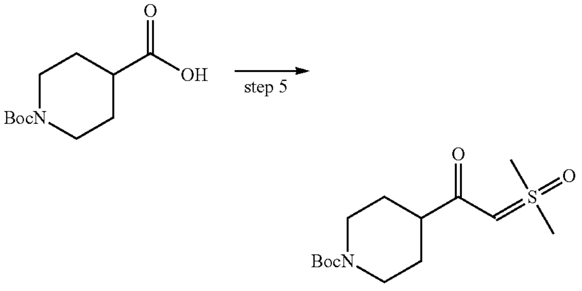

6

To a 250 mL single-neck flask were added 5 (5.00 g, 21.8 mmol), HATU (8.3 g, 21.8 mmol), triethylamine (7.72 g, 76.3 mmol) and THE (60 mL), and the mixture was reacted at room temperature for 3 h to give an activated ester. To another 1000 mL single-neck flask were added trimethylsulfoxonium iodide (14.4 g, 65.4 mmol), potassium tert-butoxide (7.70 g, 68.7 mmol) and THF (80 mL), and the mixture was reacted at 65° C. for 3 h, then cooled to 0° C. in an ice bath, and added dropwise with the activated ester. The resulting mixture was reacted at room temperature for 16 h, added with ice water to quench the reaction, stirred at room temperature for 5 h, concentrated, extracted with dichloromethane (100 mL×5), washed with saturated brine (100 mL×2), dried over anhydrous sodium sulfate, and spin-dried to give a target product (4.70 g, yield: 71.2%) in the form of a yellow solid. LC-MS: 304 $[M+H]^+$.

Step 6

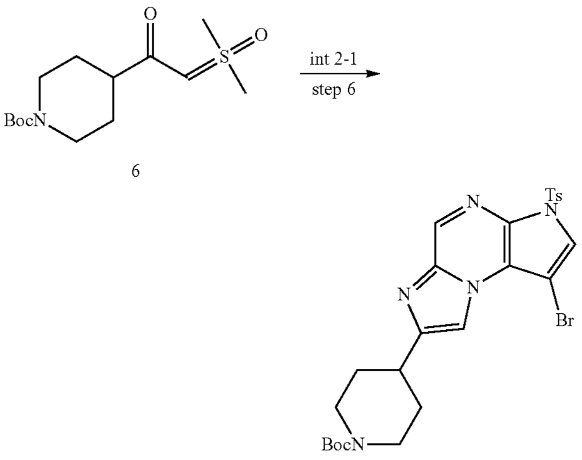

6

7

To a 100 mL single-neck flask were added 6 (1.98 g, 6.55 mmol), int 2-1 (600 mg, 1.64 mmol), chloro(1,5-cyclooctadiene)iridium(I) dimer (330 mg, 0.491 mmol), 1,10-phenanthroline (462 mg, 2.13 mmol), sodium triflate (524 mg, 3.05 mmol), dichloroethane (20 mL) and MS-4A, the mixture was reacted at 80° C. for 36 h under nitrogen atmosphere, and filtered under vacuum, and the filtrate was concentrated, and purified by TLC (petroleum ether:ethyl acetate=1:1) to give a target product (500 mg, yield: 13.5%) in the form of a yellow oil. LC-MS: 574 $[M+H]^+$.

Step 7

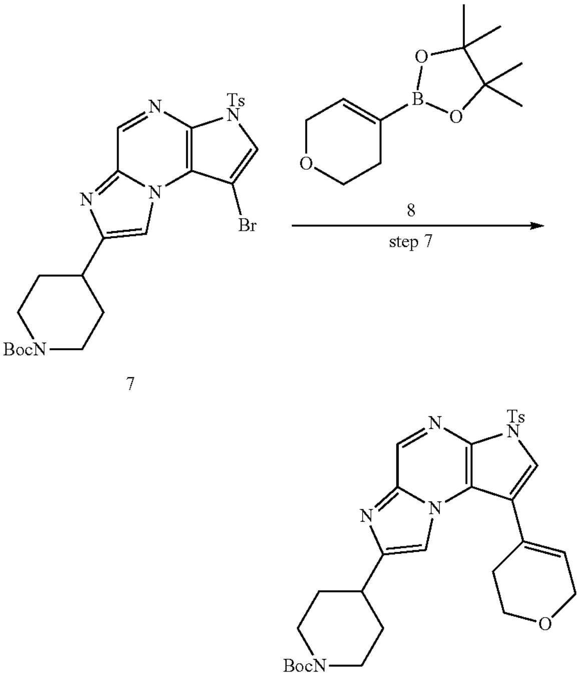

8

7

9

To a 100 mL single-neck flask were added 7 (500 mg, 0.870 mmol), 8 (274 mg, 1.305 mmol), $Pd_2(dppf)Cl_2 \cdot CH_2Cl_2$ (35.8 mg, 0.0435 mmol), $K_2CO_3$ (360 mg, 2.61 mmol), dioxane (10 mL) and $H_2O$ (2 mL), and the mixture was reacted at 80° C. for 16 h under nitrogen atmosphere, added with ice water to quench the reaction, extracted with dichloromethane (50 mL×3), washed with saturated brine (50 mL×2), dried over anhydrous sodium sulfate, spin-dried, and purified by TLC (petroleum ether:ethyl acetate=1:1) to give a target product (345 mg, yield: 68.7%) in the form of a yellow solid. LC-MS: 578 $[M+H]^+$.

Step 8

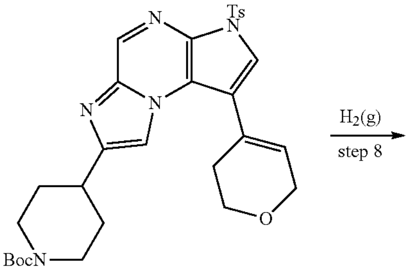

9

-continued

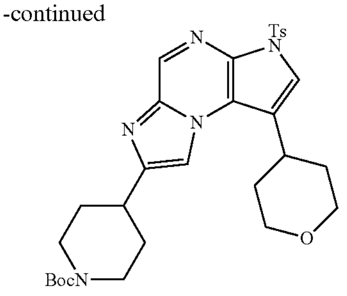

10

To a 100 mL single-neck flask were added 9 (345 mg, 0.597 mmol), $Pd(OH)_2$ (125 mg, 1.49 mmol) and THE (10 mL), the mixture was reacted at room temperature for 24 h under hydrogen atmosphere, and filtered under vacuum, and the filtrate was concentrated, and purified by TLC (petroleum ether:ethyl acetate=1:1) to give a target product (183 mg, yield: 52.8%) in the form of a yellow oil. LC-MS: 579 $[M+H]^+$.

Step 9

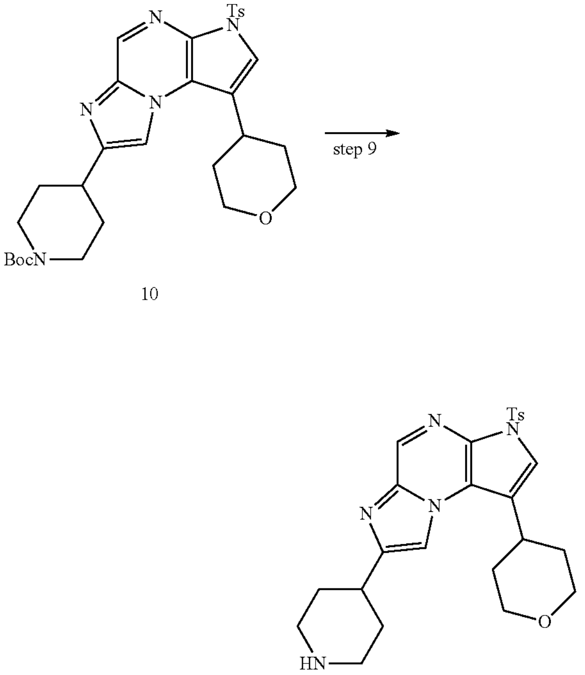

10

11

To a 100 mL single-neck flask were added 10 (183 mg, 0.315 mmol), TFA (1.0 mL) and DCM (5 mL), and the mixture was reacted at room temperature for 5 h, added with ice water to quench the reaction, adjusted to pH=9 with a saturated $Na_2CO_3$ solution, extracted with dichloromethane (20 mL×3), washed with saturated brine (20 mL×2), dried over anhydrous sodium sulfate, concentrated, and purified by TLC (petroleum ether:ethyl acetate=1:1) to give a target product (64 mg, yield: 42.3%) in the form of a yellow oil. LC-MS: 480 $[M+H]^+$.

Step 10

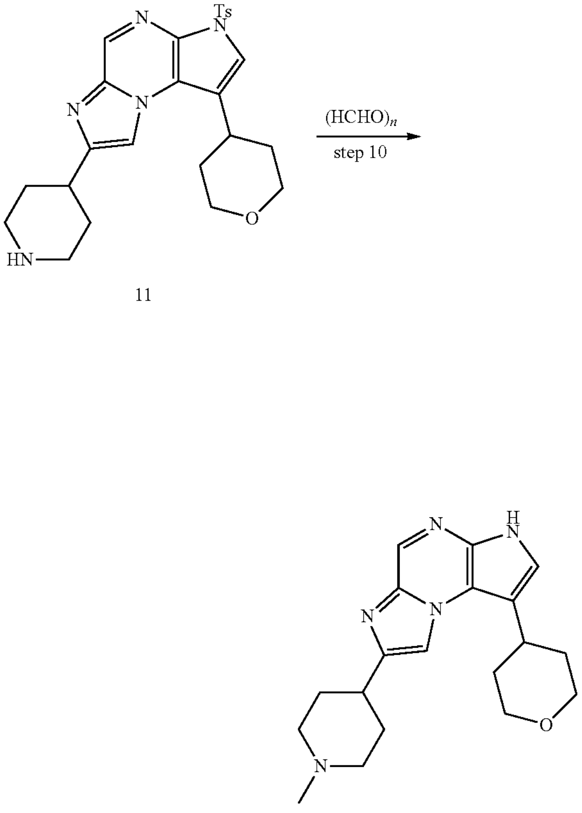

11

12

To a 100 mL single-neck flask were added 11 (64 mg, 0.133 mmol), $(CH_2O)_n$(40 mg, 1.33 mmol), AcOH (24 mg, 0.400 mmol), tetraisopropyl titanate (113.8 mg, 0.400 mmol) and methanol (10 mL), the mixture was stirred at room temperature for 1 h, then added with sodium cyanoborohydride (25 mg, 0.400 mmol), reacted at room temperature for 16 h, and filtered under vacuum, and the filtrate was concentrated, and purified by TLC (dichloromethane:methanol=15:1) to give a target product (50 mg, yield: 75.9%) in the form of a yellow oil. LC-MS: 494 $[M+H]^+$.

Step 11

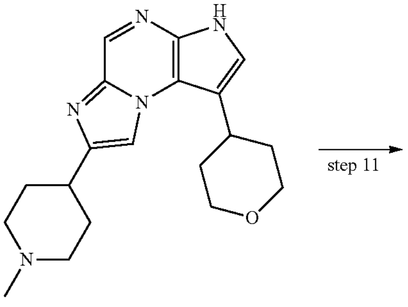

12

-continued

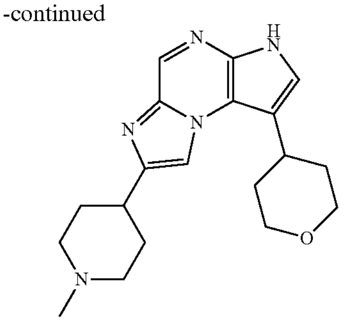

J

To a 100 mL single-neck flask were added 12 (50 mg, 0.101 mmol) and TBAF (2.0 mL), and the mixture was reacted at 70° C. for 16 h, concentrated, and subjected to high pressure liquid chromatography to give a target product (5 mg, yield: 14.7%) in the form of a white solid. LC-MS: 340 $[M+H]^+$, 1H NMR (400 MHz, DMSO) δ 12.23 (s, 1H), 9.61 (s, 1H), 8.62 (s, 1H), 8.16 (s, 1H), 7.38 (d, J=2.8 Hz, 1H), 3.98-3.95 (m, 2H), 3.41 (dd, J=11.6, 8.1, 3.6 Hz, 2H), 3.19 (d, J=7.0 Hz, 1H), 3.13 (dd, J=17.2, 6.1 Hz, 3H), 2.85 (d, J=3.6 Hz, 3H), 2.35-2.18 (m, 3H), 2.00 (dd, J=19.4, 6.4 Hz, 2H), 1.88 (d, J=12.6 Hz, 2H), 1.72 (dd, J=12.6, 3.8 Hz, 2H).

Example 11: Preparation of IRAK4 Kinase Inhibitor

The synthetic route is as follows:

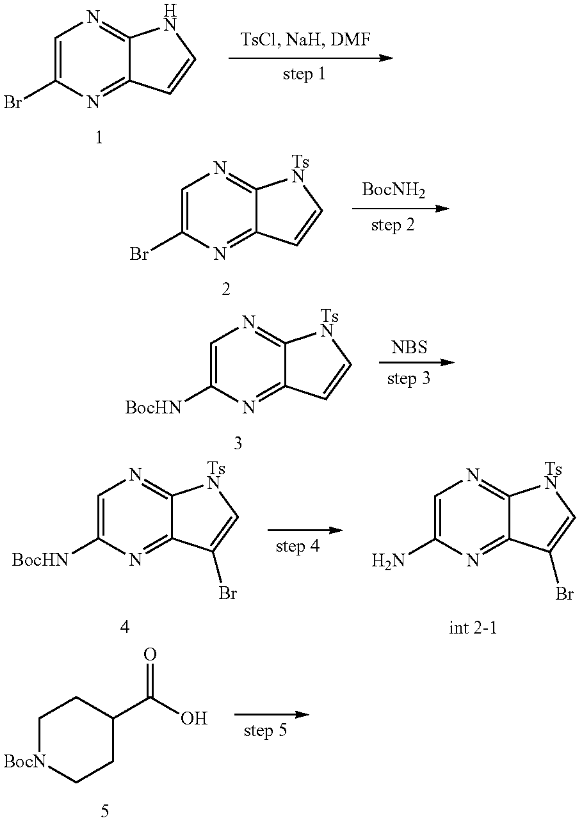

-continued

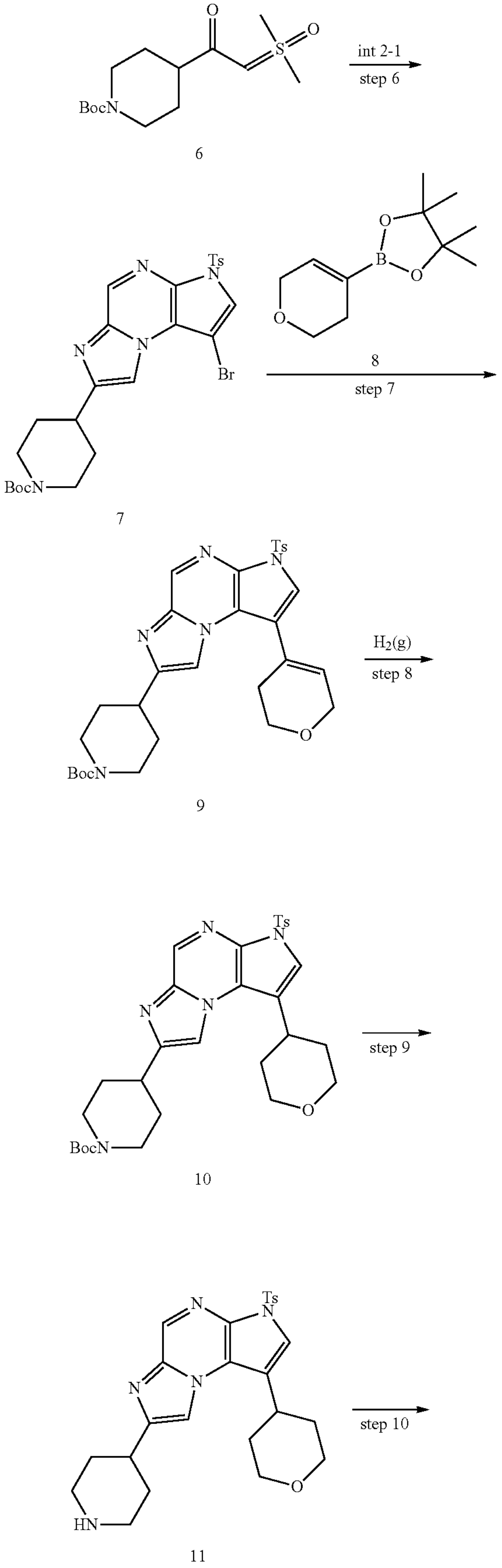

-continued

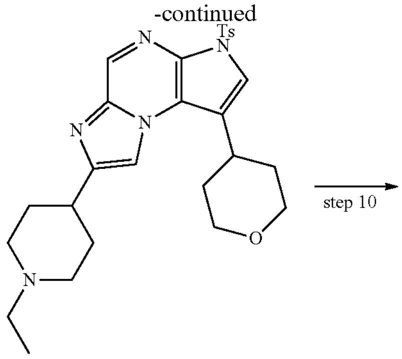

12

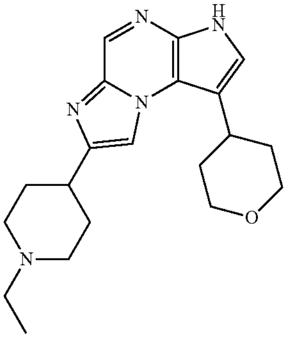

K

Step 1

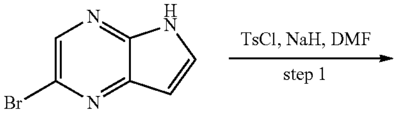

1

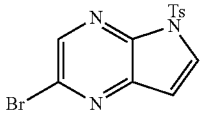

2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352 $[M+H]^+$.

Step 2

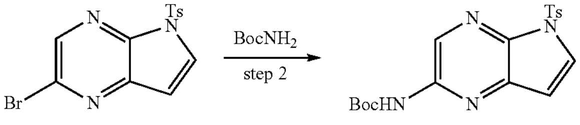

2 3

To a 500 mL single-neck round-bottom flask were added 2 (22.70 g, 64.6 mmol), $BocNH_2$ (11.3 g, 97.0 mmol), $Pd(OAc)_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 $[M+H]^+$.

Step 3

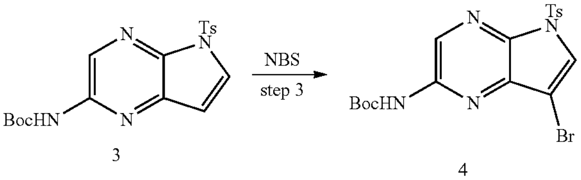

3 4

In a 500 mL single-neck flask, 3 (12.80 g, 32.9 mmol) was dissolved in DMF (100 mL), and added with NBS (7.04 g, 39.5 mmol) at 0° C. The mixture was reacted at room temperature for 1.5 h, added with ice water to quench the reaction, and filtered to give a target product (15.0 g, crude) in the form of a yellow solid. LC-MS: 467 $[M+H]^+$.

Step 4

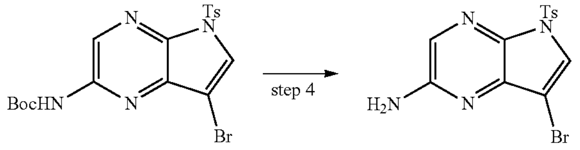

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 $[M+H]^+$.

Step 5

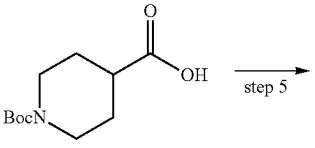

-continued

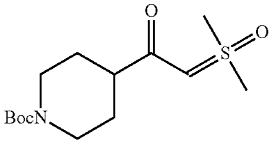

6

To a 250 mL single-neck flask were added 5 (50 g, 218.055 mmol), HATU (83.7 g, 220.235 mmol), triethylamine (77.1 g, 763.192 mmol) and THE (1400 mL), and the mixture was reacted at room temperature for 3 h to give an activated ester. To another 1000 mL single-neck flask were added trimethylsulfoxonium iodide (144 g, 654.165 mmol), potassium tert-butoxide (75.8 g, 675.970 mmol) and THE (600 mL), and the mixture was reacted at 65° C. for 3 h, then cooled to 0° C. in an ice bath, and added dropwise with the activated ester. The resulting mixture was reacted at room temperature for 16 h, added with ice water to quench the reaction, stirred at room temperature for 5 h, concentrated, extracted with dichloromethane (500 mL×5), washed with saturated brine (200 mL×2), dried over anhydrous sodium sulfate, and spin-dried to give a target product (58 g, yield: 72%) in the form of a yellow solid. LC-MS: 304 $[M+H]^+$.

Step 6

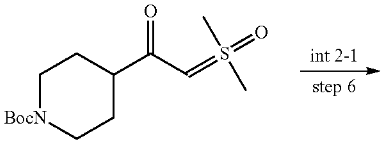

6

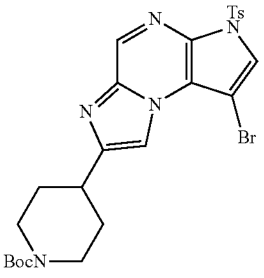

7

To a 100 mL single-neck flask were added 6 (13.22 g, 10.89 mmol), int 2-1 (4 g, 43.56 mmol), chloro(1,5-cyclooctadiene)iridium(I) dimer (2.19 g, 3.267 mmol), 1,10-phenanthroline (2.55 mg, 14.157 mmol), sodium triflate (3.49 mg, 20.2554 mmol), dichloroethane (250 mL) and MS-4A, the mixture was reacted at 80° C. for 36 h under nitrogen atmosphere, and filtered under vacuum, and the filtrate was concentrated, and purified by TLC (petroleum ether:ethyl acetate=1:1) to give a target product (2.45 g, yield: 39%) in the form of a yellow oil. LC-MS: 574 $[M+H]^+$.

Step 7

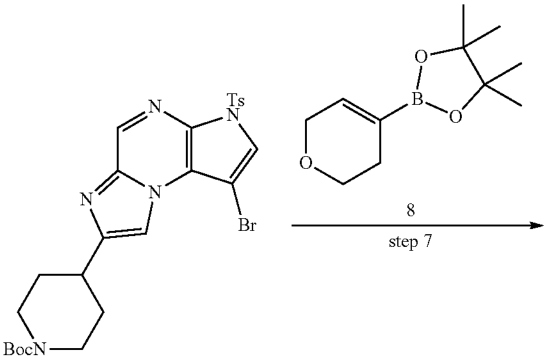

7

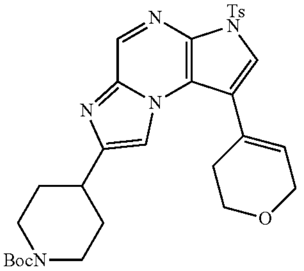

9

To a 100 mL single-neck flask were added 7 (2.45 g, 04.2683 mmol), 8 (1.34 g, 6.40245 mmol), $Pd_2(dppf)Cl_2 \cdot CH_2Cl_2$ (175.8 mg, 0.213415 mmol), $K_2CO_3$ (1.77 g, 12.8049 mmol), dioxane (20 mL) and $H_2O$ (4 mL), and the mixture was reacted at 80° C. for 16 h under nitrogen atmosphere, added with ice water to quench the reaction, extracted with dichloromethane (50 mL×3), washed with saturated brine (50 mL×2), dried over anhydrous sodium sulfate, spin-dried, and purified by TLC (petroleum ether: ethyl acetate=1:1) to give a target product (1.2 mg, yield: 48.8%) in the form of a yellow solid. LC-MS: 578 $[M+H]^+$.

Step 8

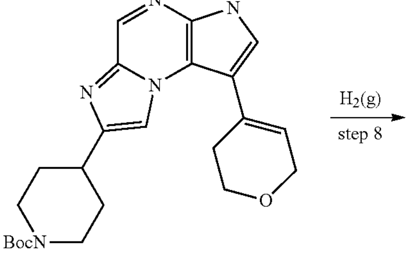

9

-continued

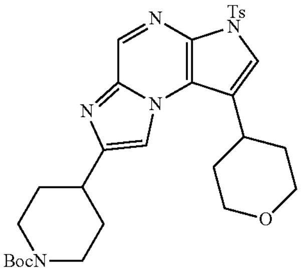

10

To a 100 mL single-neck flask were added 9 (1.2 g, 2.08 mmol), $Pd(OH)_2$ (250 mg, 2.98 mmol) and THE (15 mL), the mixture was reacted at room temperature for 24 h under hydrogen atmosphere, and filtered under vacuum, and the filtrate was concentrated, and purified by TLC (petroleum ether:ethyl acetate=1:1) to give a target product (780 mg, yield: 64.8%) in the form of a yellow oil. LC-MS: 580 $[M+H]^+$.

Step 9

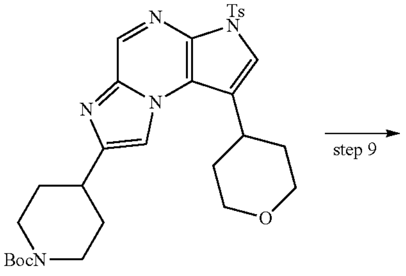

10

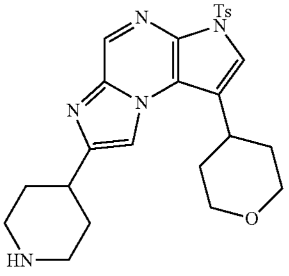

11

To a 100 mL single-neck flask were added 10 (780 mg, 1.345 mmol), TFA (1.0 mL) and DCM (5 mL), and the mixture was reacted at room temperature for 5 h, added with ice water to quench the reaction, adjusted to pH=9 with a saturated $Na_2CO_3$ solution, extracted with dichloromethane (20 mL×3), washed with saturated brine (20 mL×2), dried over anhydrous sodium sulfate, concentrated, and purified by TLC (petroleum ether:ethyl acetate=1:1) to give a target product (540 mg, yield: 83.7%) in the form of a yellow oil. LC-MS: 480 $[M+H]^+$.

Step 10

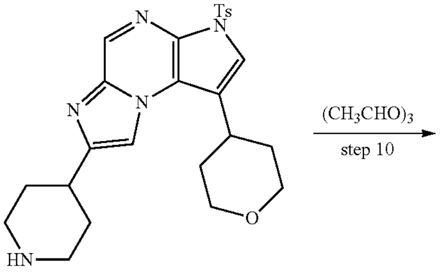

11

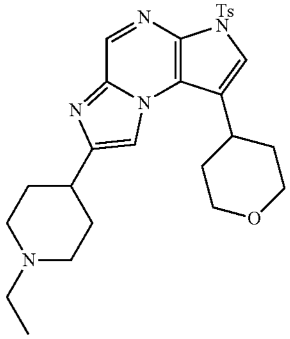

12

To a 100 mL single-neck flask were added 11 (150 mg, 0.3125 mmol), $(CH_3CHO)_n$(413 mg, 3.125 mmol), AcOH (56.3 mg, 0.9375 mmol), tetraisopropyl titanate (266.5 mg, 0.9375 mmol) and methanol (10 mL), the mixture was stirred at room temperature for 1 h, then added with sodium cyanoborohydride (58.9 mg, 0.9375 mmol), reacted at room temperature for 16 h, and filtered under vacuum, and the filtrate was concentrated, and purified by TLC (dichloromethane:methanol=15:1) to give a target product (71 mg, yield: 44.7%) in the form of a yellow oil. LC-MS: 508 $[M+H]^+$.

Step 11

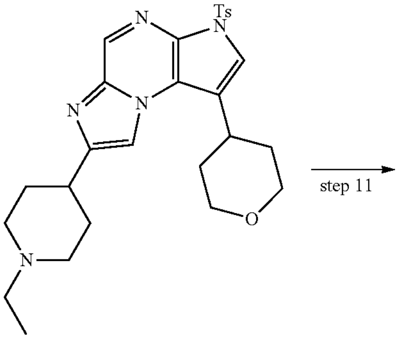

12

-continued

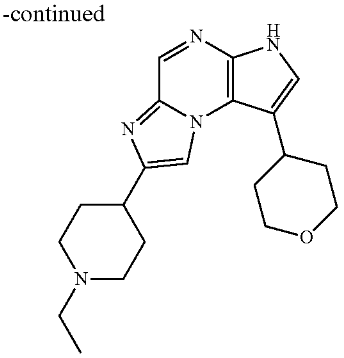

K

To a 100 mL single-neck flask were added 12 (71 mg, 0.14 mmol) and TBAF (2.0 mL), and the mixture was reacted at 70° C. for 16 h, concentrated, and subjected to high pressure liquid chromatography to give a target product (15 mg, yield: 30.6%) in the form of a white solid.

LC-MS: 354 $[M+H]^+$, $^1H$ NMR (400 MHz, DMSO) δ 12.19 (s, 1H), 8.61 (s, 1H), 8.14 (s, 1H), 7.37 (d, J=2.6 Hz, 1H), 3.65 (t, J=10.8 Hz, 4H), 3.39 (d, J=11.8 Hz, 2H), 3.17 (dd, J=12.3, 7.0 Hz, 4H), 2.70-2.66 (m, 1H), 2.34 (s, 1H), 2.00 (d, J=11.0 Hz, 2H), 1.88 (d, J=13.2 Hz, 3H), 1.73 (ddd, J=16.1, 12.4, 4.2 Hz, 3H), 1.28 (t, J=7.3 Hz, 3H).

Example 12: Preparation of IRAK4 Kinase Inhibitor

The synthetic route is as follows:

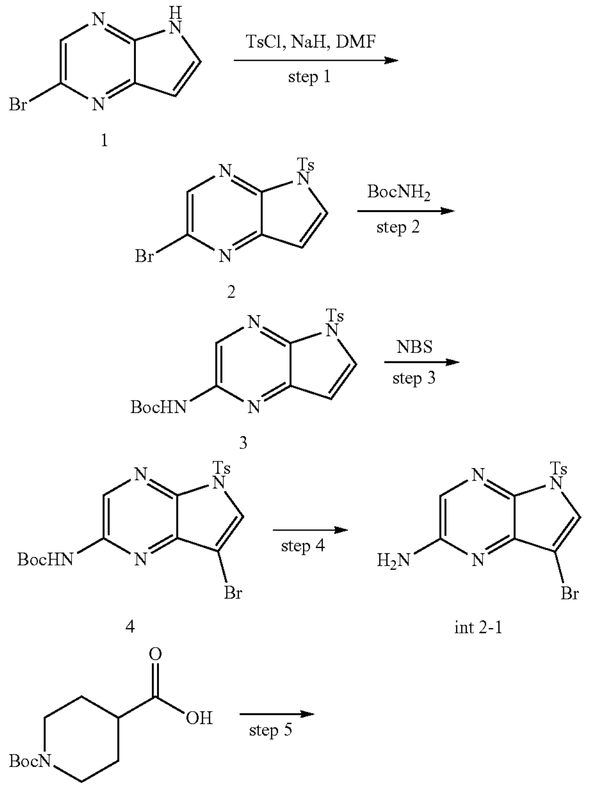

1, 2, 3, 4, int 2-1, 5

-continued

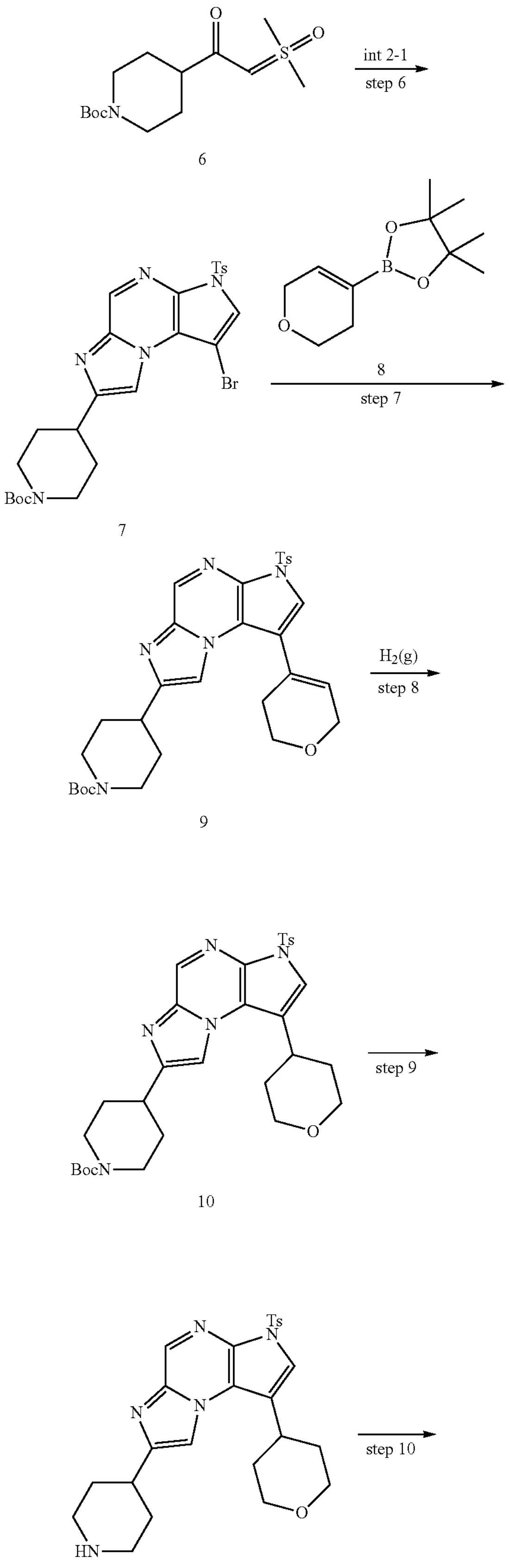

6, 7, 9, 10, 11

-continued

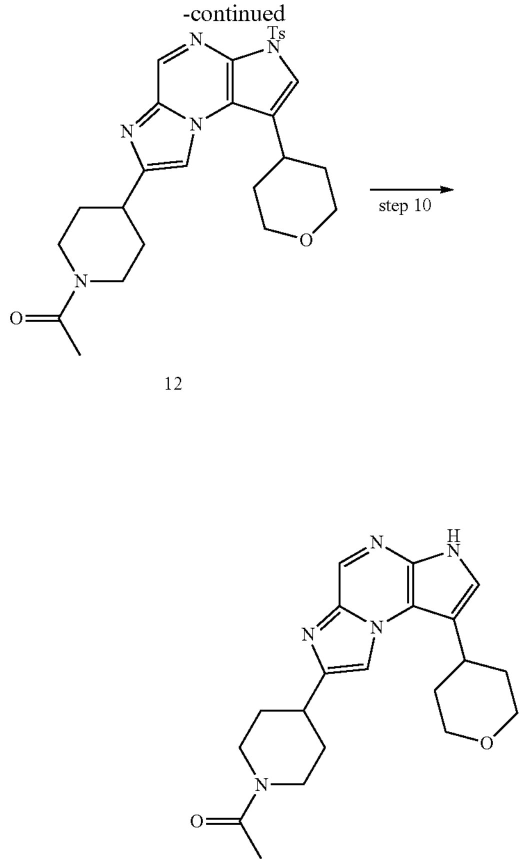

12

L

Step 1

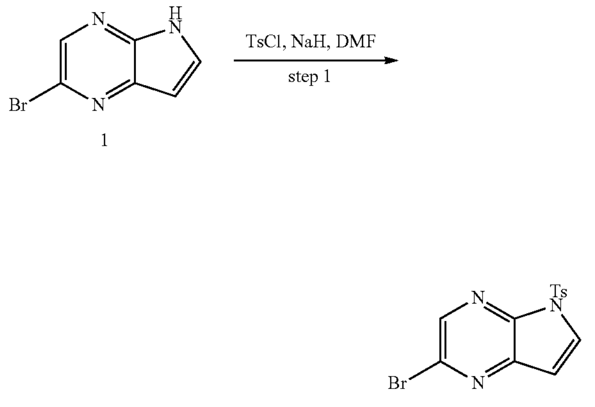

1

2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352 $[M+H]^+$.

Step 2

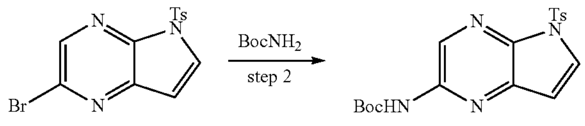

2

3

To a 500 mL single-neck round-bottom flask were added 2 (22.70 g, 64.6 mmol), $BocNH_2$ (11.3 g, 97.0 mmol), $Pd(OAc)_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 $[M+H]^+$.

Step 3

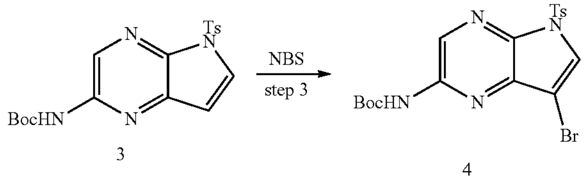

3

4

In a 500 mL single-neck flask, 3 (12.80 g, 32.9 mmol) was dissolved in DMF (100 mL), and added with NBS (7.04 g, 39.5 mmol) at 0° C. The mixture was reacted at room temperature for 1.5 h, added with ice water to quench the reaction, and filtered to give a target product (15.0 g, crude) in the form of a yellow solid. LC-MS: 467 $[M+H]^+$.

Step 4

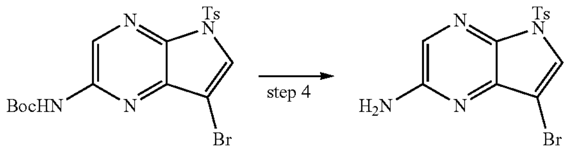

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 $[M+H]^+$.

Step 5

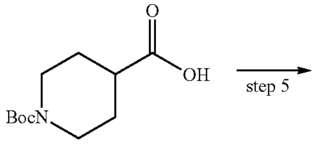

5

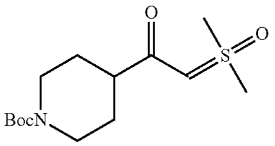

6

To a 250 mL single-neck flask were added 5 (50 g, 218.055 mmol), HATU (83.7 g, 220.235 mmol), triethylamine (77.1 g, 763.192 mmol) and THE (1400 mL), and the mixture was reacted at room temperature for 3 h to give an activated ester. To another 1000 mL single-neck flask were added trimethylsulfoxonium iodide (144 g, 654.165 mmol), potassium tert-butoxide (75.8 g, 675.970 mmol) and THE (600 mL), and the mixture was reacted at 65° C. for 3 h, then cooled to 0° C. in an ice bath, and added dropwise with the activated ester. The resulting mixture was reacted at room temperature for 16 h, added with ice water to quench the reaction, stirred at room temperature for 5 h, concentrated, extracted with dichloromethane (500 mL×5), washed with saturated brine (200 mL×2), dried over anhydrous sodium sulfate, and spin-dried to give a target product (58 g, yield: 72%) in the form of a yellow solid. LC-MS: 304 $[M+H]^+$.

Step 6

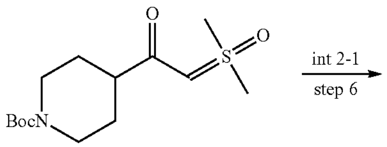

6

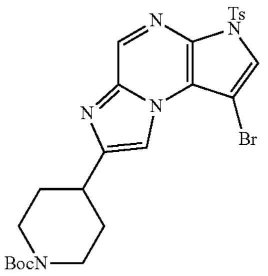

7

To a 100 mL single-neck flask were added 6 (13.22 g, 10.89 mmol), int 2-1 (4 g, 43.56 mmol), chloro(1,5-cyclooctadiene)iridium(I) dimer (2.19 g, 3.267 mmol), 1,10-phenanthroline (2.55 mg, 14.157 mmol), sodium triflate (3.49 mg, 20.2554 mmol), dichloroethane (250 mL) and MS-4A, the mixture was reacted at 80° C. for 36 h under nitrogen atmosphere, and filtered under vacuum, and the filtrate was concentrated, and purified by TLC (petroleum ether:ethyl acetate=1:1) to give a target product (2.45 g, yield: 39%) in the form of a yellow oil. LC-MS: 574 $[M+H]^+$.

Step 7

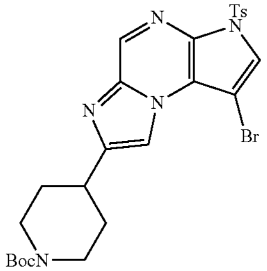

7

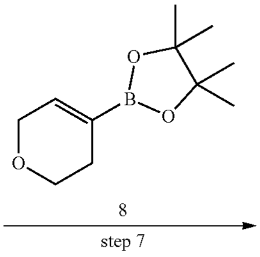

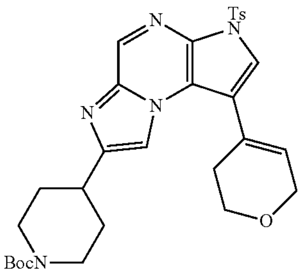

9

To a 100 mL single-neck flask were added 7 (2.45 g, 04.2683 mmol), 8 (1.34 g, 6.40245 mmol), $Pd_2(dppf)Cl_2 \cdot CH_2Cl_2$ (175.8 mg, 0.213415 mmol), $K_2CO_3$ (1.77 g, 12.8049 mmol), dioxane (20 mL) and $H_2O$ (4 mL), and the mixture was reacted at 80° C. for 16 h under nitrogen atmosphere, added with ice water to quench the reaction, extracted with dichloromethane (50 mL×3), washed with saturated brine (50 mL×2), dried over anhydrous sodium sulfate, spin-dried, and purified by TLC (petroleum ether: ethyl acetate=1:1) to give a target product (1.2 mg, yield: 48.8%) in the form of a yellow solid. LC-MS: 578 $[M+H]^+$.

Step 8

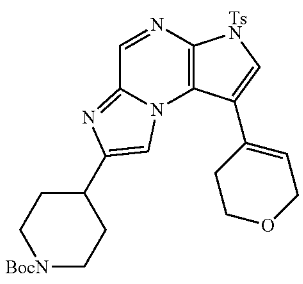

9

-continued

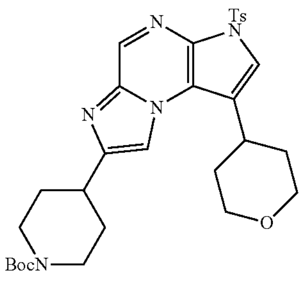

10

To a 100 mL single-neck flask were added 9 (1.2 g, 2.08 mmol), $Pd(OH)_2$ (250 mg, 2.98 mmol) and THE (15 mL), the mixture was reacted at room temperature for 24 h under hydrogen atmosphere, and filtered under vacuum, and the filtrate was concentrated, and purified by TLC (petroleum ether:ethyl acetate=1:1) to give a target product (780 mg, yield: 64.8%) in the form of a yellow oil. LC-MS: 580 $[M+H]^+$.

Step 9

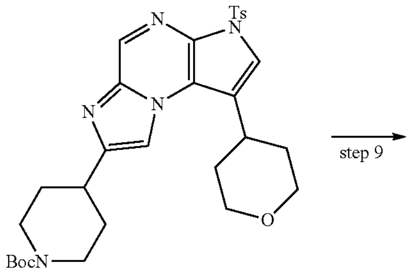

10

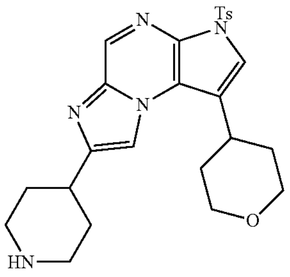

11

To a 100 mL single-neck flask were added 10 (780 mg, 1.345 mmol), TFA (1.0 mL) and DCM (5 mL), and the mixture was reacted at room temperature for 5 h, added with ice water to quench the reaction, adjusted to pH=9 with a saturated $Na_2CO_3$ solution, extracted with dichloromethane (20 mL×3), washed with saturated brine (20 mL×2), dried over anhydrous sodium sulfate, concentrated, and purified by TLC (petroleum ether:ethyl acetate=1:1) to give a target product (540 mg, yield: 83.7%) in the form of a yellow oil. LC-MS: 480 $[M+H]^+$.

Step 10

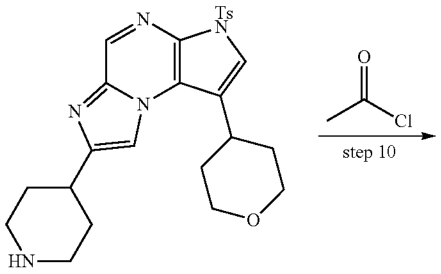

11

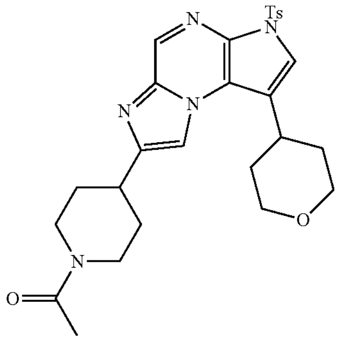

12

At 0° C., to a 100 mL single-neck flask were added 11 (200 mg, 0.4167 mmol), triethylamine (126 mg, 1.2501 mmol) and anhydrous dichloromethane (10 mL), and then added dropwise slowly acetyl chloride (49.1 mg, 0.62505 mmol), and the mixture was stirred for 30 min, added with water to quench the reaction, and extracted with dichloromethane (20 mL×3). The organic layer was concentrated, and purified by TLC (dichloromethane:methanol=15:1) to give a target product (100 mg, yield: 46.0%) in the form of a yellow oil. LC-MS: 522 $[M+H]^+$.

Step 11

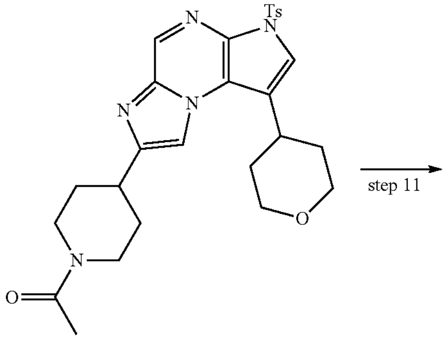

12

-continued

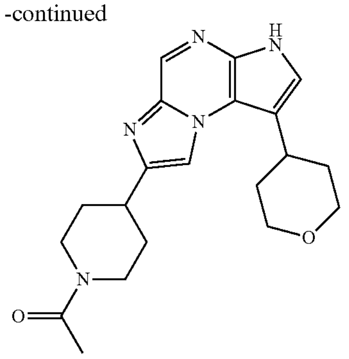

L

To a 100 mL single-neck flask were added 12 (100 mg, 0.1912 mmol) and TBAF (2.0 mL), and the mixture was reacted at 70° C. for 16 h, concentrated, and subjected to high pressure liquid chromatography to give a target product (20 mg, yield: 28.4%) in the form of a white solid.

LC-MS: 368 $[M+H]^+$, $^1H$ NMR (400 MHz, DMSO) δ 12.60 (s, 1H), 8.76 (s, 1H), 8.32 (s, 1H), 7.63 (d, J=2.3 Hz, 1H), 4.02-3.94 (m, 4H), 3.67 (dd, J=11.6, 10.0 Hz, 2H), 3.49-3.43 (m, 1H), 3.23 (dd, J=15.9, 7.6 Hz, 2H), 2.75-2.68 (m, 1H), 2.13-2.00 (m, 5H), 1.88 (d, J=12.8 Hz, 2H), 1.83-1.64 (m, 4H).

Example 13: Preparation of IRAK4 Kinase Inhibitor

The synthetic route is as follows:

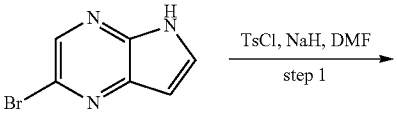

1

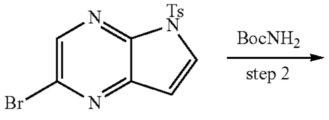

2

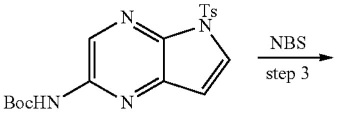

3

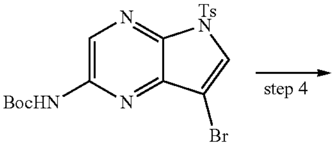

4

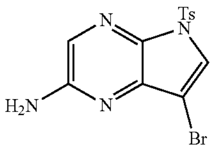

int 2-1

-continued

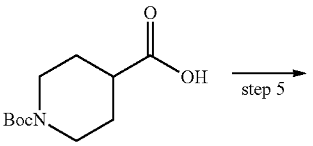

5

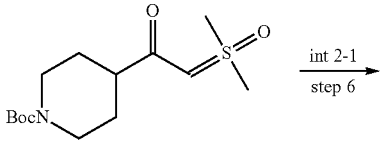

6

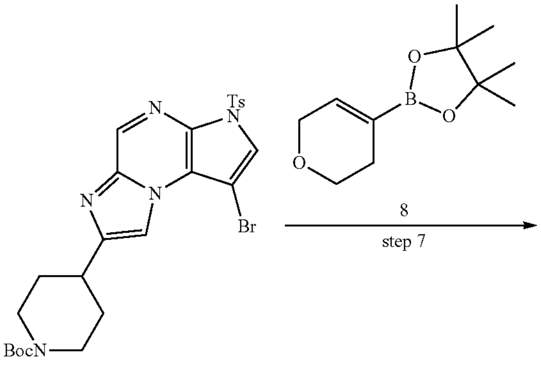

7

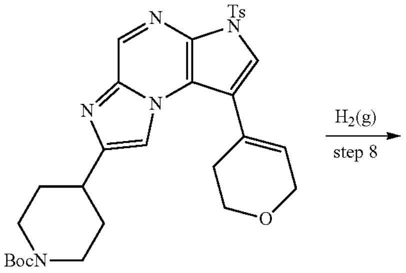

9

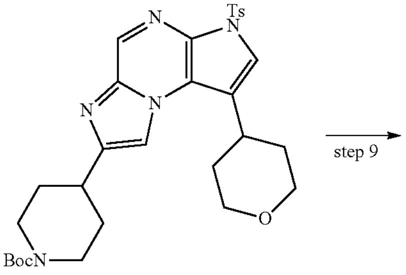

10

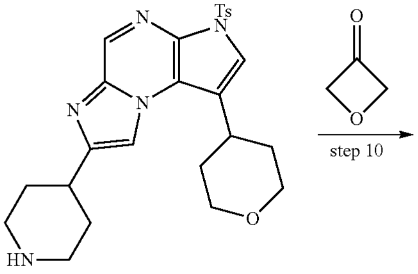

11

-continued

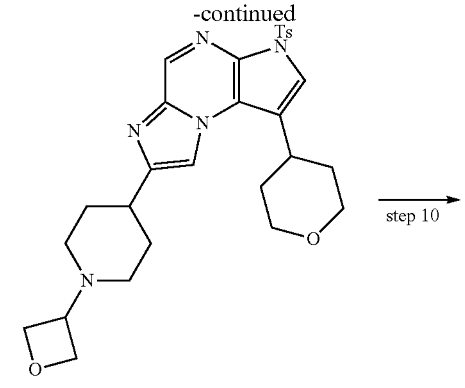

12

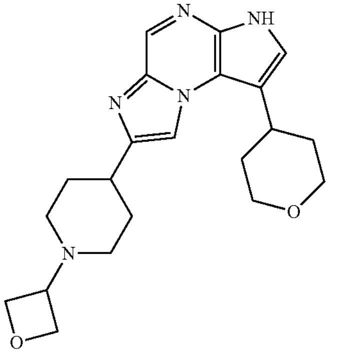

M

Step 1

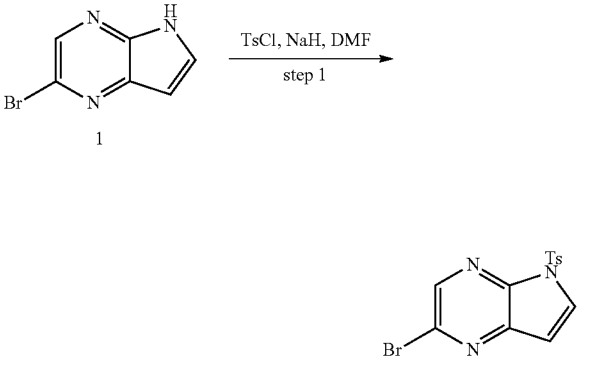

1

2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352 $[M+H]^+$.

Step 2

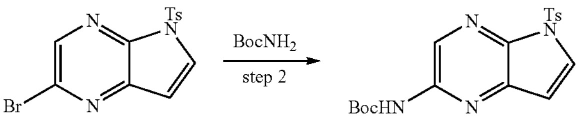

2 3

To a 500 mL single-neck round-bottom flask were added 2 (22.70 g, 64.6 mmol), $BocNH_2$ (11.3 g, 97.0 mmol), $Pd(OAc)_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 $[M+H]^+$.

Step 3

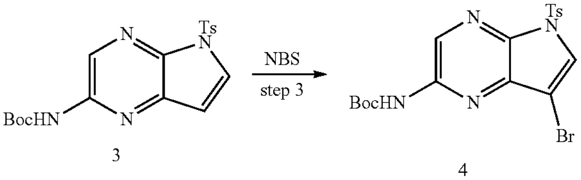

3 4

In a 500 mL single-neck flask, 3 (12.80 g, 32.9 mmol) was dissolved in DMF (100 mL), and added with NBS (7.04 g, 39.5 mmol) at 0° C. The mixture was reacted at room temperature for 1.5 h, added with ice water to quench the reaction, and filtered to give a target product (15.0 g, crude) in the form of a yellow solid. LC-MS: 467 $[M+H]^+$.

Step 4

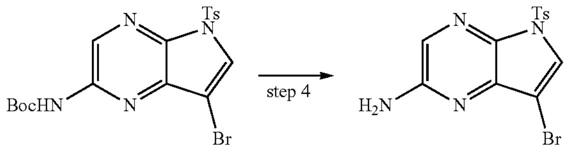

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 $[M+H]^+$.

Step 5

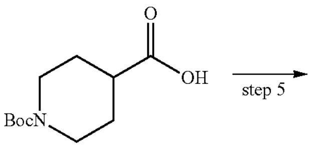

5

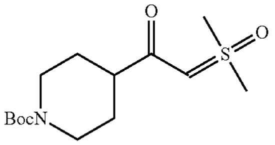

6

To a 250 mL single-neck flask were added 5 (50 g, 218.055 mmol), HATU (83.7 g, 220.235 mmol), triethylamine (77.1 g, 763.192 mmol) and THE (1400 mL), and the mixture was reacted at room temperature for 3 h to give an activated ester. To another 1000 mL single-neck flask were added trimethylsulfoxonium iodide (144 g, 654.165 mmol), potassium tert-butoxide (75.8 g, 675.970 mmol) and THE (600 mL), and the mixture was reacted at 65° C. for 3 h, then cooled to 0° C. in an ice bath, and added dropwise with the activated ester. The resulting mixture was reacted at room temperature for 16 h, added with ice water to quench the reaction, stirred at room temperature for 5 h, concentrated, extracted with dichloromethane (500 mL×5), washed with saturated brine (200 mL×2), dried over anhydrous sodium sulfate, and spin-dried to give a target product (58 g, yield: 72%) in the form of a yellow solid. LC-MS: 304 $[M+H]^+$.

Step 6

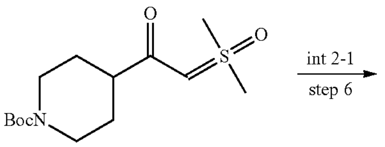

6

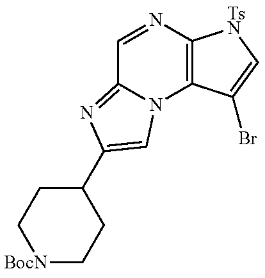

7

To a 100 mL single-neck flask were added 6 (13.22 g, 10.89 mmol), int 2-1 (4 g, 43.56 mmol), chloro(1,5-cyclooctadiene)iridium(I) dimer (2.19 g, 3.267 mmol), 1,10-phenanthroline (2.55 mg, 14.157 mmol), sodium triflate (3.49 mg, 20.2554 mmol), dichloroethane (250 mL) and MS-4A, the mixture was reacted at 80° C. for 36 h under nitrogen atmosphere, and filtered under vacuum, and the filtrate was concentrated, and purified by TLC (petroleum ether:ethyl acetate=1:1) to give a target product (2.45 g, yield: 39%) in the form of a yellow oil. LC-MS: 574 $[M+H]^+$.

Step 7

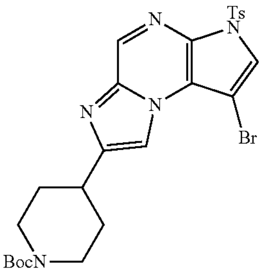

7

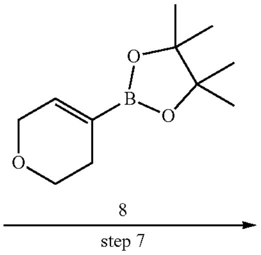

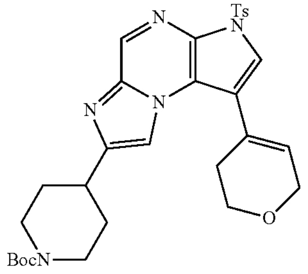

9

To a 100 mL single-neck flask were added 7 (2.45 g, 04.2683 mmol), 8 (1.34 g, 6.40245 mmol), $Pd_2(dppf)Cl_2 \cdot CH_2Cl_2$ (175.8 mg, 0.213415 mmol), $K_2CO_3$ (1.77 g, 12.8049 mmol), dioxane (20 mL) and $H_2O$ (4 mL), and the mixture was reacted at 80° C. for 16 h under nitrogen atmosphere, added with ice water to quench the reaction, extracted with dichloromethane (50 mL×3), washed with saturated brine (50 mL×2), dried over anhydrous sodium sulfate, spin-dried, and purified by TLC (petroleum ether: ethyl acetate=1:1) to give a target product (1.2 mg, yield: 48.8%) in the form of a yellow solid. LC-MS: 578 $[M+H]^+$.

Step 8

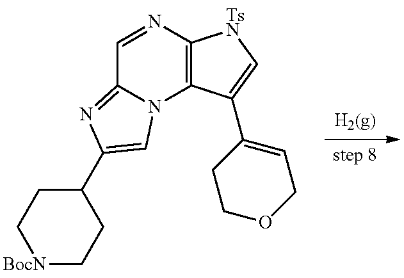

9

-continued

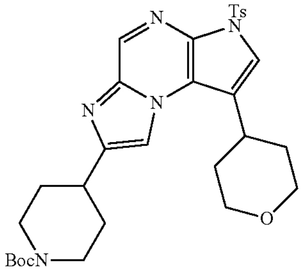

10

To a 100 mL single-neck flask were added 9 (1.2 g, 2.08 mmol), $Pd(OH)_2$ (250 mg, 2.98 mmol) and THE (15 mL), the mixture was reacted at room temperature for 24 h under hydrogen atmosphere, and filtered under vacuum, and the filtrate was concentrated, and purified by TLC (petroleum ether:ethyl acetate=1:1) to give a target product (780 mg, yield: 64.8%) in the form of a yellow oil. LC-MS: 580 $[M+H]^+$.

Step 9

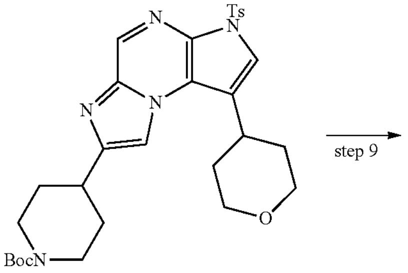

10

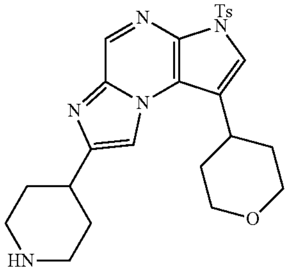

11

To a 100 mL single-neck flask were added 10 (780 mg, 1.345 mmol), TFA (1.0 mL) and DCM (5 mL), and the mixture was reacted at room temperature for 5 h, added with ice water to quench the reaction, adjusted to pH=9 with a saturated $Na_2CO_3$ solution, extracted with dichloromethane (20 mL×3), washed with saturated brine (20 mL×2), dried over anhydrous sodium sulfate, concentrated, and purified by TLC (petroleum ether:ethyl acetate=1:1) to give a target product (540 mg, yield: 83.7%) in the form of a yellow oil. LC-MS: 480 $[M+H]^+$.

Step 10

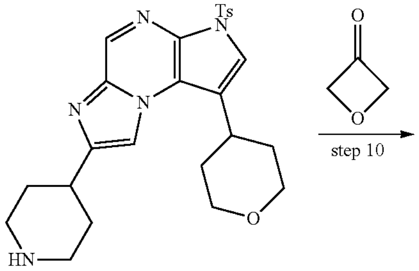

11

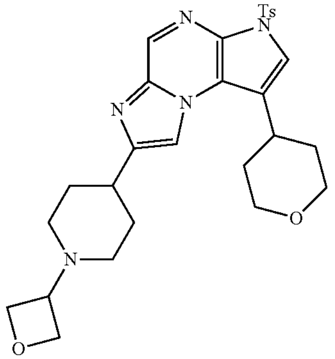

12

To a 100 mL single-neck flask were added 11 (150 mg, 0.3125 mmol), oxetan-3-one (45 mg, 0.625 mmol), sodium triacetoxyborohydride (199 mg, 0.9375 mmol) and dichloromethane (5 mL), and the mixture was stirred at room temperature for 3 h, concentrated, and purified by TLC (dichloromethane:methanol=15:1) to give a target product (138 mg, yield: 82.4%) in the form of a yellow oil. LC-MS: 536 $[M+H]^+$.

Step 11

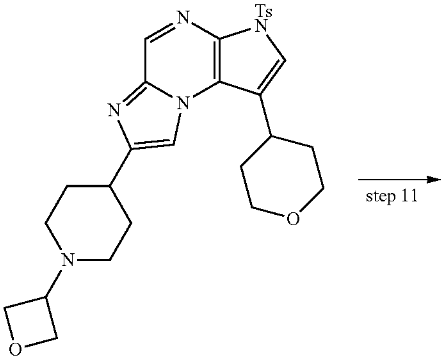

12

-continued

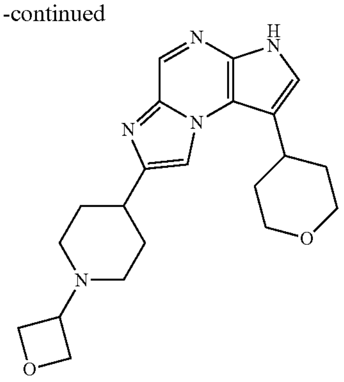

M

To a 100 mL single-neck flask were added 12 (138 mg, 0.14 mmol) and TBAF (3.0 mL), and the mixture was reacted at 70° C. for 16 h, concentrated, and subjected to high pressure liquid chromatography to give a target product (28 mg, yield: 28.6%) in the form of a white solid.

LC-MS: 382 $[M+H]^+$, $^1H$ NMR (400 MHz, DMSO) δ 12.35 (s, 1H), 8.68 (s, 1H), 8.21 (s, 1H), 7.48 (s, 1H), 4.80 (d, J=6.6 Hz, 4H), 3.97 (d, J=8.2 Hz, 2H), 3.65 (t, J=11.0 Hz, 2H), 3.56 (d, J=11.5 Hz, 2H), 3.48-3.37 (m, 2H), 3.24 (t, J=12.0 Hz, 1H), 3.04 (s, 2H), 2.35 (dd, J=11.4, 9.4 Hz, 2H), 2.03 (dd, J=24.1, 11.9 Hz, 2H), 1.88 (d, J=12.8 Hz, 2H), 1.78-1.70 (m, 2H).

Example 14: Preparation of IRAK4 Kinase Inhibitor

The synthetic route is as follows:

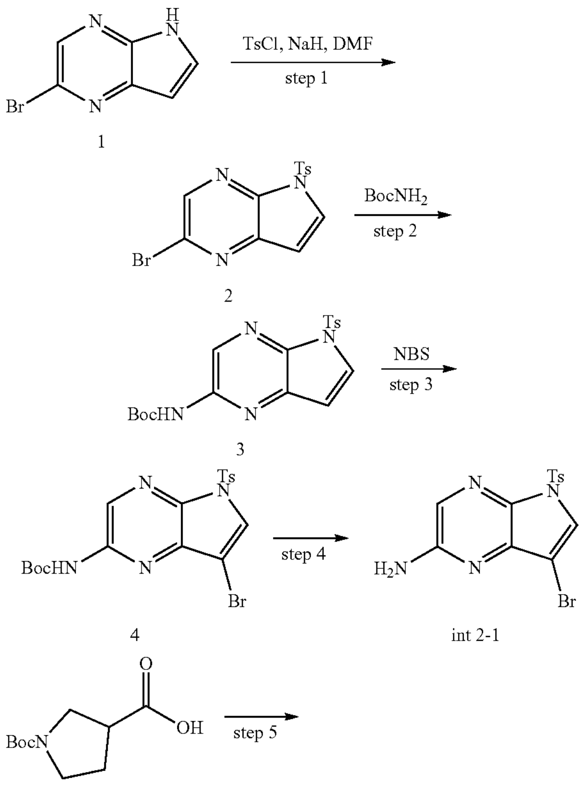

-continued

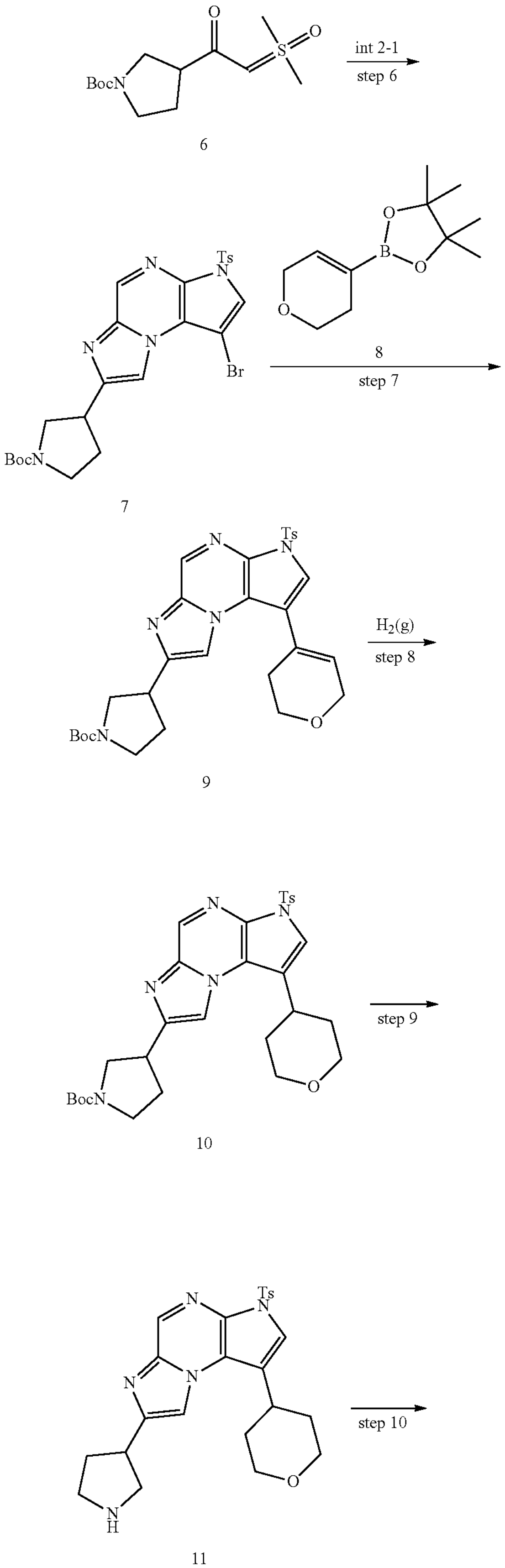

-continued

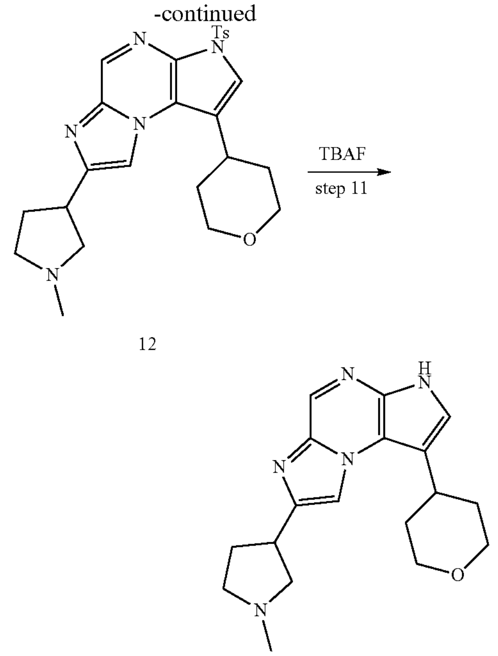

12

N

Step 1

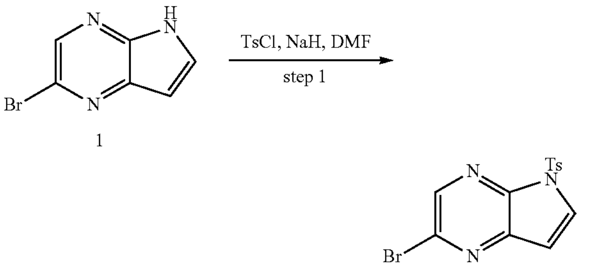

1

2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352 $[M+H]^+$.

Step 2

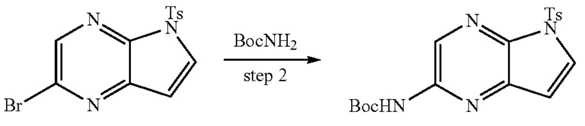

2

3

To a 500 mL single-neck round-bottom flask were added 2 (22.70 g, 64.6 mmol), $BocNH_2$ (11.3 g, 97.0 mmol), $Pd(OAc)_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 $[M+H]^+$.

Step 3

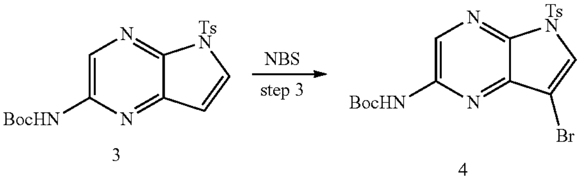

3

4

In a 500 mL single-neck flask, 3 (12.80 g, 32.9 mmol) was dissolved in DMF (100 mL), and added with NBS (7.04 g, 39.5 mmol) at 0° C. The mixture was reacted at room temperature for 1.5 h, added with ice water to quench the reaction, and filtered to give a target product (15.0 g, crude) in the form of a yellow solid. LC-MS: 467 $[M+H]^+$.

Step 4

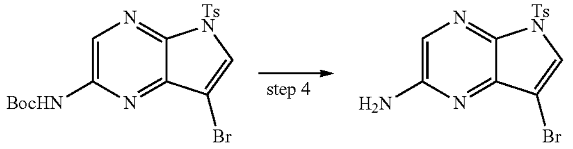

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 $[M+H]^+$.

Step 5

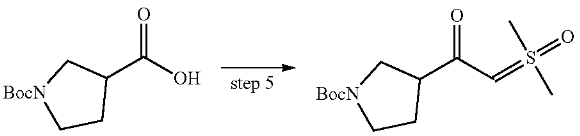

5

6

To a 250 mL single-neck flask were added 5 (5.00 g, 23.2 mmol), HATU (8.8 g, 23.2 mmol), triethylamine (8.82 g, 81.3 mmol) and THE (30 mL), and the mixture was reacted at room temperature for 3 h to give an activated ester. To another 1000 mL single-neck flask were added trimethylsulfoxonium iodide (15.3 g, 69.6 mmol), potassium tert-butoxide (8.20 g, 73.0 mmol) and THF (60 mL), and the mixture was reacted at 65° C. for 3 h, then cooled to 0° C. in an ice bath, and added dropwise with the activated ester. The resulting mixture was reacted at room temperature for 16 h, added with ice water to quench the reaction, stirred at room temperature for 5 h, concentrated, extracted with dichloromethane (100 mL×5), washed with saturated brine (100 mL×2), dried over anhydrous sodium sulfate, and spin-dried to give a target product (3.60 g, yield: 53.7%) in the form of a yellow solid. LC-MS: 290 $[M+H]^+$.

Step 6

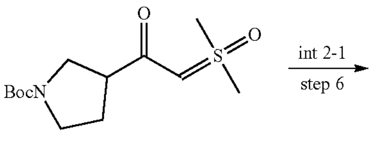

6

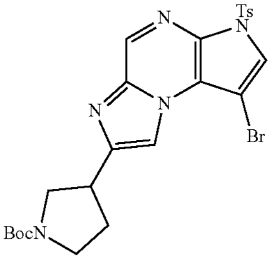

7

To a 100 mL single-neck flask were added 6 (2.52 g, 8.72 mmol), int 2-1 (800 mg, 2.17 mmol), chloro(1,5-cyclooctadiene)iridium(I) dimer (439 mg, 0.653 mmol), 1,10-phenanthroline (510 mg, 2.83 mmol), sodium triflate (562 mg, 3.26 mmol), dichloroethane (30 mL) and MS-4A, the mixture was reacted at 80° C. for 36 h under nitrogen atmosphere, and filtered under vacuum, and the filtrate was concentrated, and purified by TLC (petroleum ether:ethyl acetate=1:1) to give a target product (500 mg, yield: 41.6%) in the form of a yellow oil. LC-MS: 560 $[M+H]^+$.

Step 7

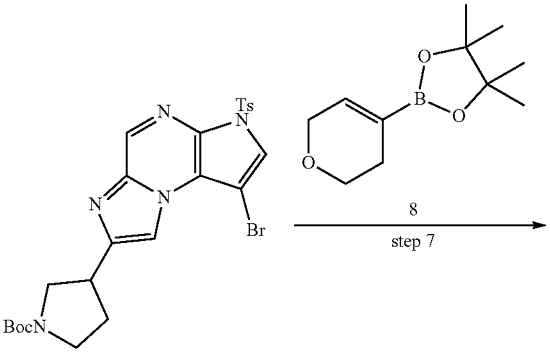

7

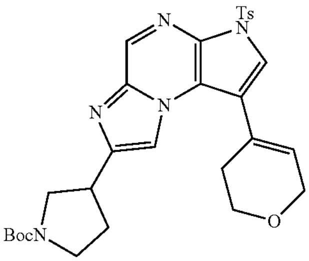

9

To a 100 mL single-neck flask were added 7 (500 mg, 0.890 mmol), 8 (281.1 mg, 1.33 mmol), $Pd_2(dppf)Cl_2 \cdot CH_2Cl_2$ (36.7 mg, 0.0446 mmol), $K_2CO_3$ (369.3 mg, 2.67 mmol), dioxane (10 mL) and $H_2O$ (2 mL), and the mixture was reacted at 80° C. for 16 h under nitrogen atmosphere, added with ice water to quench the reaction, extracted with dichloromethane (50 mL×3), washed with saturated brine (50 mL×2), dried over anhydrous sodium sulfate, spin-dried, and purified by TLC (petroleum ether: ethyl acetate=1:1) to give a target product (194 mg, yield: 38.6%) in the form of a yellow solid. LC-MS: 564 $[M+H]^+$.

Step 8

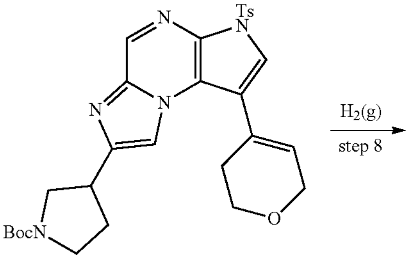

9

-continued

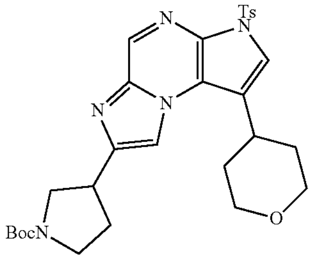

10

To a 100 mL single-neck flask were added 9 (194 mg, 0.344 mmol), $Pd(OH)_2$ (100 mg) and THE (5 mL), the mixture was reacted at room temperature for 24 h under hydrogen atmosphere, and filtered under vacuum, and the filtrate was concentrated, and purified by TLC (petroleum ether:ethyl acetate=1:1) to give a target product (154 mg, yield: 79.3%) in the form of a yellow oil. LC-MS: 566 $[M+H]^+$.

Step 9

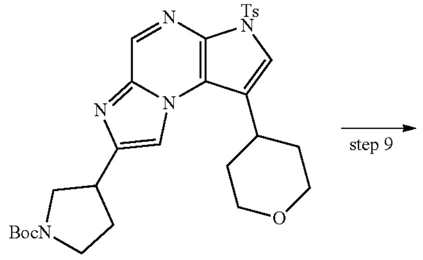

10

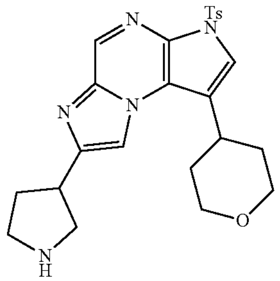

11

To a 100 mL single-neck flask were added 10 (154 mg, 0.272 mmol), TFA (1.0 mL) and DCM (5 mL), and the mixture was reacted at room temperature for 5 h, added with ice water to quench the reaction, adjusted to pH=9 with a saturated $Na_2CO_3$ solution, extracted with dichloromethane (20 mL×3), washed with saturated brine (20 mL×2), dried over anhydrous sodium sulfate, concentrated, and purified by TLC (petroleum ether:ethyl acetate=1:1) to give a target product (94 mg, yield: 74.6%) in the form of a yellow oil. LC-MS: 466 $[M+H]^+$.

Step 10

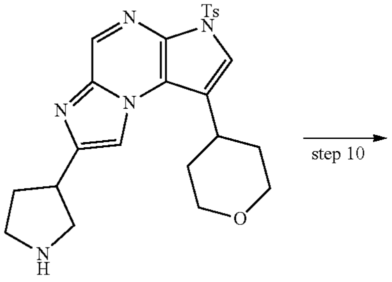

11

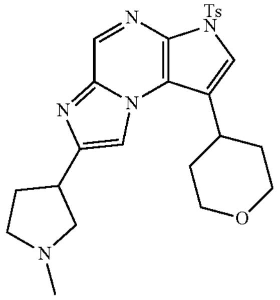

12

To a 100 mL single-neck flask were added 11 (94 mg, 0.206 mmol), $(CH_2O)_n$(61.8 mg, 2.06 mmol), AcOH (37.1 mg, 0.618 mmol), tetraisopropyl titanate (175.7 mg, 0.618 mmol) and methanol (5 mL), the mixture was stirred at room temperature for 1 h, then added with sodium cyanoborohydride (38.8 mg, 0.618 mmol), reacted at room temperature for 16 h, and filtered under vacuum, and the filtrate was concentrated, and purified by TLC (dichloromethane:methanol=15:1) to give a target product (50 mg, yield: 52.0%) in the form of a yellow oil. LC-MS: 480 $[M+H]^+$.

Step 11

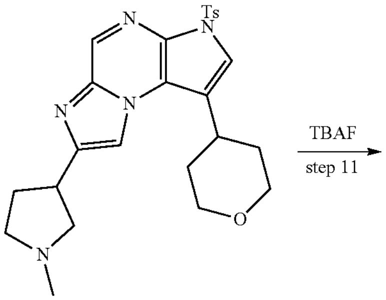

12

-continued

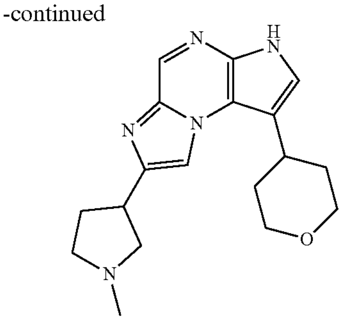

N

To a 100 mL single-neck flask were added 12 (50 mg, 0.104 mmol) and TBAF (1.5 mL), and the mixture was reacted at 70° C. for 16 h, concentrated, and subjected to high pressure liquid chromatography to give a target product (5 mg, yield: 15.0%) in the form of a white solid. LC-MS: 326 $[M+H]^+$, 1H NMR (400 MHz, DMSO) δ 12.01 (s, 1H), 8.51 (s, 1H), 8.34 (s, 2H), 8.08 (s, 1H), 7.24 (s, 1H), 3.96 (dd, J=10.9, 3.1 Hz, 2H), 3.65 (s, 2H), 3.10 (t, J=8.3 Hz, 1H), 2.85 (d, J=6.0 Hz, 1H), 2.69 (dd, J=19.3, 10.9 Hz, 2H), 2.39 (s, 2H), 2.29 (s, 1H), 2.16-2.10 (m, 1H), 1.87 (d, J=12.2 Hz, 2H), 1.70 (dd, J=20.7, 11.8 Hz, 2H), 1.24 (s, 1H).

Example 15: Preparation of IRAK4 Kinase Inhibitor

The synthetic route is as follows:

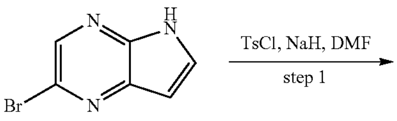

1

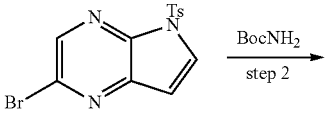

2

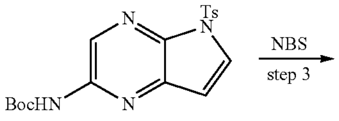

3

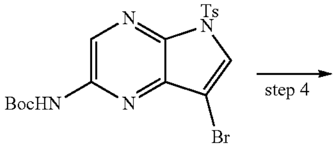

4

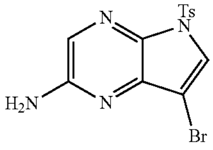

int 2-1

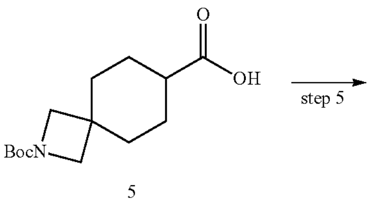

5

-continued

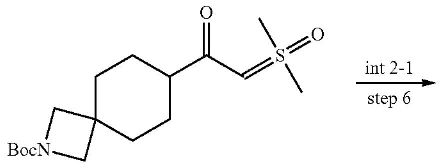

6

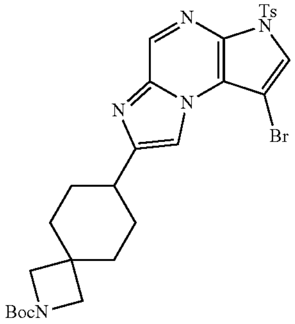

7

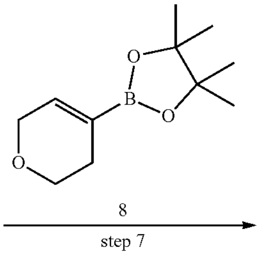

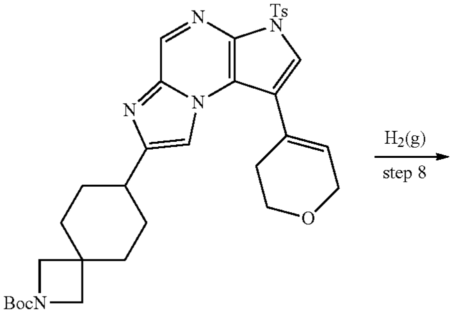

9

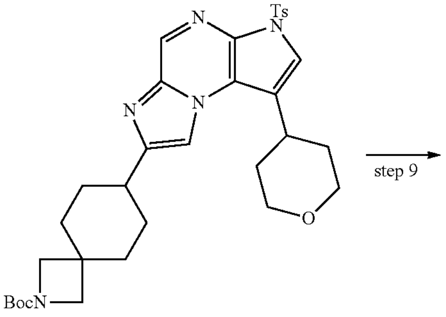

10

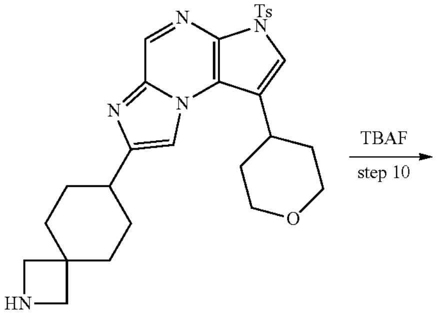

11

-continued

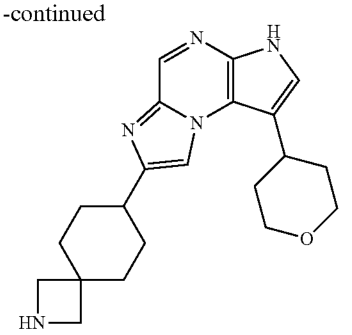

O

Step 1

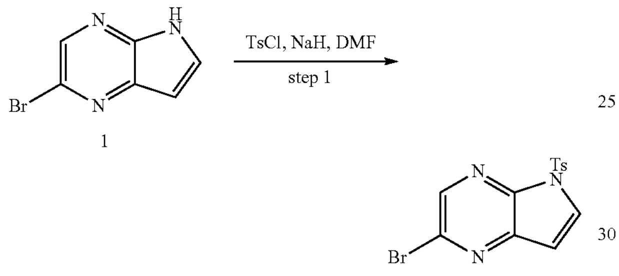

1

2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352 $[M+H]^+$.

Step 2

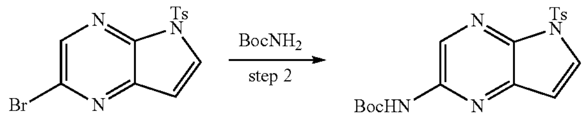

2 3

To a 500 mL single-neck round-bottom flask were added 2 (22.70 g, 64.6 mmol), $BocNH_2$ (11.3 g, 97.0 mmol), $Pd(OAc)_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 $[M+H]^+$.

Step 3

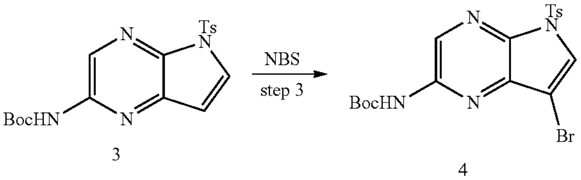

3 4

In a 500 mL single-neck flask, 3 (12.80 g, 32.9 mmol) was dissolved in DMF (100 mL), and added with NBS (7.04 g, 39.5 mmol) at 0° C. The mixture was reacted at room temperature for 1.5 h, added with ice water to quench the reaction, and filtered to give a target product (15.0 g, crude) in the form of a yellow solid. LC-MS: 467 $[M+H]^+$.

Step 4

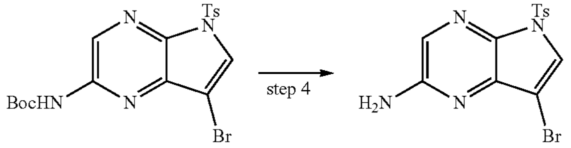

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 $[M+H]^+$.

Step 5

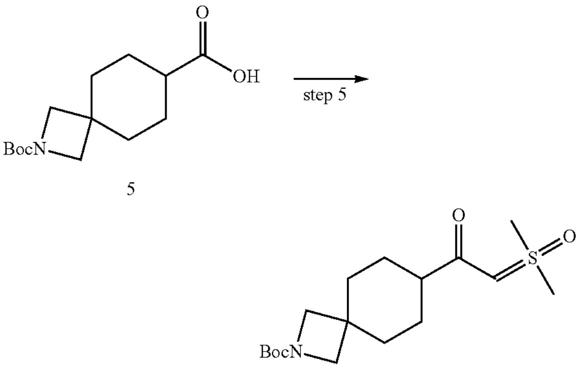

5

6

To a 100 mL single-neck flask were added 5 (1.02 g, 3.79 mmol), HATU (1.44 g, 3.79 mmol), triethylamine (13.2 g, 3.50 mmol) and THE (30 mL), and the mixture was reacted at room temperature for 3 h to give an activated ester. To another 1000 mL single-neck flask were added trimethylsulfoxonium iodide (2.50 g, 11.3 mmol), potassium tert-butoxide (1.34 g, 11.9 mmol) and THE (30 mL), and the mixture was reacted at 65° C. for 3 h, then cooled to 0° C. in an ice bath, and added dropwise with the activated ester. The resulting mixture was reacted at room temperature for 16 h, added with ice water to quench the reaction, stirred at room temperature for 5 h, and filtered under vacuum, and the filtrate was concentrated and extracted with dichloromethane (80 mL×5), washed with saturated brine (80 mL×3), dried over anhydrous sodium sulfate, and spin-dried to give a target product (1.12 g, yield: 84.6%) in the form of a white solid. LC-MS: 344 $[M+H]^+$.

Step 6

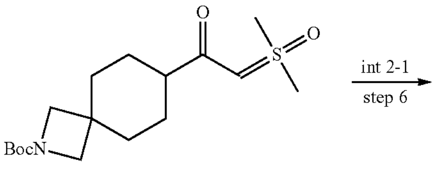

6

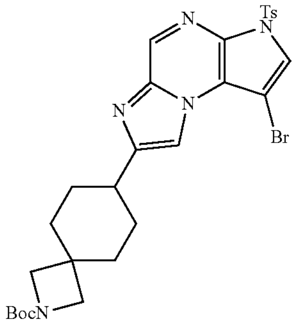

7

To a 100 mL single-neck flask were added 6 (1.12 g, 3.26 mmol), int 2-1 (300 mg, 0.816 mmol), chloro(1,5-cyclooctadiene)iridium(I) dimer (164.6 mg, 0.245 mmol), 1,10-phenanthroline (230 mg, 1.06 mmol), sodium triflate (210.7 mg, 1.22 mmol), dichloroethane (20 mL) and MS-4A, the mixture was reacted at 80° C. for 36 h under nitrogen atmosphere, and filtered under vacuum, and the filtrate was concentrated, and purified by TLC (petroleum ether:ethyl acetate=2:1) to give a target product (249 mg, yield: 49.7%) in the form of a yellow oil. LC-MS: 614 $[M+H]^+$.

Step 7

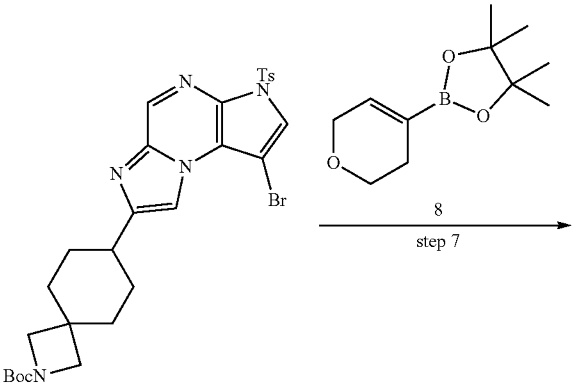

7

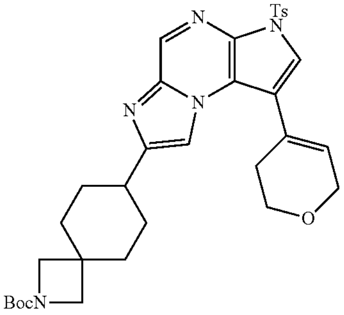

9

To a 100 mL single-neck flask were added 7 (249 mg, 0.406 mmol), 8 (128 mg, 0.609 mmol), $Pd_2$(dppf) $Cl_2 \cdot CH_2Cl_2$ (16.7 mg, 0.0203 mmol), $K_2CO_3$ (168 mg, 1.21 mmol), dioxane (10 mL) and $H_2O$ (2 mL), and the mixture was reacted at 80° C. for 16 h under nitrogen atmosphere, added with ice water to quench the reaction, extracted with ethyl acetate (20 mL×3), washed with saturated brine (20 mL×2), dried over anhydrous sodium sulfate, spin-dried, and purified by TLC (petroleum ether:ethyl acetate=2:1) to give a target product (80 mg, yield: 32%) in the form of a yellow oil. LC-MS: 618 $[M+H]^+$.

Step 8

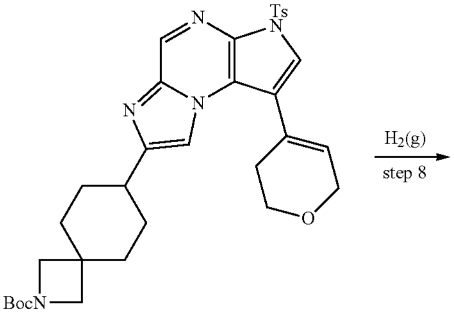

9

-continued

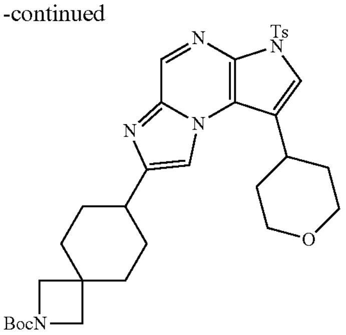

10

To a 100 mL single-neck flask were added 9 (80 mg, 0.129 mmol), $Pd(OH)_2$ (40 mg) and THE (50 mL), the mixture was reacted at room temperature for 24 h under hydrogen atmosphere, and filtered under vacuum, and the filtrate was concentrated, and purified by TLC (petroleum ether:ethyl acetate=1:1) to give a target product (24 mg, yield: 30%) in the form of a yellow oil. LC-MS: 620 $[M+H]^+$.

Step 9

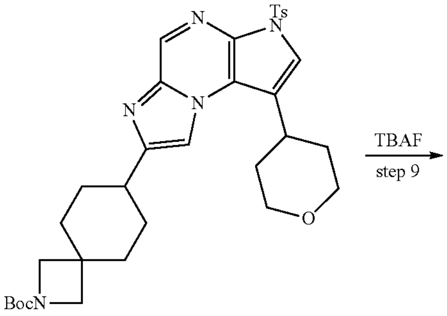

10

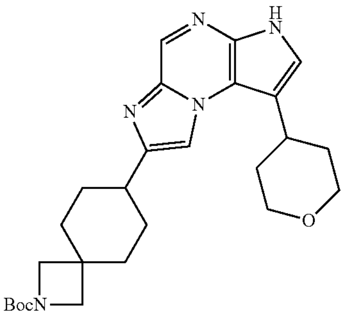

11

To a 100 mL single-neck flask were added 10 (24 mg, 0.0387 mmol) and TBAF (2.0 mL), and the mixture was reacted at 70° C. for 16 h, concentrated to give a target product (15 mg, yield: 83.0%) in the form of a yellow oil. LC-MS: 466 $[M+H]^+$.

Step 10

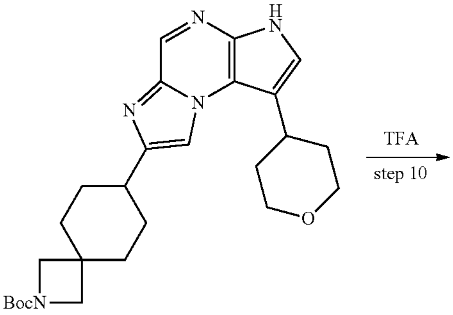

11

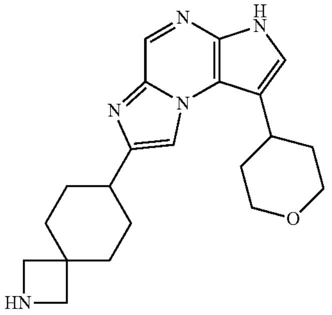

O

To a 100 mL single-neck flask were added 11 (15 mg, 0.0322 mmol), TFA (0.6 mL) and DCM (3 mL), and the mixture was reacted at room temperature for 5 h, concentrated, and subjected to prep-HPLC to give a target product (2 mg, yield: 11.7%) in the form of a white solid. LC-MS: 366 $[M+H]^+$, 1H NMR (400 MHz, DMSO) δ 12.38 (s, 1H), 8.67 (s, 1H), 8.18 (s, 1H), 7.49 (s, 1H), 3.97 (d, J=8.1 Hz, 2H), 3.79 (s, 2H), 3.66 (s, 2H), 3.41 (t, J=11.7 Hz, 2H), 2.89 (s, 2H), 2.12 (d, J=7.1 Hz, 2H), 1.99 (s, 3H), 1.87 (d, J=10.8 Hz, 3H), 1.73 (dd, J=12.6, 4.0 Hz, 2H), 1.61 (s, 2H), 1.24 (s, 1H).

Example 16: Preparation of IRAK4 Kinase Inhibitor

The synthetic route is as follows:

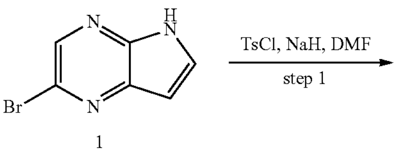

1

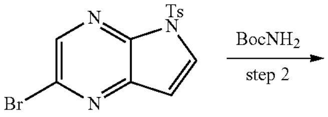

2

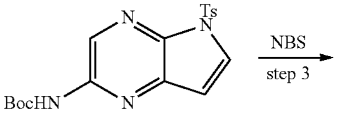

3

-continued
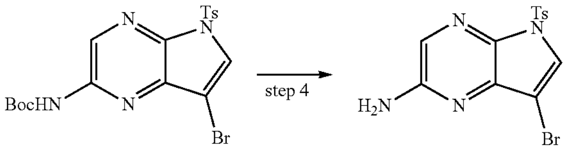
4
int 2-1
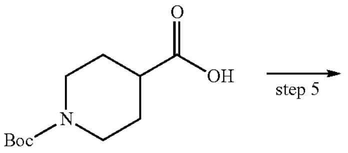
5
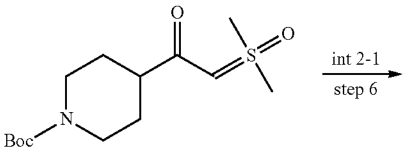
6
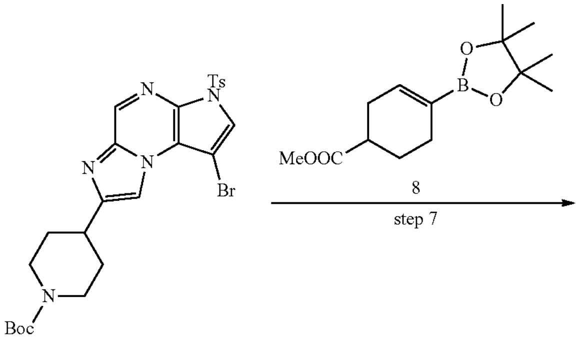
7
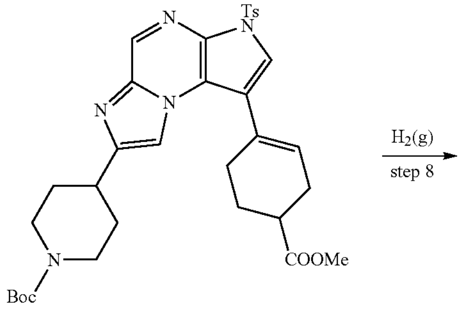
9
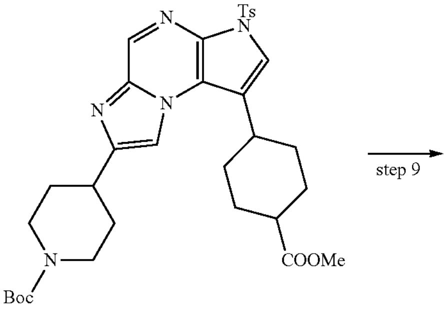
10
-continued
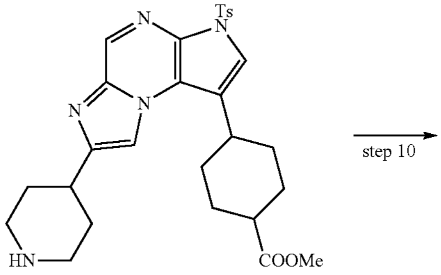
11
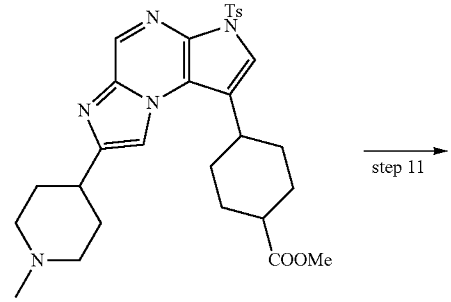
12
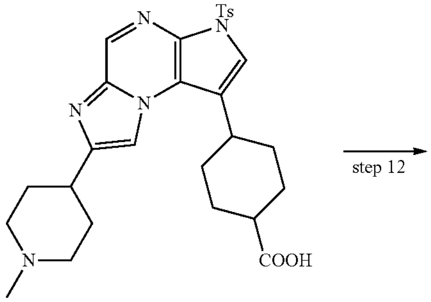
13
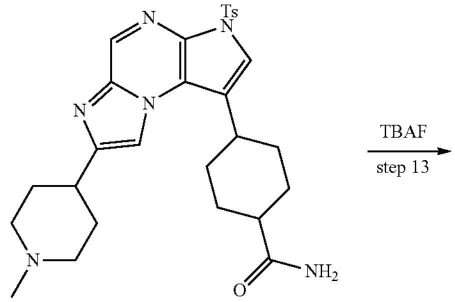
14
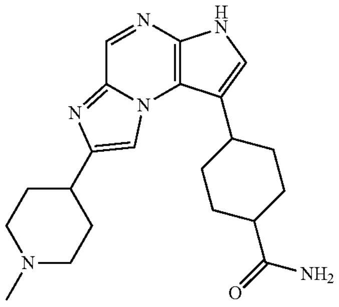
P Step 1

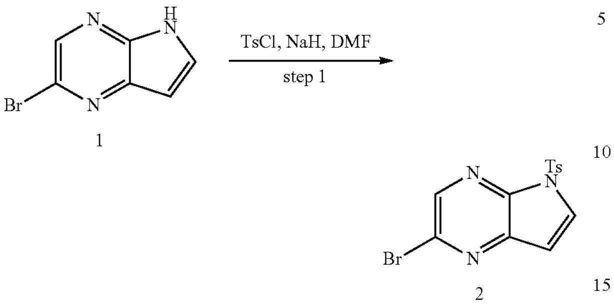

1 2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352 $[M+H]^+$.

Step 2

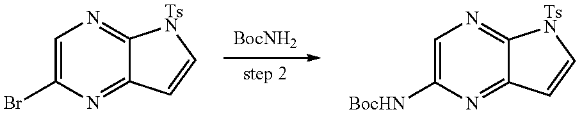

2 3

To a 500 mL single-neck round-bottom flask were added 2 (22.70 g, 64.6 mmol), $BocNH_2$ (11.3 g, 97.0 mmol), $Pd(OAc)_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 $[M+H]^+$.

Step 3

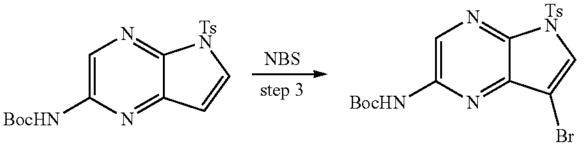

3 4

In a 500 mL single-neck flask, 3 (12.80 g, 32.9 mmol) was dissolved in DMF (100 mL), and added with NBS (7.04 g, 39.5 mmol) at 0° C. The mixture was reacted at room temperature for 1.5 h, added with ice water to quench the reaction, and filtered to give a target product (15.0 g, crude) in the form of a yellow solid. LC-MS: 467 $[M+H]^+$.

Step 4

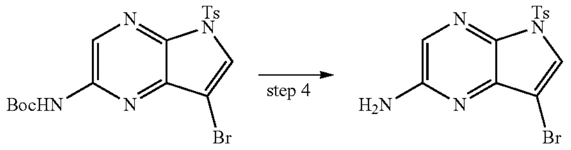

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 $[M+H]^+$.

Step 5

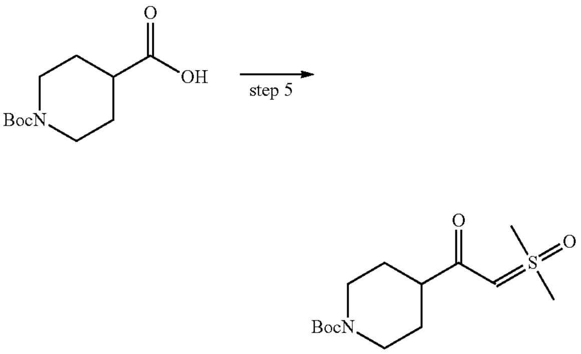

6

To a 250 mL single-neck flask were added 5 (5.00 g, 21.8 mmol), HATU (8.3 g, 21.8 mmol), triethylamine (7.72 g, 76.3 mmol) and THE (60 mL), and the mixture was reacted at room temperature for 3 h to give an activated ester. To another 1000 mL single-neck flask were added trimethylsulfoxonium iodide (14.4 g, 65.4 mmol), potassium tert-butoxide (7.70 g, 68.7 mmol) and THE (80 mL), and the mixture was reacted at 65° C. for 3 h, then cooled to 0° C. in an ice bath, and added dropwise with the activated ester. The resulting mixture was reacted at room temperature for 16 h, added with ice water to quench the reaction, stirred at room temperature for 5 h, concentrated, extracted with dichloromethane (100 mL×5), washed with saturated brine (100 mL×2), dried over anhydrous sodium sulfate, and spin-dried to give a target product (4.70 g, crude) in the form of a yellow solid. LC-MS: 304 $[M+H]^+$.

Step 6

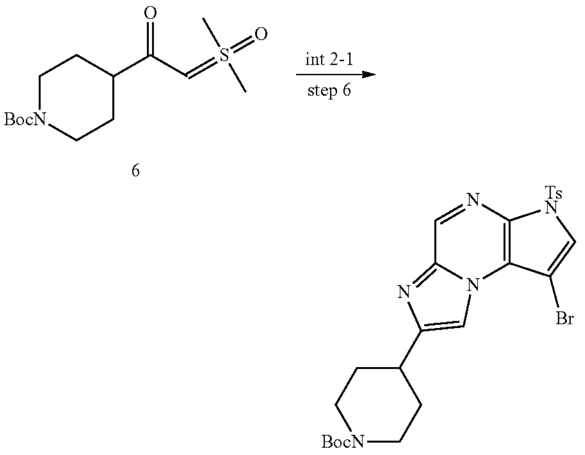

6

7

To a 100 mL single-neck flask were added 6 (4.70 g, 15.4 mmol), int 2-1 (1.42 g, 3.86 mmol), chloro(1,5-cyclooctadiene)iridium(I) dimer (778 mg, 1.16 mmol), 1,10-phenanthroline (1.09 g, 5.02 mmol), sodium triflate (1.23 g, 7.18 mmol), dichloroethane (30 mL) and MS-4A, the mixture was reacted at 80° C. for 20 h under nitrogen atmosphere, and filtered under vacuum, and the filtrate was concentrated, and purified by TLC (petroleum ether:ethyl acetate=1:1) to give a target product (422 mg, yield: 19.0%) in the form of a yellow oil. LC-MS: 574 $[M+H]^+$.

Step 7

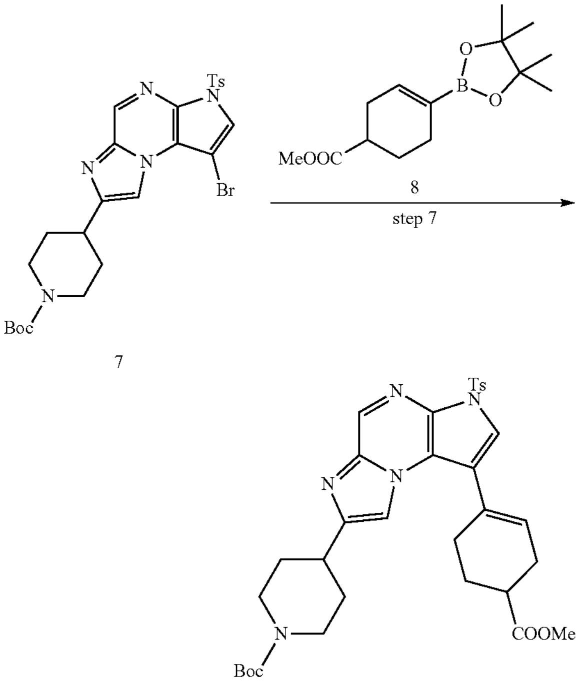

7

8

9

To a 100 mL single-neck flask were added 7 (422 mg, 0.736 mmol), 8 (294 mg, 1.10 mmol), $Pd(dppf)Cl_2 \cdot CH_2Cl_2$ (30.1 mg, 0.0368 mmol), $K_2CO_3$ (305 mg, 2.21 mmol), dioxane (7.5 mL) and $H_2O$ (1.5 mL), and the mixture was reacted at 80° C. for 16 h under nitrogen atmosphere, spin-dried, and separated by column chromatography (petroleum ether:ethyl acetate=2:1) to 15 give a target product (236 mg, yield: 50.6%) in the form of a yellow liquid. LC-MS: $634[M+H]^+$.

Step 8

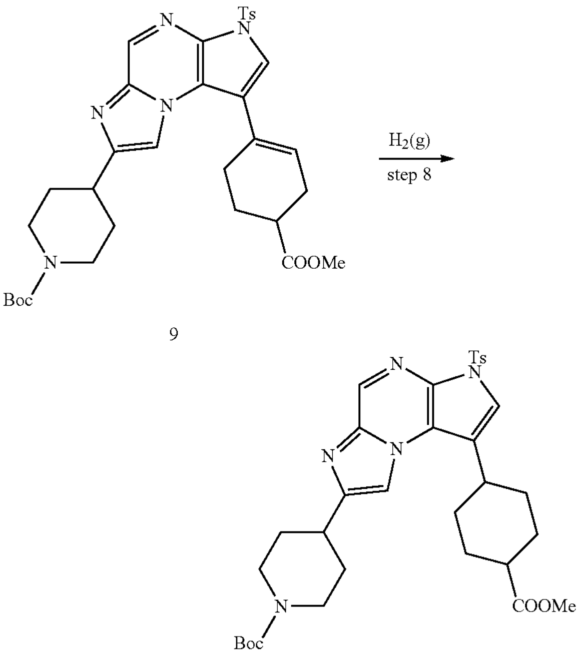

9

10

To a 100 mL single-neck flask were added 9 (236 mg, 0.37 mmol), $Pd(OH)_2$ (94.4 mg, 0.67 mmol) and THE (5 mL), the mixture was reacted at room temperature for 24 h under hydrogen atmosphere, and filtered under vacuum, and the filtrate was concentrated, and separated by column chromatography (petroleum ether:ethyl acetate=1:1) to give a target product (211 mg, yield: 89.8%) in the form of a yellow oil. LC-MS: 636 [M+H].

Step 9

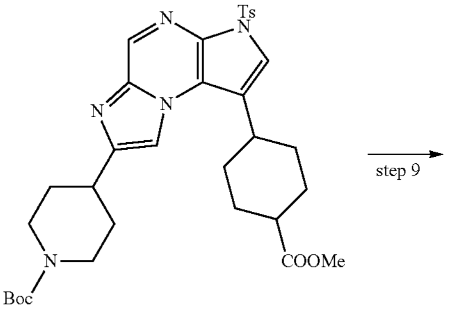

10

-continued

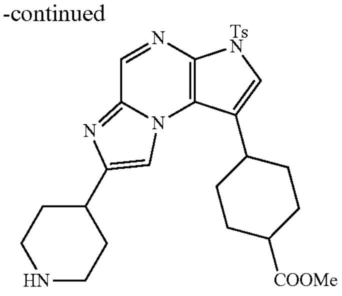

11

To a 100 mL single-neck flask were added 10 (211 mg, 0.332 mmol), TFA (1.0 mL) and DCM (5 mL), and the mixture was reacted at room temperature for 5 h, added with ice water to quench the reaction, adjusted to pH=9 with a saturated $Na_2CO_3$ solution, extracted with dichloromethane (20 mL×3), washed with saturated brine (20 mL×2), dried over anhydrous sodium sulfate, and concentrated to give a target product (82 mg, crude) in the form of a yellow solid. LC-MS: 536 $[M+H]^+$.

Step 10

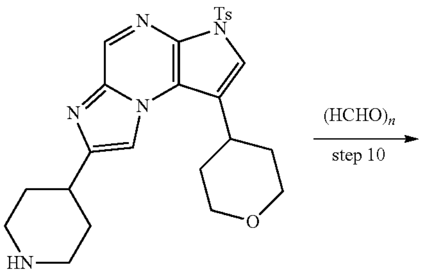

11

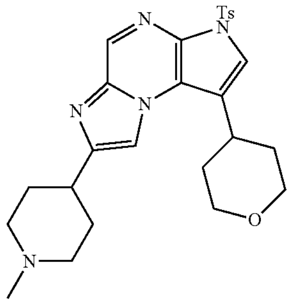

12

To a 100 mL single-neck flask were added 11 (82.0 mg, 0.150 mmol), $(CH_2O)_n$(45.0 mg, 1.50 mmol), AcOH (27.0 mg, 0.450 mmol), tetraisopropyl titanate (128 mg, 0.45 mmol) and methanol (5 mL), and the mixture was stirred at room temperature for 1 h, then added with sodium cyano-borohydride (28.3 mg, 0.450 mmol), reacted at room temperature for 16 h, and 15 added with water to quench the reaction, and extracted with dichloromethane (10 mL×3). The organic phases were combined, washed with brine (20 mL×3), dried over anhydrous sodium sulfate, filtered, spin-dried, and separated by thin-layer chromatography to give a target product (35.0 mg, yield: 43.0%) in the form of a white solid. LC-MS: 550 $[M+H]^+$.

Step 11

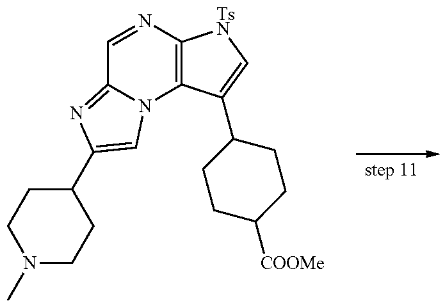

12

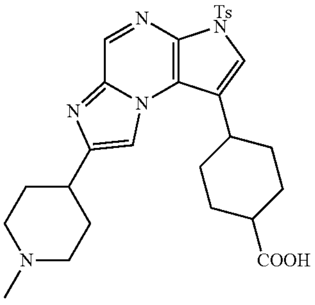

13

To a 100 mL single-neck flask were added 12 (35.0 mg, 0.0638 mmol), lithium hydroxide (7.66 mg, 0.319 mmol), tetrahydrofuran (5 mL) and water (0.5 mL), and the mixture was stirred at room temperature for 24 h, and spin-dried to give a target product (26.0 mg, crude) in the form of a white solid. LC-MS: 536 [M+H].

Step 12

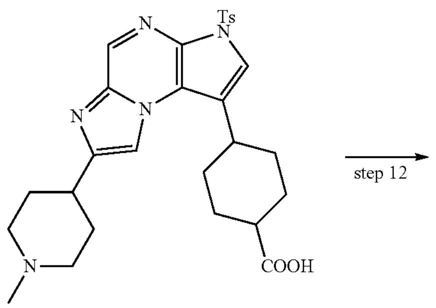

13

-continued

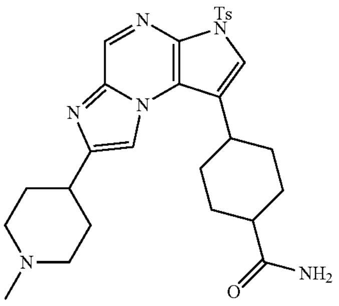

14

To a 100 mL single-neck flask were added 13 (26.0 mg, 0.0486 mmol), ammonium chloride (3.41 mg, 0.0638 mmol), HATU (36.4 mg, 0.0657 mmol), DIEA (24.7 mg, 0.191 mmol) and DMF (3 mL), and the mixture was stirred at room temperature for 3 h, and concentrated to give a target product (15.0 mg, crude) in the form of a white solid. LC-MS: 535 [M+H]$^+$.

Step 13

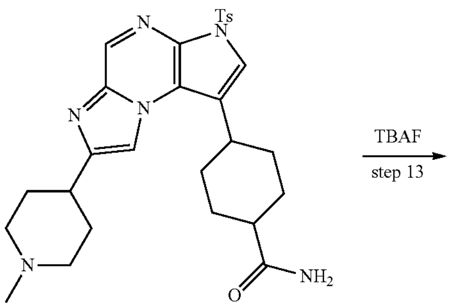

14

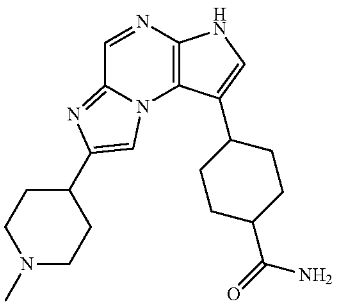

P

To a 100 mL single-neck flask were added 14 (15.0 mg, 0.0280 mmol) and TBAF (2.0 mL), and the mixture was reacted at 70° C. for 16 h, concentrated, and subjected to high pressure liquid chromatography to give a target product (2.00 mg, yield: 20.0%) in the form of a white solid. LC-MS: 381 [M+H]$^+$, $^1$H NMR (400 MHz, MeOD) δ 8.50 (s, 1H), 8.12 (s, 1H), 7.25 (s, 1H), 3.67 (d, J=12.6 Hz, 2H), 3.23 (d, J=10.4 Hz, 2H), 3.15-3.11 (m, 1H), 2.96 (s, 3H), 2.65-2.62 (m, 1H), 2.38 (d, J=13.3 Hz, 2H), 2.19-2.09 (m, 4H), 2.03 (s, 2H), 2.00 (s, 1H), 1.98-1.93 (m, 2H), 1.89-1.82 (m, 2H).

Example 17: Preparation of IRAK4 Kinase Inhibitor

The synthetic route is as follows:

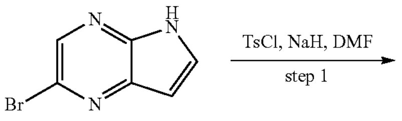

1

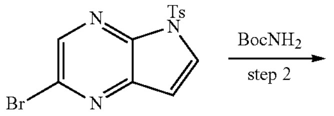

2

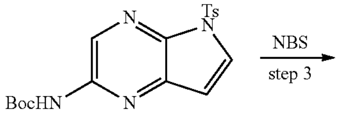

3

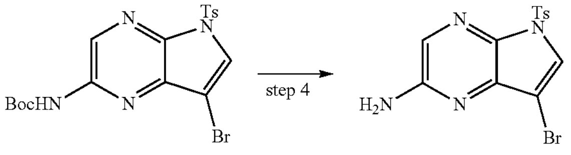

4 int 2-1

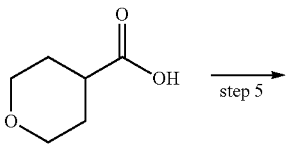

6

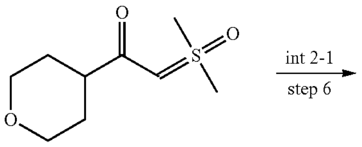

7

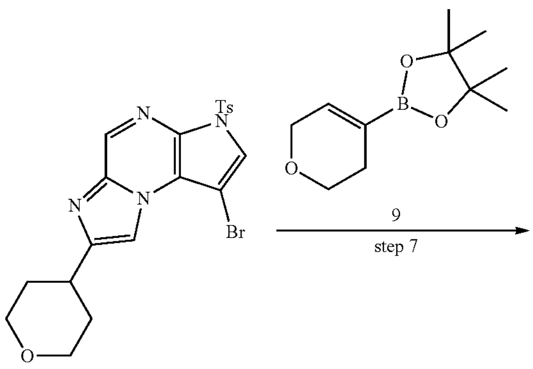

9

8

-continued

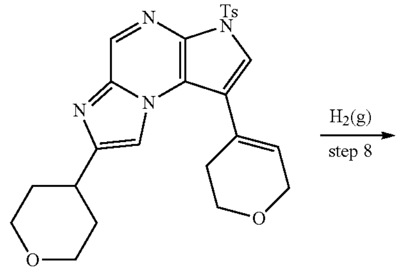

10

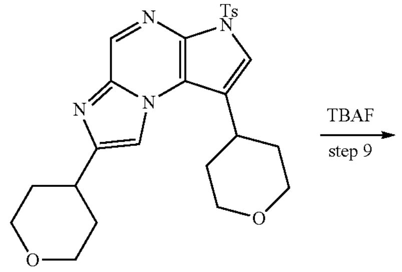

11

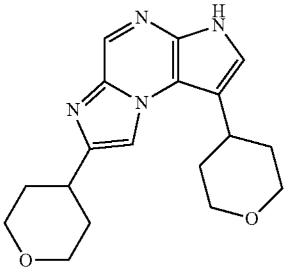

Q

Step 1

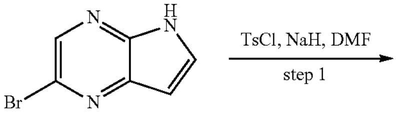

1

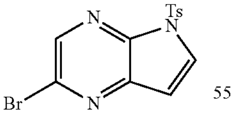

2

In a 500 mL three-neck flask, 1 (12.30 g, 62.1 mmol) was dissolved in DMF (100 mL), cooled to 0° C. in an ice bath, and added with NaH (2.98 g, 74.5 mmol). After stirring at room temperature for 1 h, the mixture was added with TsCl (14.2 g, 74.5 mmol) and reacted at room temperature for 16 h, added with ice water to quench the reaction, and filtered to give a target product (22.70 g, crude) in the form of a yellow solid. LC-MS: 352 $[M+H]^+$.

Step 2

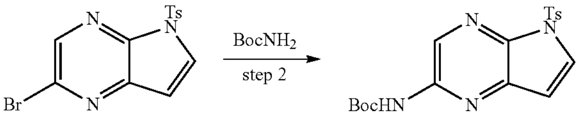

2 3

To a 500 mL single-neck round-bottom flask were added 2 (22.70 g, 64.6 mmol), $BocNH_2$ (11.3 g, 97.0 mmol), $Pd(OAc)_2$ (145 mg, 0.646 mmol), xantphos (1.12 g, 1.94 mmol), $K_2CO_3$ (26.7 g, 194 mmol) and dioxane (150 mL), and the mixture was reacted at 95° C. for 18 h under nitrogen atmosphere, added with ice water to quench the reaction, extracted with ethyl acetate (200 mL×3), washed with saturated brine (200 mL×3), dried over anhydrous sodium sulfate, spin-dried, and purified by column chromatography (petroleum ether:ethyl acetate=15:1) to give a target product (12.8 g, yield: 51.2%) in the form of a yellow solid. LC-MS: 389 $[M+H]^+$.

Step 3

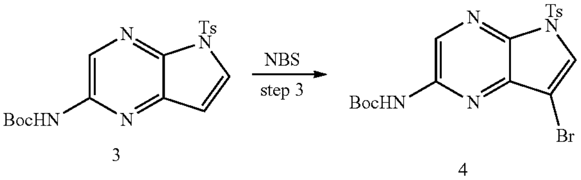

3 4

In a 500 mL single-neck flask, 3 (12.80 g, 32.9 mmol) was dissolved in DMF (100 mL), and added with NBS (7.04 g, 39.5 mmol) at 0° C. The reaction system was reacted at room temperature for 1.5 h, added with ice water to quench the reaction, and filtered to give a target product (15.0 g, crude) in the form of a yellow solid. LC-MS: 467 $[M+H]^+$.

Step 4

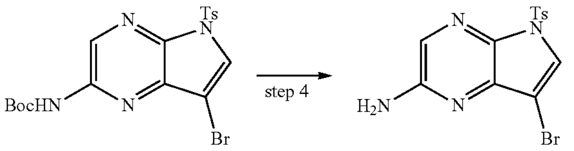

4 int 2-1

In a 500 mL single-neck flask, 4 (15.0 g, 32.1 mmol) was dissolved in dichloromethane (130 mL), and added dropwise with trifluoroacetic acid (26 mL) at 0° C. The mixture was reacted at room temperature for 16 h, added with ice water to quench the reaction, adjusted to pH=9 with a saturated $Na_2CO_3$ solution, extracted with dichloromethane (150 mL×3), washed with saturated brine (150 mL×2), dried over anhydrous sodium sulfate, spin-dried, and purified by column chromatography (petroleum ether:ethyl acetate=2:1) to give a target product (9.5 g, yield: 80.5%) in the form of a yellow solid. LC-MS: 367 $[M+H]^+$.

Step 5

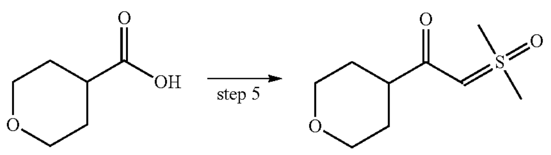

6 7

To a 250 mL single-neck flask were added 5 (5.00 g, 38.5 mmol), HATU (14.6 g, 38.5 mmol), triethylamine (13.8 g, 135 mmol) and THE (60 mL), and the mixture was reacted at room temperature for 3 h to give an activated ester. To another 1000 mL single-neck flask were added trimethylsulfoxonium iodide (25.5 g, 116 mmol), potassium tert-butoxide (13.6 g, 121 mmol) and THE (60 mL), and the mixture was reacted at 65° C. for 3 h, cooled to 0° C. in an ice bath, and added dropwise with the activated ester. The resulting mixture was reacted at room temperature for 16 h, added with ice water to quench the reaction, stirred at room temperature for 5 h, concentrated, extracted with dichloromethane (100 mL×5), washed with saturated brine (100 mL×2), dried over anhydrous sodium sulfate, and spin-dried to give a target product (12.6 g, crude) in the form of a white solid. LC-MS: 205 $[M+H]^+$.

Step 6

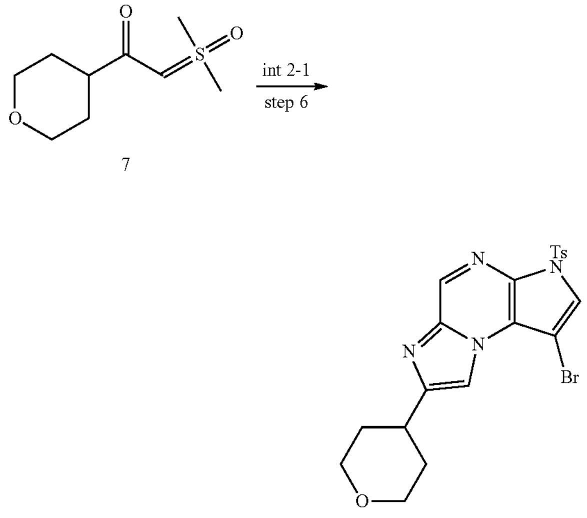

7

8

To a 100 mL single-neck flask were added 7 (3.16 g, 15.4 mmol), int 2-1 (1.42 g, 3.86 mmol), chloro(1,5-cyclooctadiene)iridium(I) dimer (778 mg, 1.16 mmol), 1,10-phenanthroline (1.09 g, 5.02 mmol), sodium triflate (1.23 g, 7.18 mmol), dichloroethane (40 mL) and MS-4A, the mixture was reacted at 80° C. for 40 h under nitrogen atmosphere, and filtered under vacuum, and the filtrate was concentrated to give a target product (1.01 g, crude) in the form of a yellow solid. LC-MS: 475 $[M+H]^+$.

Step 7

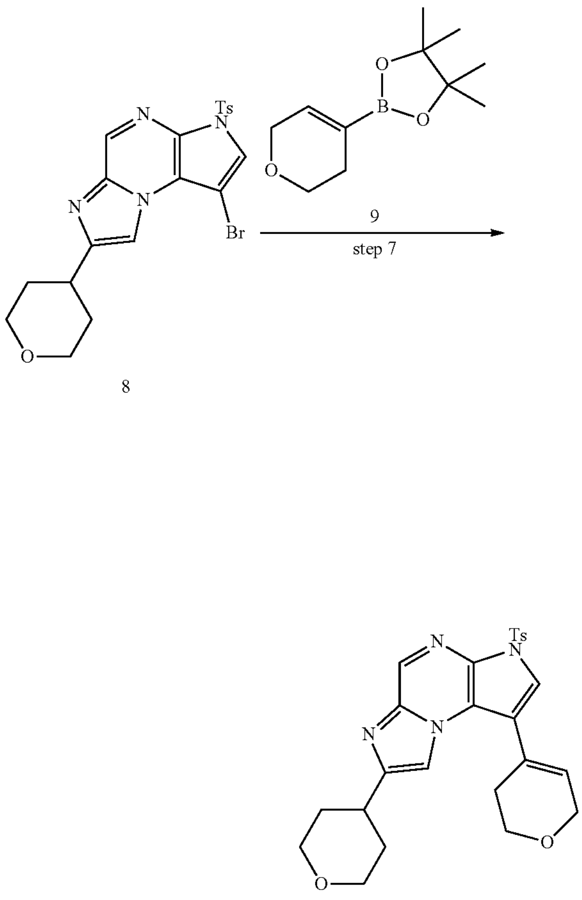

8 9 10

To a 100 mL single-neck flask were added 8 (400 mg, 0.844 mmol), 9 (267 mg, 1.27 mmol), $Pd(dppf)Cl_2$ (30.9 mg, 0.0422 mmol), $K_2CO_3$ (349 mg, 2.53 mmol), dioxane (20 mL) and $H_2O$ (4 mL), the mixture was reacted at 80° C. for 20 h under nitrogen atmosphere, and the reaction solution was spin-dried, and subjected to PTLC (petroleum ether: ethyl acetate=1:1) to give a target product (122 mg, yield: 30.3%) in the form of a yellow solid. LC-MS: 479 $[M+H]^+$.

Step 8

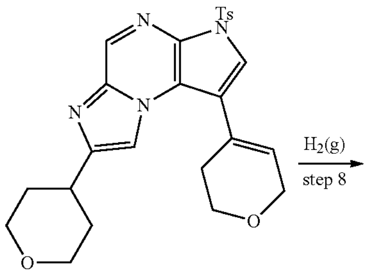

10

-continued

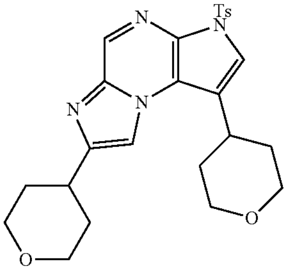

11

To a 100 mL single-neck flask were added 10 (122 mg, 0.255 mmol), $Pd(OH)_2$ (93.0 mg, 0.664 mmol) and THE (5 mL), the mixture was reacted at room temperature for 48 h under hydrogen atmosphere, and filtered under vacuum, and the filtrate was concentrated to give a target product (46.0 mg, yield: 37.7%) in the form of a yellow solid. LC-MS: 481 $[M+H]^+$.

Step 9

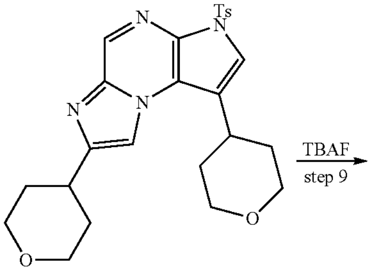

11

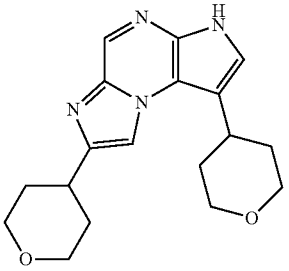

Q

To a 100 mL single-neck flask were added 11 (46.0 mg, 0.0958 mmol) and TBAF (3.0 mL), and the mixture was reacted at 70° C. for 30 h, concentrated, and subjected to high pressure liquid chromatography to give a target product (20.0 mg, yield: 64.5%) in the form of a white solid. LC-MS: 327 $[M+H]^+$, $^1H$ NMR (400 MHz, DMSO) δ 12.62 (s, 1H), 8.78 (s, 1H), 8.34 (s, 1H), 7.63 (s, 1H), 4.06-3.89 (m, 4H), 3.67 (t, J=10.8 Hz, 2H), 3.55-3.48 (m, 2H), 3.48-3.43 (m, 1H), 3.24 (d, J=11.0 Hz, 1H), 1.96 (d, J=13.7 Hz, 2H), 1.89 (dd, J=15.3, 8.4 Hz, 4H), 1.79-1.67 (m, 2H).

Example 18: Preparation of IRAK4 Kinase Inhibitor

The synthetic route is as follows:

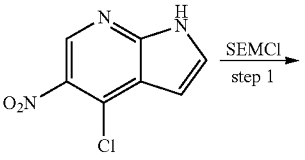

1

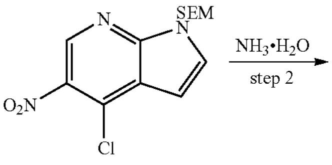

2

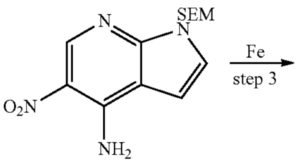

3

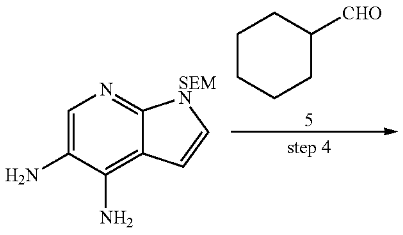

4

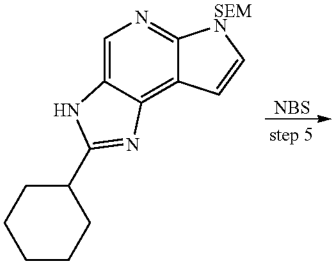

6

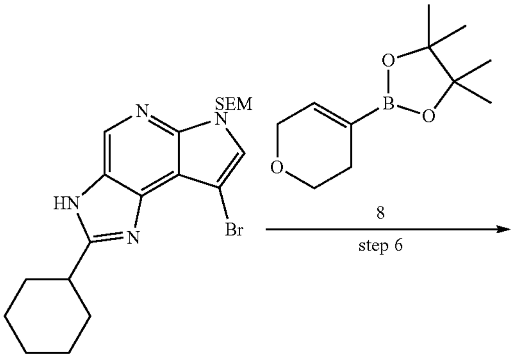

7

-continued

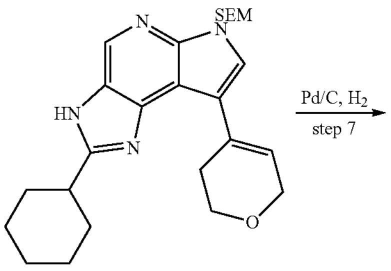

9

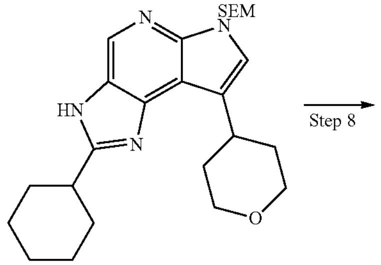

10

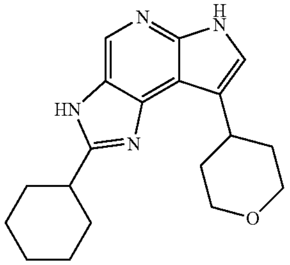

R

Step 1

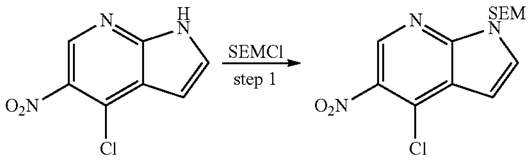

1 2

In a 100 mL three-neck flask, 1 (740 mg, 3.74 mmol) was dissolved in DMF (8 mL), cooled to 0° C. in an ice bath, and added with NaH (239.7 mg, 5.99 mmol). After stirring at room temperature for 1 h, the mixture was added with SEM-Cl (750 mg, 4.49 mmol), reacted at room temperature for 16 h, added with ice water to quench the reaction, extracted with ethyl acetate (20 mL×3), washed with saturated brine (20 mL×3), dried over anhydrous sodium sulfate, spin-dried, and purified by column chromatography (petroleum ether:ethyl acetate=1:1) to give a target product (980 mg, yield: 81.6%) in the form of a yellow oil. LC-MS: 328[M+H]+.

Step 2

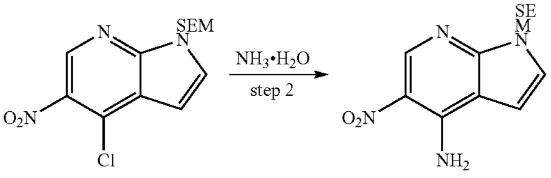

2 3

To a 100 mL single-neck round-bottom flask were added 2 (780 mg, 2.38 mmol), $NH_3H_2O$ (4 mL) and dioxane (4 mL), and the mixture was reacted at 80° C. for 18 h, concentrated, added with ice water to quench the reaction, extracted with dichloromethane (20 mL×3), washed with saturated saline (20 mL×3), dried over anhydrous sodium sulfate, and spin-dried to give a target product (1.1 g, crude) in the form of a yellow solid. LC-MS: 309 $[M+H]^+$.

Step 3

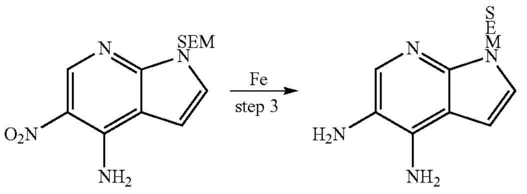

3 4

In a 100 mL single-neck flask, 3 (1.10 g, 3.31 mmol), Fe (0.927 g, 16.5 mmol) and $NH_4Cl$ (0.878 g, 16.5 mmol) were added to ethanol/water (30 mL/10 mL), and the mixture was reacted at 80° C. for 16 h, filtered under vacuum, concentrated, added with ice water to quench the reaction, extracted with DCM/MeOH (15:1), washed with saturated saline (20 mL×3), dried over anhydrous sodium sulfate, and spin-dried to give a target product (680 mg, crude) in the form of a yellow oil. LC-MS: 279 $[M+H]^+$.

Step 4

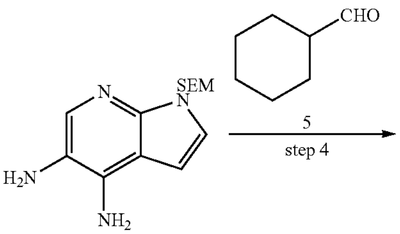

4

-continued

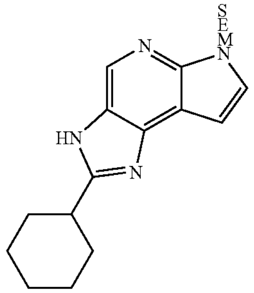

6

To a 100 mL single-neck flask were added 4 (0.681 mg, 2.44 mmol), 5 (274 mg, 2.44 mmol), AcOH (440 mg, 7.34 mmol) and methanol (10 mL), and the mixture was reacted at room temperature for 16 h, concentrated, added with ice water to quench the reaction, extracted with dichloromethane (30 mL×4), washed with saturated saline (30 mL×2), dried over anhydrous sodium sulfate, spin-dried, and purified by column chromatography (dichloromethane:methanol=20:1) to give a target product (640 mg, yield: 70%) in the form of a yellow oil. LC-MS: 371 [M+H]+.

Step 5

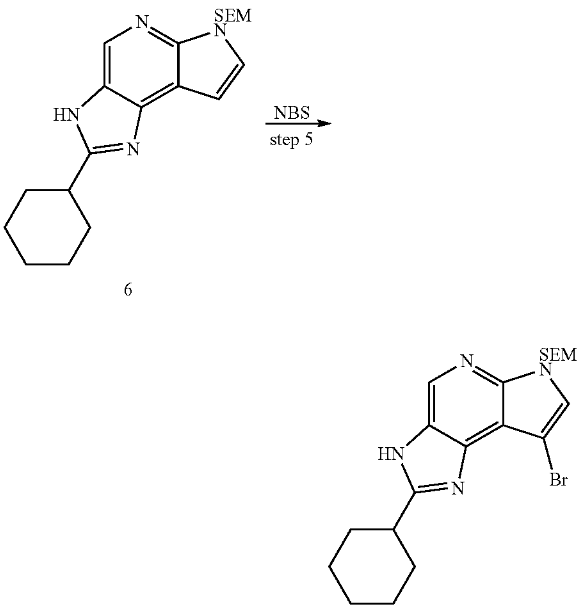

6

7

To a 100 mL single-neck flask were added 6 (640 mg, 1.73 mmol), NBS (369 mg, 2.07 mmol) and DMF (10 mL), and the mixture was reacted at room temperature for 16 h, added with ice water to quench the reaction, extracted with ethyl acetate (20 mL×3), washed with saturated brine (20 mL×3), dried over anhydrous sodium sulfate, spin-dried, and purified by column 15 chromatography (dichloromethane: methanol=20:1) to give a target product (374 mg, yield: 47%) in the form of a yellow oil. LC-MS: 451 [M+H]+.

Step 6

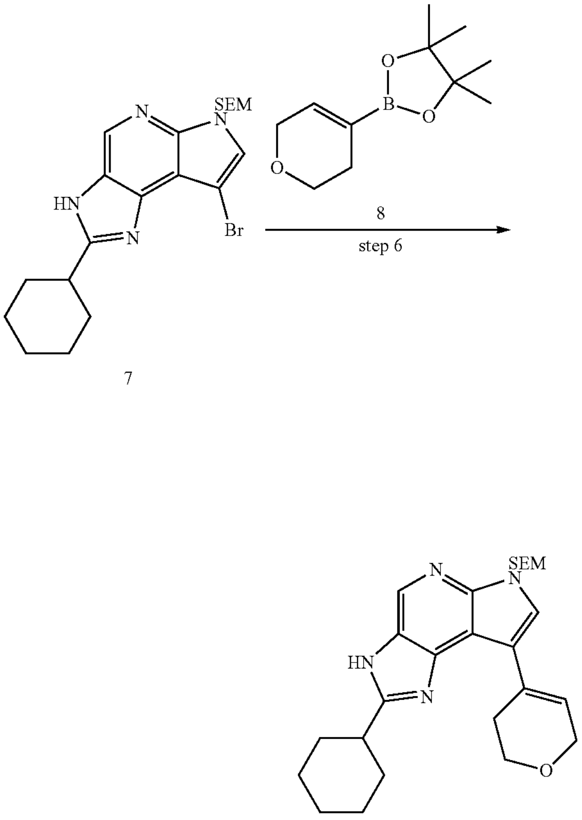

7

8

9

To a 100 mL single-neck flask were added 7 (374 mg, 0.834 mmol), 8 (263 mg, 1.25 mmol), $Pd_2(dppf)Cl_2 \cdot CH_2Cl_2$ (34.4 mg, 0.0417 mmol), $K_2CO_3$ (345.6 mg, 2.05 mmol), dioxane (10 mL) and $H_2O$ (2 mL), and the mixture was reacted at 80° C. for 16 h under nitrogen atmosphere, added with ice water to quench the reaction, extracted with ethyl acetate (50 mL×3), washed with saturated brine (50 mL×2), dried over anhydrous sodium sulfate, spin-dried, and purified by TLC (petroleum ether:ethyl acetate=1:1) to give a target product (130 mg, yield: 34.6%) in the form of a yellow oil. LC-MS: 453 [M+H]+.

Step 7

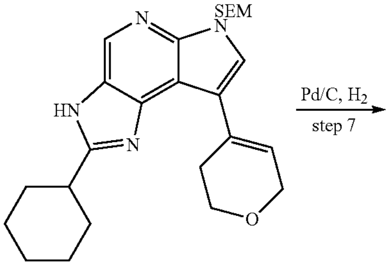

9

-continued

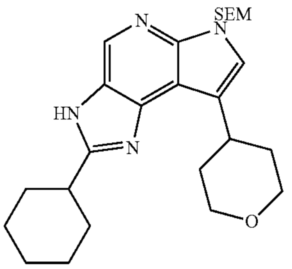

10

To a 100 mL single-neck flask were added 9 (130 mg, 0.287 mmol), $Pd(OH)_2$ (52 mg) and THE (5 mL), the mixture was reacted at room temperature for 16 h under hydrogen atmosphere, and filtered under vacuum, and the filtrate was concentrated, and purified by TLC (dichloromethane:methanol=20:1) to give a target product (45 mg, yield: 34.6%) in the form of a yellow oil. LC-MS: 455 $[M+H]^+$.

Step 8

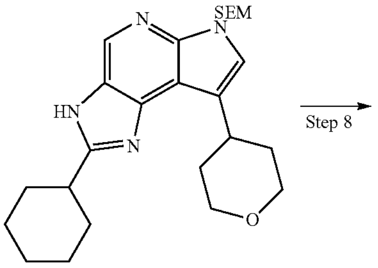

10

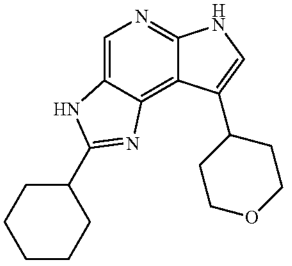

R

To a 100 mL single-neck flask were added 10 (45 mg, 0.0991 mmol), TFA (0.5 mL) and DCM (2.5 mL), and the mixture was reacted at room temperature for 16 h, and concentrated to give a crude product (35 mg) in the form of a yellow oil. The crude product was added with $NH_3H_2O$ (0.5 mL) and dioxane (3 mL), reacted at 70° C. for 16 h, concentrated, and subjected to high pressure liquid chromatography to give a target product (5.0 mg, yield: 20.8%) in the form of a white solid. LC-MS: 325 $[M+H]^+$, 1H NMR (400 MHz, DMSO) δ 11.52 (s, 1H), 8.49 (s, 1H), 8.14 (s, 1H), 7.21 (s, 1H), 3.96 (s, 2H), 3.59 (s, 2H), 3.30 (s, 1H), 3.01 (s, 1H), 2.08 (s, 2H), 1.99 (s, 2H), 1.85 (d, J=6.3 Hz, 2H), 1.74 (s, 2H), 1.65 (s, 2H), 1.45-1.41 (m, 3H), 1.31 (d, J=3.2 Hz, 1H).

Example 19: Preparation of IRAK4 Kinase Inhibitor

The synthetic route is as follows:

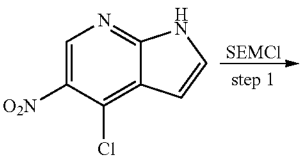

1

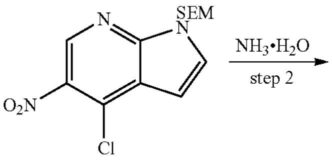

2

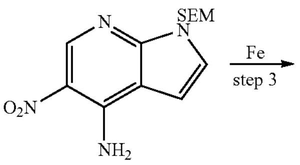

3

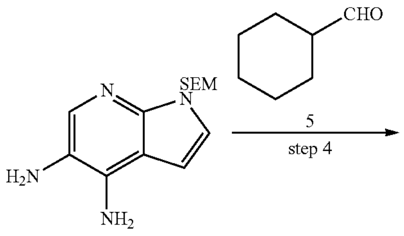

4

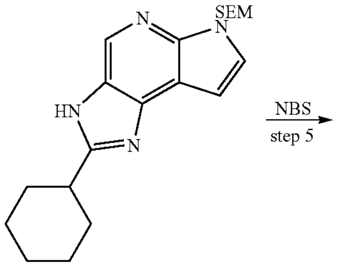

6

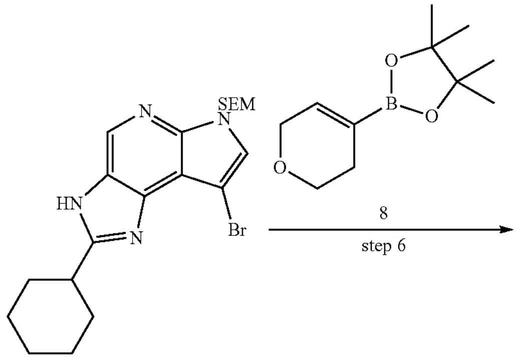

7

-continued

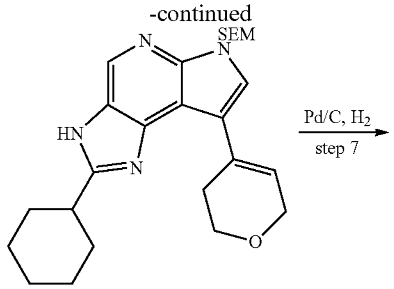

9

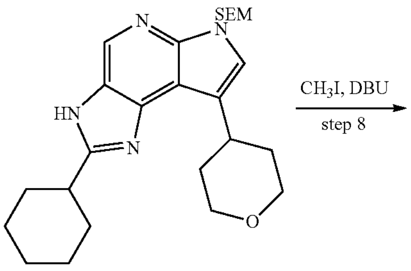

10

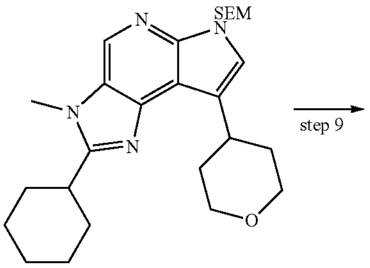

11

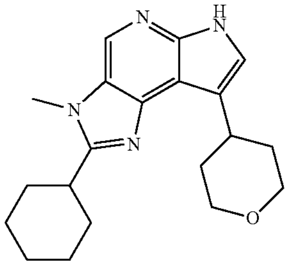

S

Step 1

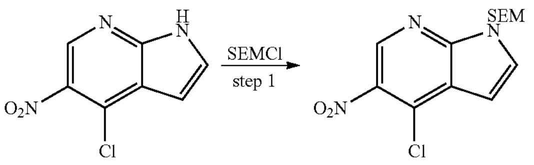

1 2

In a 500 mL three-neck flask, 1 (5.08 g, 25.7 mmol) was dissolved in DMF (70 mL), cooled to 0° C. in an ice bath, and added with NaH (1.64 g, 41.1 mmol). After stirring at room temperature for 1 h, the mixture was added with SEM-Cl (5.14 g, 3.08 mmol), reacted at room temperature for 16 h, added with ice water to quench the reaction, extracted with ethyl acetate (100 mL×3), washed with saturated brine (100 mL×3), dried over anhydrous sodium sulfate, spin-dried, and purified by column chromatography (petroleum ether:ethyl acetate=1:1) to give a target product (5.38 g, yield: 64%) in the form of a yellow oil. LC-MS: 328[M+H]$^+$.

Step 2

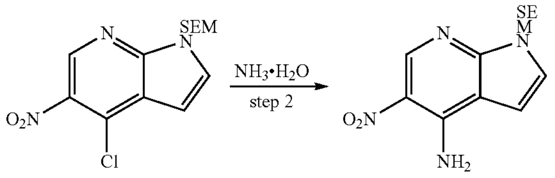

2 3

To a 500 mL single-neck round-bottom flask were added 2 (5.38 g, 16.4 mmol), $NH_3H_2O$ (40 mL) and dioxane (40 mL), and the mixture was reacted at 80° C. for 18 h, concentrated, added with ice water to quench the reaction, extracted with dichloromethane (100 mL×3), washed with saturated brine (100 mL×3), dried over anhydrous sodium sulfate, spin-dried, and purified by column chromatography (petroleum ether:ethyl acetate=10:1) to give a target product (4.48 g) in the form of a yellow solid. LC-MS: 309 [M+H]$^+$.

Step 3

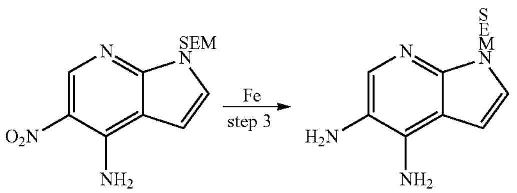

3 4

In a 500 mL single-neck flask, 3 (4.48 g, 14.5 mmol), Fe (4.07 g, 72.7 mmol) and $NH_4Cl$ (3.85 g, 72.7 mmol) were added to ethanol/water (60 mL/20 mL), and the mixture was reacted at 80° C. for 16 h, filtered under vacuum, concentrated, and purified by column chromatography (dichloromethane:methanol=50:1) to give a target product (3.4 g) in the form of a yellow solid. LC-MS: 279 [M+H]$^+$.

Step 4

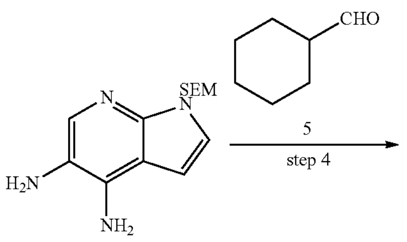

4

-continued

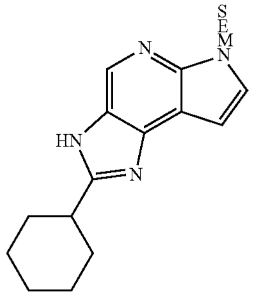

6

To a 250 mL single-neck flask were added 4 (3 g, 10.7 mmol), 5 (1.2 g, 10.7 mmol), AcOH (1.94 g, 32.3 mmol) and methanol (50 mL), and the mixture was reacted at room temperature for 16 h, concentrated, added with ice water to quench the reaction, extracted with dichloromethane (100 mL×4), washed with saturated saline (100 mL×2), dried over anhydrous sodium sulfate, spin-dried, and purified by column chromatography (dichloromethane:methanol=100:1) to give a target product (2.36 g, yield: 70%) in the form of a white solid. LC-MS: 371 $[M+H]^+$.

Step 5

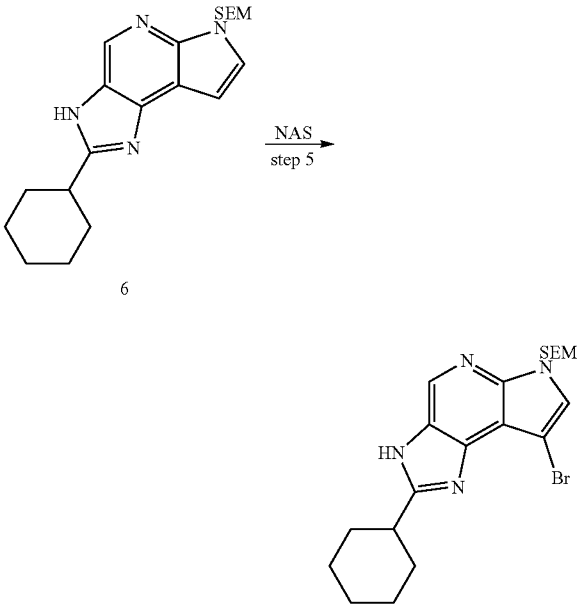

6

7

To a 250 mL single-neck flask were added 6 (2.36 g, 6.36 mmol), NBS (1.36 g, 7.64 mmol) and DMF (30 mL), and the mixture was reacted at room temperature for 16 h, added with ice water to quench the reaction, extracted with ethyl acetate (80 mL×3), washed with saturated brine (80 mL×3), dried over anhydrous sodium sulfate, spin-dried, and purified by column chromatography (dichloromethane:methanol=80:1) to give a target product (2.7 g, yield: 96%) in the form of a yellow oil. LC-MS: 451 $[M+H]^+$.

Step 6

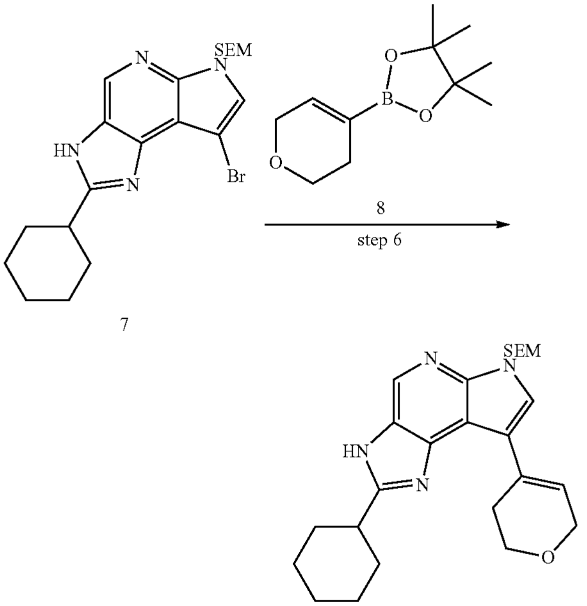

7

8

9

To a 250 mL single-neck flask were added 7 (3.6 g, 8.03 mmol), 8 (2.5 mg, 12.0 mmol), $Pd_2(dppf)Cl_2 \cdot CH_2Cl_2$ (331 mg, 0.401 mmol), $K_2CO_3$ (3.3 g, 24.1 mmol), dioxane (50 mL) and $H_2O$ (10 mL), and the mixture was reacted at 80° C. for 16 h under nitrogen atmosphere, spin-dried, and purified by column chromatography (petroleum ether:ethyl acetate=1:1) to give a target product (841 mg, yield: 31%) in the form of a yellow oil. LC-MS: 453 $[M+H]^+$.

Step 7

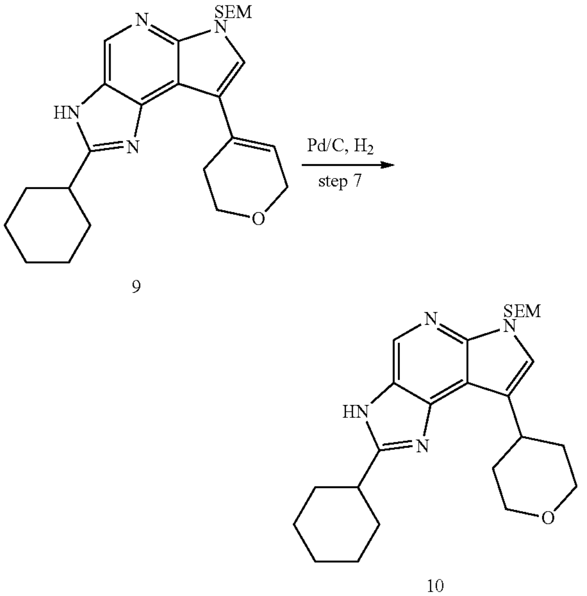

9

10

To a 250 mL single-neck flask were added 9 (841 mg, 1.86 mmol), $Pd(OH)_2$ (400 mg) and THE (15 mL), the mixture was reacted at room temperature for 16 h under hydrogen atmosphere, and filtered under vacuum, and the filtrate was concentrated to give a target product (723 mg, yield: 85.6%) in the form of a yellow oil. LC-MS: 455 $[M+H]^+$.

Step 8

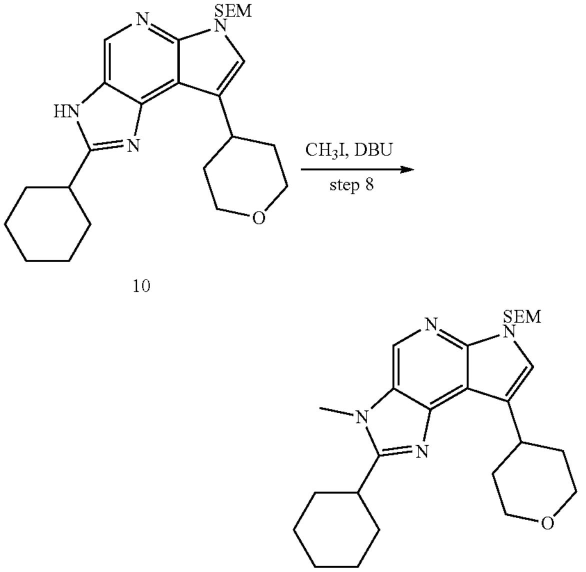

10

11

In a 100 mL three-neck flask, 10 (150 mg, 0.330 mmol) was dissolved in DMF (2.5 mL), cooled to 0° C. in an ice bath, and added with NaH (19.8 mg, 0.495 mmol). After stirring at room temperature for 30 min, the mixture was added with $CH_3I$ (51.6 mg, 0.363 mmol) and reacted at room temperature for 1 h, added with ice water to quench the reaction, extracted with ethyl acetate (50 mL×3), washed with saturated brine (50 mL×3), dried over anhydrous sodium sulfate, spin-dried, and purified by column chromatography (petroleum ether:ethyl acetate=1:1) to give a target product (100 mg, yield: 97%) in the form of a white solid. LC-MS: 469 $[M+H]^+$.

Step 9

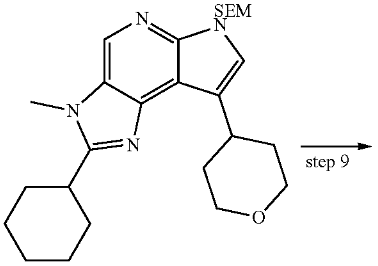

11

-continued

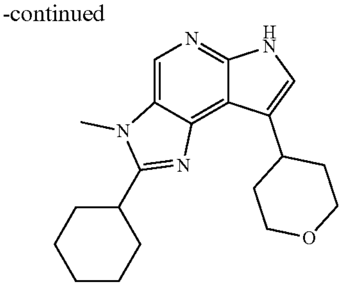

S

To a 100 mL single-neck flask were added 11 (100 mg, 0.213 mmol), TFA (1 mL) and DCM (3 mL), and the mixture was reacted at room temperature for 16 h, and concentrated to give a crude product (90 mg) in the form of a yellow oil. The crude product was added with $NH_3H_2O$ (1 mL) and dioxane (5 mL), reacted at 70° C. for 16 h, concentrated, and subjected to high pressure liquid chromatography to give a target product (3.0 mg) in the form of a white solid. LC-MS: 469 $[M+H]^+$. 1H NMR (400 MHz, DMSO) δ 12.03 (s, 1H), 8.82 (s, 1H), 7.37 (d, J=1.9 Hz, 1H), 3.99 (s, 3H), 3.97 (d, J=4.1 Hz, 2H), 3.56 (t, J=10.9 Hz, 2H), 3.34 (s, 1H), 3.19 (s, 1H), 2.09 (d, J=11.6 Hz, 2H), 1.99 (d, J=12.8 Hz, 2H), 1.89-1.81 (m, 4H), 1.74 (s, 2H), 1.51-1.33 (m, 4H).

Example 20: Enzymatic Experiment for IRAK4 Kinase Inhibitor

Experimental materials: IRAK4 recombinant human proteases, purchased from Carna (Cat #09-145); ATP, purchased from Sigma (Cat #A7699-5G); Compound 26, purchased from Merck Millipore (Cat #531237); and HTRF KinEASE-STK Si kit, purchased from Cisbio (Cat #62ST1PEC).

Experimental method: Phosphorylation of STK1 can be detected using an HTRF assay kit. The experimental reaction was carried out in a 384-well plate (Greiner, Cat #784075) with a total reaction system of 20 uL. The reaction system mainly comprised 1× kinase buffer, 1 M $MgCl_2$, 1 M DTT, 0.4 uM STK1 and 80 uM ATP. The target product prepared in Example 1 was serially diluted with DMSO at 10 concentration points, and transferred to an experimental assay plate at 100 nL. The reaction was started after 6 nM IRAK4 was added and stopped by adding a detection reagent (0.25×STK Antibody-Cryptate, 25 nM Streptavidin-XL665) after being in process at 37° C. for 90 min. After standing at room temperature for 60 min, an FRET signal was read on a Spark 10M or envision plate reader. (HTRF 665/615=signal value at 665 nm/signal value at 615 nm).

Data analysis: signal ratio (665/615) was converted to a percent rejection.

$$\text{Inhibition } \%=(\text{max}-\text{sample})/(\text{max}-\text{min})\times 100.$$

"min" represents a ratio of signal values (665/615) for control well without enzyme, and "max" represents a ratio of signal values (665/615) for control well with DMIC. 5C50 values for compounds were calculated by XLFit in the Excel.

$$Y=\text{Bottom}+(\text{Top}-\text{Bottom})/(1+(\text{IC50}/X)^\wedge\text{HillSlope}) \quad \text{Equation:}$$

Result: the IC50 of the compounds determined according to the above experimental method is as follows:
TABLE 1
| IC50 values of compounds | |
|---|---|
| Compound | Relative IC50 (nM) |
| 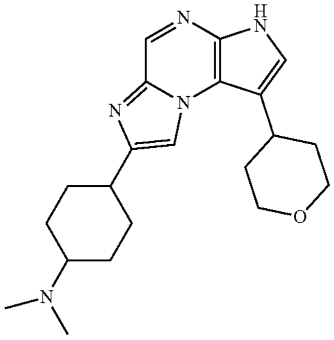 A | IC50 < 100 |
| 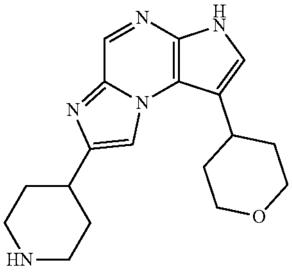 B | IC50 < 100 |
| 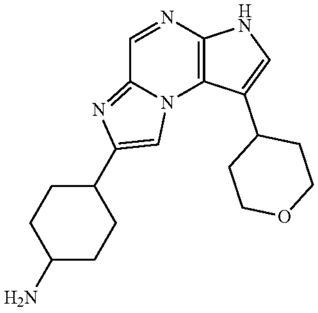 C | IC50 < 100 |
| 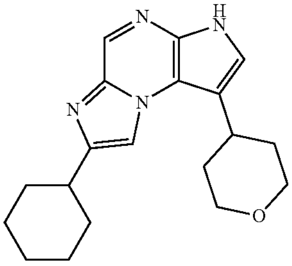 D | IC50 < 100 |
TABLE 1-continued
| IC50 values of compounds | |
|---|---|
| Compound | Relative IC50 (nM) |
| 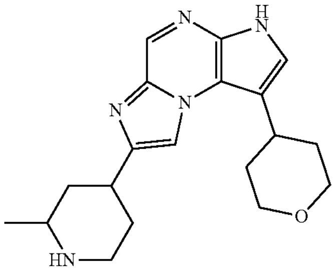 E-1 | 100 < IC50 < 1,000 |
| 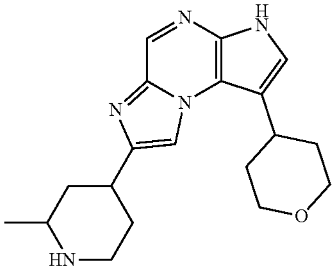 E-2 | 100 < IC50 < 1,000 |
| 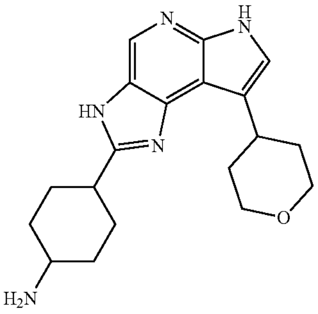 F-1 | IC50 < 100 |
| 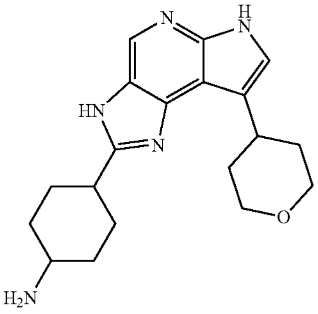 F-2 | IC50 < 100 |

TABLE 1-continued
IC50 values of compounds
| Compound | Relative IC50 (nM) |
| --- | --- |
| 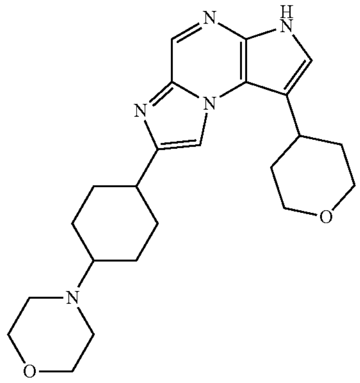 G | 100 < IC50 < 1000 |
| 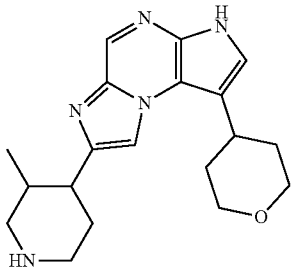 H | IC50 < 100 |
| 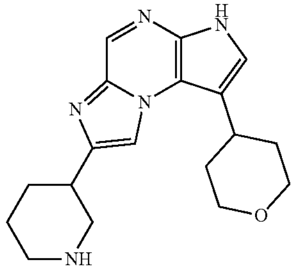 I | IC50 < 100 |
| 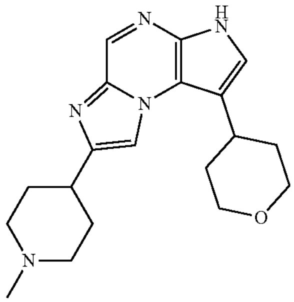 J | 100 < IC50 < 1000 |
TABLE 1-continued
IC50 values of compounds
| Compound | Relative IC50 (nM) |
| --- | --- |
| 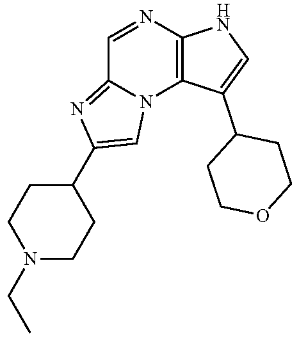 K | 100 < IC50 < 1000 |
| 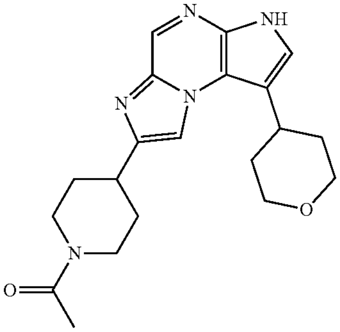 L | IC50 > 1000 |
| 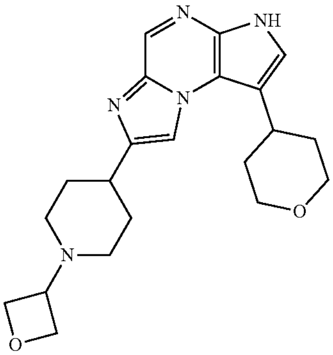 M | IC50 > 1000 |
| 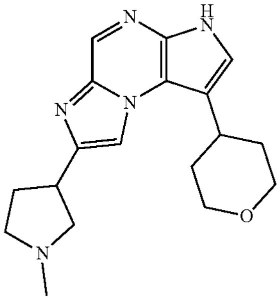 N | 100 < IC50 < 1000 |

TABLE 1-continued

| IC50 values of compounds | |
|---|---|
| Compound | Relative IC50 (nM) |
| 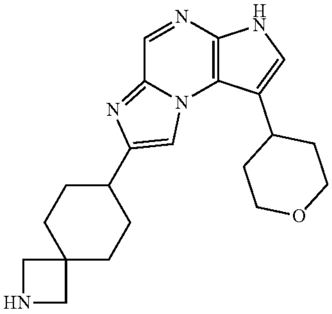 O | IC50 < 100 |
| 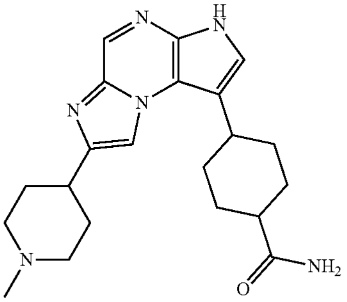 P | IC50 > 1000 |
| 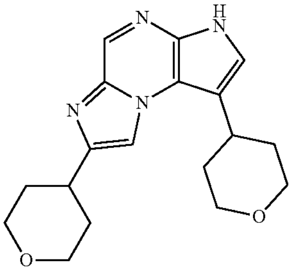 Q | 100 < IC50 < 1000 |
| 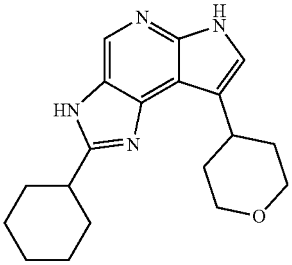 R | 100 < IC50 < 1000 |
| 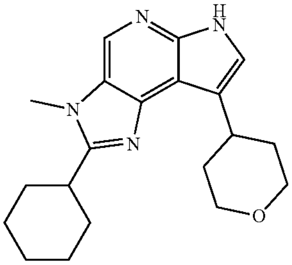 S | 100 < IC50 < 1000 |

Finally, it should be noted that, the above examples are only used to illustrate the technical solutions of the present invention, and should not limit the same; although the present invention is described in detail with reference to the examples described above, it will be understood by those skilled in the art that, the technical solutions in the examples described above can still be modified, or some or all of the technical features can be equivalently replaced; and these modifications or replacements do not make the technical solutions corresponding thereto depart from the scope of the technical solutions in the examples of the present invention.

The invention claimed is:

1. A compound, or a pharmaceutically acceptable salt thereof, wherein the compound has the following structural formula:

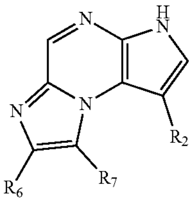 , or 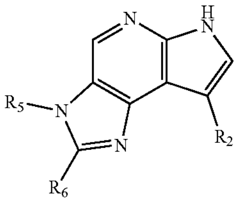 , wherein, $R_2$ is selected from

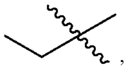 , 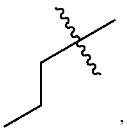 , 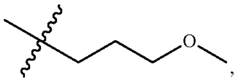 , 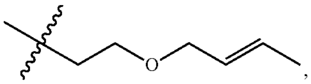 , 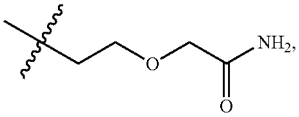 , 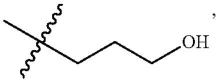 , 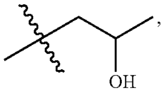 , 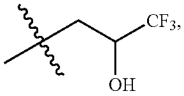

-continued
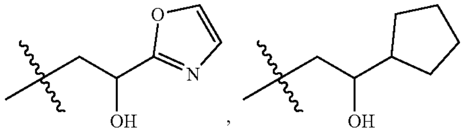
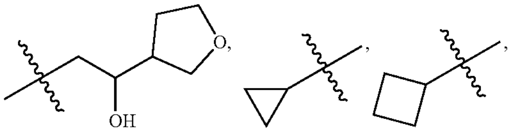
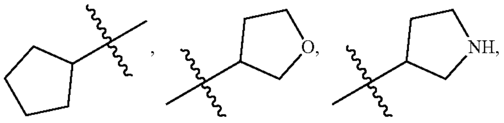
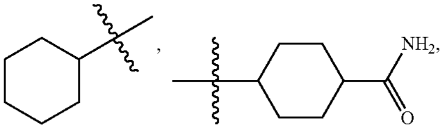
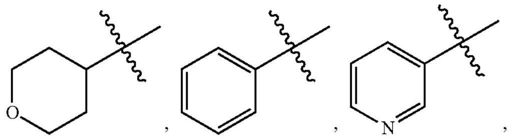
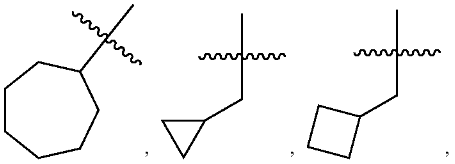
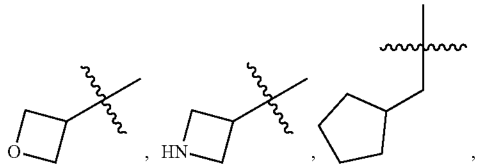
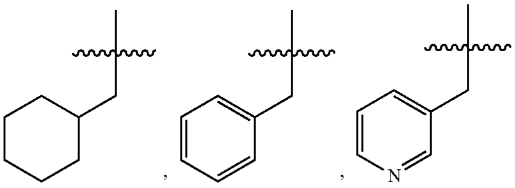
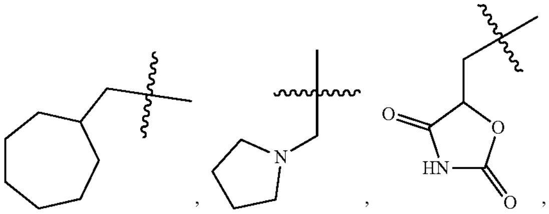
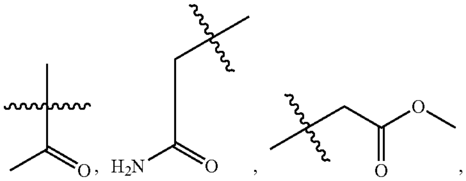
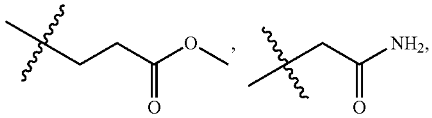
-continued
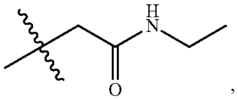, 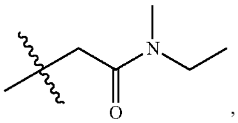,
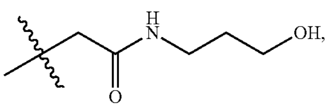 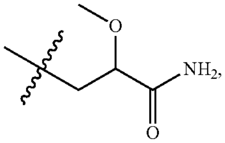
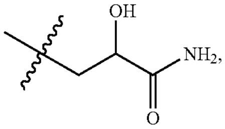 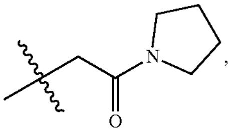,
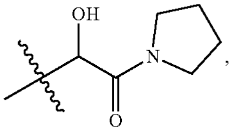, 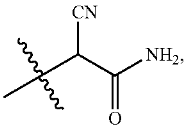
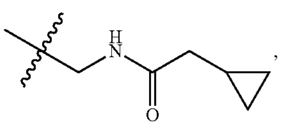, 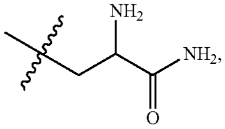
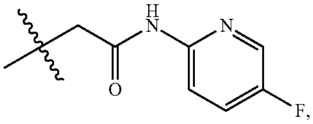
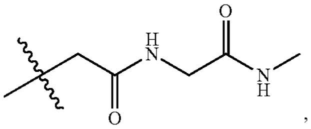,
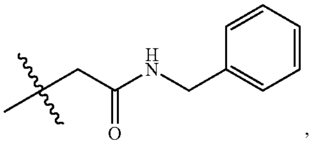,
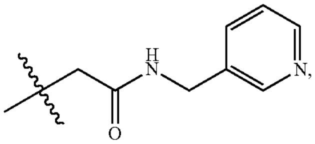 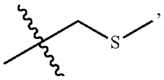
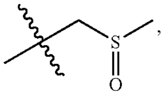 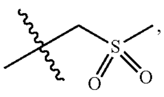 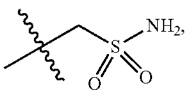
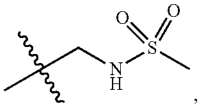, 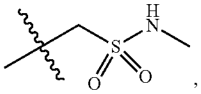,
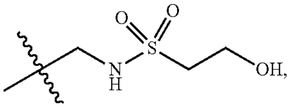 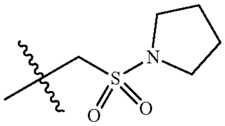 and -continued
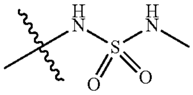;
$R_5$ is selected from —H, —$CH_3$,
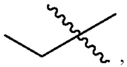, 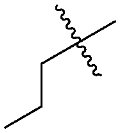, 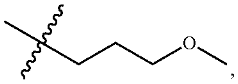,
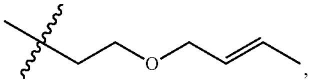,
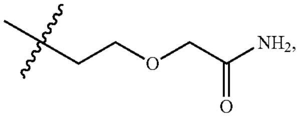, 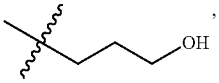,
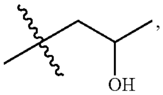, 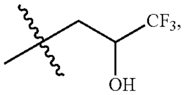
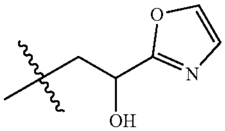, 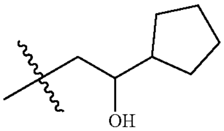,
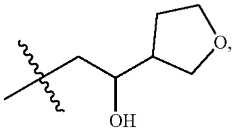, 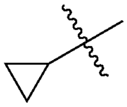, 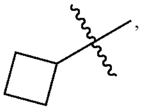,
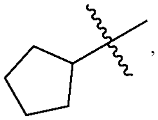, 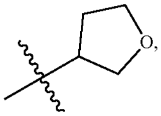, 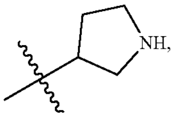
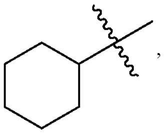, 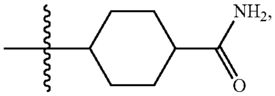
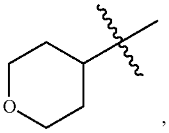, 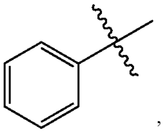, 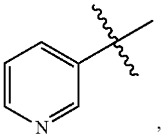,
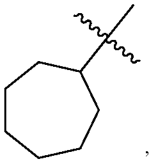, 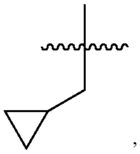, 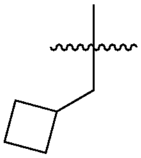,
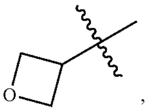, 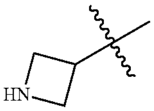, 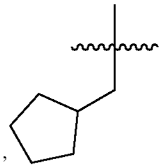,
-continued
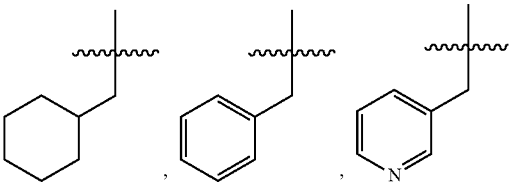,
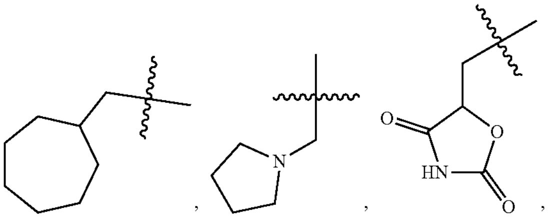,
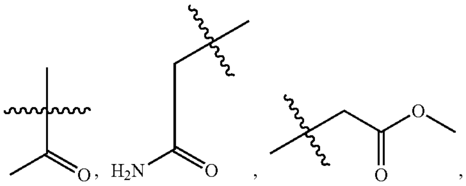,
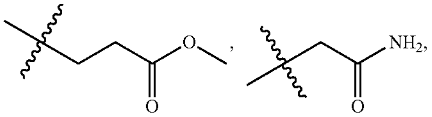
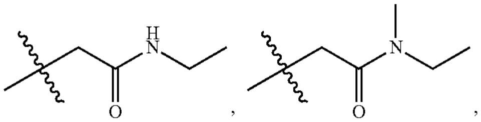,
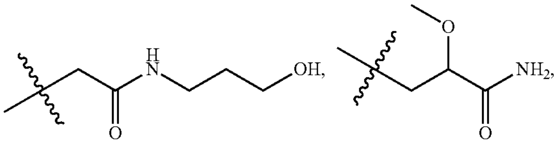
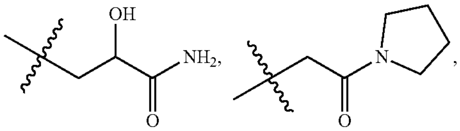,
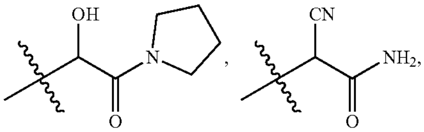
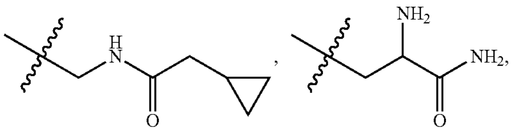
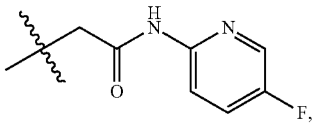
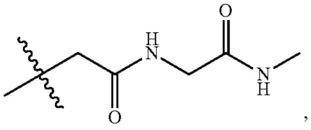, -continued
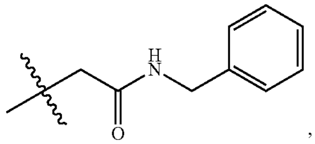
,
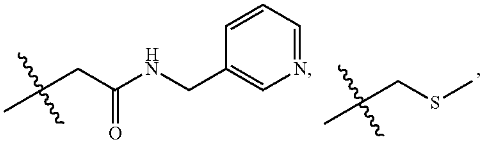
,
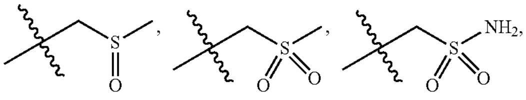
,
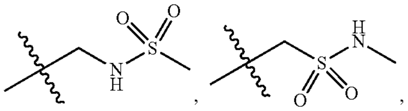
,
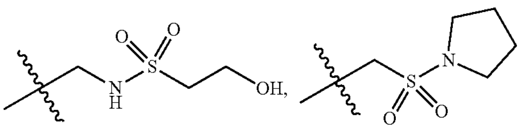
and
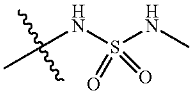
;
R$_6$ is selected from —$CF_3$, —$CHF_2$, —$CH_2F$, —$CH_2CF_3$, —CN,
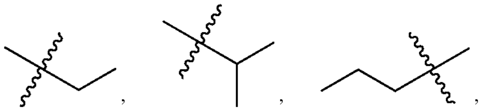
,
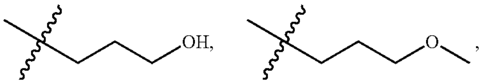
,
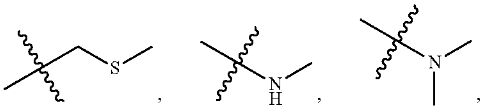
,
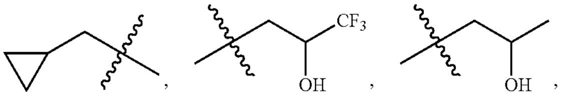
,
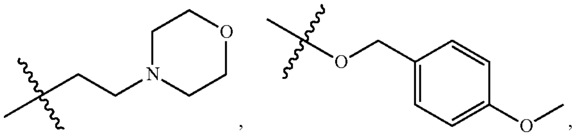
,
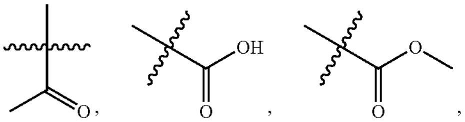
,
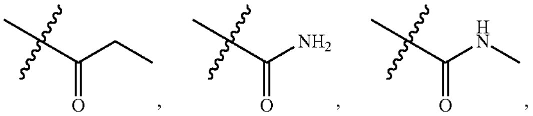
,
-continued
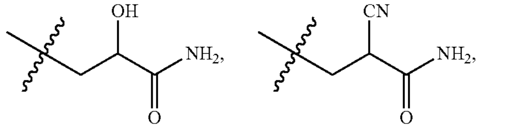
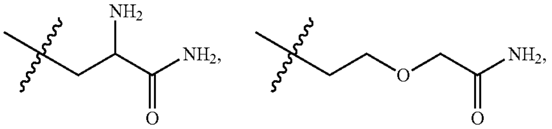
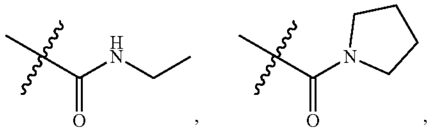
,
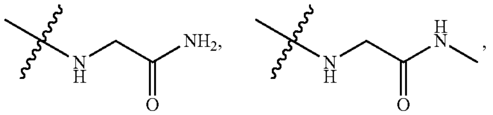
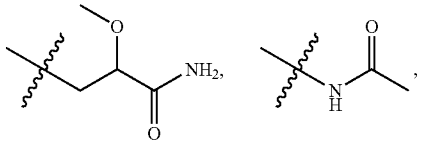
,
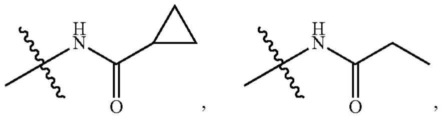
,
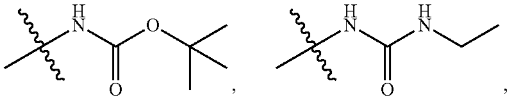
,
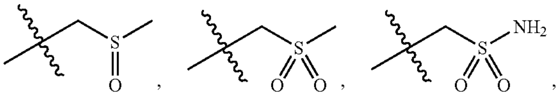
,
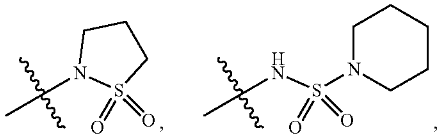
,
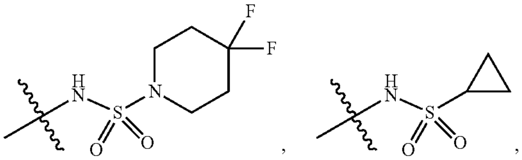
,
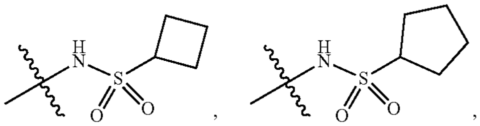
,
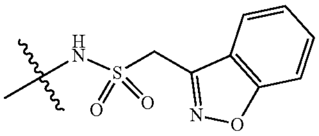
,
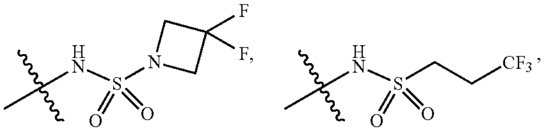

-continued
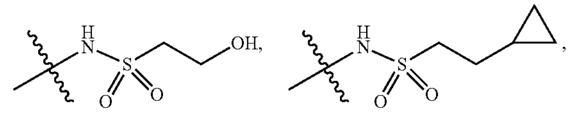
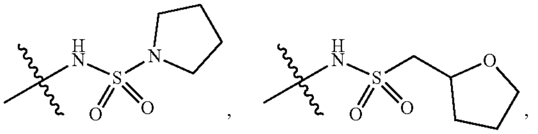
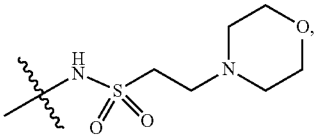
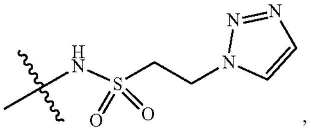
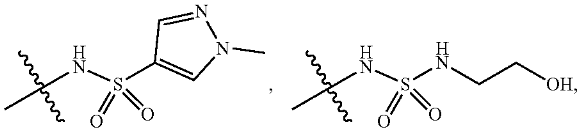
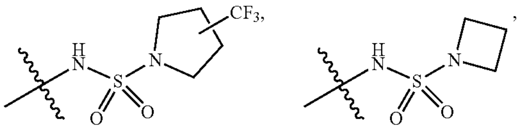
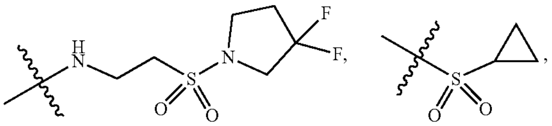
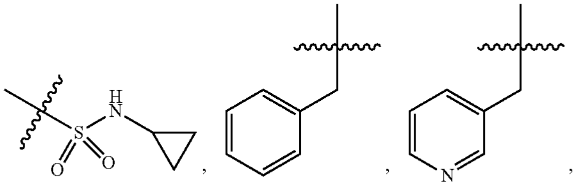
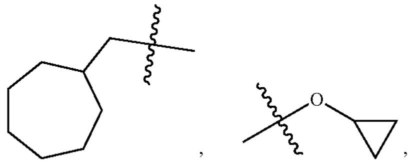
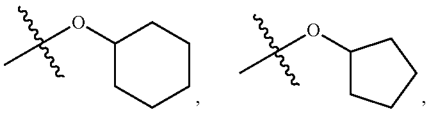
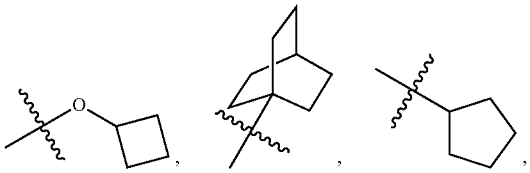
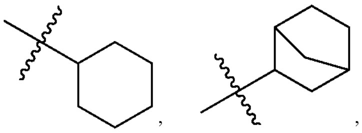
-continued
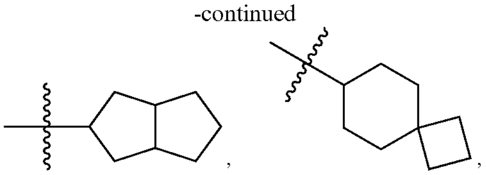
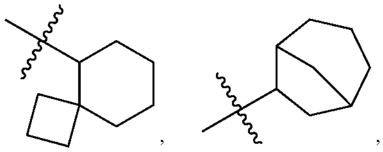
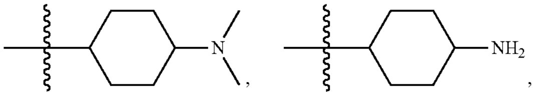
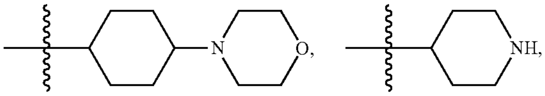
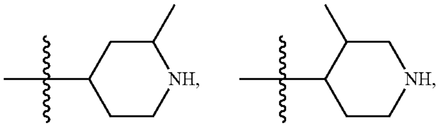
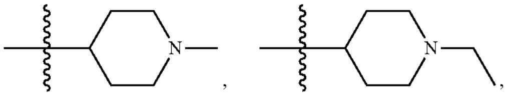
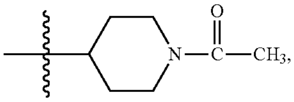
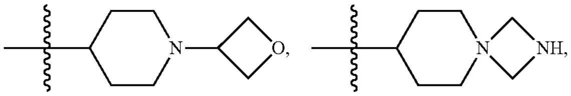
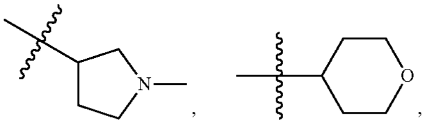
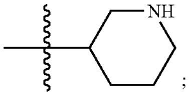
and
$R_7$ is —H.
2. The compound, or the pharmaceutically acceptable salt thereof according to claim 1, wherein
$R_2$ is selected from
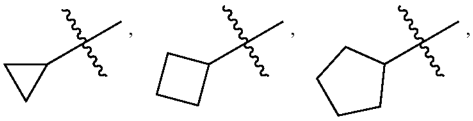
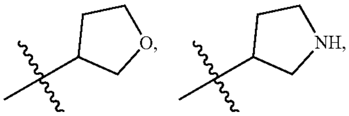
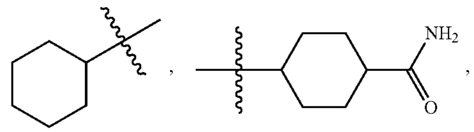

-continued
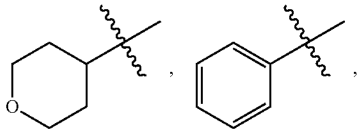
,
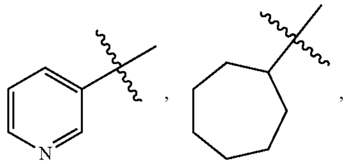
,
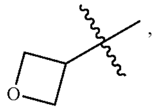
, and
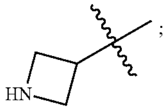
;
$R_5$ is selected from —H, —$CH_3$,
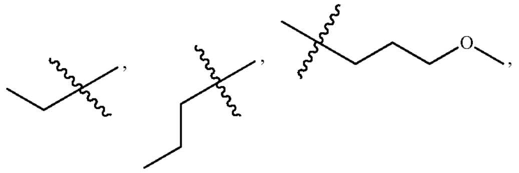
,
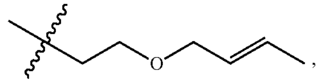
,
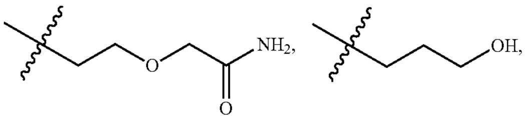
,
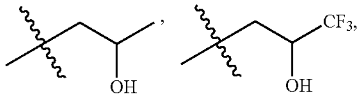
,
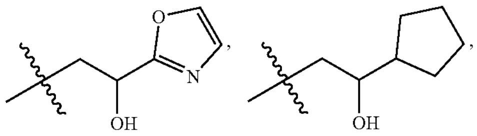
,
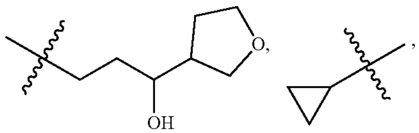
,
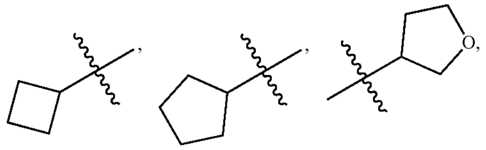
,
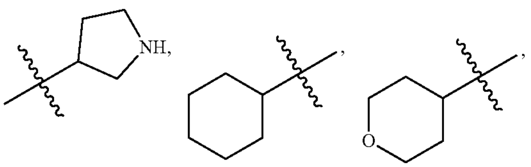
,
-continued
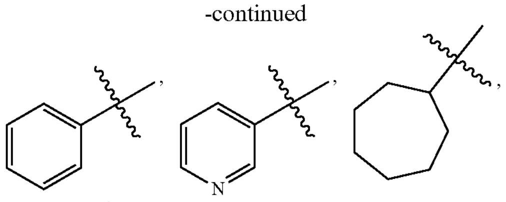
,
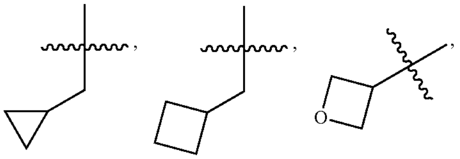
,
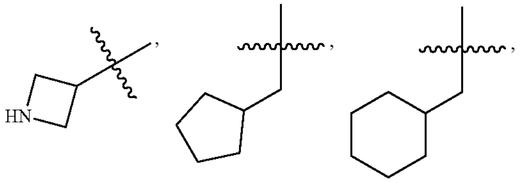
,
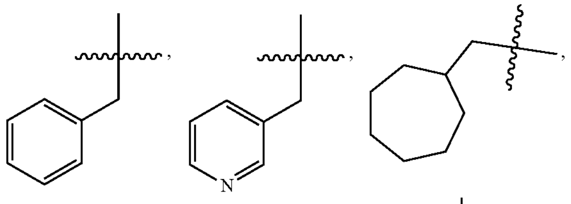
,
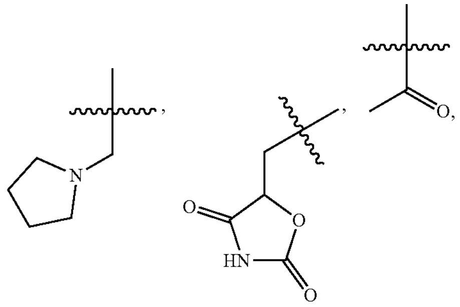
,
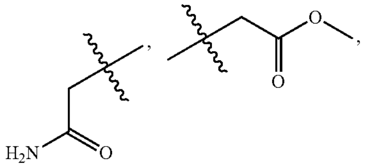
,
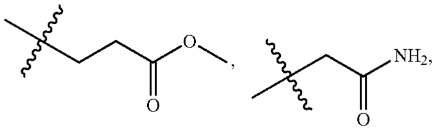
,
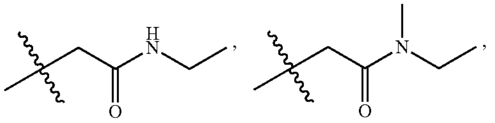
,
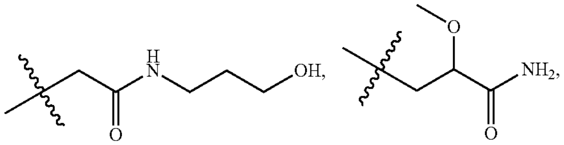
,
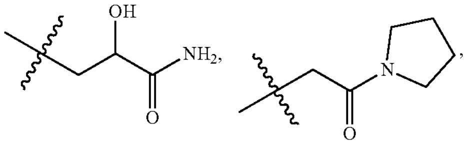
, -continued
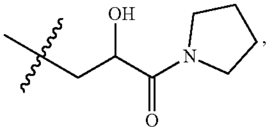, 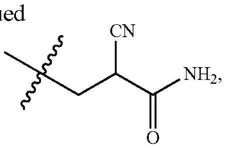
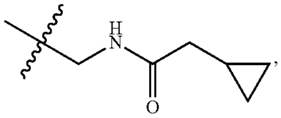, 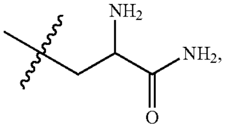
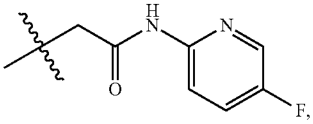
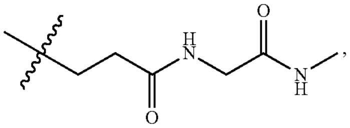,
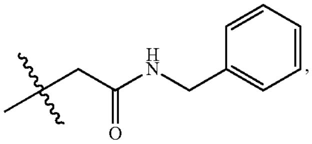,
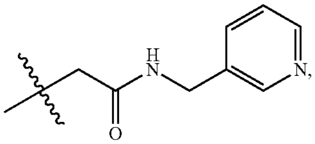, 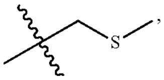,
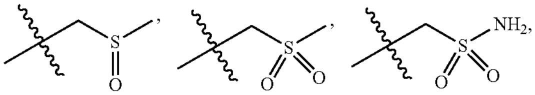
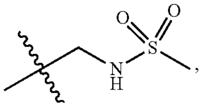, 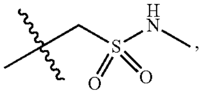,
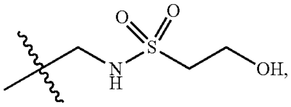 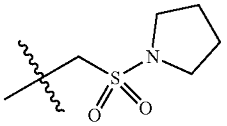 and
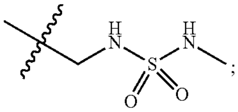;
R$_6$ is selected from
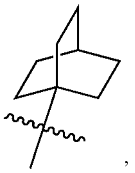, 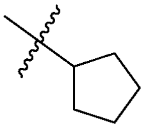, 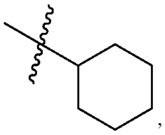,
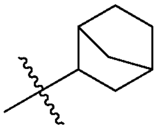, 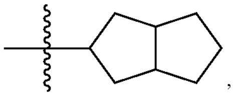,
-continued
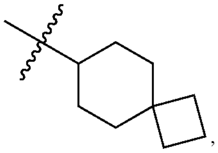, 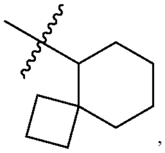,
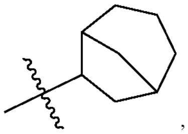, 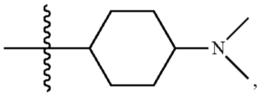,
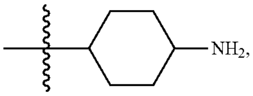 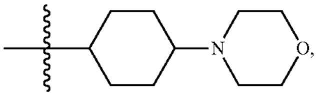
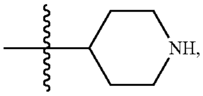 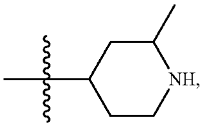
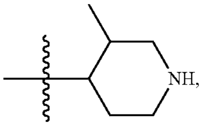 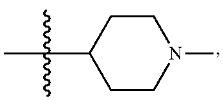
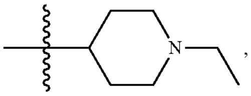, 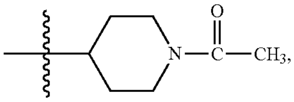
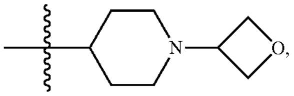 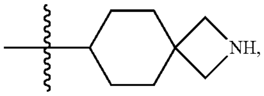
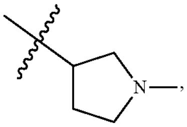 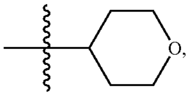
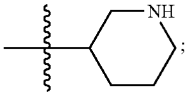;
and
R$_7$ is —H.
3. The compound, or the pharmaceutically acceptable salt thereof according to claim 2,
wherein:
R$_2$ is
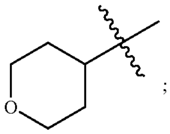 [SMILES: *C1CCOCC1];
R$_5$ is —H or —CH$_3$;
R$_6$ is selected from
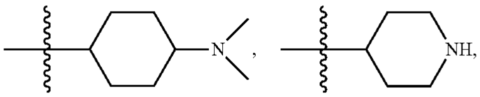

-continued
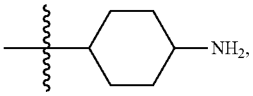,
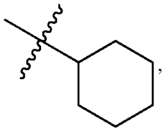,
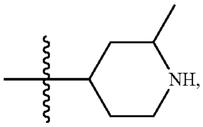,
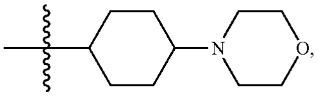,
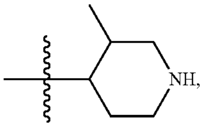,
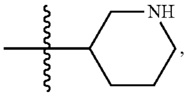,
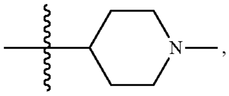,
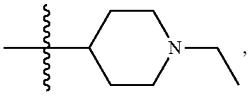,
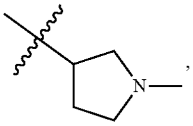,
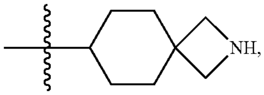, and
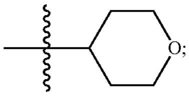;
and
$R_7$ is —H.
4. A pharmaceutical composition, comprising the compound, or the pharmaceutically acceptable salt thereof according to claim 1, and further comprising a pharmaceutically acceptable excipient.
5. A compound, or a pharmaceutically acceptable salt thereof, wherein the compound is selected from the following structures:
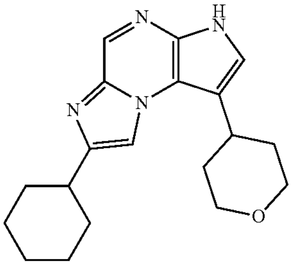,
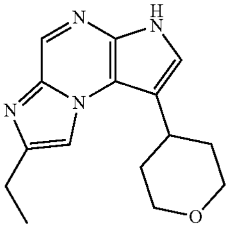,
-continued
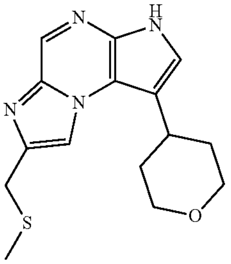,
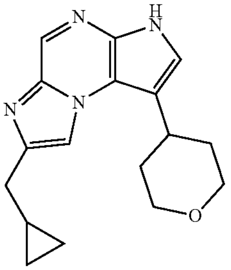,
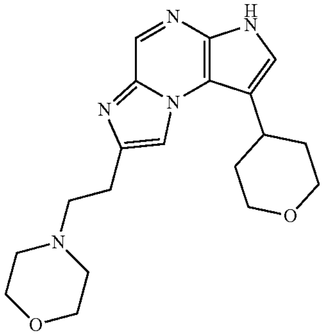,
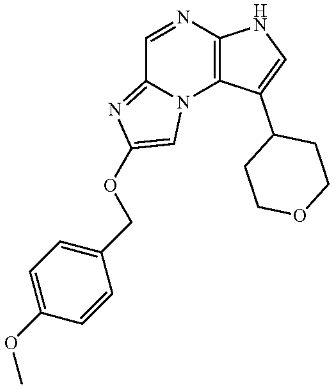,
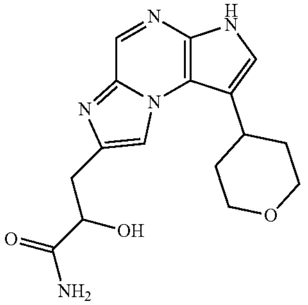, -continued
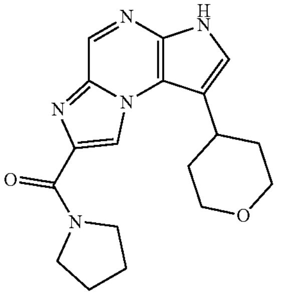
,
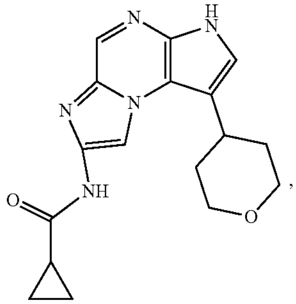
,
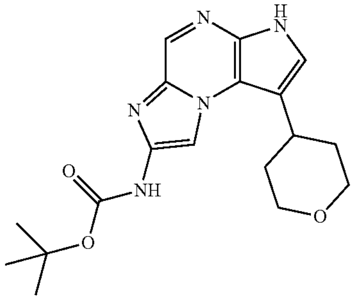
,
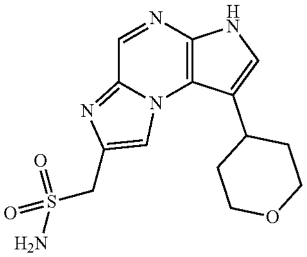
,
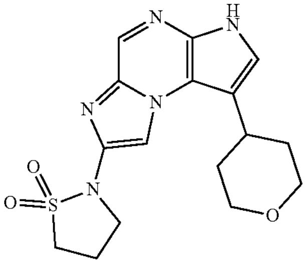
,
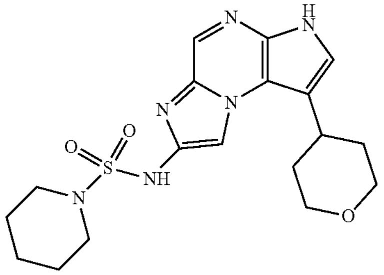
,
-continued
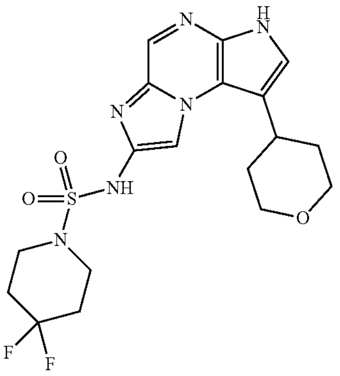
,
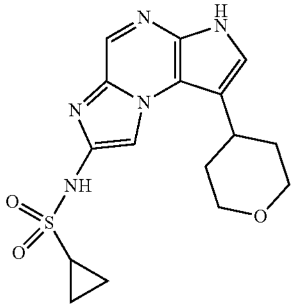
,
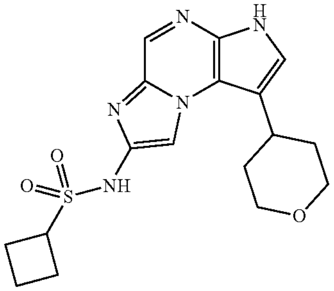
,
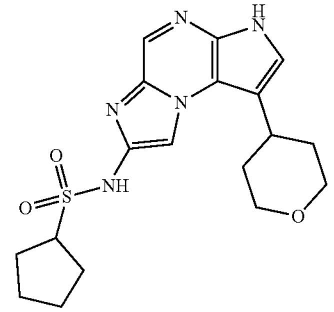
,
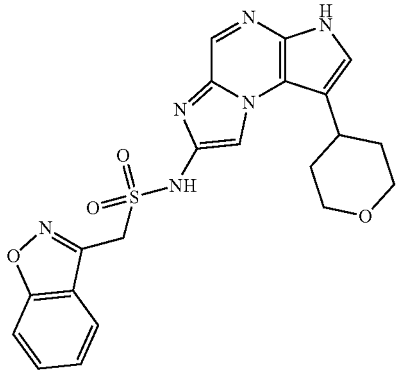
, -continued
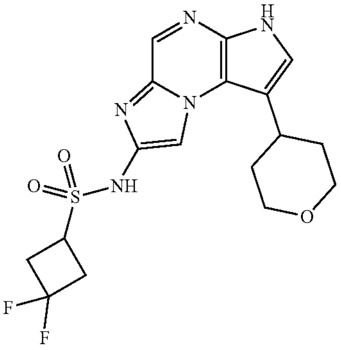
,
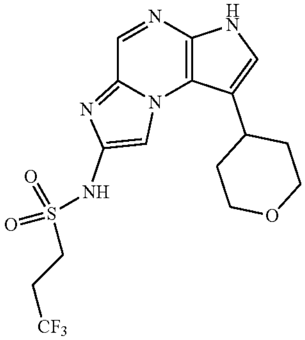
,
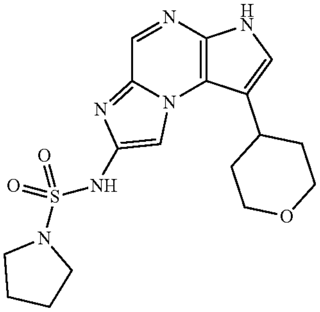
,
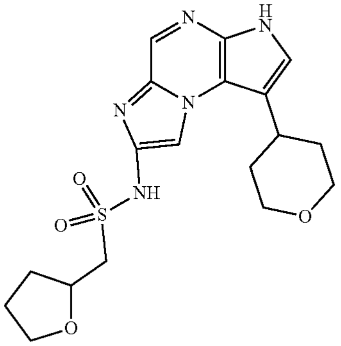
,
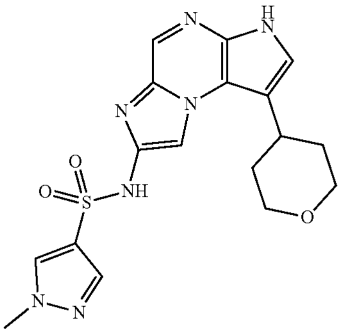
,
-continued
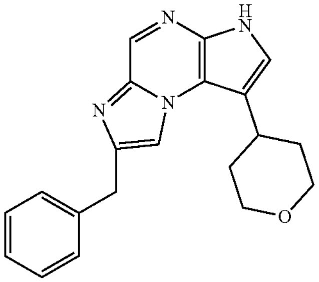
,
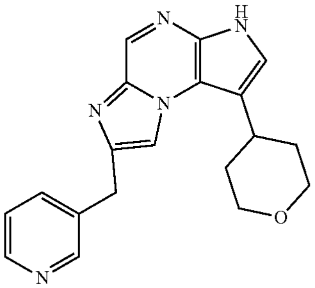
,
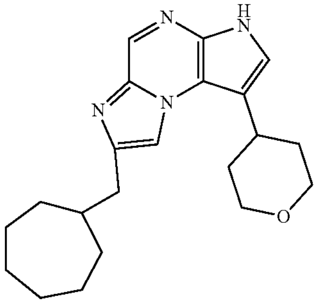
,
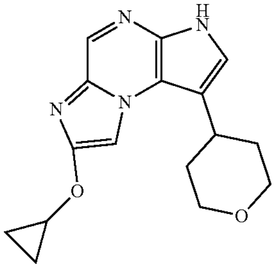
,
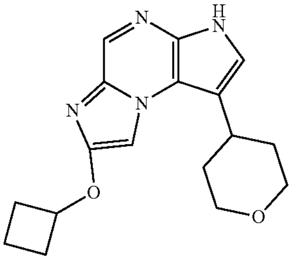
,
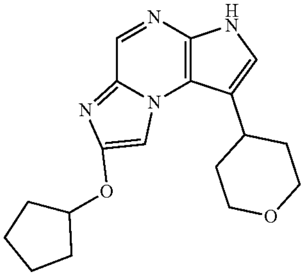
, -continued
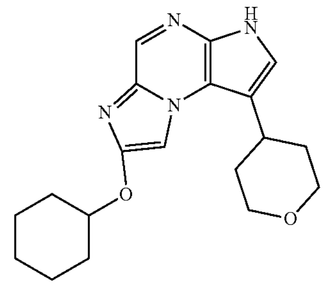
,
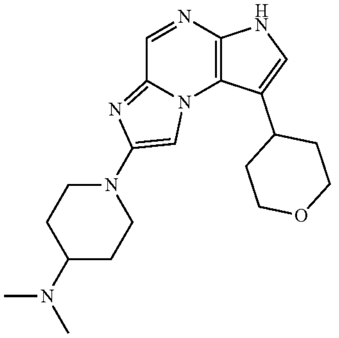
,
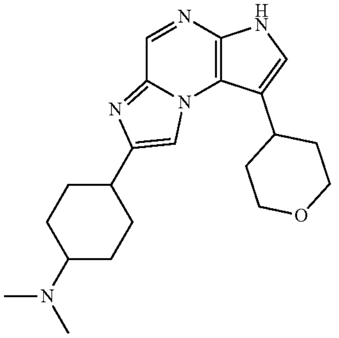
,
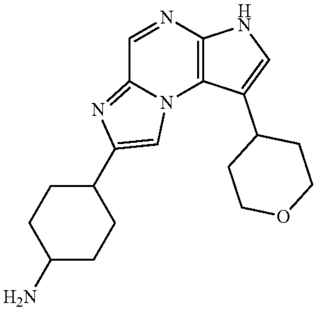
,
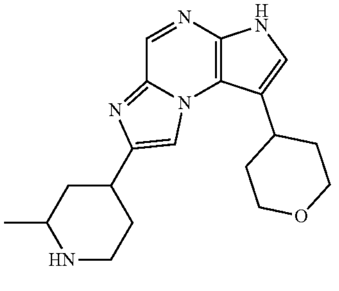
,
-continued
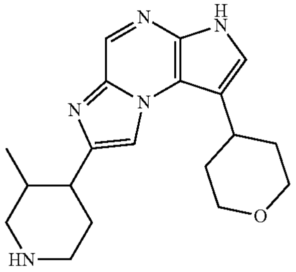
,
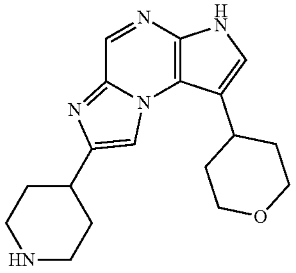
,
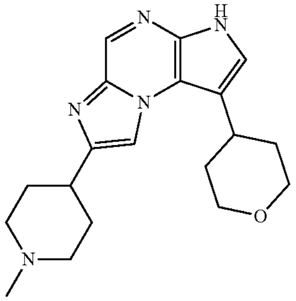
,
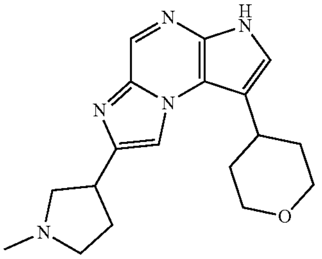
,
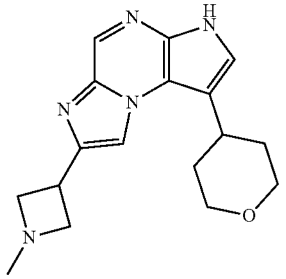
,
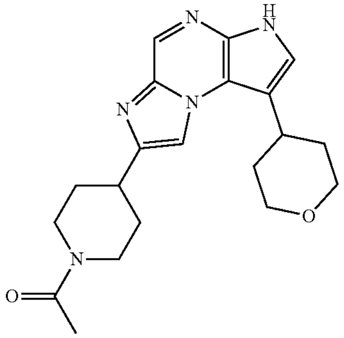
, -continued
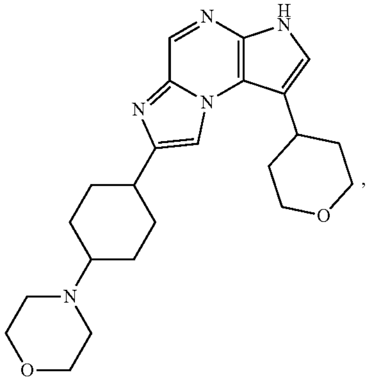
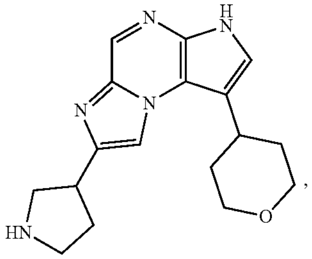
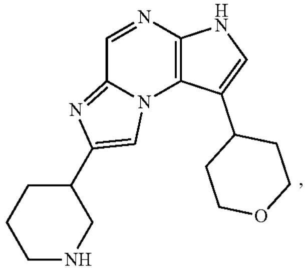
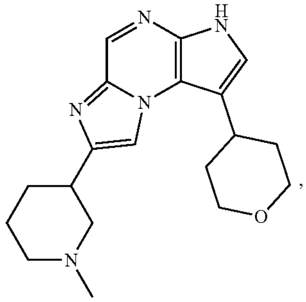
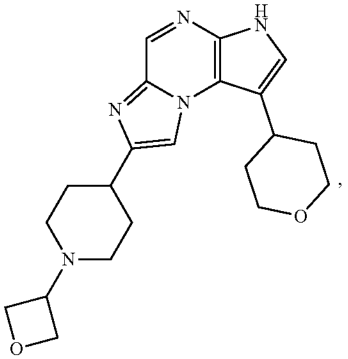
-continued
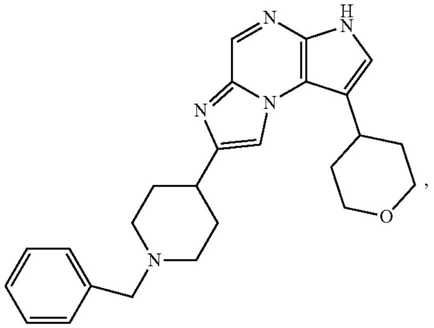
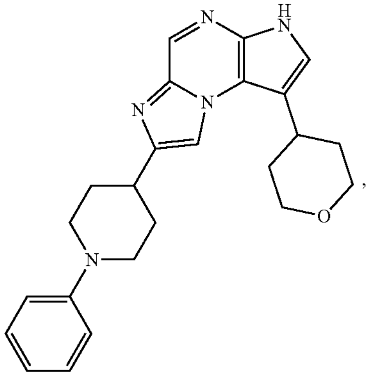
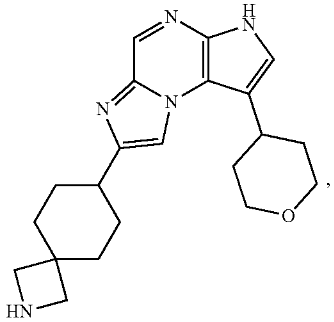
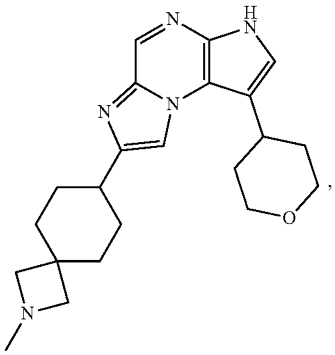
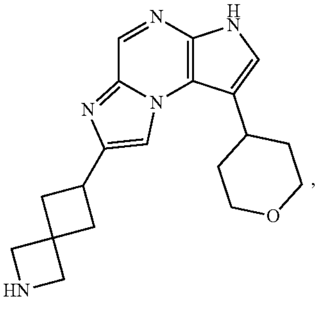

-continued
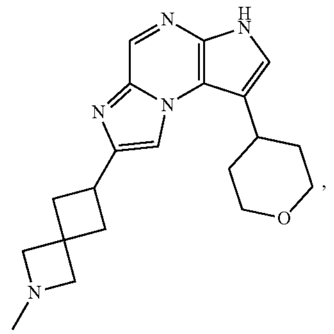
,
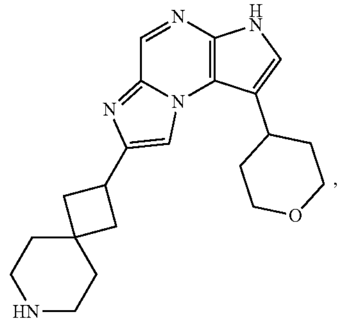
,
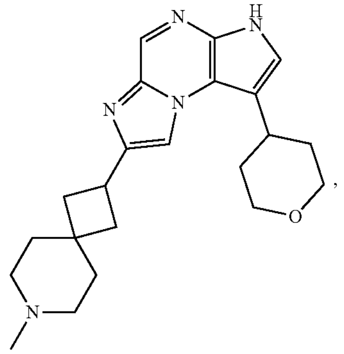
,
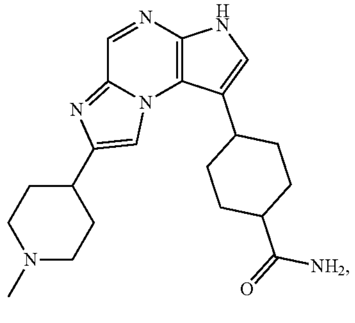
,
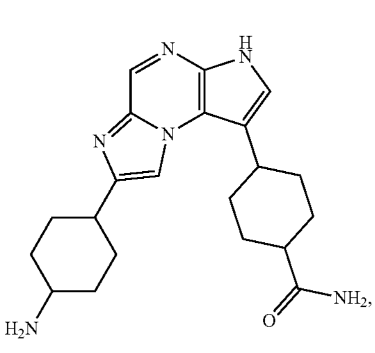
,
-continued
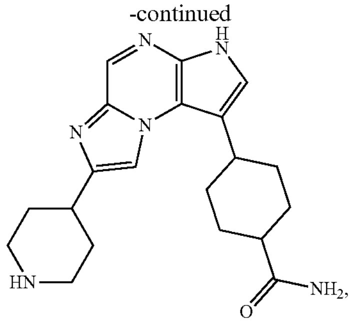
,
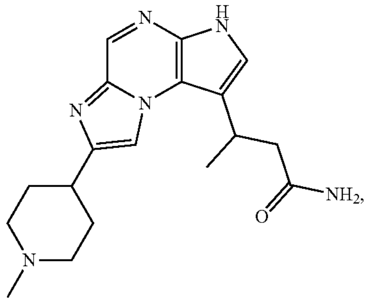
,
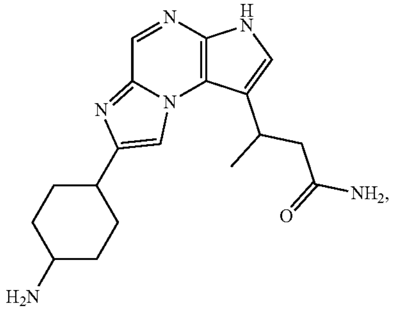
,
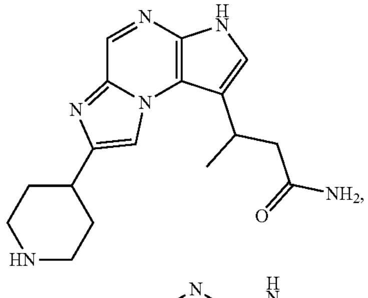
,
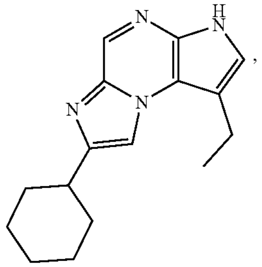
,
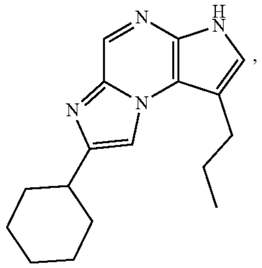
, -continued
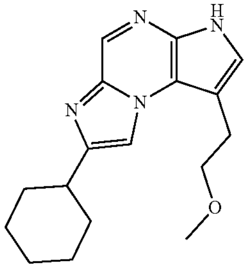
,
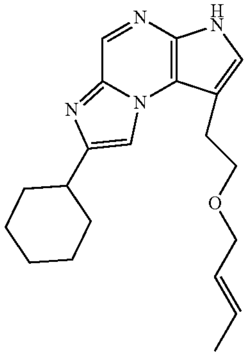
,
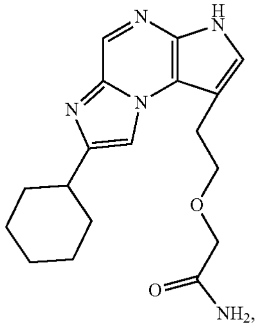
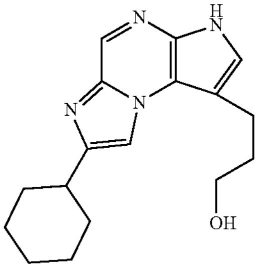
,
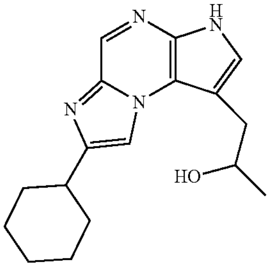
,
-continued
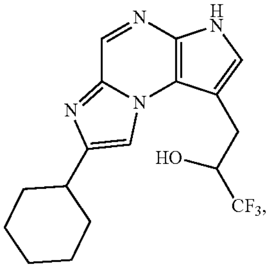
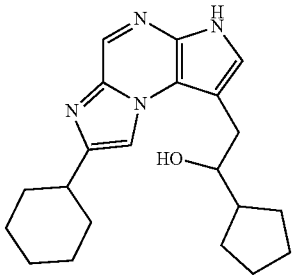
,
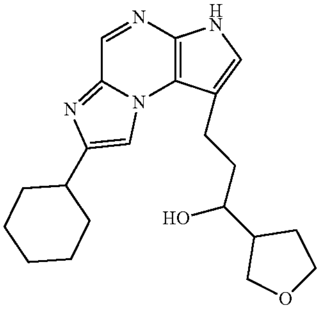
,
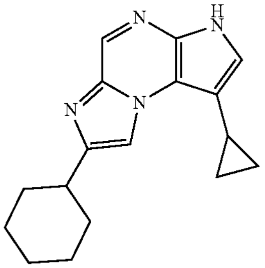
,
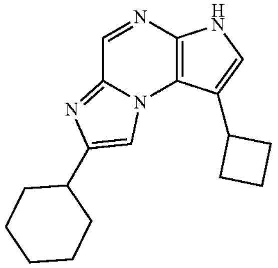
,
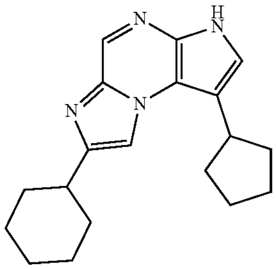
, -continued
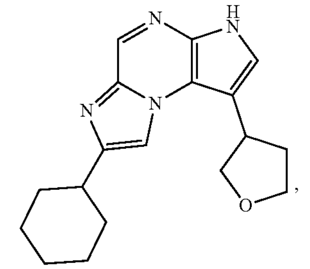
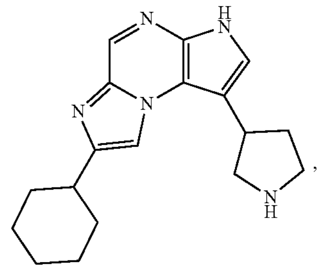
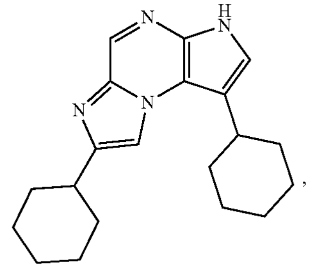
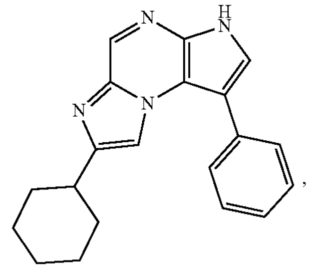
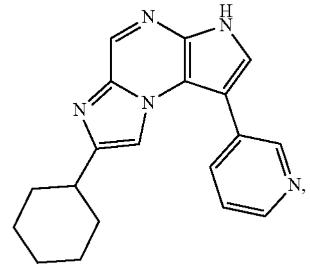
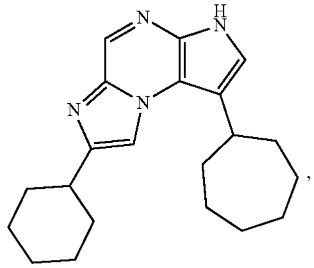
-continued
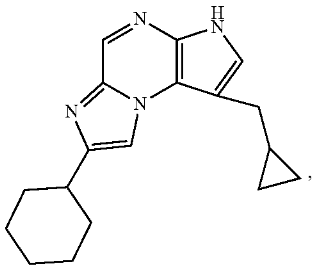
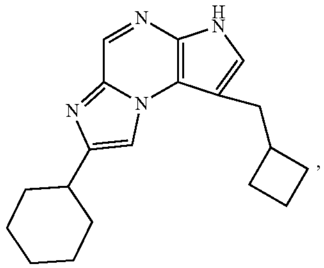
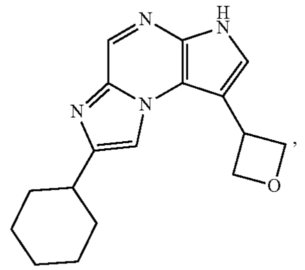
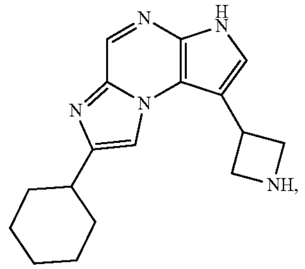
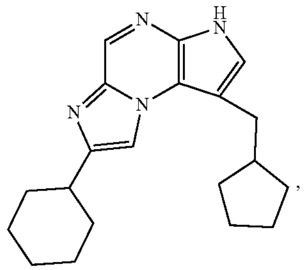
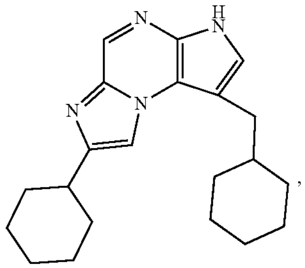

-continued
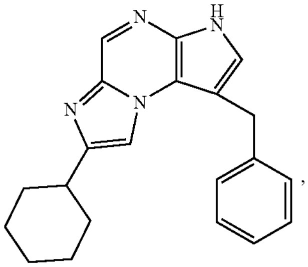
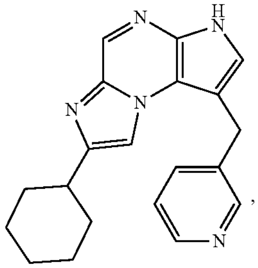
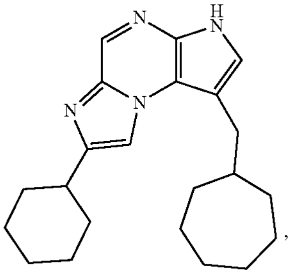
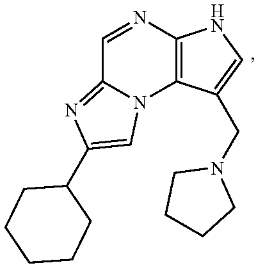
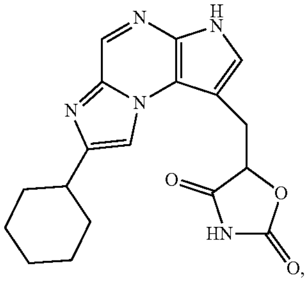
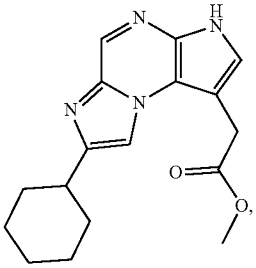
-continued
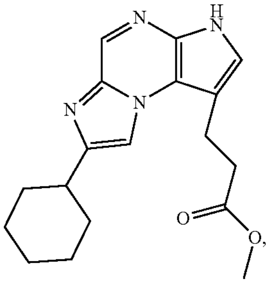
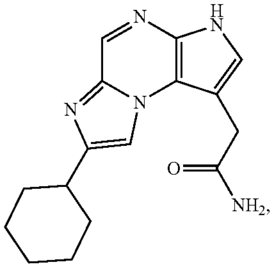
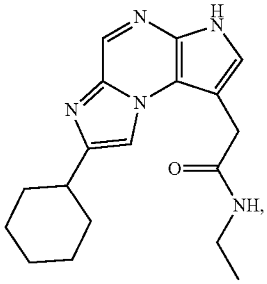
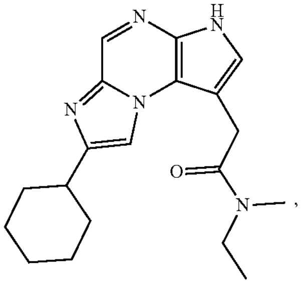
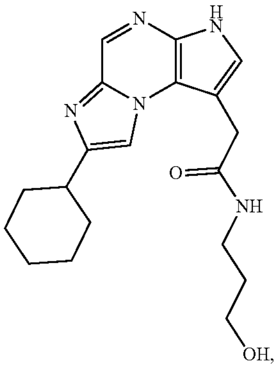

-continued
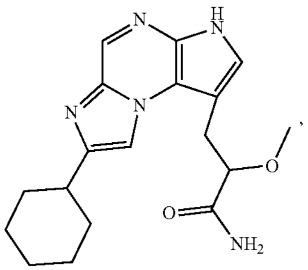
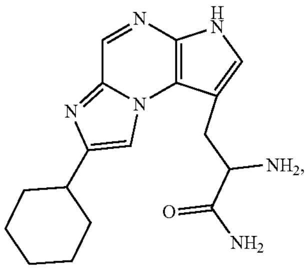
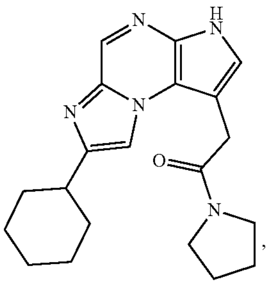
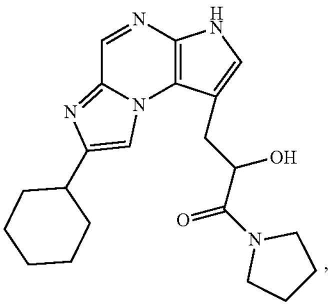
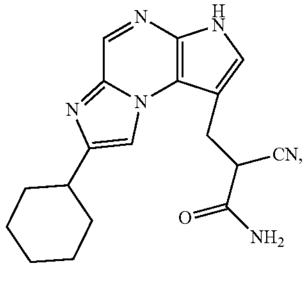
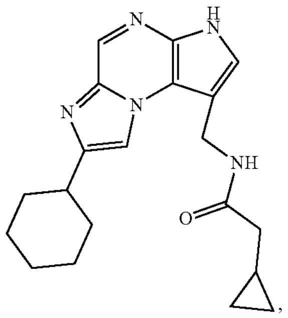
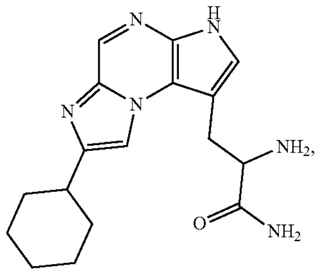
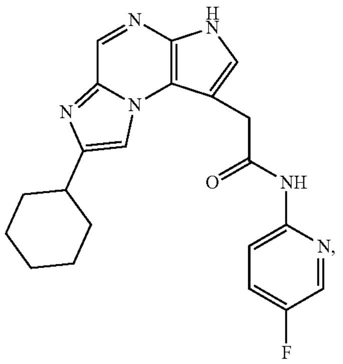
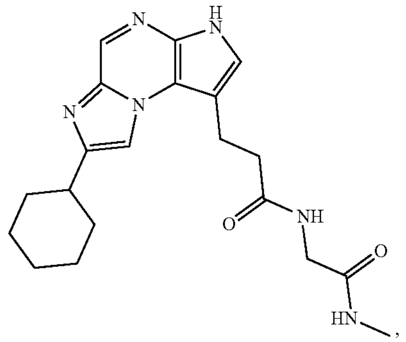
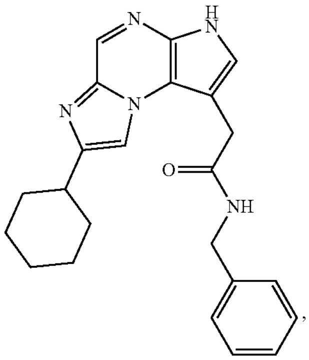

-continued
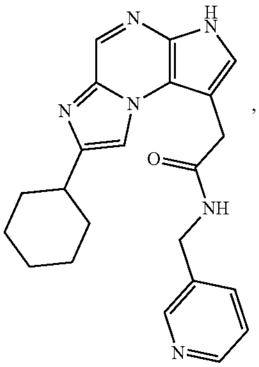
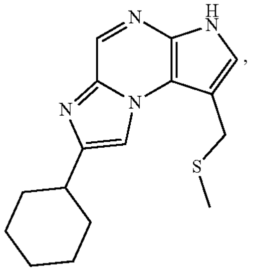
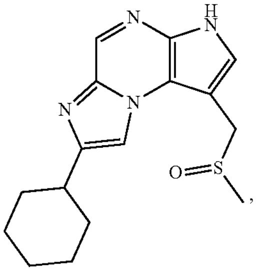
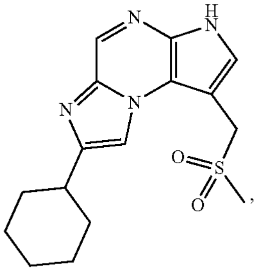
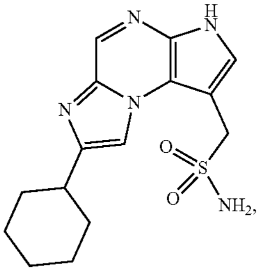
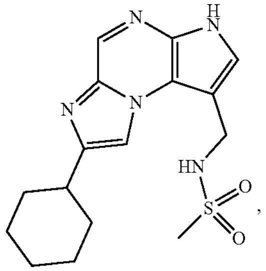
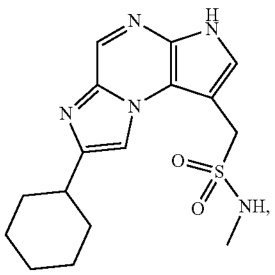
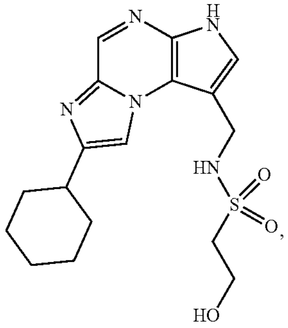
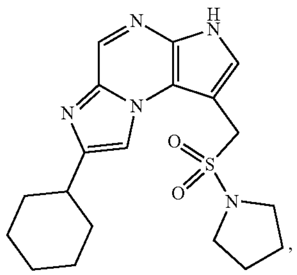
-continued
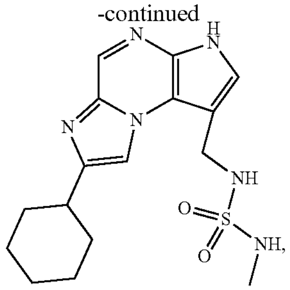
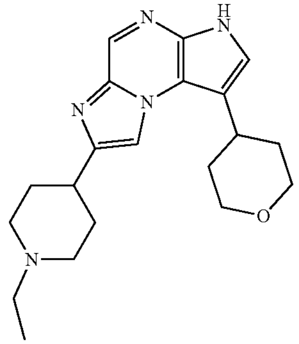
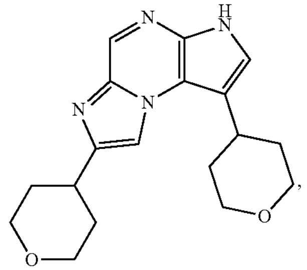
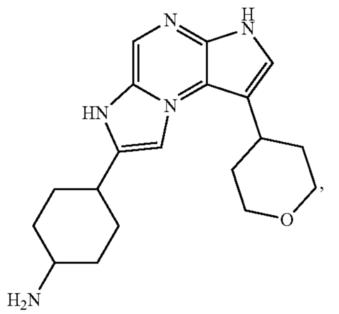
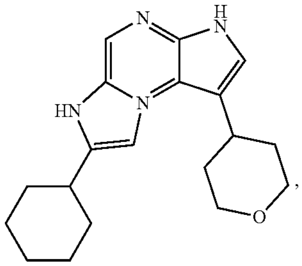
or -continued
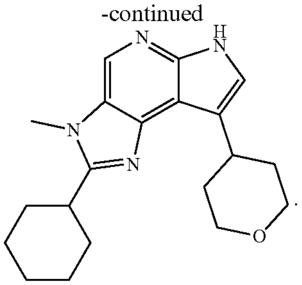
.
6. The compound, or the pharmaceutically acceptable salt thereof according to claim 5, wherein the compound has the following specific structural formula:
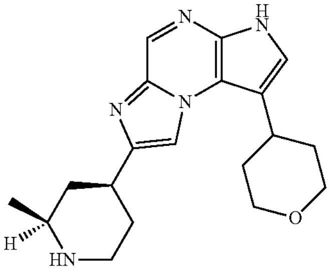
,
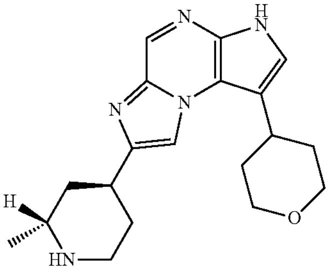
,
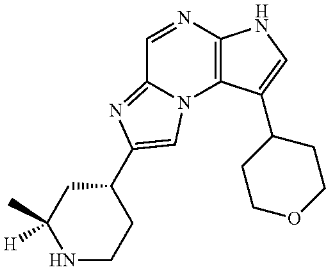
or
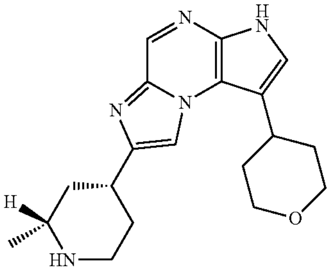
.
7. The compound, or the pharmaceutically acceptable salt thereof according to claim 5, wherein the compound is selected from the following structures:
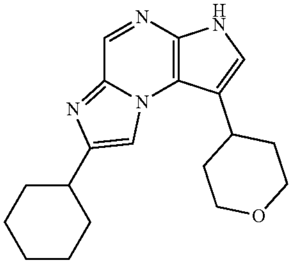
,
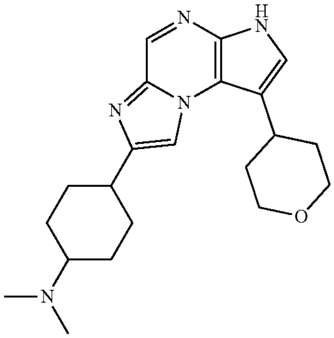
,
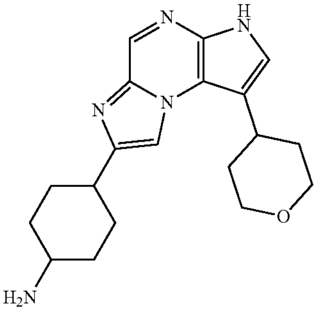
,
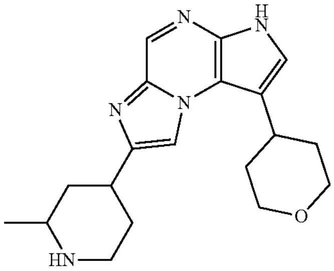
,
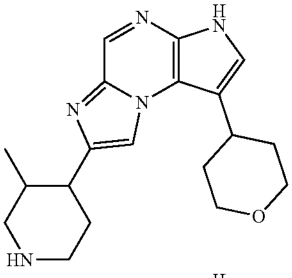
,
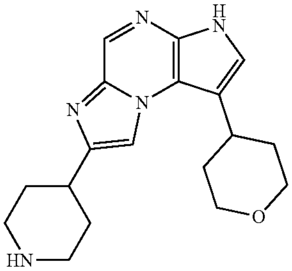
, -continued
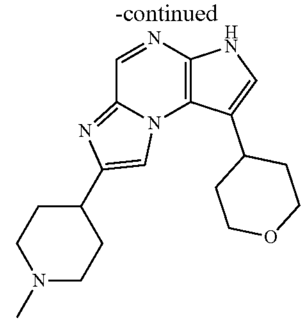
,
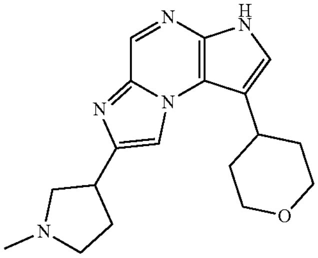
,
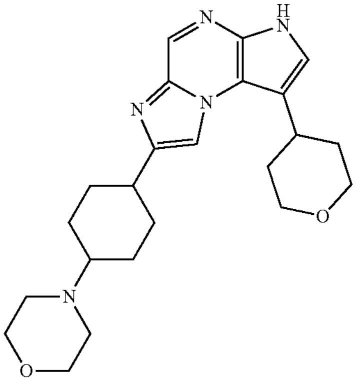
,
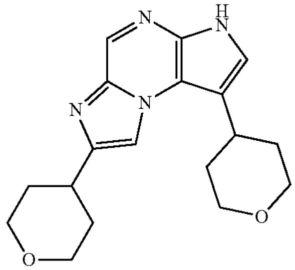
,
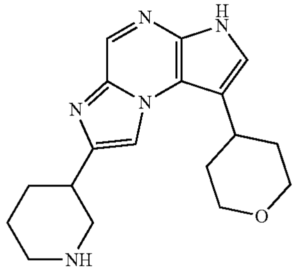
,
-continued
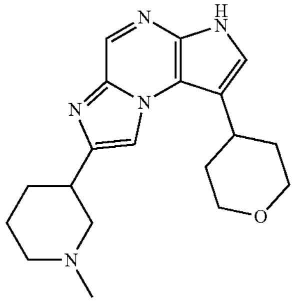
,
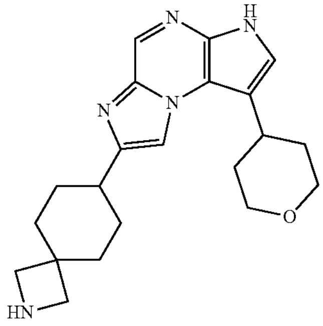
,
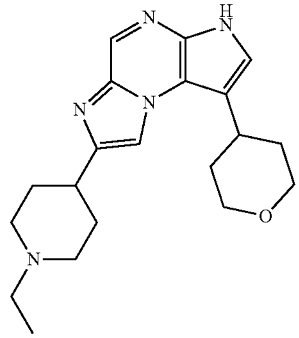
,
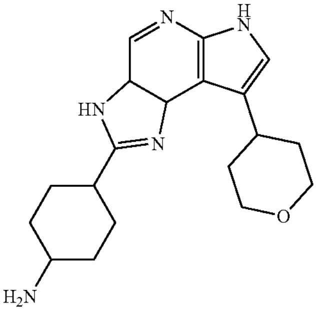
,
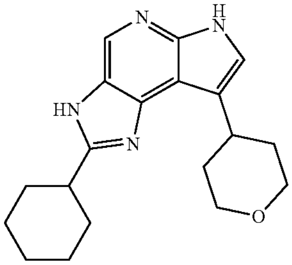
, or -continued

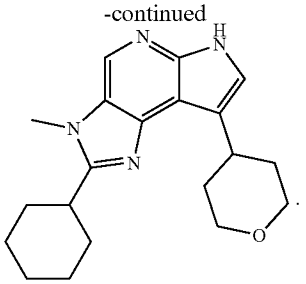

8. A method for treating a disease associated with interleukin-1 receptor-associated kinase-4 (IRAK4), comprising administering the compound, or the pharmaceutically acceptable salt thereof according to claim 5, wherein the disease associated with IRAK4 is selected from autoimmune diseases, inflammatory diseases, cancers, heteroimmune diseases, thromboembolism, atherosclerosis, myocardial infarction and metabolic syndrome.

9. The method according to claim 8, further comprising administering one or more pharmaceutical formulations selected from agonists and inhibitors of TLRs.

10. A compound, or a pharmaceutically acceptable salt, a stereoisomer, a solvate, or a deuterated compound thereof, wherein the compound has the following structural formula:

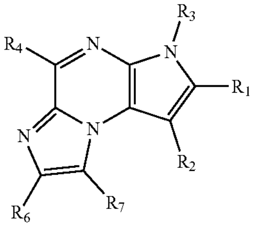

or

-continued

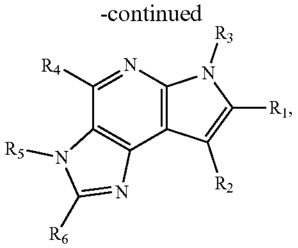

wherein:

$R_2$ is $C_{3-8}$ cycloalkyl or heterocycloalkyl, wherein H of the groups can be substituted with one or two or more of the following substituents: —OH, —$NH_2$, halogen, —CN, —$NO_2$, —$CF_3$, —$OCF_3$, ═O, —N alkyl, —O alkyl, —S alkyl, —SO-alkyl, —$SO_2$-alkyl, —COO-alkyl, —CON alkyl, —CO-alkyl, —OCO-alkyl, —N-alkyl-CON-alkyl, —N-alkyl-CO-alkyl, —N alkyl-$SO_2$-alkyl, substituted or unsubstituted aryl, and substituted or unsubstituted cycloalkyl;

$R_6$ is selected from $C_{3-8}$ cycloalkyl or heterocycloalkyl, wherein H of the groups can be substituted with one or two or more of the following substituents: —OH, —$NH_2$, halogen, —CN, —$NO_2$, —$CF_3$, —$OCF_3$, ═O, —N alkyl, —O alkyl, —S alkyl, —SO-alkyl, —$SO_2$-alkyl, —COO-alkyl, —CON alkyl, —CO-alkyl, —OCO-alkyl, —N-alkyl-CON-alkyl, —N alkyl-CO-alkyl, —N alkyl-$SO_2$-alkyl, substituted or unsubstituted aryl, and substituted or unsubstituted cycloalkyl, $R_1$, $R_3$, and $R_4$ are each —H, $R_7$ is —H, and $R_5$ is —H or —$CH_3$.

* * * * *